US008697654B2

(12) United States Patent
Cheng et al.

(10) Patent No.: US 8,697,654 B2
(45) Date of Patent: Apr. 15, 2014

(54) PEPTIDE LINKERS FOR EFFECTIVE MULTIVALENT PEPTIDE BINDING

(75) Inventors: Qiong Cheng, Wilmington, DE (US); Stephen R. Fahnestock, Wilmington, DE (US); Hongxian He, Wilmington, DE (US); Kristy N. Kostichka, Wilmington, DE (US); Hong Wang, Kennett Square, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 981 days.

(21) Appl. No.: 12/632,831

(22) Filed: Dec. 8, 2009

(65) Prior Publication Data

US 2010/0158823 A1 Jun. 24, 2010

Related U.S. Application Data

(60) Provisional application No. 61/138,633, filed on Dec. 18, 2008.

(51) Int. Cl.
| | | |
|---|---|---|
| A61K 38/16 | (2006.01) |
| A61K 8/00 | (2006.01) |
| A61Q 5/00 | (2006.01) |
| A61C 9/00 | (2006.01) |
| A61P 17/00 | (2006.01) |

(52) U.S. Cl.
USPC ........... 514/21.3; 530/324; 514/20.7; 424/47; 424/70.6; 433/215; 434/100

(58) Field of Classification Search
None
See application file for complete search history.

(56) References Cited

U.S. PATENT DOCUMENTS

| | | | |
|---|---|---|---|
| 5,192,332 | A | 3/1993 | Lang et al. |
| 5,597,386 | A | 1/1997 | Igarashi et al. |
| 6,258,558 | B1 | 7/2001 | Szostak et al. |
| 7,129,326 | B2 | 10/2006 | Janssen et al. |
| 7,220,405 | B2 | 5/2007 | Huang et al. |
| 7,285,264 | B2 | 10/2007 | O'Brien et al. |
| 7,297,847 | B1 | 11/2007 | Ludevid et al. |
| 7,309,482 | B2 | 12/2007 | Buseman-Williams et al. |
| 7,341,604 | B2 | 3/2008 | Rothe et al. |
| 7,585,495 | B2 | 9/2009 | O'Brien et al. |
| 7,759,460 | B2* | 7/2010 | Huang et al. ............ 530/324 |
| 8,263,056 | B2* | 9/2012 | Benson et al. ............ 424/70.9 |
| 8,273,337 | B2* | 9/2012 | Benson et al. ............ 424/70.9 |
| 8,287,845 | B2* | 10/2012 | Fahnestock et al. ....... 424/70.6 |
| 2002/0098524 | A1 | 7/2002 | Murray et al. |
| 2003/0185870 | A1 | 10/2003 | Grinstaff et al. |
| 2004/0115345 | A1 | 6/2004 | Huang et al. |
| 2005/0050656 | A1* | 3/2005 | Huang et al. ............ 8/406 |
| 2005/0054752 | A1 | 3/2005 | O'Brien et al. |
| 2005/0226839 | A1 | 10/2005 | Huang et al. |
| 2005/0249682 | A1 | 11/2005 | Buseman-Williams et al. |
| 2006/0073111 | A1 | 4/2006 | O'Brien et al. |
| 2006/0084115 | A1 | 4/2006 | DeNardo et al. |
| 2006/0140889 | A1 | 6/2006 | Houtzager et al. |
| 2006/0171885 | A1 | 8/2006 | Janssen et al. |
| 2006/0199206 | A1 | 9/2006 | Wang et al. |
| 2007/0048236 | A1* | 3/2007 | Huang et al. ............ 424/61 |
| 2007/0053857 | A1 | 3/2007 | Huang et al. |
| 2007/0065387 | A1 | 3/2007 | Beck et al. |
| 2007/0067924 | A1 | 3/2007 | Beck et al. |
| 2007/0110686 | A1 | 5/2007 | Lowe et al. |
| 2007/0141628 | A1 | 6/2007 | Cunningham et al. |
| 2007/0141629 | A1 | 6/2007 | Cunningham et al. |
| 2007/0196305 | A1 | 8/2007 | Wang et al. |
| 2007/0249805 | A1 | 10/2007 | Ittel et al. |
| 2007/0261775 | A1 | 11/2007 | Cunningham et al. |
| 2007/0264720 | A1 | 11/2007 | Cunningham et al. |
| 2007/0265431 | A1 | 11/2007 | Cunningham et al. |
| 2008/0075684 | A1 | 3/2008 | Barg et al. |
| 2008/0107614 | A1 | 5/2008 | Fahnestock et al. |
| 2008/0175798 | A1 | 7/2008 | Beck et al. |
| 2008/0206809 | A1 | 8/2008 | DeCarolis et al. |
| 2008/0207872 | A1 | 8/2008 | Cunningham et al. |
| 2008/0280810 | A1 | 11/2008 | O'Brien et al. |
| 2009/0074694 | A1 | 3/2009 | Benson et al. |
| 2009/0221477 | A1 | 9/2009 | Artymiuk et al. |

FOREIGN PATENT DOCUMENTS

| | | |
|---|---|---|
| JP | 08-104614 | 4/1996 |
| JP | 09-003100 | 1/1997 |
| JP | 2002-363026 | 12/2002 |
| WO | WO 97/28247 A2 | 8/1997 |
| WO | WO 00/48558 A1 | 8/2000 |
| WO | WO 01/79479 A2 | 10/2001 |
| WO | WO 03/050283 A2 | 6/2003 |
| WO | WO 04/000257 A2 | 12/2003 |
| WO | WO 2006/010891 A2 | 2/2006 |
| WO | WO 2006/031689 * | 3/2006 |
| WO | WO 2006/053613 A2 | 5/2006 |
| WO | WO 2007/126641 A1 | 11/2007 |
| WO | WO 2008/054746 A1 | 5/2008 |

OTHER PUBLICATIONS

Arai, 2001, Protein Engineering, 14, 529-532.*
Brinz, H. Kaspar et al., Engineering novel binding proteins from nonimmunoglobulin domains, Nature Biotechnology, Oct. 2005, pp. 1257-1268, vol. 23, No. 10.
Dani, Maria, Biological Libraries, J. of Receptor & Signal Transduction Research, 2001, pp. 447-468, vol. 21, No. 4.
Arai, Ryoichi et al., Design of the linkers which effectively separate domains of a bifunctional fusion, Protein Engineering, 2001, pp. 529-532, vol. 14, No. 8, Oxford University Press.
Beyermann, Michael et al., A Role for a Helical Connector between Two Receptor Binding Sites of a Long-chain Peptide Hormone, The Journal of Biological Chemistry, Feb. 25, 2000, pp. 5702-5709, vol. 275, No. 8, The American Society for Biochemistry and Molecular Biology, Inc.

(Continued)

*Primary Examiner* — Satyanarayana R Gudibande

(57) ABSTRACT

Short single chain peptides having affinity for a target surface often lack the binding durability required for certain commercial applications. One way to improve durability is to promote multivalent binding by linking together binding sequences using peptide linkers. However, the resulting single chain binding peptides often suffer from linker entropy. It has been discovered that the use of rigid peptide linkers when linking together multiple binding sequences enhances the binding affinity of the resulting single chain peptide.

21 Claims, 5 Drawing Sheets

(56) References Cited

OTHER PUBLICATIONS

Ihalainen, Janne A. et al., α-Helix folding in the presence of structural constraints, Proceedings of the National Academy of Science, Jul. 15, 2008, pp. 9588-9593, vol. 105, No. 28.

Mammen, Mathai et al., Polyvalent Interactions in Biological Systems: Implications for Design and Use of Multivalent Ligands and Inhibitors, Angew. Chem. Int. Ed., 1998, pp. 2754-2794, vol. 37, Wiley-VCH Verlag GmbH.

Mammen, Mathai et al., Using a Convenient, Quantitative Model for Torsional Entropy to Establish Qualitative Trends for Molecular Processes That Restrict Conformational Freedom, Journal of Organic Chemistry, 1998, pp. 3168-3175, vol. 63, American Chemical Society.

Mammen, Mathai et al., Estimating the Entropic Cost of Self-Assembly of Multiparticle Hydrogen-Bonded Aggregates Based on the Cyanuric Acid-Melamine Lattice, Journal of Organic Chemistry, 1998, pp. 3821-3830, vol. 53, American Chemical Society.

Marqusee, Susan et al., Helix stabilization by Glu—Lys+ salt bridges in short peptides of de novo design, Proceedings of the National Academy of Science, 1987, pp. 8898-8902, vol. 84.

Miller, Benjamin T. et al., CHARMMing: A New, Flexible Web Portal for CHARMM, Journal of Chemical Information and Modeling, Dec. 2008, pp. 1920-1929, vol. 48, American Chemical Society.

Minami, Toshiaki et al., Anti-nociceptive responses produced by human putative counterpart of nocistatin, British Journal of Pharmacology, 1998, pp. 1016-1018, vol. 124, Stockton Press.

Yan, Wei et al., α-Helical Linker of an Artificial 6-Zinc Finger Peptide Contributes to Selective DNA Binding to a Discontinuous Recognition Sequence, Biochemistry, 2007, pp. 8517-8524, vol. 46, American Chemical Society.

International Search Report dated Apr. 7, 2010, International Application No. PCT/US2009/068194.

\* cited by examiner

SEQUENCE LISTING

<160> NUMBER OF SEQ ID NOS: 595

<210> SEQ ID NO 1
<211> LENGTH: 19
<212> TYPE: PRT
<213> ORGANISM: artificial sequence
<220> FEATURE:
<223> OTHER INFORMATION: synthetic construct peptide linker

<400> SEQUENCE: 1

Gly Pro Glu Ala Ala Ala Lys Glu Ala Ala Lys Glu Ala Ala Ala
1               5                   10                  15

Lys Pro Ala

<210> SEQ ID NO 2
<211> LENGTH: 15
<212> TYPE: PRT
<213> ORGANISM: artificial sequence

```
<220> FEATURE:
<223> OTHER INFORMATION: synthetic linker

<400> SEQUENCE: 2

Glu Ala Ala Ala Lys Glu Ala Ala Lys Glu Ala Ala Ala Lys
1               5                   10                  15

<210> SEQ ID NO 3
<211> LENGTH: 29
<212> TYPE: PRT
<213> ORGANISM: artificial sequence
<220> FEATURE:
<223> OTHER INFORMATION: synthetic linker

<400> SEQUENCE: 3

Gly Pro Glu Ala Ala Ala Lys Glu Ala Ala Ala Lys Glu Ala Ala Ala
1               5                   10                  15

Lys Glu Ala Ala Ala Lys Glu Ala Ala Ala Lys Pro Ala
                20                  25

<210> SEQ ID NO 4
<211> LENGTH: 25
<212> TYPE: PRT
<213> ORGANISM: artificial sequence
<220> FEATURE:
<223> OTHER INFORMATION: synthetic linker

<400> SEQUENCE: 4

Glu Ala Ala Ala Lys Glu Ala Ala Ala Lys Glu Ala Ala Ala Lys Glu
1               5                   10                  15

Ala Ala Ala Lys Glu Ala Ala Ala Lys
                20                  25

<210> SEQ ID NO 5
<211> LENGTH: 34
<212> TYPE: PRT
<213> ORGANISM: artificial sequence
<220> FEATURE:
<223> OTHER INFORMATION: synthetic linker

<400> SEQUENCE: 5

Gly Pro Glu Ala Ala Ala Lys Glu Ala Ala Ala Lys Glu Ala Ala Ala
1               5                   10                  15

Lys Glu Ala Ala Ala Lys Glu Ala Ala Ala Lys Glu Ala Ala Ala Lys
                20                  25                  30

Pro Ala

<210> SEQ ID NO 6
<211> LENGTH: 30
<212> TYPE: PRT
<213> ORGANISM: artificial sequence
<220> FEATURE:
<223> OTHER INFORMATION: synthetic linker

<400> SEQUENCE: 6

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys
                20                  25                  30

<210> SEQ ID NO 7
<211> LENGTH: 16
<212> TYPE: PRT
<213> ORGANISM: artificial sequence
```

-continued

```
<220> FEATURE:
<223> OTHER INFORMATION: synthetic linker

<400> SEQUENCE: 7

Gly Pro Glu Glu Ala Ala Lys Lys Glu Glu Ala Ala Lys Lys Pro Ala
1               5                   10                  15

<210> SEQ ID NO 8
<211> LENGTH: 12
<212> TYPE: PRT
<213> ORGANISM: artificial sequence
<220> FEATURE:
<223> OTHER INFORMATION: synthetic linker

<400> SEQUENCE: 8

Glu Glu Ala Ala Lys Lys Glu Glu Ala Ala Lys Lys
1               5                   10

<210> SEQ ID NO 9
<211> LENGTH: 28
<212> TYPE: PRT
<213> ORGANISM: artificial sequence
<220> FEATURE:
<223> OTHER INFORMATION: synthetic linker

<400> SEQUENCE: 9

Gly Pro Glu Glu Ala Ala Lys Lys Glu Glu Ala Ala Lys Lys Glu Glu
1               5                   10                  15

Ala Ala Lys Lys Glu Glu Ala Ala Lys Lys Pro Ala
            20                  25

<210> SEQ ID NO 10
<211> LENGTH: 24
<212> TYPE: PRT
<213> ORGANISM: artificial sequence
<220> FEATURE:
<223> OTHER INFORMATION: synthetic linker

<400> SEQUENCE: 10

Glu Glu Ala Ala Lys Lys Glu Glu Ala Ala Lys Lys Glu Glu Ala Ala
1               5                   10                  15

Lys Lys Glu Glu Ala Ala Lys Lys
            20

<210> SEQ ID NO 11
<211> LENGTH: 34
<212> TYPE: PRT
<213> ORGANISM: artificial sequence
<220> FEATURE:
<223> OTHER INFORMATION: synthetic linker

<400> SEQUENCE: 11

Gly Pro Glu Glu Ala Ala Lys Lys Glu Glu Ala Ala Lys Lys Glu Glu
1               5                   10                  15

Ala Ala Lys Lys Glu Glu Ala Ala Lys Lys Glu Glu Ala Ala Lys Lys
            20                  25                  30

Pro Ala

<210> SEQ ID NO 12
<211> LENGTH: 30
<212> TYPE: PRT
<213> ORGANISM: artificial sequence
<220> FEATURE:
<223> OTHER INFORMATION: synthetic linker
```

```
<400> SEQUENCE: 12

Glu Glu Ala Ala Lys Lys Glu Glu Ala Ala Lys Glu Glu Ala Ala
1               5                   10                  15
Lys Lys Glu Glu Ala Ala Lys Lys Glu Glu Ala Ala Lys Lys
                20                  25                  30

<210> SEQ ID NO 13
<211> LENGTH: 12
<212> TYPE: PRT
<213> ORGANISM: artificial sequence
<220> FEATURE:
<223> OTHER INFORMATION: synthetic linker

<400> SEQUENCE: 13

Gly Pro Lys Pro Lys Pro Lys Pro Lys Pro Pro Ala
1               5                   10

<210> SEQ ID NO 14
<211> LENGTH: 8
<212> TYPE: PRT
<213> ORGANISM: artificial sequence
<220> FEATURE:
<223> OTHER INFORMATION: synthetic linker

<400> SEQUENCE: 14

Lys Pro Lys Pro Lys Pro Lys Pro
1               5

<210> SEQ ID NO 15
<211> LENGTH: 20
<212> TYPE: PRT
<213> ORGANISM: artificial sequence
<220> FEATURE:
<223> OTHER INFORMATION: synthetic linker

<400> SEQUENCE: 15

Gly Pro Lys Pro Lys Pro Lys Pro Lys Pro Lys Pro Lys Pro Lys Pro
1               5                   10                  15
Lys Pro Pro Ala
                20

<210> SEQ ID NO 16
<211> LENGTH: 16
<212> TYPE: PRT
<213> ORGANISM: artificial sequence
<220> FEATURE:
<223> OTHER INFORMATION: synthetic linker

<400> SEQUENCE: 16

Lys Pro Lys Pro Lys Pro Lys Pro Lys Pro Lys Pro Lys Pro Lys Pro
1               5                   10                  15

<210> SEQ ID NO 17
<211> LENGTH: 28
<212> TYPE: PRT
<213> ORGANISM: artificial sequence
<220> FEATURE:
<223> OTHER INFORMATION: synthetic linker

<400> SEQUENCE: 17

Gly Pro Lys Pro Lys Pro Lys Pro Lys Pro Lys Pro Lys Pro Lys Pro
1               5                   10                  15
Lys Pro Lys Pro Lys Pro Lys Pro Lys Pro Pro Ala
                20                  25
```

```
<210> SEQ ID NO 18
<211> LENGTH: 24
<212> TYPE: PRT
<213> ORGANISM: artificial sequence
<220> FEATURE:
<223> OTHER INFORMATION: synthetic linker

<400> SEQUENCE: 18

Lys Pro Lys Pro Lys Pro Lys Pro Lys Pro Lys Pro Lys Pro Lys Pro
1               5                   10                  15

Lys Pro Lys Pro Lys Pro Lys Pro
            20

<210> SEQ ID NO 19
<211> LENGTH: 36
<212> TYPE: PRT
<213> ORGANISM: artificial sequence
<220> FEATURE:
<223> OTHER INFORMATION: synthetic linker

<400> SEQUENCE: 19

Gly Pro Lys Pro Lys Pro Lys Pro Lys Pro Lys Pro Lys Pro Lys Pro
1               5                   10                  15

Lys Pro Lys Pro Lys Pro Lys Pro Lys Pro Lys Pro Lys Pro Lys Pro
            20                  25                  30

Lys Pro Pro Ala
        35

<210> SEQ ID NO 20
<211> LENGTH: 32
<212> TYPE: PRT
<213> ORGANISM: artificial sequence
<220> FEATURE:
<223> OTHER INFORMATION: synthetic linker

<400> SEQUENCE: 20

Lys Pro Lys Pro Lys Pro Lys Pro Lys Pro Lys Pro Lys Pro Lys Pro
1               5                   10                  15

Lys Pro Lys Pro Lys Pro Lys Pro Lys Pro Lys Pro Lys Pro Lys Pro
            20                  25                  30

<210> SEQ ID NO 21
<211> LENGTH: 12
<212> TYPE: PRT
<213> ORGANISM: artificial sequence
<220> FEATURE:
<223> OTHER INFORMATION: synthetic linker

<400> SEQUENCE: 21

Gly Pro Gly Gly Gly Ser Gly Gly Gly Ser Pro Ala
1               5                   10

<210> SEQ ID NO 22
<211> LENGTH: 8
<212> TYPE: PRT
<213> ORGANISM: artificial sequence
<220> FEATURE:
<223> OTHER INFORMATION: synthetic linker

<400> SEQUENCE: 22

Gly Gly Gly Ser Gly Gly Gly Ser
1               5

<210> SEQ ID NO 23
<211> LENGTH: 20
<212> TYPE: PRT
```

<213> ORGANISM: artificial sequence
<220> FEATURE:
<223> OTHER INFORMATION: synthetic linker

<400> SEQUENCE: 23

Gly Pro Gly Gly Gly Ser Gly Gly Gly Ser Gly Gly Gly Ser Gly Gly
1               5                   10                  15

Gly Ser Pro Ala
            20

<210> SEQ ID NO 24
<211> LENGTH: 16
<212> TYPE: PRT
<213> ORGANISM: artificial sequence
<220> FEATURE:
<223> OTHER INFORMATION: synthetic linker

<400> SEQUENCE: 24

Gly Gly Gly Ser Gly Gly Gly Ser Gly Gly Gly Ser Gly Gly Gly Ser
1               5                   10                  15

<210> SEQ ID NO 25
<211> LENGTH: 28
<212> TYPE: PRT
<213> ORGANISM: artificial sequence
<220> FEATURE:
<223> OTHER INFORMATION: synthetic linker

<400> SEQUENCE: 25

Gly Pro Gly Gly Gly Ser Gly Gly Gly Ser Gly Gly Gly Ser Gly Gly
1               5                   10                  15

Gly Ser Gly Gly Gly Ser Gly Gly Gly Ser Pro Ala
            20                  25

<210> SEQ ID NO 26
<211> LENGTH: 24
<212> TYPE: PRT
<213> ORGANISM: artificial sequence
<220> FEATURE:
<223> OTHER INFORMATION: synthetic linker

<400> SEQUENCE: 26

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 27
<211> LENGTH: 14
<212> TYPE: PRT
<213> ORGANISM: artificial sequence
<220> FEATURE:
<223> OTHER INFORMATION: synthetic linker

<400> SEQUENCE: 27

Gly Pro Glu Gly Gly Gly Ser Glu Gly Gly Gly Ser Pro Ala
1               5                   10

<210> SEQ ID NO 28
<211> LENGTH: 10
<212> TYPE: PRT
<213> ORGANISM: artificial sequence
<220> FEATURE:
<223> OTHER INFORMATION: synthetic linker

<400> SEQUENCE: 28

```
Glu Gly Gly Gly Ser Glu Gly Gly Gly Ser
1               5                   10

<210> SEQ ID NO 29
<211> LENGTH: 26
<212> TYPE: PRT
<213> ORGANISM: artificial sequence
<220> FEATURE:
<223> OTHER INFORMATION: synthetic linker

<400> SEQUENCE: 29

Gly Pro Pro Glu Gly Gly Gly Ser Glu Gly Gly Gly Ser Pro Glu Gly
1               5                   10                  15

Gly Gly Ser Glu Gly Gly Gly Ser Pro Ala
            20                  25

<210> SEQ ID NO 30
<211> LENGTH: 22
<212> TYPE: PRT
<213> ORGANISM: artificial sequence
<220> FEATURE:
<223> OTHER INFORMATION: synthetic linker

<400> SEQUENCE: 30

Pro Glu Gly Gly Gly Ser Glu Gly Gly Gly Ser Pro Glu Gly Gly Gly
1               5                   10                  15

Ser Glu Gly Gly Gly Ser
            20

<210> SEQ ID NO 31
<211> LENGTH: 34
<212> TYPE: PRT
<213> ORGANISM: artificial sequence
<220> FEATURE:
<223> OTHER INFORMATION: synthetic linker

<400> SEQUENCE: 31

Gly Pro Glu Gly Gly Gly Ser Glu Gly Gly Gly Ser Glu Gly Gly Gly
1               5                   10                  15

Ser Glu Gly Gly Gly Ser Glu Gly Gly Gly Ser Glu Gly Gly Gly Ser
            20                  25                  30

Pro Ala

<210> SEQ ID NO 32
<211> LENGTH: 30
<212> TYPE: PRT
<213> ORGANISM: artificial sequence
<220> FEATURE:
<223> OTHER INFORMATION: synthetic linker

<400> SEQUENCE: 32

Glu Gly Gly Gly Ser Glu Gly Gly Gly Ser Glu Gly Gly Gly Ser Glu
1               5                   10                  15

Gly Gly Gly Ser Glu Gly Gly Gly Ser Glu Gly Gly Gly Ser
            20                  25                  30

<210> SEQ ID NO 33
<211> LENGTH: 14
<212> TYPE: PRT
<213> ORGANISM: artificial sequence
<220> FEATURE:
<223> OTHER INFORMATION: synthetic linker

<400> SEQUENCE: 33

Gly Pro Lys Gly Gly Gly Ser Lys Gly Gly Gly Ser Pro Ala
```

```
<210> SEQ ID NO 34
<211> LENGTH: 10
<212> TYPE: PRT
<213> ORGANISM: artificial sequence
<220> FEATURE:
<223> OTHER INFORMATION: synthetic linker

<400> SEQUENCE: 34

Lys Gly Gly Gly Ser Lys Gly Gly Gly Ser
1               5                   10

<210> SEQ ID NO 35
<211> LENGTH: 24
<212> TYPE: PRT
<213> ORGANISM: artificial sequence
<220> FEATURE:
<223> OTHER INFORMATION: synthetic linker

<400> SEQUENCE: 35

Gly Pro Lys Gly Gly Gly Ser Lys Gly Gly Gly Ser Lys Gly Gly
1               5                   10                  15

Ser Lys Gly Gly Gly Ser Pro Ala
            20

<210> SEQ ID NO 36
<211> LENGTH: 20
<212> TYPE: PRT
<213> ORGANISM: artificial sequence
<220> FEATURE:
<223> OTHER INFORMATION: synthetic linker

<400> SEQUENCE: 36

Lys Gly Gly Gly Ser Lys Gly Gly Gly Ser Lys Gly Gly Gly Ser Lys
1               5                   10                  15

Gly Gly Gly Ser
            20

<210> SEQ ID NO 37
<211> LENGTH: 34
<212> TYPE: PRT
<213> ORGANISM: artificial sequence
<220> FEATURE:
<223> OTHER INFORMATION: synthetic linker

<400> SEQUENCE: 37

Gly Pro Lys Gly Gly Gly Ser Lys Gly Gly Gly Ser Lys Gly Gly
1               5                   10                  15

Ser Lys Gly Gly Gly Ser Lys Gly Gly Gly Ser Lys Gly Gly Gly Ser
            20                  25                  30

Pro Ala

<210> SEQ ID NO 38
<211> LENGTH: 30
<212> TYPE: PRT
<213> ORGANISM: artificial sequence
<220> FEATURE:
<223> OTHER INFORMATION: synthetic linker

<400> SEQUENCE: 38

Lys Gly Gly Gly Ser Lys Gly Gly Gly Ser Lys Gly Gly Gly Ser Lys
1               5                   10                  15

Gly Gly Gly Ser Lys Gly Gly Gly Ser Lys Gly Gly Gly Ser
            20                  25                  30
```

```
<210> SEQ ID NO 39
<211> LENGTH: 15
<212> TYPE: PRT
<213> ORGANISM: artificial sequence
<220> FEATURE:
<223> OTHER INFORMATION: synthetic linker

<400> SEQUENCE: 39

Gly Pro Gly Ala Gly Gly Ala Gly Gly Ser Gly Gly Ser Pro Ala
1               5                   10                  15

<210> SEQ ID NO 40
<211> LENGTH: 11
<212> TYPE: PRT
<213> ORGANISM: artificial sequence
<220> FEATURE:
<223> OTHER INFORMATION: synthetic linker

<400> SEQUENCE: 40

Gly Ala Gly Gly Ala Gly Gly Ser Gly Gly Ser
1               5                   10

<210> SEQ ID NO 41
<211> LENGTH: 26
<212> TYPE: PRT
<213> ORGANISM: artificial sequence
<220> FEATURE:
<223> OTHER INFORMATION: synthetic linker

<400> SEQUENCE: 41

Gly Pro Gly Ala Gly Gly Ala Gly Gly Ser Gly Gly Ser Gly Ala Gly
1               5                   10                  15

Gly Ala Gly Gly Ser Gly Gly Ser Pro Ala
            20                  25

<210> SEQ ID NO 42
<211> LENGTH: 22
<212> TYPE: PRT
<213> ORGANISM: artificial sequence
<220> FEATURE:
<223> OTHER INFORMATION: synthetic linker

<400> SEQUENCE: 42

Gly Ala Gly Gly Ala Gly Ser Gly Gly Ser Gly Ala Gly Gly Ala
1               5                   10                  15

Gly Gly Ser Gly Gly Ser
            20

<210> SEQ ID NO 43
<211> LENGTH: 37
<212> TYPE: PRT
<213> ORGANISM: artificial sequence
<220> FEATURE:
<223> OTHER INFORMATION: synthetic linker

<400> SEQUENCE: 43

Gly Pro Gly Ala Gly Gly Ala Gly Gly Ser Gly Gly Ser Gly Ala Gly
1               5                   10                  15

Gly Ala Gly Gly Ser Gly Gly Ser Gly Ala Gly Gly Ala Gly Gly Ser
            20                  25                  30

Gly Gly Ser Pro Ala
        35

<210> SEQ ID NO 44
```

```
<211> LENGTH: 33
<212> TYPE: PRT
<213> ORGANISM: artificial sequence
<220> FEATURE:
<223> OTHER INFORMATION: synthetic linker

<400> SEQUENCE: 44

Gly Ala Gly Gly Ala Gly Gly Ser Gly Gly Ser Gly Ala Gly Gly Ala
1               5                   10                  15

Gly Gly Ser Gly Gly Ser Gly Ala Gly Gly Ala Gly Gly Ser Gly Gly
            20                  25                  30

Ser

<210> SEQ ID NO 45
<211> LENGTH: 15
<212> TYPE: PRT
<213> ORGANISM: artificial sequence
<220> FEATURE:
<223> OTHER INFORMATION: synthetic linker

<400> SEQUENCE: 45

Gly Pro Ala Gly Pro Ala Pro Gly Ser Pro Gly Ser Pro Pro Ala
1               5                   10                  15

<210> SEQ ID NO 46
<211> LENGTH: 11
<212> TYPE: PRT
<213> ORGANISM: artificial sequence
<220> FEATURE:
<223> OTHER INFORMATION: synthetic linker

<400> SEQUENCE: 46

Ala Gly Pro Ala Pro Gly Ser Pro Gly Ser Pro
1               5                   10

<210> SEQ ID NO 47
<211> LENGTH: 26
<212> TYPE: PRT
<213> ORGANISM: artificial sequence
<220> FEATURE:
<223> OTHER INFORMATION: synthetic linker

<400> SEQUENCE: 47

Gly Pro Ala Gly Pro Ala Pro Gly Ser Pro Gly Ser Pro Ala Gly Pro
1               5                   10                  15

Ala Pro Gly Ser Pro Gly Ser Pro Pro Ala
            20                  25

<210> SEQ ID NO 48
<211> LENGTH: 22
<212> TYPE: PRT
<213> ORGANISM: artificial sequence
<220> FEATURE:
<223> OTHER INFORMATION: synthetic linker

<400> SEQUENCE: 48

Ala Gly Pro Ala Pro Gly Ser Pro Gly Ser Pro Ala Gly Pro Ala Pro
1               5                   10                  15

Gly Ser Pro Gly Ser Pro
            20

<210> SEQ ID NO 49
<211> LENGTH: 37
<212> TYPE: PRT
<213> ORGANISM: artificial sequence
<220> FEATURE:
```

<223> OTHER INFORMATION: synthetic linker

<400> SEQUENCE: 49

Gly Pro Ala Gly Pro Ala Pro Gly Ser Pro Gly Ser Pro Ala Gly Pro
1               5                   10                  15
Ala Pro Gly Ser Pro Gly Ser Pro Ala Gly Pro Ala Pro Gly Ser Pro
            20                  25                  30
Gly Ser Pro Pro Ala
        35

<210> SEQ ID NO 50
<211> LENGTH: 33
<212> TYPE: PRT
<213> ORGANISM: artificial sequence
<220> FEATURE:
<223> OTHER INFORMATION: synthetic linker

<400> SEQUENCE: 50

Ala Gly Pro Ala Pro Gly Ser Pro Gly Ser Pro Ala Gly Pro Ala Pro
1               5                   10                  15
Gly Ser Pro Gly Ser Pro Ala Gly Pro Ala Pro Gly Ser Pro Gly Ser
            20                  25                  30
Pro

<210> SEQ ID NO 51
<211> LENGTH: 32
<212> TYPE: PRT
<213> ORGANISM: artificial sequence
<220> FEATURE:
<223> OTHER INFORMATION: synthetic linker

<400> SEQUENCE: 51

Gly Pro Lys Pro Lys Pro Lys Pro Lys Pro Lys Pro Lys Pro Gly Gly
1               5                   10                  15
Lys Pro Lys Pro Lys Pro Lys Pro Lys Pro Lys Pro Gly Gly Pro Ala
            20                  25                  30

<210> SEQ ID NO 52
<211> LENGTH: 28
<212> TYPE: PRT
<213> ORGANISM: artificial sequence
<220> FEATURE:
<223> OTHER INFORMATION: synthetic linker

<400> SEQUENCE: 52

Lys Pro Lys Pro Lys Pro Lys Pro Lys Pro Lys Pro Gly Gly Lys Pro
1               5                   10                  15
Lys Pro Lys Pro Lys Pro Lys Pro Lys Pro Gly Gly
            20                  25

<210> SEQ ID NO 53
<211> LENGTH: 37
<212> TYPE: PRT
<213> ORGANISM: artificial sequence
<220> FEATURE:
<223> OTHER INFORMATION: synthetic linker

<400> SEQUENCE: 53

Gly Pro Glu Pro Glu Pro Glu Pro Glu Pro Ile Pro Glu Pro Pro Lys
1               5                   10                  15
Glu Ala Pro Val Val Ile Glu Lys Pro Lys Pro Lys Pro Lys Pro Lys
            20                  25                  30
Pro Lys Pro Pro Ala

<210> SEQ ID NO 54
<211> LENGTH: 33
<212> TYPE: PRT
<213> ORGANISM: artificial sequence
<220> FEATURE:
<223> OTHER INFORMATION: synthetic linker

<400> SEQUENCE: 54

Glu Pro Glu Pro Glu Pro Glu Pro Ile Pro Glu Pro Pro Lys Glu Ala
1               5                   10                  15

Pro Val Val Ile Glu Lys Pro Lys Pro Lys Pro Lys Pro Lys Pro Lys
            20                  25                  30

Pro

<210> SEQ ID NO 55
<211> LENGTH: 25
<212> TYPE: PRT
<213> ORGANISM: artificial sequence
<220> FEATURE:
<223> OTHER INFORMATION: synthetic linker

<400> SEQUENCE: 55

Gly Pro Glu Ala Ala Ala Lys Leu Leu Glu Ala Ala Ala Lys Leu Leu
1               5                   10                  15

Glu Ala Ala Ala Lys Leu Leu Pro Ala
            20                  25

<210> SEQ ID NO 56
<211> LENGTH: 21
<212> TYPE: PRT
<213> ORGANISM: artificial sequence
<220> FEATURE:
<223> OTHER INFORMATION: synthetic linker

<400> SEQUENCE: 56

Glu Ala Ala Ala Lys Leu Leu Glu Ala Ala Ala Lys Leu Leu Glu Ala
1               5                   10                  15

Ala Ala Lys Leu Leu
            20

<210> SEQ ID NO 57
<211> LENGTH: 32
<212> TYPE: PRT
<213> ORGANISM: artificial sequence
<220> FEATURE:
<223> OTHER INFORMATION: synthetic linker

<400> SEQUENCE: 57

Gly Pro Glu Ala Ala Ala Lys Leu Leu Glu Ala Ala Ala Lys Leu Leu
1               5                   10                  15

Glu Ala Ala Ala Lys Leu Leu Glu Ala Ala Ala Lys Leu Leu Pro Ala
            20                  25                  30

<210> SEQ ID NO 58
<211> LENGTH: 28
<212> TYPE: PRT
<213> ORGANISM: artificial sequence
<220> FEATURE:
<223> OTHER INFORMATION: synthetic linker

<400> SEQUENCE: 58

Glu Ala Ala Ala Lys Leu Leu Glu Ala Ala Ala Lys Leu Leu Glu Ala
1               5                   10                  15

```
Ala Ala Lys Leu Leu Glu Ala Ala Ala Lys Leu Leu
            20                  25
```

<210> SEQ ID NO 59
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 59

```
Thr Pro Pro Glu Leu Leu His Gly Ala Pro Arg Ser
1               5                   10
```

<210> SEQ ID NO 60
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 60

```
Thr Pro Pro Thr Asn Val Leu Met Leu Ala Thr Lys
1               5                   10
```

<210> SEQ ID NO 61
<211> LENGTH: 7
<212> TYPE: PRT
<213> ORGANISM: artificial sequence
<220> FEATURE:
<223> OTHER INFORMATION: synthetic hair-binding peptide

<400> SEQUENCE: 61

```
Asn Thr Ser Gln Leu Ser Thr
1               5
```

<210> SEQ ID NO 62
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 62

```
Gly Met Pro Ala Met His Trp Ile His Pro Phe Ala
1               5                   10
```

<210> SEQ ID NO 63
<211> LENGTH: 15
<212> TYPE: PRT
<213> ORGANISM: artificial sequence
<220> FEATURE:
<223> OTHER INFORMATION: synthetic hair-binding peptide

<400> SEQUENCE: 63

```
His Asp His Lys Asn Gln Lys Glu Thr His Gln Arg His Ala Ala
1               5                   10                  15
```

<210> SEQ ID NO 64
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 64

```
His Asn His Met Gln Glu Arg Tyr Thr Ala Pro Gln His Ser Pro Ser
```

```
1               5                   10                  15
Val Asn Gly Leu
            20

<210> SEQ ID NO 65
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 65

Thr Ala Glu Ile Gln Ser Ser Lys Asn Pro Asn Pro His Pro Gln Arg
1               5                   10                  15

Ser Trp Thr Asn
            20

<210> SEQ ID NO 66
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 66

Gly Ser Cys Val Asp Thr His Lys Ala Asp Ser Cys Val Ala Asn Asn
1               5                   10                  15

Gly Pro Ala Thr
            20

<210> SEQ ID NO 67
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 67

Ala Gln Ser Gln Leu Pro Asp Lys His Ser Gly Leu His Glu Arg Ala
1               5                   10                  15

Pro Gln Arg Tyr
            20

<210> SEQ ID NO 68
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 68

Thr Asp Met Met His Asn His Ser Asp Asn Ser Pro Pro His Arg Arg
1               5                   10                  15

Ser Pro Arg Asn
            20

<210> SEQ ID NO 69
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 69

Thr Pro Pro Glu Leu Ala His Thr Pro His His Leu Ala Gln Thr Arg
```

<210> SEQ ID NO 70
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 70

His Ile Asn Lys Thr Asn Pro His Gln Gly Asn His His Ser Glu Lys
1               5                   10                  15

Thr Gln Arg Gln
            20

<210> SEQ ID NO 71
<211> LENGTH: 3604
<212> TYPE: DNA
<213> ORGANISM: artificial sequence
<220> FEATURE:
<223> OTHER INFORMATION: synthetic construct

<400> SEQUENCE: 71

```
ggcactttc  ggggaaatgt  gcgcggaacc  cctatttgtt  tattttctta  aatacattca    60
aatatgtatc  cgctcatgag  acaataaccc  tgataaatgc  ttcaataata  ttgaaaaagg   120
aagagtatga  gtattcaaca  tttccgtgtc  gcccttattc  ccttttttgc  ggcatttgc    180
cttcctgttt  ttgctcaccc  agaaacgctg  gtgaaagtaa  aagatgctga  agatcagttg   240
ggtgcacgag  tgggttacat  cgaactggat  ctcaacagcg  gtaagatcct  tgagagtttt   300
cgccccgaag  aacgttttcc  aatgatgagc  acttttaaag  ttctgctatg  tggcgcggta   360
ttatcccgta  ttgacgccgg  gcaagagcaa  ctcggtcgcc  gcatacacta  ttctcagaat   420
gacttggttg  agtactcacc  agtcacagaa  aagcatctta  cggatggcat  gacagtaaga   480
gaattatgca  gtgctgccat  aaccatgagt  gataacactg  cggccaactt  acttctgaca   540
acgatcggag  gaccgaagga  gctaaccgct  ttttgcaca   acatggggga  tcatgtaact   600
cgccttgatc  gttgggaacc  ggagctgaat  gaagccatac  caaacgacga  gcgtgacacc   660
acgatgcctg  tagcaatggc  aacaacgttg  cgcaaactat  taactggcga  actacttact   720
ctagcttccc  ggcaacaatt  aatagactgg  atggaggcgg  ataaagttgc  aggaccactt   780
ctgcgctcgg  cccttccggc  tggctggttt  attgctgata  aatctggagc  cggtgagcgt   840
gggtctcgcg  gtatcattgc  agcactgggg  ccagatggta  agccctcccg  tatcgtagtt   900
atctacacga  cggggagtca  ggcaactatg  gatgaacgaa  atagacagat  cgctgagata   960
ggtgcctcac  tgattaagca  ttggtaactg  tcagaccaag  tttactcata  tatactttag  1020
attgatttaa  aacttcattt  ttaatttaaa  aggatctagg  tgaagatcct  ttttgataat  1080
ctcatgacca  aaatccctta  acgtgagttt  tcgttccact  gagcgtcaga  ccccgtagaa  1140
aagatcaaag  gatcttcttg  agatcctttt  tttctgcgcg  taatctgctg  cttgcaaaca  1200
aaaaaaccac  cgctaccagc  ggtggtttgt  ttgccggatc  aagagctacc  aactcttttt  1260
ccgaaggtaa  ctggcttcag  cagagcgcag  ataccaaata  ctgtccttct  agtgtagccg  1320
tagttaggcc  accacttcaa  gaactctgta  gcaccgccta  catacctcgc  tctgctaatc  1380
ctgttaccag  tggctgctgc  cagtggcgat  aagtcgtgtc  ttaccgggtt  ggactcaaga  1440
cgatagttac  cggataaggc  gcagcggtcg  ggctgaacgg  ggggttcgtg  cacacagccc  1500
```

```
agcttggagc gaacgaccta caccgaactg agatacctac agcgtgagct atgagaaagc    1560
gccacgcttc ccgaagggag aaaggcggac aggtatccgg taagcggcag ggtcggaaca    1620
ggagagcgca cgagggagct tccagggga aacgcctggt atctttatag tcctgtcggg     1680
tttcgccacc tctgacttga gcgtcgattt tgtgatgct cgtcaggggg gcggagccta     1740
tggaaaaacg ccagcaacgc ggcctttta cggttcctgg ccttttgctg gccttttgct     1800
cacatgttct ttcctgcgtt atccctgat tctgtggata accgtattac cgcctttgag     1860
tgagctgata ccgctcgccg cagccgaacg accgagcgca gcgagtcagt gagcgaggaa    1920
gcggaagagc gcccaatacg caaaccgcct ctccccgcgc gttggccgat tcattaatgc    1980
agctggcacg acaggtttcc cgactggaaa gcgggcagtg agcgcaacgc aattaatgtg    2040
agttagctca ctcattaggc accccaggct ttacacttta tgcttccggc tcgtatgttg    2100
tgtggaattg tgagcggata acaatttcac acaggaaaca gctatgacca tgattacgcc    2160
aagctcgaaa ttaaccctca ctaaagggaa caaaagctgg agctctaaga aggagatata    2220
catgtgaaaa aattattatt cgcaattcct ttagttgttc ctttctattc tcactcccct    2280
agggcggccg catggatccg gtggcggtgg ctctccattc gtttgtgaat atcaaggcca    2340
atcgtctgac ctgcctcaac ctcctgtcaa tgctggcggc ggctctggtg gtggttctgg    2400
tggcggctct gagggtggtg gctctgaggg tggcggttct gagggtggcg gctctgaggg    2460
aggcggttcc ggtggtggct ctggttccgg tgattttgat tatgaaaaga tggcaaacgc    2520
taataagggg gctatgaccg aaaatgccga tgaaaacgcg ctacagtctg acgctaaagg    2580
caaacttgat tctgtcgcta ctgattacgg tgctgctatc gatggtttca ttggtgacgt    2640
ttccggcctt gctaatggta atggtgctac tggtgatttt gctggctcta attcccaaat    2700
ggctcaagtc ggtgacggtg ataattcacc tttaatgaat aatttccgtc aatatttacc    2760
ttccctccct caatcggttg aatgtcgccc ttttgtcttt agcgctggta accatatga    2820 attttctatt gattgtgaca aaataaactt attccgtggt gtctttgcgt ttcttttata    2880
tgttgccacc tttatgtatg tattttctac gtttgctaac atactgcgta ataaggagtc    2940
ttaataaggt acccaattcg ccctatagtg agtcgtatta caattcactg gccgtcgttt    3000
tacaacgtcg tgactgggaa aaccctggcg ttacccaact taatcgcctt gcagcacatc    3060
cccctttcgc cagctggcgt aatagcgaag aggcccgcac cgatcgccct tcccaacagt    3120
tgcgcagcct gaatggcgaa tgggacgcgc cctgtagcgg cgcattaagc gcggcgggtg    3180
tggtggttac gcgcagcgtg accgctacac ttgccagcgc cctagcgccc gctcctttcg    3240
ctttcttccc ttcctttctc gccacgttcg ccggctttcc ccgtcaagct ctaaatcggg    3300
ggctcccttt agggttccga tttagtgctt tacggcacct cgaccccaaa aaacttgatt    3360
agggtgatgg ttcacgtagt gggccatcgc cctgatagac ggttttcgc cctttgacgt     3420 tggagtccac gttctttaat agtggactct tgttccaaac tggaacaaca ctcaacccta    3480
tctcggtcta ttcttttgat ttataaggga ttttgccgat ttcggcctat tggttaaaaa    3540
atgagctgat ttaacaaaaa tttaacgcga attttaacaa aatattaacg cttacaattt    3600
aggt                                                                3604
```

<210> SEQ ID NO 72
<211> LENGTH: 65
<212> TYPE: PRT
<213> ORGANISM: artificial sequence
<220> FEATURE:
<223> OTHER INFORMATION: synthetic construct

```
<400> SEQUENCE: 72

Pro Ser Ala Gln Ser Gln Leu Pro Asp Lys His Ser Gly Leu His Glu
1               5                   10                  15

Arg Ala Pro Gln Arg Tyr Gly Pro Gly Ala Gly Gly Ala Gly Gly Ser
                20                  25                  30

Gly Gly Ser Gly Ala Gly Gly Ala Gly Gly Ser Gly Gly Ser Pro Ala
            35                  40                  45

His Asp His Lys Asn Gln Lys Glu Thr His Gln Arg His Ala Ala Gly
        50                  55                  60

Ser
65

<210> SEQ ID NO 73
<211> LENGTH: 64
<212> TYPE: PRT
<213> ORGANISM: artificial sequence
<220> FEATURE:
<223> OTHER INFORMATION: synthetic construct

<400> SEQUENCE: 73

Pro Ser Ala Gln Ser Gln Leu Pro Asp Lys His Ser Gly Leu His Glu
1               5                   10                  15

Arg Ala Pro Gln Arg Tyr Gly Pro Glu Glu Ala Ala Lys Lys Glu Glu
                20                  25                  30

Ala Ala Lys Lys Glu Glu Ala Ala Lys Lys Glu Glu Ala Ala Lys Lys
            35                  40                  45

Pro Ala Gly Met Pro Ala Met His Trp Ile His Pro Phe Ala Gly Ser
        50                  55                  60

<210> SEQ ID NO 74
<211> LENGTH: 78
<212> TYPE: PRT
<213> ORGANISM: artificial sequence
<220> FEATURE:
<223> OTHER INFORMATION: synthetic construct

<400> SEQUENCE: 74

Pro Ser Ala Gln Ser Gln Leu Pro Asp Lys His Ser Gly Leu His Glu
1               5                   10                  15

Arg Ala Pro Gln Arg Tyr Gly Pro Glu Glu Ala Ala Lys Lys Glu Glu
                20                  25                  30

Ala Ala Lys Lys Glu Glu Ala Ala Lys Lys Glu Glu Ala Ala Lys Lys
            35                  40                  45

Glu Glu Ala Ala Lys Lys Pro Ala His Asn His Met Gln Glu Arg Tyr
        50                  55                  60

Thr Ala Pro Gln His Ser Pro Ser Val Asn Gly Leu Gly Ser
65                  70                  75

<210> SEQ ID NO 75
<211> LENGTH: 72
<212> TYPE: PRT
<213> ORGANISM: artificial sequence
<220> FEATURE:
<223> OTHER INFORMATION: synthetic construct

<400> SEQUENCE: 75

Pro Ser Ala Gln Ser Gln Leu Pro Asp Lys His Ser Gly Leu His Glu
1               5                   10                  15

Arg Ala Pro Gln Arg Tyr Gly Pro Glu Glu Ala Ala Lys Lys Glu Glu
                20                  25                  30
```

```
Ala Ala Lys Lys Glu Glu Ala Ala Lys Lys Glu Glu Ala Ala Lys Lys
            35                  40                  45

Pro Ala His Ile Asn Lys Thr Asn Pro His Gln Gly Asn His His Ser
    50                  55                  60

Glu Lys Thr Gln Arg Gln Gly Ser
65                  70

<210> SEQ ID NO 76
<211> LENGTH: 60
<212> TYPE: PRT
<213> ORGANISM: artificial sequence
<220> FEATURE:
<223> OTHER INFORMATION: synthetic construct

<400> SEQUENCE: 76

Pro Ser Ala Gln Ser Gln Leu Pro Asp Lys His Ser Gly Leu His Glu
1               5                   10                  15

Arg Ala Pro Gln Arg Tyr Gly Pro Glu Glu Ala Ala Lys Lys Glu Glu
            20                  25                  30

Ala Ala Lys Lys Pro Ala His Ile Asn Lys Thr Asn Pro His Gln Gly
            35                  40                  45

Asn His His Ser Glu Lys Thr Gln Arg Gln Gly Ser
    50                  55                  60

<210> SEQ ID NO 77
<211> LENGTH: 48
<212> TYPE: PRT
<213> ORGANISM: artificial sequence
<220> FEATURE:
<223> OTHER INFORMATION: synthetic construct

<400> SEQUENCE: 77

Pro Ser Gly Met Pro Ala Met His Trp Ile His Pro Phe Ala Gly Pro
1               5                   10                  15

Lys Pro Lys Pro Lys Pro Lys Pro Lys Pro Lys Pro Lys Pro Lys Pro
            20                  25                  30

Pro Ala Gly Met Pro Ala Met His Trp Ile His Pro Phe Ala Gly Ser
            35                  40                  45

<210> SEQ ID NO 78
<211> LENGTH: 76
<212> TYPE: PRT
<213> ORGANISM: artificial sequence
<220> FEATURE:
<223> OTHER INFORMATION: synthetic construct

<400> SEQUENCE: 78

Pro Ser Thr Ala Glu Ile Gln Ser Ser Lys Asn Pro Asn Pro His Pro
1               5                   10                  15

Gln Arg Ser Trp Thr Asn Gly Pro Lys Pro Lys Pro Lys Pro Lys Pro
            20                  25                  30

Lys Pro Lys Pro Gly Gly Lys Pro Lys Pro Lys Pro Lys Pro Lys Pro
            35                  40                  45

Lys Pro Gly Gly Pro Ala His Asn His Met Gln Glu Arg Tyr Thr Ala
            50                  55                  60

Pro Gln His Ser Pro Ser Val Asn Gly Leu Gly Ser
65                  70                  75

<210> SEQ ID NO 79
<211> LENGTH: 63
<212> TYPE: PRT
```

<213> ORGANISM: artificial sequence
<220> FEATURE:
<223> OTHER INFORMATION: synthetic construct

<400> SEQUENCE: 79

Pro Ser Asn Thr Ser Gln Leu Ser Thr Gly Pro Lys Pro Lys Pro Lys
1               5                   10                  15

Pro Lys Pro Lys Pro Lys Pro Gly Gly Lys Pro Lys Pro Lys Pro Lys
            20                  25                  30

Pro Lys Pro Lys Pro Gly Gly Pro Ala His Asn His Met Gln Glu Arg
        35                  40                  45

Tyr Thr Ala Pro Gln His Ser Pro Ser Val Asn Gly Leu Gly Ser
    50                  55                  60

<210> SEQ ID NO 80
<211> LENGTH: 63
<212> TYPE: PRT
<213> ORGANISM: artificial sequence
<220> FEATURE:
<223> OTHER INFORMATION: synthetic construct

<400> SEQUENCE: 80

Pro Ser Asn Thr Ser Gln Leu Ser Thr Gly Pro Lys Pro Lys Pro Lys
1               5                   10                  15

Pro Lys Pro Lys Pro Lys Pro Gly Gly Lys Pro Lys Pro Lys Pro Lys
            20                  25                  30

Pro Lys Pro Lys Pro Gly Gly Pro Ala Thr Ala Glu Ile Gln Ser Ser
        35                  40                  45

Lys Asn Pro Asn Pro His Pro Gln Arg Ser Trp Thr Asn Gly Ser
    50                  55                  60

<210> SEQ ID NO 81
<211> LENGTH: 63
<212> TYPE: PRT
<213> ORGANISM: artificial sequence
<220> FEATURE:
<223> OTHER INFORMATION: synthetic construct

<400> SEQUENCE: 81

Pro Ser Asn Thr Ser Gln Leu Ser Thr Gly Pro Lys Pro Lys Pro Lys
1               5                   10                  15

Pro Lys Pro Lys Pro Lys Pro Gly Gly Lys Pro Lys Pro Lys Pro Lys
            20                  25                  30

Pro Lys Pro Lys Pro Gly Gly Pro Ala Thr Ala Glu Ile Gln Ser Ser
        35                  40                  45

Lys Asn Pro Asn Pro His Pro Arg Arg Ser Trp Thr Asn Gly Ser
    50                  55                  60

<210> SEQ ID NO 82
<211> LENGTH: 55
<212> TYPE: PRT
<213> ORGANISM: artificial sequence
<220> FEATURE:
<223> OTHER INFORMATION: synthetic construct

<400> SEQUENCE: 82

Pro Ser Asn Thr Ser Gln Leu Ser Thr Gly Pro Lys Pro Lys Pro Lys
1               5                   10                  15

Pro Lys Pro Lys Pro Lys Pro Gly Gly Lys Pro Lys Pro Lys Pro Lys
            20                  25                  30

Pro Lys Pro Lys Pro Gly Gly Pro Ala Thr Pro Pro Thr Asn Val Leu
        35                  40                  45

```
Met Leu Ala Thr Lys Gly Ser
    50              55

<210> SEQ ID NO 83
<211> LENGTH: 58
<212> TYPE: PRT
<213> ORGANISM: artificial sequence
<220> FEATURE:
<223> OTHER INFORMATION: synthetic construct

<400> SEQUENCE: 83

Pro Ser His Asp His Lys Asn Gln Lys Glu Thr His Gln Arg His Ala
1               5                   10                  15

Ala Gly Pro Lys Pro Lys Pro Lys Pro Lys Pro Lys Pro Lys Pro Gly
                20                  25                  30

Gly Lys Pro Lys Pro Lys Pro Lys Pro Lys Pro Lys Pro Gly Gly Pro
            35                  40                  45

Ala Asn Thr Ser Gln Leu Ser Thr Gly Ser
    50                  55

<210> SEQ ID NO 84
<211> LENGTH: 63
<212> TYPE: PRT
<213> ORGANISM: artificial sequence
<220> FEATURE:
<223> OTHER INFORMATION: synthetic construct

<400> SEQUENCE: 84

Pro Ser Thr Asp Met Met His Asn His Ser Asp Asn Ser Pro Pro His
1               5                   10                  15

Arg Arg Ser Pro Arg Asn Gly Pro Lys Pro Lys Pro Lys Pro Lys Pro
                20                  25                  30

Lys Pro Lys Pro Gly Gly Lys Pro Lys Pro Lys Pro Lys Pro Lys Pro
            35                  40                  45

Lys Pro Gly Gly Pro Ala Asn Thr Ser Gln Leu Ser Thr Gly Ser
    50                  55                  60

<210> SEQ ID NO 85
<211> LENGTH: 76
<212> TYPE: PRT
<213> ORGANISM: artificial sequence
<220> FEATURE:
<223> OTHER INFORMATION: synthetic construct

<400> SEQUENCE: 85

Pro Ser Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro Glu Pro
                20                  25                  30

Ile Pro Glu Pro Pro Lys Glu Ala Pro Val Val Ile Glu Lys Pro Lys
            35                  40                  45

Pro Lys Pro Lys Pro Lys Pro Lys Pro Pro Ala His Asp His Lys Asn
    50                  55                  60

Gln Lys Glu Thr His Gln Arg His Ala Ala Gly Ser
65                  70                  75

<210> SEQ ID NO 86
<211> LENGTH: 76
<212> TYPE: PRT
<213> ORGANISM: artificial sequence
<220> FEATURE:
<223> OTHER INFORMATION: synthetic construct
```

<400> SEQUENCE: 86

Pro Ser His Asp His Lys Asn Gln Lys Glu Thr His Gln Arg His Ala
1               5                   10                  15

Ala Gly Pro Glu Pro Glu Pro Glu Pro Ile Pro Glu Pro Pro
            20                  25                  30

Lys Glu Ala Pro Val Val Ile Glu Lys Pro Lys Pro Lys Pro Lys Pro
        35                  40                  45

Lys Pro Lys Pro Pro Ala Gly Ser Cys Val Asp Thr His Lys Ala Asp
    50                  55                  60

Ser Cys Val Ala Asn Asn Gly Pro Ala Thr Gly Ser
65                  70                  75

<210> SEQ ID NO 87
<211> LENGTH: 73
<212> TYPE: PRT
<213> ORGANISM: artificial sequence
<220> FEATURE:
<223> OTHER INFORMATION: synthetic construct

<400> SEQUENCE: 87

Pro Ser Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro Glu Pro
            20                  25                  30

Ile Pro Glu Pro Pro Lys Glu Ala Pro Val Val Ile Glu Lys Pro Lys
        35                  40                  45

Pro Lys Pro Lys Pro Lys Pro Lys Pro Ala Pro Thr Pro Pro Thr Asn
    50                  55                  60

Val Leu Met Leu Ala Thr Lys Gly Ser
65                  70

<210> SEQ ID NO 88
<211> LENGTH: 73
<212> TYPE: PRT
<213> ORGANISM: artificial sequence
<220> FEATURE:
<223> OTHER INFORMATION: synthetic construct

<400> SEQUENCE: 88

Pro Ser Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro Glu Pro
            20                  25                  30

Ile Pro Glu Pro Pro Lys Glu Ala Pro Val Val Ile Glu Lys Pro Lys
        35                  40                  45

Pro Lys Pro Lys Pro Lys Pro Lys Pro Ala Pro Thr Pro Pro Glu Leu
    50                  55                  60

Leu His Gly Ala Pro Arg Ser Gly Ser
65                  70

<210> SEQ ID NO 89
<211> LENGTH: 81
<212> TYPE: PRT
<213> ORGANISM: artificial sequence
<220> FEATURE:
<223> OTHER INFORMATION: synthetic construct

<400> SEQUENCE: 89

Pro Ser Ala Gln Ser Gln Leu Pro Asp Lys His Ser Gly Leu His Glu
1               5                   10                  15

```
Arg Ala Pro Gln Arg Tyr Gly Pro Glu Pro Glu Pro Glu Pro
        20                  25                  30

Ile Pro Glu Pro Pro Lys Glu Ala Pro Val Val Ile Glu Lys Pro Lys
            35                  40                  45

Pro Lys Pro Lys Pro Lys Pro Lys Pro Pro Ala His Ile Asn Lys Thr
 50                  55                  60

Asn Pro His Gln Gly Asn His His Ser Glu Lys Thr Gln Arg Gln Gly
 65              70                  75                  80

Ser
```

```
<210> SEQ ID NO 90
<211> LENGTH: 69
<212> TYPE: PRT
<213> ORGANISM: artificial sequence
<220> FEATURE:
<223> OTHER INFORMATION: synthetic construct

<400> SEQUENCE: 90

Pro Ser Thr Ala Glu Ile Gln Ser Ser Lys Asn Pro Asn Pro His Pro
 1               5                  10                  15

Gln Arg Ser Trp Thr Asn Gly Pro Glu Ala Ala Ala Lys Leu Leu Glu
            20                  25                  30

Ala Ala Ala Lys Leu Leu Glu Ala Ala Ala Lys Leu Leu Pro Ala His
            35                  40                  45

Ile Asn Lys Thr Asn Pro His Gln Gly Asn His His Ser Glu Lys Thr
 50                  55                  60

Gln Arg Gln Gly Ser
 65
```

```
<210> SEQ ID NO 91
<211> LENGTH: 81
<212> TYPE: PRT
<213> ORGANISM: artificial sequence
<220> FEATURE:
<223> OTHER INFORMATION: synthetic construct

<400> SEQUENCE: 91

Pro Ser Ala Gln Ser Gln Leu Pro Asp Lys His Ser Gly Leu His Glu
 1               5                  10                  15

Arg Ala Pro Gln Arg Tyr Gly Pro Glu Pro Glu Pro Glu Pro Glu Pro
            20                  25                  30

Ile Pro Glu Pro Pro Lys Glu Ala Pro Val Val Ile Glu Lys Pro Lys
            35                  40                  45

Pro Lys Pro Lys Pro Lys Pro Lys Pro Pro Ala Ala Gln Ser Gln Leu
 50                  55                  60

Pro Asp Lys His Ser Gly Leu His Glu Arg Ala Pro Gln Arg Tyr Gly
 65              70                  75                  80

Ser
```

```
<210> SEQ ID NO 92
<211> LENGTH: 64
<212> TYPE: PRT
<213> ORGANISM: artificial sequence
<220> FEATURE:
<223> OTHER INFORMATION: synthetic construct

<400> SEQUENCE: 92

Pro Ser Thr Ala Glu Ile Gln Ser Ser Lys Asn Pro Asn Pro His Pro
 1               5                  10                  15
```

```
Gln Arg Ser Trp Thr Asn Gly Pro Glu Ala Ala Lys Leu Leu Glu
            20                  25                  30

Ala Ala Ala Lys Leu Leu Glu Ala Ala Lys Leu Leu Pro Ala His
        35                  40                  45

Asp His Lys Asn Gln Lys Glu Thr His Gln Arg His Ala Ala Gly Ser
    50                  55                  60
```

<210> SEQ ID NO 93
<211> LENGTH: 73
<212> TYPE: PRT
<213> ORGANISM: artificial sequence
<220> FEATURE:
<223> OTHER INFORMATION: synthetic construct

<400> SEQUENCE: 93

```
Pro Ser Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro Glu Pro
            20                  25                  30

Ile Pro Glu Pro Pro Lys Glu Ala Pro Val Val Ile Glu Lys Pro Lys
        35                  40                  45

Pro Lys Pro Lys Pro Lys Pro Lys Pro Pro Ala Thr Pro Pro Thr Asn
    50                  55                  60

Val Leu Met Leu Ala Thr Lys Gly Ser
65                  70
```

<210> SEQ ID NO 94
<211> LENGTH: 61
<212> TYPE: PRT
<213> ORGANISM: artificial sequence
<220> FEATURE:
<223> OTHER INFORMATION: synthetic construct

<400> SEQUENCE: 94

```
Pro Ser His Ile Asn Lys Thr Asn Pro His Gln Gly Asn His His Ser
1               5                   10                  15

Glu Lys Thr Gln Arg Gln Gly Pro Glu Ala Ala Ala Lys Leu Leu Glu
            20                  25                  30

Ala Ala Ala Lys Leu Leu Glu Ala Ala Lys Leu Leu Pro Ala Thr
        35                  40                  45

Pro Pro Glu Leu Leu His Gly Ala Pro Arg Ser Gly Ser
    50                  55                  60
```

<210> SEQ ID NO 95
<211> LENGTH: 60
<212> TYPE: PRT
<213> ORGANISM: artificial sequence
<220> FEATURE:
<223> OTHER INFORMATION: synthetic construct

<400> SEQUENCE: 95

```
Pro Ser Thr Pro Pro Thr Asn Val Leu Met Leu Ala Thr Lys Gly Pro
1               5                   10                  15

Lys Gly Gly Gly Ser Lys Gly Gly Gly Ser Lys Gly Gly Gly Ser Lys
            20                  25                  30

Gly Gly Gly Ser Pro Ala Ala Gln Ser Gln Leu Pro Asp Lys His Ser
        35                  40                  45

Gly Leu His Glu Arg Ala Pro Gln Arg Tyr Gly Ser
    50                  55                  60
```

<210> SEQ ID NO 96

```
<211> LENGTH: 56
<212> TYPE: PRT
<213> ORGANISM: artificial sequence
<220> FEATURE:
<223> OTHER INFORMATION: synthetic construct

<400> SEQUENCE: 96

Pro Ser Thr Pro Pro Thr Asn Val Leu Met Leu Ala Thr Lys Gly Pro
1               5                   10                  15

Lys Pro Lys Pro Lys Pro Lys Pro Lys Pro Lys Pro Lys Pro Lys Pro
            20                  25                  30

Lys Pro Lys Pro Lys Pro Lys Pro Pro Ala Thr Pro Pro Glu Leu Leu
        35                  40                  45

His Gly Ala Pro Arg Ser Gly Ser
    50                  55

<210> SEQ ID NO 97
<211> LENGTH: 63
<212> TYPE: PRT
<213> ORGANISM: artificial sequence
<220> FEATURE:
<223> OTHER INFORMATION: synthetic construct

<400> SEQUENCE: 97

Pro Ser Asn Thr Ser Gln Leu Ser Thr Gly Pro Lys Pro Lys Pro Lys
1               5                   10                  15

Pro Lys Pro Lys Pro Lys Pro Gly Gly Lys Pro Lys Pro Lys Pro Lys
            20                  25                  30

Pro Lys Pro Lys Pro Gly Gly Pro Ala His Asn His Met Gln Glu Arg
        35                  40                  45

Tyr Thr Ala Pro Gln His Ser Pro Ser Val Asn Gly Leu Gly Ser
    50                  55                  60

<210> SEQ ID NO 98
<211> LENGTH: 76
<212> TYPE: PRT
<213> ORGANISM: artificial sequence
<220> FEATURE:
<223> OTHER INFORMATION: synthetic construct

<400> SEQUENCE: 98

Pro Ser His Asp His Lys Asn Gln Lys Glu Thr His Gln Arg His Ala
1               5                   10                  15

Ala Gly Pro Glu Pro Glu Pro Glu Pro Glu Pro Ile Pro Glu Pro Pro
            20                  25                  30

Lys Glu Ala Pro Val Val Ile Glu Lys Pro Lys Pro Lys Pro Lys Pro
        35                  40                  45

Lys Pro Lys Pro Pro Ala Gly Ser Cys Val Asp Thr His Lys Ala Asp
    50                  55                  60

Ser Cys Val Ala Asn Asn Gly Pro Ala Thr Gly Ser
65                  70                  75

<210> SEQ ID NO 99
<211> LENGTH: 76
<212> TYPE: PRT
<213> ORGANISM: artificial sequence
<220> FEATURE:
<223> OTHER INFORMATION: synthetic construct

<400> SEQUENCE: 99

Pro Ser Thr Ala Glu Ile Gln Ser Ser Lys Asn Pro Asn Pro His Pro
1               5                   10                  15
```

-continued

Gln Arg Ser Trp Thr Asn Gly Pro Lys Pro Lys Pro Lys Pro
            20                  25                  30

Lys Pro Lys Pro Gly Gly Lys Pro Lys Pro Lys Pro Lys Pro
            35                  40                  45

Lys Pro Gly Gly Pro Ala Ala Gln Ser Gln Leu Pro Asp Lys His Ser
        50                  55                  60

Gly Leu His Glu Arg Ala Pro Gln Arg Tyr Gly Ser
65                  70                  75

<210> SEQ ID NO 100
<211> LENGTH: 63
<212> TYPE: PRT
<213> ORGANISM: artificial sequence
<220> FEATURE:
<223> OTHER INFORMATION: synthetic construct

<400> SEQUENCE: 100

Pro Ser His Asp His Lys Asn Gln Lys Glu Thr His Gln Arg His Ala
1               5                   10                  15

Ala Gly Pro Glu Ala Ala Ala Lys Leu Leu Glu Ala Ala Ala Lys Leu
            20                  25                  30

Leu Glu Ala Ala Ala Lys Leu Leu Glu Ala Ala Ala Lys Leu Leu Pro
        35                  40                  45

Ala Thr Pro Pro Thr Asn Val Leu Met Leu Ala Thr Lys Gly Ser
    50                  55                  60

<210> SEQ ID NO 101
<211> LENGTH: 50
<212> TYPE: PRT
<213> ORGANISM: artificial sequence
<220> FEATURE:
<223> OTHER INFORMATION: synthetic construct

<400> SEQUENCE: 101

Pro Ser Asn Thr Ser Gln Leu Ser Thr Gly Pro Lys Pro Lys Pro Lys
1               5                   10                  15

Pro Lys Pro Lys Pro Lys Pro Gly Gly Lys Pro Lys Pro Lys Pro Lys
            20                  25                  30

Pro Lys Pro Lys Pro Gly Gly Pro Ala Asn Thr Ser Gln Leu Ser Thr
        35                  40                  45

Gly Ser
    50

<210> SEQ ID NO 102
<211> LENGTH: 76
<212> TYPE: PRT
<213> ORGANISM: artificial sequence
<220> FEATURE:
<223> OTHER INFORMATION: synthetic construct

<400> SEQUENCE: 102

Pro Ser His Ile Asn Lys Thr Asn Pro His Gln Gly Asn His His Ser
1               5                   10                  15

Glu Lys Thr Gln Arg Gln Gly Pro Lys Pro Lys Pro Lys Pro Lys Pro
            20                  25                  30

Lys Pro Lys Pro Gly Gly Lys Pro Lys Pro Lys Pro Lys Pro Lys Pro
        35                  40                  45

Lys Pro Gly Gly Pro Ala His Ile Asn Lys Thr Asn Pro His Gln Gly
    50                  55                  60

Asn His His Ser Glu Lys Thr Gln Arg Gln Gly Ser
65                  70                  75

<210> SEQ ID NO 103
<211> LENGTH: 12
<212> TYPE: PRT
<213> ORGANISM: artificial sequence
<220> FEATURE:
<223> OTHER INFORMATION: synthetic pigment binding peptide

<400> SEQUENCE: 103

Trp Ala Pro Glu Lys Asp His Met Gln Leu Met Lys
1               5                   10

<210> SEQ ID NO 104
<211> LENGTH: 8
<212> TYPE: PRT
<213> ORGANISM: artificial sequence
<220> FEATURE:
<223> OTHER INFORMATION: synthetic peptide bridge

<400> SEQUENCE: 104

Gly Ser Gly Gly Gly Gly Ser Pro
1               5

<210> SEQ ID NO 105
<211> LENGTH: 21
<212> TYPE: PRT
<213> ORGANISM: artificial sequence
<220> FEATURE:
<223> OTHER INFORMATION: synthetic peptide linker

<400> SEQUENCE: 105

Gly Lys Gly Lys Gly Lys Gly Lys Gly Lys Gly Lys Gly Lys Gly Lys
1               5                   10                  15

Gly Lys Gly Lys Gly
            20

<210> SEQ ID NO 106
<211> LENGTH: 129
<212> TYPE: PRT
<213> ORGANISM: artificial sequence
<220> FEATURE:
<223> OTHER INFORMATION: synthetic peptide-based reagent HC353

<400> SEQUENCE: 106

Pro Ser Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro Glu Pro
                20                  25                  30

Ile Pro Glu Pro Pro Lys Glu Ala Pro Val Val Ile Glu Lys Pro Lys
            35                  40                  45

Pro Lys Pro Lys Pro Lys Pro Lys Pro Pro Ala His Asp His Lys Asn
        50                  55                  60

Gln Lys Glu Thr His Gln Arg His Ala Ala Gly Ser Gly Gly Gly Gly
65                  70                  75                  80

Ser Pro Trp Ala Pro Glu Lys Asp His Met Gln Leu Met Lys Gly Lys
                85                  90                  95

Gly Lys Gly Lys Gly Lys Gly Lys Gly Lys Gly Lys Gly Lys Gly Lys
            100                 105                 110

Gly Lys Gly Trp Ala Pro Glu Lys Asp His Met Gln Leu Met Lys Gly
        115                 120                 125

Lys

<210> SEQ ID NO 107
<211> LENGTH: 393
<212> TYPE: DNA
<213> ORGANISM: artificial sequence
<220> FEATURE:
<223> OTHER INFORMATION: synthetic nucleic acid sequence encoding HC353

<400> SEQUENCE: 107

```
ccttctgctc aatctcaact gcctgataaa cattctggtc tgcacgagcg cgctccgcag      60
cgctatggcc ctgaaccgga acctgagcca gagccgattc cggaaccgcc gaaagaggcg     120
ccagtagtta tcgaaaaacc taaaccaaaa ccaaaaccga aaccgaaacc tccggcccac     180
gaccacaaaa accagaaaga aacccatcag cgtcacgccg ctggttctgg tggtggcggt     240
agcccgtggg ctccggaaaa ggatcacatg cagctgatga aggcaaagg taagggcaaa     300 ggtaaaggta agggtaaagg caaaggcaaa ggcaagggca agggttgggc accagagaaa     360
gaccacatgc aactgatgaa gggtaaataa tga                                  393
```

<210> SEQ ID NO 108
<211> LENGTH: 6368
<212> TYPE: DNA
<213> ORGANISM: artificial sequence
<220> FEATURE:
<223> OTHER INFORMATION: synthetic construct plasmid

<400> SEQUENCE: 108

```
agatctcgat cccgcgaaat taatacgact cactataggg agaccacaac ggtttccctc      60
tagaaataat tttgtttaac tttaagaagg agatatacat atgcacactc agaacatat     120 caccgcagta gtacagcgtt ttgtggcagc tctgaacgcg ggcgagctgg aaggtattgt     180
ggcgctgttc gcggaagaag ccaccgtgga agaaccggtg ggttctgaac cgcgttccgg     240
caccgcagcc tgccgtgaat tttacgcaaa cagcctgaag ctgccgctgg cggttgaact     300
gacccaagaa tgtcgtgcgg tggctaacga agccgctttc gcgttcaccg tgtccttcga     360
ataccagggt cgtaagaccg ttgtggcgcc atgcgaacac tttcgtttca acggcgcagg     420
caaagtggtt tccatccgcg cactgttcgg tgaaaagaac atccatgctt gtcagggatc     480
cgatccgact ccgccgacga atgtactgat gctggcaacc aaaggcggtg gtacgcattc     540
cacgcacaac catggcagcc gcgccacac gaatgctgac gcaggcaatc cgggcggcgg     600 cacccccacca accaatgtcc tgatgctggc tactaaaggc ggcggcacgc attctaccca     660
caaccatggt agcccgcgcc atactaatgc agatgccggc aacccgggcg gtggtacccc     720
gccaaccaac gttctgatgc tggcgacgaa aggtggcggt accccattcca cgcataatca     780 tggcagccct cgccacacca acgctgatgc tggtaatcct ggtggcggta agaagaaata     840
ataaggcgcg ccgacccagc tttcttgtac aaagtggttg attcgaggct gctaacaaag     900
cccgaaagga agctgagttg gctgctgcca ccgctgagca ataactagca taacccttg      960 gggcctctaa acgggtcttg aggggttttt tgctgaaagg aggaactata tccggatatc    1020
cacaggacgg gtgtggtcgc catgatcgcg tagtcgatag tggctccaag tagcgaagcg    1080
agcaggactg ggcggcggcc aaagcggtcg acagtgctcc gagaacggg tgcgcataga    1140 aattgcatca acgcatatag cgctagcagc acgccatagt gactggcgat gctgtcggaa    1200
tggacgatat cccgcaagag gcccggcagt accggcataa ccaagcctat gcctacagca    1260
tccagggtga cggtgccgag gatgacgatg agcgcattgt tagatttcat acacggtgcc    1320
tgactgcgtt agcaatttaa ctgtgataaa ctaccgcatt aaagcttgca gtggcggttt    1380
tcatggcttg ttatgactgt ttttttgggg tacagtctat gcctcgggca tccaagcagc    1440
```

```
aagcgcgtta cgccgtgggt cgatgtttga tgttatggag cagcaacgat gttacgcagc    1500
agggcagtcg ccctaaaaca aagttaaaca tcatgaggga agcggtgatc gccgaagtat    1560
cgactcaact atcagaggta gttggcgtca tcgagcgcca tctcgaaccg acgttgctgg    1620
ccgtacattt gtacggctcc gcagtggatg gcggcctgaa gccacacagt gatattgatt    1680
tgctggttac ggtgaccgta aggcttgatg aaacaacgcg gcgagctttg atcaacgacc    1740
ttttggaaac ttcggcttcc cctggagaga gcgagattct ccgcgctgta gaagtcacca    1800
ttgttgtgca cgacgacatc attccgtggc gttatccagc taagcgcgaa ctgcaatttg    1860
gagaatggca gcgcaatgac attcttgcag gtatcttcga gccagccacg atcgacattg    1920
atctggctat cttgctgaca aaagcaagag aacatagcgt tgccttggta ggtccagcgg    1980
cggaggaact ctttgatccg gttcctgaac aggatctatt tgaggcgcta aatgaaacct    2040
taacgctatg gaactcgccg cccgactggg ctggcgatga gcgaaatgta gtgcttacgt    2100
tgtcccgcat ttggtacagc gcagtaaccg gcaaaatcgc gccgaaggat gtcgctgccg    2160
actgggcaat ggagcgcctg ccggcccagt atcagcccgt catacttgaa gctagacagg    2220
cttatcttgg acaagaagaa gatcgcttgg cctcgcgcgc agatcagttg gaagaatttg    2280
tccactacgt gaaaggcgag atcaccaagg tagtcggcaa ataatgtcta acaattcgtt    2340
caagcttatc gatgataagc tgtcaaacat gagaattctt gaagacgaaa gggcctcgtg    2400
atacgcctat ttttataggt taatgtcatg ataataatgg tttcttagac gtcaggtggc    2460
acttttcggg gaaatgtgcg cggaacccct atttgtttat ttttctaaat acattcaaat    2520
atgtatccgc tcatgagaca ataaccctga taaatgcttc aataatattg aaaaaggaag    2580
agtatgagta ttcaacattt ccgtgtcgcc cttattccct ttttttgcggc attttgcctt    2640 cctgtttttg ctcacccaga aacgctggtg aaagtaaaag atgctgaaga tcagttgggt    2700
gcacgagtgg gttacatcga actggatctc aacagcggta agatccttga gttttcgc    2760 cccgaagaac gttttccaat gatgagcact tttaaagttc tgctatgtgg cgcggtatta    2820
tcccgtgttg acgccgggca agagcaactc ggtcgccgca tacactattc tcagaatgac    2880
ttggttgagt actcaccagt cacagaaaag catcttacgg atggcatgac agtaagagaa    2940
ttatgcagtg ctgccataac catgagtgat aacactgcgg ccaacttact tctgacaacg    3000
atcggaggac cgaaggagct aaccgctttt ttgcacaaca tgggggatca tgtaactcgc    3060
cttgatcgtt gggaaccgga gctgaatgaa gccataccaa acgacgagcg tgacaccacg    3120
atgcctgcag caatggcaac aacgttgcgc aaactattaa ctggcgaact acttactcta    3180
gcttcccggc aacaattaat agactggatg gaggcggata agttgcagg accacttctg    3240 cgctcggccc ttccggctgg ctggtttatt gctgataaat ctggagccgg tgagcgtggg    3300
tctcgcggta tcattgcagc actggggcca gatggtaagc cctcccgtat cgtagttatc    3360
tacacgacgg ggagtcaggc aactatggat gaacgaaata gacagatcgc tgagataggt    3420
gcctcactga ttaagcattg gtaactgtca gaccaagttt actcatatat actttagatt    3480
gatttaaaac ttcatttta atttaaaagg atctaggtga agatccttttt tgataatctc    3540 atgaccaaaa tcccttaacg tgagttttcg ttccactgag cgtcagaccc cgtagaaaag    3600
atcaaaggat cttcttgaga tcctttttt ctgcgcgtaa tctgctgctt gcaaacaaaa    3660
aaaccaccgc taccagcggt ggtttgtttg ccggatcaag agctaccaac tcttttccg    3720 aaggtaactg gcttcagcag agcgcagata ccaaatactg tccttctagt gtagccgtag    3780
ttaggccacc acttcaagaa ctctgtagca ccgcctacat acctcgctct gctaatcctg    3840
```

```
ttaccagtgg ctgctgccag tggcgataag tcgtgtctta ccgggttgga ctcaagacga   3900
tagttaccgg ataaggcgca gcggtcgggc tgaacggggg gttcgtgcac acagcccagc   3960
ttggagcgaa cgacctacac cgaactgaga tacctacagc gtgagctatg agaaagcgcc   4020
acgcttcccg aagggagaaa ggcggacagg tatccggtaa gcggcagggt cggaacagga   4080
gagcgcacga gggagcttcc aggggggaaac gcctggtatc tttatagtcc tgtcgggttt   4140
cgccacctct gacttgagcg tcgattttttg tgatgctcgt caggggggcg gagcctatgg   4200
aaaaacgcca gcaacgcggc cttttttacgg ttcctggcct tttgctggcc ttttgctcac   4260
atgttctttc ctgcgttatc ccctgattct gtggataacc gtattaccgc ctttgagtga   4320
gctgataccg ctcgccgcag ccgaacgacc gagcgcagcg agtcagtgag cgaggaagcg   4380
gaagagcgcc tgatgcggta ttttctcctt acgcatctgt gcggtatttc acaccgcata   4440
tatggtgcac tctcagtaca atctgctctg atgccgcata gttaagccag tatacactcc   4500
gctatcgcta cgtgactggg tcatggctgc gccccgacac ccgccaacac ccgctgacgc   4560
gccctgacgg gcttgtctgc tcccggcatc cgcttacaga caagctgtga ccgtctccgg   4620
gagctgcatg tgtcagaggt tttcaccgtc atcaccgaaa cgcgcgaggc agctgcggta   4680
aagctcatca gcgtggtcgt gaagcgattc acagatgtct gcctgttcat ccgcgtccag   4740
ctcgttgagt ttctccagaa gcgttaatgt ctggcttctg ataaagcggg ccatgttaag   4800
ggcggttttt tcctgtttgg tcactgatgc ctccgtgtaa ggggggatttc tgttcatggg   4860 ggtaatgata ccgatgaaac gagagaggat gctcacgata cgggttactg atgatgaaca   4920
tgcccggtta ctggaacgtt gtgagggtaa acaactggcg gtatggatgc ggcgggacca   4980
gagaaaaatc actcagggtc aatgccagcg cttcgttaat acagatgtag gtgttccaca   5040
gggtagccag cagcatcctg cgatgcagat ccggaacata atggtgcagg gcgctgactt   5100 ccgcgttttcc agactttacg aaacacggaa accgaagacc attcatgttg ttgctcaggt   5160
cgcagacgtt ttgcagcagc agtcgcttca cgttcgctcg cgtatcggtg attcattctg   5220
ctaaccagta aggcaacccc gccagcctag ccgggtcctc aacgacagga gcacgatcat   5280
gcgcacccgt ggccaggacc caacgctgcc cgagatgcgc cgcgtgcggc tgctggagat   5340
ggcggacgcg atggatatgt tctgccaagg gttggtttgc gcattcacag ttctccgcaa   5400
gaattgattg gctccaattc ttggagtggt gaatccgtta gcgaggtgcc gccggcttcc   5460
attcaggtcg aggtggcccg gctccatgca ccgcgacgca acgcggggag gcagacaagg   5520
tatagggcgg cgcctacaat ccatgccaac ccgttccatg tgctcgccga ggcggcataa   5580
atcgccgtga cgatcagcgg tccagtgatc gaagttaggc tggtaagagc cgcgagcgat   5640
ccttgaagct gtccctgatg gtcgtcatct acctgcctgg acagcatggc ctgcaacgcg   5700
ggcatcccga tgccgccgga agcgagaaga atcataatgg ggaaggccat ccagcctcgc   5760
gtcgcgaacg ccagcaagac gtagcccagc gcgtcggccg ccatgccggc gataatggcc   5820
tgcttctcgc cgaaacgttt ggtggcggga ccagtgacga aggcttgagc gagggcgtgc   5880
aagattccga ataccgcaag cgacaggccg atcatcgtcg cgctccagcg aaagcggtcc   5940
tcgccgaaaa tgacccagag cgctgccggc acctgtccta cgagttgcat gataaagaag   6000
acagtcataa gtgcggcgac gatagtcatg ccccgcgccc accggaagga gctgactggg   6060
ttgaaggctc tcaagggcat cggtcgatcg acgctctccc ttatgcgact cctgcattag   6120
gaagcagccc agtagtaggt tgaggccgtt gagcaccgcc gccgcaagga atggtgcatg   6180
caaggagatg gcgcccaaca gtcccccggc cacggggcct gccaccatac ccacgccgaa   6240
```

```
acaagcgctc atgagcccga agtggcgagc ccgatcttcc ccatcggtga tgtcggcgat    6300
ataggcgcca gcaaccgcac ctgtggcgcc ggtgatgccg ccacgatgc gtccggcgta     6360 gaggatcg                                                             6368

<210> SEQ ID NO 109
<211> LENGTH: 127
<212> TYPE: PRT
<213> ORGANISM: artificial sequence
<220> FEATURE:
<223> OTHER INFORMATION: synthetic construct inclusion body tag

<400> SEQUENCE: 109

Met His Thr Pro Glu His Ile Thr Ala Val Val Gln Arg Phe Val Ala
1               5                   10                  15

Ala Leu Asn Ala Gly Glu Leu Glu Gly Ile Val Ala Leu Phe Ala Glu
            20                  25                  30

Glu Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Glu His Phe Arg Phe Asn Gly Ala Gly Lys Val Val Ser Ile
            100                 105                 110

Arg Ala Leu Phe Gly Glu Lys Asn Ile His Ala Cys Gln Gly Ser
        115                 120                 125

<210> SEQ ID NO 110
<211> LENGTH: 6401
<212> TYPE: DNA
<213> ORGANISM: artificial sequence
<220> FEATURE:
<223> OTHER INFORMATION: synthetic construct plasmid

<400> SEQUENCE: 110
agatctcgat cccgcgaaat taatacgact cactataggg agaccacaac ggtttccctc    60
tagaaataat tttgtttaac tttaagaagg agatatacat atgcacactc cagaacatat    120
caccgcagta gtacagcgtt ttgtggcagc tctgaacgcg ggcgagctgg aaggtattgt    180
ggcgctgttc gcggaagaag ccaccgtgga agaaccggtg ggttctgaac cgcgttccgg    240
caccgcagcc tgccgtgaat tttacgcaaa cagcctgaag ctgccgctgg cggttgaact    300
gacccaagaa tgtcgtgcgg tggctaacga agccgctttc gcgttcaccg tgtccttcga    360
ataccagggt cgtaagaccg ttgtggcgcc atgcgaacac tttcgtttca acggcgcagg    420
caaagtggtt tccatccgcg cactgttcgg tgaaaagaac atccatgctt gtcagggatc    480
cgatccttct gctcaatctc aactgcctga taaacattct ggtctgcacg agcgcgctcc    540
gcagcgctat ggccctgaac cggaacctga gccagagccg attccggaac cgccgaaaga    600
ggcgccagta gttatcgaaa acctaaaacc aaaaccaaaa ccgaaaccga aacctccggc    660
ccacgaccac aaaaaccaga agaaaaccca tcagcgtcac gccgctggtt ctggtggtgg    720
cggtagcccg tgggctccgg aaaaggatca catgcagctg atgaaaggca aggtaaggg     780 caaaggtaaa ggtaagggta aaggcaaagg caaaggcaag gcaagggtt gggcaccaga    840 gaaagaccac atgcaactga tgaagggtaa ataatgaggc gcgccgaccc agctttcttg    900
```

```
tacaaagtgg ttgattcgag gctgctaaca aagcccgaaa ggaagctgag ttggctgctg    960
ccaccgctga gcaataacta gcataacccc ttggggcctc taaacgggtc ttgaggggtt   1020
ttttgctgaa aggaggaact atatccggat atccacagga cgggtgtggt cgccatgatc   1080
gcgtagtcga tagtggctcc aagtagcgaa gcgagcagga ctgggcggcg ccaaagcgg    1140 tcggacagtg ctccgagaac gggtgcgcat agaaattgca tcaacgcata tagcgctagc   1200
agcacgccat agtgactggc gatgctgtcg gaatggacga tatcccgcaa gaggcccggc   1260
agtaccggca taaccaagcc tatgcctaca gcatccaggg tgacggtgcc gaggatgacg   1320
atgagcgcat tgttagattt catacacggt gcctgactgc gttagcaatt taactgtgat   1380
aaactaccgc attaaagctt gcagtggcgg ttttcatggc ttgttatgac tgttttttg    1440 gggtacagtc tatgcctcgg gcatccaagc agcaagcgcg ttacgccgtg ggtcgatgtt   1500
tgatgttatg gagcagcaac gatgttacgc agcagggcag tcgccctaaa acaaagttaa   1560
acatcatgag ggaagcggtg atcgccgaag tatcgactca actatcagag gtagttggcg   1620
tcatcgagcg ccatctcgaa ccgacgttgc tggccgtaca tttgtacggc tccgcagtgg   1680
atggcggcct gaagccacac agtgatattg atttgctggt tacggtgacc gtaaggcttg   1740
atgaaacaac gcggcgagct ttgatcaacg accttttgga aacttcggct tccctggag    1800 agagcgagat tctccgcgct gtagaagtca ccattgttgt gcacgacgac atcattccgt   1860
ggcgttatcc agctaagcgc gaactgcaat ttggagaatg gcagcgcaat gacattcttg   1920
caggtatctt cgagccagcc acgatcgaca ttgatctggc tatcttgctg acaaaagcaa   1980
gagaacatag cgttgccttg gtaggtccag cggcggagga actctttgat ccggttcctg   2040
aacaggatct atttgaggcg ctaaatgaaa ccttaacgct atggaactcg ccgcccgact   2100
gggctggcga tgagcgaaat gtagtgctta cgttgtcccg catttggtac agcgcagtaa   2160
ccggcaaaat cgcgccgaag gatgtcgctg ccgactgggc aatggagcgc ctgccggccc   2220
agtatcagcc cgtcatactt gaagctagac aggcttatct tggacaagaa gaagatcgct   2280
tggcctcgcg cgcagatcag ttggaagaat ttgtccacta cgtgaaaggc gagatcacca   2340
aggtagtcgg caaataatgt ctaacaattc gttcaagctt atcgatgata agctgtcaaa   2400
catgagaatt cttgaagacg aaagggcctc gtgatacgcc tatttttata ggttaatgtc   2460
atgataataa tggtttctta cgtcaggt ggcacttttc ggggaaatgt gcgcggaacc    2520
cctatttgtt tatttttcta aatacattca aatatgtatc cgctcatgag acaataaccc   2580
tgataaatgc ttcaataata ttgaaaaagg aagagtatga gtattcaaca tttccgtgtc   2640
gcccttattc ccttttttgc ggcattttgc cttcctgttt ttgctcaccc agaaacgctg   2700
gtgaaagtaa aagatgctga agatcagttg ggtgcacgag tgggttacat cgaactggat   2760
ctcaacagcg gtaagatcct tgagagtttt cgccccgaag aacgttttcc aatgatgagc   2820
acttttaaag ttctgctatg tggcgcggta ttatcccgtg ttgacgccgg caagagcaa    2880 ctcggtcgcc gcatacacta ttctcagaat gacttggttg agtactcacc agtcacagaa   2940
aagcatctta cggatggcat gacagtaaga gaattatgca gtgctgccat aaccatgagt   3000
gataacactg cggccaactt acttctgaca acgatcggag gaccgaagga gctaaccgct   3060 ttttttgcaca acatggggga tcatgtaact cgccttgatc gttgggaacc ggagctgaat   3120
gaagccatac caaacgacga gcgtgacacc acgatgcctg cagcaatggc aacaacgttg   3180
cgcaaactat taactggcga actacttact ctagcttccc ggcaacaatt aatagactgg   3240
atggaggcgg ataaagttgc aggaccactt ctgcgctcgg cccttccggc tggctggttt   3300
```

```
attgctgata aatctggagc cggtgagcgt gggtctcgcg gtatcattgc agcactgggg    3360
ccagatggta agccctcccg tatcgtagtt atctacacga cggggagtca ggcaactatg    3420
gatgaacgaa atagacagat cgctgagata ggtgcctcac tgattaagca ttggtaactg    3480
tcagaccaag tttactcata tatactttag attgatttaa aacttcattt ttaatttaaa    3540
aggatctagg tgaagatcct ttttgataat ctcatgacca aaatcccttaa cgtgagttt    3600 tcgttccact gagcgtcaga ccccgtagaa aagatcaaag gatcttcttg agatcctttt    3660
tttctgcgcg taatctgctg cttgcaaaca aaaaaaccac cgctaccagc ggtggtttgt    3720
ttgccggatc aagagctacc aactctttt ccgaaggtaa ctggcttcag cagagcgcag    3780
ataccaaata ctgtccttct agtgtagccg tagttaggcc accacttcaa gaactctgta    3840
gcaccgccta catacctcgc tctgctaatc ctgttaccag tggctgctgc cagtggcgat    3900
aagtcgtgtc ttaccgggtt ggactcaaga cgatagttac cggataaggc gcagcggtcg    3960
ggctgaacgg ggggttcgtg cacacagccc agcttggagc gaacgaccta caccgaactg    4020
agatacctac agcgtgagct atgagaaagc gccacgcttc ccgaagggag aaaggcggac    4080
aggtatccgg taagcggcag ggtcggaaca ggagagcgca cgagggagct tccaggggga    4140
aacgcctggt atctttatag tcctgtcggg tttcgccacc tctgacttga gcgtcgattt    4200
ttgtgatgct cgtcaggggg gcggagccta tggaaaaacg ccagcaacgc ggcctttta    4260 cggttcctgg ccttttgctg gccttttgct cacatgttct ttcctgcgtt atccctgat    4320 tctgtggata accgtattac cgcctttgag tgagctgata ccgctcgccg cagccgaacg    4380
accgagcgca gcgagtcagt gagcgaggaa gcggaagagc gcctgatgcg gtattttctc    4440
cttacgcatc tgtgcggtat ttcacaccgc atatatggtg cactctcagt acaatctgct    4500
ctgatgccgc atagttaagc cagtatacac tccgctatcg ctacgtgact gggtcatggc    4560
tgcgccccga cacccgccaa cacccgctga cgcgccctga cgggcttgtc tgctcccggc    4620
atccgcttac agacaagctg tgaccgtctc cgggagctgc atgtgtcaga ggttttcacc    4680
gtcatcaccg aaacgcgcga ggcagctgcg gtaaagctca tcagcgtggt cgtgaagcga    4740
ttcacagatg tctgcctgtt catccgcgtc cagctcgttg agtttctcca gaagcgttaa    4800
tgtctggctt ctgataaagc gggccatgtt aagggcggtt ttttcctgtt ggtcactga    4860 tgcctccgtg taagggggat tctgttcat ggggtaatg ataccgatga acgagagag     4920 gatgctcacg atacgggtta ctgatgatga acatgcccgg ttactggaac gttgtgaggg    4980
taaacaactg gcggtatgga tgcggcggga ccagagaaaa atcactcagg gtcaatgcca    5040
gcgcttcgtt aatacagatg taggtgttcc acagggtagc cagcagcatc ctgcgatgca    5100
gatccggaac ataatggtgc agggcgctga cttccgcgtt tccagacttt acgaaacacg    5160
gaaaccgaag accattcatg ttgttgctca ggtcgcagac gttttgcagc agcagtcgct    5220
tcacgttcgc tcgcgtatcg gtgattcatt ctgctaacca gtaaggcaac cccgccagcc    5280
tagccgggtc tcaacgaca ggagcacgat catgcgcacc cgtggccagg acccaacgct    5340
gcccgagatg cgccgcgtgc ggctgctgga gatggcggac gcgatggata tgttctgcca    5400
agggttggtt tgcgcattca cagttctccg caagaattga ttggctccaa ttcttggagt    5460
ggtgaatccg ttagcgaggt gccgccggct tccattcagg tcgaggtggc ccggctccat    5520
gcaccgcgac gcaacgcggg gaggcagaca aggtataggg cggcgcctac aatccatgcc    5580
aacccgttcc atgtgctcgc cgaggcggca taaatcgccg tgacgatcag cggtccagtg    5640
atcgaagtta ggctggtaag agccgcgagc gatccttgaa gctgtccctg atggtcgtca    5700
```

```
tctacctgcc tggacagcat ggcctgcaac gcgggcatcc cgatgccgcc ggaagcgaga    5760
agaatcataa tggggaaggc catccagcct cgcgtcgcga acgccagcaa gacgtagccc    5820
agcgcgtcgg ccgccatgcc ggcgataatg gcctgcttct cgccgaaacg tttggtggcg    5880
ggaccagtga cgaaggcttg agcgagggcg tgcaagattc cgaataccgc aagcgacagg    5940
ccgatcatcg tcgcgctcca gcgaaagcgg tcctcgccga aaatgaccca gagcgctgcc    6000
ggcacctgtc ctacgagttg catgataaag aagacagtca taagtgcggc gacgatagtc    6060
atgccccgcg cccaccggaa ggagctgact gggttgaagg ctctcaaggg catcggtcga    6120
tcgacgctct cccttatgcg actcctgcat taggaagcag cccagtagta ggttgaggcc    6180
gttgagcacc gccgccgcaa ggaatggtgc atgcaaggag atggcgccca acagtccccc    6240
ggccacgggg cctgccacca tacccacgcc gaaacaagcg ctcatgagcc cgaagtggcg    6300
agcccgatct tccccatcgg tgatgtcggc gatataggcg ccagcaaccg cacctgtggc    6360
gccggtgatg ccggccacga tgcgtccggc gtagaggatc g                       6401
```

<210> SEQ ID NO 111
<211> LENGTH: 31
<212> TYPE: PRT
<213> ORGANISM: artificial sequence
<220> FEATURE:
<223> OTHER INFORMATION: Synthetic hair-binding constructs with his tag

<400> SEQUENCE: 111

Pro Gly Thr Pro Pro Glu Leu Leu His Gly Ala Pro Arg Ser Gly Gly
1               5                   10                  15

Gly Gly Ser Gly Gly Gly Gly Ser Gly His His His His His His
            20                  25                  30

<210> SEQ ID NO 112
<211> LENGTH: 46
<212> TYPE: PRT
<213> ORGANISM: artificial sequence
<220> FEATURE:
<223> OTHER INFORMATION: Synthetic hair-binding constructs with his tag

<400> SEQUENCE: 112

Pro Gly Thr Pro Pro Glu Leu Leu His Gly Ala Pro Arg Ser Gly Gly
1               5                   10                  15

Gly Thr Pro Pro Glu Leu Leu His Gly Ala Pro Arg Ser Gly Gly Gly
            20                  25                  30

Gly Ser Gly Gly Gly Gly Ser Gly His His His His His His
        35                  40                  45

<210> SEQ ID NO 113
<211> LENGTH: 34
<212> TYPE: PRT
<213> ORGANISM: artificial sequence
<220> FEATURE:
<223> OTHER INFORMATION: Synthetic hair-binding constructs with his tag

<400> SEQUENCE: 113

Pro Gly His Ala His Lys Asn Gln Lys Glu Thr His Gln Arg His Ala
1               5                   10                  15

Ala Gly Gly Gly Gly Ser Gly Gly Gly Gly Ser Gly His His His His
            20                  25                  30

His His

<210> SEQ ID NO 114

```
<211> LENGTH: 52
<212> TYPE: PRT
<213> ORGANISM: artificial sequence
<220> FEATURE:
<223> OTHER INFORMATION: Synthetic hair-binding constructs with his tag

<400> SEQUENCE: 114

Pro Gly His Ala His Lys Asn Gln Lys Glu Thr His Gln Arg His Ala
1               5                   10                  15

Ala Gly Gly Gly His Ala His Lys Asn Gln Lys Glu Thr His Gln Arg
            20                  25                  30

His Ala Ala Gly Gly Gly Ser Gly Gly Gly Gly Ser Gly His His
        35                  40                  45

His His His His
    50

<210> SEQ ID NO 115
<211> LENGTH: 52
<212> TYPE: PRT
<213> ORGANISM: artificial sequence
<220> FEATURE:
<223> OTHER INFORMATION: Synthetic hair-binding constructs with his tag

<400> SEQUENCE: 115

Pro Gly His Asp His Lys Asn Gln Lys Glu Thr His Gln Arg His Ala
1               5                   10                  15

Ala Gly Gly Gly His Asp His Lys Asn Gln Lys Glu Thr His Gln Arg
            20                  25                  30

His Ala Ala Gly Gly Gly Ser Gly Gly Gly Gly Ser Gly His His
        35                  40                  45

His His His His
    50

<210> SEQ ID NO 116
<211> LENGTH: 77
<212> TYPE: PRT
<213> ORGANISM: artificial sequence
<220> FEATURE:
<223> OTHER INFORMATION: Synthetic hair-binding constructs with his tag

<400> SEQUENCE: 116

Pro Ser Ala Gln Ser Gln Leu Pro Asp Lys His Ser Gly Leu His Glu
1               5                   10                  15

Arg Ala Pro Gln Arg Tyr Gly Pro Gly Ala Gly Gly Ala Gly Gly Ser
            20                  25                  30

Gly Gly Ser Gly Ala Gly Gly Ala Gly Ser Gly Gly Ser Pro Ala
        35                  40                  45

His Asp His Lys Asn Gln Lys Glu Thr His Gln Arg His Ala Ala Gly
    50                  55                  60

Ser Gly Gly Gly Ser Pro His His His His His His
65                  70                  75

<210> SEQ ID NO 117
<211> LENGTH: 88
<212> TYPE: PRT
<213> ORGANISM: artificial sequence
<220> FEATURE:
<223> OTHER INFORMATION: Synthetic hair-binding constructs with his tag

<400> SEQUENCE: 117

Pro Ser Ala Gln Ser Gln Leu Pro Asp Lys His Ser Gly Leu His Glu
1               5                   10                  15
```

Arg Ala Pro Gln Arg Tyr Gly Pro Glu Pro Glu Pro Glu Pro
            20                  25                  30

Ile Pro Glu Pro Pro Lys Glu Ala Pro Val Val Ile Glu Lys Pro Lys
        35                  40                  45

Pro Lys Pro Lys Pro Lys Pro Lys Pro Ala His Asp His Lys Asn
50                  55                  60

Gln Lys Glu Thr His Gln Arg His Ala Ala Gly Ser Gly Gly Gly Gly
65                  70                  75                  80

Ser Pro His His His His His
            85

<210> SEQ ID NO 118
<211> LENGTH: 67
<212> TYPE: PRT
<213> ORGANISM: artificial sequence
<220> FEATURE:
<223> OTHER INFORMATION: Synthetic hair-binding constructs with his tag

<400> SEQUENCE: 118

Pro Ser Thr Pro Pro Glu Leu Ala His Thr Pro His His Leu Ala Gln
1               5                   10                  15

Thr Arg Leu Thr Asp Arg Gly Pro Glu Gly Gly Ser Glu Gly Gly
            20                  25                  30

Gly Ser Glu Gly Gly Gly Ser Glu Gly Gly Gly Ser Pro Ala Asn Thr
        35                  40                  45

Ser Gln Leu Ser Thr Gly Ser Gly Gly Gly Ser Pro His His His
    50                  55                  60

His His His
65

<210> SEQ ID NO 119
<211> LENGTH: 85
<212> TYPE: PRT
<213> ORGANISM: ARTIFICIAL SEQUENCE
<220> FEATURE:
<223> OTHER INFORMATION: Synthetic hair-binding constructs with his tag

<400> SEQUENCE: 119

Pro Arg Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro
            20                  25                  30

Ile Pro Glu Pro Pro Lys Glu Ala Pro Val Val Ile Glu Lys Pro Lys
        35                  40                  45

Pro Lys Pro Lys Pro Lys Pro Lys Pro Pro Ala Thr Pro Pro Glu Leu
50                  55                  60

Leu His Gly Ala Pro Arg Ser Gly Ser Gly Gly Gly Ser Pro His
65                  70                  75                  80

His His His His His
            85

<210> SEQ ID NO 120
<211> LENGTH: 93
<212> TYPE: PRT
<213> ORGANISM: ARTIFICIAL SEQUENCE
<220> FEATURE:
<223> OTHER INFORMATION: Synthetic hair-binding constructs with his tag

<400> SEQUENCE: 120

Pro Arg Ala Gln Ser Gln Leu Pro Asp Lys His Ser Gly Leu His Glu
1               5                   10                  15

-continued

```
Arg Ala Pro Gln Arg Tyr Gly Pro Glu Pro Glu Pro Glu Pro
        20                  25                  30

Ile Pro Glu Pro Pro Lys Glu Ala Pro Val Val Ile Glu Lys Pro Lys
        35                  40                  45

Pro Lys Pro Lys Pro Lys Pro Lys Pro Pro Ala Ala Gln Ser Gln Leu
    50                  55                  60

Pro Asp Lys His Ser Gly Leu His Glu Arg Ala Pro Gln Arg Tyr Gly
65                  70                  75                  80

Ser Gly Gly Gly Ser Pro His His His His His
                85                  90

<210> SEQ ID NO 121
<211> LENGTH: 84
<212> TYPE: PRT
<213> ORGANISM: ARTIFICIAL SEQUENCE
<220> FEATURE:
<223> OTHER INFORMATION: Synthetic hair-binding constructs with his tag

<400> SEQUENCE: 121

Pro Arg Ala Gln Ser Gln Leu Pro Asp Lys His Ser Gly Leu His Glu
1               5                   10                  15

Arg Ala Pro Gln Arg Tyr Gly Pro Glu Glu Ala Ala Lys Lys Glu Glu
        20                  25                  30

Ala Ala Lys Lys Glu Glu Ala Ala Lys Lys Glu Glu Ala Ala Lys Lys
        35                  40                  45

Pro Ala His Ile Asn Lys Thr Asn Pro His Gln Gly Asn His His Ser
    50                  55                  60

Glu Lys Thr Gln Arg Gln Gly Ser Gly Gly Gly Ser Pro His His
65                  70                  75                  80

His His His His

<210> SEQ ID NO 122
<211> LENGTH: 85
<212> TYPE: PRT
<213> ORGANISM: ARTIFICIAL SEQUENCE
<220> FEATURE:
<223> OTHER INFORMATION: Synthetic hair-binding constructs with his tag

<400> SEQUENCE: 122

Pro Arg Ala Gln Ser Gln Leu Pro Asp Lys His Ser Gly Leu His Glu
1               5                   10                  15

Arg Ala Pro Gln Arg Tyr Gly Pro Glu Pro Glu Pro Glu Pro Glu Pro
        20                  25                  30

Ile Pro Glu Pro Pro Lys Glu Ala Pro Val Val Ile Lys Lys Pro Lys
        35                  40                  45

Pro Lys Pro Lys Pro Lys Pro Lys Pro Pro Ala Thr Pro Pro Thr Asn
    50                  55                  60

Val Leu Met Leu Ala Thr Lys Gly Ser Gly Gly Gly Ser Pro His
65                  70                  75                  80

His His His His His
            85

<210> SEQ ID NO 123
<211> LENGTH: 90
<212> TYPE: PRT
<213> ORGANISM: ARTIFICIAL SEQUENCE
<220> FEATURE:
<223> OTHER INFORMATION: Synthetic hair-binding constructs with his tag

<400> SEQUENCE: 123
```

```
Pro Arg Ala Gln Ser Gln Leu Pro Asp Lys His Ser Gly Leu His Glu
1               5                   10                  15

Arg Ala Pro Gln Arg Tyr Gly Pro Glu Glu Ala Ala Lys Lys Glu Glu
                20                  25                  30

Ala Ala Lys Lys Glu Glu Ala Ala Lys Lys Glu Glu Ala Ala Lys Lys
            35                  40                  45

Glu Glu Ala Ala Lys Lys Pro Ala His Asn His Met Gln Glu Arg Tyr
50                      55                  60

Thr Ala Pro Gln His Ser Pro Ser Val Asn Gly Leu Gly Ser Gly Gly
65                  70                  75                  80

Gly Gly Ser Pro His His His His His His
                85                  90
```

<210> SEQ ID NO 124
<211> LENGTH: 72
<212> TYPE: PRT
<213> ORGANISM: ARTIFICIAL SEQUENCE
<220> FEATURE:
<223> OTHER INFORMATION: Synthetic hair-binding constructs with his tag

<400> SEQUENCE: 124

```
Pro Arg Ala Gln Ser Gln Leu Pro Asp Lys His Ser Gly Leu His Glu
1               5                   10                  15

Arg Ala Pro Gln Arg Tyr Gly Pro Glu Glu Ala Ala Lys Lys Glu Glu
                20                  25                  30

Ala Ala Lys Lys Pro Ala His Ile Asn Lys Thr Asn Pro His Gln Gly
            35                  40                  45

Asn His His Ser Glu Lys Thr Gln Arg Gln Gly Ser Gly Gly Gly Gly
        50                  55                  60

Ser Pro His His His His His His
65                  70
```

<210> SEQ ID NO 125
<211> LENGTH: 38
<212> TYPE: DNA
<213> ORGANISM: artificial sequence
<220> FEATURE:
<223> OTHER INFORMATION: primer

<400> SEQUENCE: 125
cgcgcctagg atcggaaccc tgacaagcat ggatgttc                        38

<210> SEQ ID NO 126
<211> LENGTH: 26
<212> TYPE: DNA
<213> ORGANISM: artificial sequence
<220> FEATURE:
<223> OTHER INFORMATION: primer

<400> SEQUENCE: 126
aatggatccg gtggcggcgg tagccc                                     26

<210> SEQ ID NO 127
<211> LENGTH: 30
<212> TYPE: DNA
<213> ORGANISM: artificial sequence
<220> FEATURE:
<223> OTHER INFORMATION: primer

<400> SEQUENCE: 127
cggcctaggg gtatgcctgc tatgcattgg                                 30
```

<210> SEQ ID NO 128
<211> LENGTH: 30
<212> TYPE: DNA
<213> ORGANISM: artificial sequence
<220> FEATURE:
<223> OTHER INFORMATION: primer

<400> SEQUENCE: 128
cggcctaggc atgatcataa aaaccaaaag                                    30

<210> SEQ ID NO 129
<211> LENGTH: 29
<212> TYPE: DNA
<213> ORGANISM: artificial sequence
<220> FEATURE:
<223> OTHER INFORMATION: primer

<400> SEQUENCE: 129
cggcctagga ctgcagaaat ccaatctag                                     29

<210> SEQ ID NO 130
<211> LENGTH: 29
<212> TYPE: DNA
<213> ORGANISM: artificial sequence
<220> FEATURE:
<223> OTHER INFORMATION: primer

<400> SEQUENCE: 130
cggcctaggg cacaatctca actgcctga                                     29

<210> SEQ ID NO 131
<211> LENGTH: 28
<212> TYPE: DNA
<213> ORGANISM: artificial sequence
<220> FEATURE:
<223> OTHER INFORMATION: primer

<400> SEQUENCE: 131
cggcctagga ctgatatgat gcacaacc                                      28

<210> SEQ ID NO 132
<211> LENGTH: 30
<212> TYPE: DNA
<213> ORGANISM: artificial sequence
<220> FEATURE:
<223> OTHER INFORMATION: primer

<400> SEQUENCE: 132
cggcctagga ctccaccaac taatgttctg                                    30

<210> SEQ ID NO 133
<211> LENGTH: 29
<212> TYPE: DNA
<213> ORGANISM: artificial sequence
<220> FEATURE:
<223> OTHER INFORMATION: primer

<400> SEQUENCE: 133
cggcctagga atacctccca gctgtccac                                     29

<210> SEQ ID NO 134
<211> LENGTH: 29
<212> TYPE: DNA
<213> ORGANISM: artificial sequence
<220> FEATURE:
<223> OTHER INFORMATION: primer -continued

<400> SEQUENCE: 134
cggcctaggc atatcaataa aactaatcc                              29

<210> SEQ ID NO 135
<211> LENGTH: 25
<212> TYPE: DNA
<213> ORGANISM: artificial sequence
<220> FEATURE:
<223> OTHER INFORMATION: primer

<400> SEQUENCE: 135
aatggatcct gcgaacggat gaatc                                  25

<210> SEQ ID NO 136
<211> LENGTH: 25
<212> TYPE: DNA
<213> ORGANISM: artificial sequence
<220> FEATURE:
<223> OTHER INFORMATION: primer

<400> SEQUENCE: 136
aatggatccc gcagcgtgac gctgg                                  25

<210> SEQ ID NO 137
<211> LENGTH: 23
<212> TYPE: DNA
<213> ORGANISM: artificial sequence
<220> FEATURE:
<223> OTHER INFORMATION: primer

<400> SEQUENCE: 137
aatggatccc agaccgttca cag                                    23

<210> SEQ ID NO 138
<211> LENGTH: 23
<212> TYPE: DNA
<213> ORGANISM: artificial sequence
<220> FEATURE:
<223> OTHER INFORMATION: primer

<400> SEQUENCE: 138
aatggatccg ttagtccagg agc                                    23

<210> SEQ ID NO 139
<211> LENGTH: 22
<212> TYPE: DNA
<213> ORGANISM: artificial sequence
<220> FEATURE:
<223> OTHER INFORMATION: primer

<400> SEQUENCE: 139
aatggatccc gtcgctggac cg                                     22

<210> SEQ ID NO 140
<211> LENGTH: 23
<212> TYPE: DNA
<213> ORGANISM: artificial sequence
<220> FEATURE:
<223> OTHER INFORMATION: primer

<400> SEQUENCE: 140
aatggatccg tagcgttgcg gtg                                    23

<210> SEQ ID NO 141
<211> LENGTH: 23
<212> TYPE: DNA

```
<213> ORGANISM: artificial sequence
<220> FEATURE:
<223> OTHER INFORMATION: primer

<400> SEQUENCE: 141
aatggatcca cggtcagtca gac                                          23

<210> SEQ ID NO 142
<211> LENGTH: 22
<212> TYPE: DNA
<213> ORGANISM: artificial sequence
<220> FEATURE:
<223> OTHER INFORMATION: primer

<400> SEQUENCE: 142
aatggatcct ttggttgcca gc                                           22

<210> SEQ ID NO 143
<211> LENGTH: 23
<212> TYPE: DNA
<213> ORGANISM: artificial sequence
<220> FEATURE:
<223> OTHER INFORMATION: primer

<400> SEQUENCE: 143
aatggatccg gagcgtggag cac                                          23

<210> SEQ ID NO 144
<211> LENGTH: 23
<212> TYPE: DNA
<213> ORGANISM: artificial sequence
<220> FEATURE:
<223> OTHER INFORMATION: primer

<400> SEQUENCE: 144
aatggatccg gtggacagct ggc                                          23

<210> SEQ ID NO 145
<211> LENGTH: 28
<212> TYPE: DNA
<213> ORGANISM: artificial sequence
<220> FEATURE:
<223> OTHER INFORMATION: primer

<400> SEQUENCE: 145
aatggatccc tgacgctgag ttttctcg                                     28

<210> SEQ ID NO 146
<211> LENGTH: 72
<212> TYPE: PRT
<213> ORGANISM: ARTIFICIAL SEQUENCE
<220> FEATURE:
<223> OTHER INFORMATION: synthetic hair-binding construct

<400> SEQUENCE: 146

Pro Arg Ala Gln Ser Gln Leu Pro Asp Lys His Ser Gly Leu His Glu
1               5                   10                  15

Arg Ala Pro Gln Arg Tyr Gly Pro Glu Glu Ala Ala Lys Lys Glu Glu
            20                  25                  30

Ala Ala Lys Lys Glu Glu Ala Ala Lys Lys Glu Glu Ala Ala Lys Lys
        35                  40                  45

Pro Ala His Ile Asn Lys Thr Asn Pro His Gln Gly Asn His His Ser
    50                  55                  60

Glu Lys Thr Gln Arg Gln Gly Ser
65                  70
```

```
<210> SEQ ID NO 147
<211> LENGTH: 76
<212> TYPE: PRT
<213> ORGANISM: ARTIFICIAL SEQUENCE
<220> FEATURE:
<223> OTHER INFORMATION: synthetic hair-binding construct

<400> SEQUENCE: 147

Pro Arg Ala Gln Ser Gln Leu Pro Asp Lys His Ser Gly Leu His Glu
1               5                   10                  15

Arg Ala Pro Gln Arg Tyr Gly Pro Lys Pro Lys Pro Lys Pro Lys Pro
            20                  25                  30

Lys Pro Lys Pro Gly Gly Lys Pro Lys Pro Lys Pro Lys Pro Lys Pro
        35                  40                  45

Lys Pro Gly Gly Pro Ala His Asn His Met Gln Glu Arg Tyr Thr Ala
    50                  55                  60

Pro Gln His Ser Pro Ser Val Asn Gly Leu Gly Ser
65                  70                  75

<210> SEQ ID NO 148
<211> LENGTH: 76
<212> TYPE: PRT
<213> ORGANISM: ARTIFICIAL SEQUENCE
<220> FEATURE:
<223> OTHER INFORMATION: synthetic hair-binding construct

<400> SEQUENCE: 148

Pro Arg Thr Ala Glu Ile Gln Ser Ser Lys Asn Pro Asn Pro His Pro
1               5                   10                  15

Gln Arg Ser Trp Thr Asn Gly Pro Lys Pro Lys Pro Lys Pro Lys Pro
            20                  25                  30

Lys Pro Lys Pro Gly Gly Lys Pro Lys Pro Lys Pro Lys Pro Lys Pro
        35                  40                  45

Lys Pro Gly Gly Pro Ala His Asn His Met Gln Glu Arg Tyr Thr Ala
    50                  55                  60

Pro Gln His Ser Pro Ser Val Asn Gly Leu Gly Ser
65                  70                  75

<210> SEQ ID NO 149
<211> LENGTH: 15
<212> TYPE: PRT
<213> ORGANISM: ARTIFICIAL SEQUENCE
<220> FEATURE:
<223> OTHER INFORMATION: synthetic cellulose acetate-binding peptide

<400> SEQUENCE: 149

Ser Asp Glu Thr Gly Pro Gln Ile Pro His Arg Arg Pro Thr Trp
1               5                   10                  15

<210> SEQ ID NO 150
<211> LENGTH: 33
<212> TYPE: PRT
<213> ORGANISM: ARTIFICIAL SEQUENCE
<220> FEATURE:
<223> OTHER INFORMATION: synethic cellulose acetate-binding construct

<400> SEQUENCE: 150

Ser Asp Glu Thr Gly Pro Gln Ile Pro His Arg Arg Pro Thr Trp Gly
1               5                   10                  15

Gly Gly Ser Asp Glu Thr Gly Pro Gln Ile Pro His Arg Arg Pro Thr
            20                  25                  30
```

Trp

<210> SEQ ID NO 151
<211> LENGTH: 36
<212> TYPE: PRT
<213> ORGANISM: ARTIFICIAL SEQUENCE
<220> FEATURE:
<223> OTHER INFORMATION: synethic cellulose acetate-binding construct

<400> SEQUENCE: 151

Ser Asp Glu Thr Gly Pro Gln Ile Pro His Arg Arg Pro Thr Trp Gly
1               5                   10                  15

Ser Pro Gly Gly Gly Ser Asp Glu Thr Gly Pro Gln Ile Pro His Arg
            20                  25                  30

Arg Pro Thr Trp
        35

<210> SEQ ID NO 152
<211> LENGTH: 39
<212> TYPE: PRT
<213> ORGANISM: ARTIFICIAL SEQUENCE
<220> FEATURE:
<223> OTHER INFORMATION: synethic cellulose acetate-binding construct

<400> SEQUENCE: 152

Ser Asp Glu Thr Gly Pro Gln Ile Pro His Arg Arg Pro Thr Trp Gly
1               5                   10                  15

Ser Pro Gly Gly Gly Thr Gly Gly Ser Asp Glu Thr Gly Pro Gln Ile
            20                  25                  30

Pro His Arg Arg Pro Thr Trp
        35

<210> SEQ ID NO 153
<211> LENGTH: 67
<212> TYPE: PRT
<213> ORGANISM: ARTIFICIAL SEQUENCE
<220> FEATURE:
<223> OTHER INFORMATION: synethic cellulose acetate-binding construct

<400> SEQUENCE: 153

Ser Asp Glu Thr Gly Pro Gln Ile Pro His Arg Arg Pro Thr Trp Gly
1               5                   10                  15

Pro Glu Pro Glu Pro Glu Pro Glu Pro Ile Pro Glu Pro Pro Lys Glu
            20                  25                  30

Ala Pro Val Val Ile Glu Lys Pro Lys Pro Lys Pro Lys Pro Lys Pro
        35                  40                  45

Lys Pro Pro Ala Ser Asp Glu Thr Gly Pro Gln Ile Pro His Arg Arg
    50                  55                  60

Pro Thr Trp
65

<210> SEQ ID NO 154
<211> LENGTH: 51
<212> TYPE: PRT
<213> ORGANISM: ARTIFICIAL SEQUENCE
<220> FEATURE:
<223> OTHER INFORMATION: synethic cellulose acetate-binding construct

<400> SEQUENCE: 154

Ser Asp Glu Thr Gly Pro Gln Ile Pro His Arg Arg Pro Thr Trp Gly
1               5                   10                  15

Gly Gly Ser Asp Glu Thr Gly Pro Gln Ile Pro His Arg Arg Pro Thr
            20                  25                  30

```
Trp Gly Gly Gly Ser Asp Glu Thr Gly Pro Gln Ile Pro His Arg Arg
            35                  40                  45

Pro Thr Trp
    50

<210> SEQ ID NO 155
<211> LENGTH: 179
<212> TYPE: PRT
<213> ORGANISM: Escherichia coli

<400> SEQUENCE: 155

Pro Trp Pro Thr Leu Leu Ser Val Cys Ile His Gly Ala Val Val Ala
1               5                   10                  15

Gly Leu Leu Tyr Thr Ser Val His Gln Val Ile Glu Leu Pro Ala Pro
            20                  25                  30

Ala Gln Pro Ile Ser Val Thr Met Val Thr Pro Ala Asp Leu Glu Pro
        35                  40                  45

Pro Gln Ala Val Gln Pro Pro Glu Pro Val Val Glu Pro Glu Pro
    50                  55                  60

Glu Pro Glu Pro Ile Pro Glu Pro Pro Lys Glu Ala Pro Val Val Ile
65                  70                  75                  80

Glu Lys Pro Lys Pro Lys Pro Lys Pro Lys Pro Val Lys Lys
                85                  90                  95

Val Gln Glu Gln Pro Lys Arg Asp Val Lys Pro Val Glu Ser Arg Pro
                100                 105                 110

Ala Ser Pro Phe Glu Asn Thr Ala Pro Ala Arg Leu Thr Ser Ser Thr
            115                 120                 125

Ala Thr Ala Ala Thr Ser Lys Pro Val Thr Ser Val Ala Ser Gly Pro
130                 135                 140

Arg Ala Leu Ser Arg Asn Gln Pro Gln Tyr Pro Ala Arg Ala Gln Ala
145                 150                 155                 160

Leu Arg Ile Glu Gly Gln Val Lys Val Lys Phe Asp Val Thr Pro Asp
                165                 170                 175

Gly Arg Val

<210> SEQ ID NO 156
<211> LENGTH: 60
<212> TYPE: PRT
<213> ORGANISM: artificial sequence
<220> FEATURE:
<223> OTHER INFORMATION: synthetic alpha helix forming sequence
<220> FEATURE:
<221> NAME/KEY: MISC_FEATURE
<222> LOCATION: (1)..(1)
<223> OTHER INFORMATION: Xaa = Glu or Asp
<220> FEATURE:
<221> NAME/KEY: MISC_FEATURE
<222> LOCATION: (1)..(2)
<223> OTHER INFORMATION: Xaa of residue positions 1 and 2 have opposite
      charge of Xaa at positions 5 and 6
<220> FEATURE:
<221> NAME/KEY: MISC_FEATURE
<222> LOCATION: (2)..(2)
<223> OTHER INFORMATION: Xaa = Glu or Asp
<220> FEATURE:
<221> NAME/KEY: MISC_FEATURE
<222> LOCATION: (5)..(5)
<223> OTHER INFORMATION: Xaa = Lys or Arg
<220> FEATURE:
<221> NAME/KEY: MISC_FEATURE
<222> LOCATION: (6)..(6)
<223> OTHER INFORMATION: Xaa = Lys or Arg
<220> FEATURE:
<221> NAME/KEY: MISC_FEATURE
```

```
<222> LOCATION: (7)..(8)
<223> OTHER INFORMATION: Xaa of residue positions 7 and 8 have opposite
      charge of Xaa at positions 11 and 12
<220> FEATURE:
<221> NAME/KEY: MISC_FEATURE
<222> LOCATION: (8)..(8)
<223> OTHER INFORMATION: Xaa = Glu or Asp
<220> FEATURE:
<221> NAME/KEY: MISC_FEATURE
<222> LOCATION: (11)..(11)
<223> OTHER INFORMATION: Xaa = Lys or Arg
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = Glu or Asp
<220> FEATURE:
<221> NAME/KEY: MISC_FEATURE
<222> LOCATION: (13)..(14)
<223> OTHER INFORMATION: Xaa of residue positions 13 and 13 have
      opposite charge of Xaa at positions 17 and 18
<220> FEATURE:
<221> NAME/KEY: MISC_FEATURE
<222> LOCATION: (13)..(18)
<223> OTHER INFORMATION: optionally present
<220> FEATURE:
<221> NAME/KEY: MISC_FEATURE
<222> LOCATION: (14)..(14)
<223> OTHER INFORMATION: Xaa = Glu or Asp
<220> FEATURE:
<221> NAME/KEY: MISC_FEATURE
<222> LOCATION: (17)..(17)
<223> OTHER INFORMATION: Xaa = Lys or Arg
<220> FEATURE:
<221> NAME/KEY: MISC_FEATURE
<222> LOCATION: (18)..(18)
<223> OTHER INFORMATION: Xaa = Lys or Arg
<220> FEATURE:
<221> NAME/KEY: MISC_FEATURE
<222> LOCATION: (19)..(19)
<223> OTHER INFORMATION: Xaa = Glu or Asp
<220> FEATURE:
<221> NAME/KEY: MISC_FEATURE
<222> LOCATION: (19)..(20)
<223> OTHER INFORMATION: Xaa of residue positions 19 and 20 have
      opposite charge of Xaa at positions 23 and 24
<220> FEATURE:
<221> NAME/KEY: MISC_FEATURE
<222> LOCATION: (19)..(24)
<223> OTHER INFORMATION: optionally present
<220> FEATURE:
<221> NAME/KEY: MISC_FEATURE
<222> LOCATION: (20)..(20)
<223> OTHER INFORMATION: Xaa = Glu or Asp
<220> FEATURE:
<221> NAME/KEY: MISC_FEATURE
<222> LOCATION: (23)..(23)
<223> OTHER INFORMATION: Xaa = Lys or Arg
<220> FEATURE:
<221> NAME/KEY: MISC_FEATURE
<222> LOCATION: (24)..(24)
<223> OTHER INFORMATION: Xaa = Lys or Arg
<220> FEATURE:
<221> NAME/KEY: MISC_FEATURE
<222> LOCATION: (25)..(25)
<223> OTHER INFORMATION: Xaa = Glu or Asp
<220> FEATURE:
<221> NAME/KEY: MISC_FEATURE
<222> LOCATION: (25)..(26)
<223> OTHER INFORMATION: Xaa of residue positions 25 and 26 have
      opposite charge of Xaa at positions 29 and 30
<220> FEATURE:
<221> NAME/KEY: MISC_FEATURE
<222> LOCATION: (25)..(30)
<223> OTHER INFORMATION: optionally present
<220> FEATURE:
<221> NAME/KEY: MISC_FEATURE
```

```
<222> LOCATION: (26)..(26)
<223> OTHER INFORMATION: Xaa = Glu or Asp
<220> FEATURE:
<221> NAME/KEY: MISC_FEATURE
<222> LOCATION: (29)..(29)
<223> OTHER INFORMATION: Xaa = Lys or Arg
<220> FEATURE:
<221> NAME/KEY: MISC_FEATURE
<222> LOCATION: (30)..(30)
<223> OTHER INFORMATION: Xaa = Lys or Arg
<220> FEATURE:
<221> NAME/KEY: MISC_FEATURE
<222> LOCATION: (31)..(31)
<223> OTHER INFORMATION: Xaa = Glu or Asp
<220> FEATURE:
<221> NAME/KEY: MISC_FEATURE
<222> LOCATION: (31)..(32)
<223> OTHER INFORMATION: Xaa of residue positions 31 and 32 have
      opposite charge of Xaa at positions 36 and 36
<220> FEATURE:
<221> NAME/KEY: MISC_FEATURE
<222> LOCATION: (31)..(36)
<223> OTHER INFORMATION: optionally present
<220> FEATURE:
<221> NAME/KEY: MISC_FEATURE
<222> LOCATION: (32)..(32)
<223> OTHER INFORMATION: Xaa = Glu or Asp
<220> FEATURE:
<221> NAME/KEY: MISC_FEATURE
<222> LOCATION: (35)..(35)
<223> OTHER INFORMATION: Xaa = Lys or Arg
<220> FEATURE:
<221> NAME/KEY: MISC_FEATURE
<222> LOCATION: (36)..(36)
<223> OTHER INFORMATION: Xaa = Lys or Arg
<220> FEATURE:
<221> NAME/KEY: MISC_FEATURE
<222> LOCATION: (37)..(37)
<223> OTHER INFORMATION: Xaa = Glu or Asp
<220> FEATURE:
<221> NAME/KEY: MISC_FEATURE
<222> LOCATION: (37)..(38)
<223> OTHER INFORMATION: Xaa of residue positions 37 and 38 have
      opposite charge of Xaa at positions 41 and 42
<220> FEATURE:
<221> NAME/KEY: MISC_FEATURE
<222> LOCATION: (37)..(42)
<223> OTHER INFORMATION: optionally present
<220> FEATURE:
<221> NAME/KEY: MISC_FEATURE
<222> LOCATION: (38)..(38)
<223> OTHER INFORMATION: Xaa = Glu or Asp
<220> FEATURE:
<221> NAME/KEY: MISC_FEATURE
<222> LOCATION: (41)..(41)
<223> OTHER INFORMATION: Xaa = Lys or Arg
<220> FEATURE:
<221> NAME/KEY: MISC_FEATURE
<222> LOCATION: (42)..(42)
<223> OTHER INFORMATION: Xaa = Lys or Arg
<220> FEATURE:
<221> NAME/KEY: MISC_FEATURE
<222> LOCATION: (43)..(43)
<223> OTHER INFORMATION: Xaa = Glu or Asp
<220> FEATURE:
<221> NAME/KEY: MISC_FEATURE
<222> LOCATION: (43)..(44)
<223> OTHER INFORMATION: Xaa of residue positions 43 and 44 have
      opposite charge of Xaa at positions 47 and 48
<220> FEATURE:
<221> NAME/KEY: MISC_FEATURE
<222> LOCATION: (43)..(48)
<223> OTHER INFORMATION: optionally present
<220> FEATURE:
<221> NAME/KEY: MISC_FEATURE
<222> LOCATION: (44)..(44)
<223> OTHER INFORMATION: Xaa = Glu or Asp
<220> FEATURE:
<221> NAME/KEY: MISC_FEATURE
<222> LOCATION: (47)..(47)
```

```
<223> OTHER INFORMATION: Xaa = Lys or Arg
<220> FEATURE:
<221> NAME/KEY: MISC_FEATURE
<222> LOCATION: (48)..(48)
<223> OTHER INFORMATION: Xaa = Lys or Arg
<220> FEATURE:
<221> NAME/KEY: MISC_FEATURE
<222> LOCATION: (49)..(49)
<223> OTHER INFORMATION: Xaa = Glu or Asp
<220> FEATURE:
<221> NAME/KEY: MISC_FEATURE
<222> LOCATION: (49)..(50)
<223> OTHER INFORMATION: Xaa of residue positions 49 and 50 have
      opposite charge of Xaa at positions 53 and 54
<220> FEATURE:
<221> NAME/KEY: MISC_FEATURE
<222> LOCATION: (49)..(54)
<223> OTHER INFORMATION: optionally present
<220> FEATURE:
<221> NAME/KEY: MISC_FEATURE
<222> LOCATION: (50)..(50)
<223> OTHER INFORMATION: Xaa = Glu or Asp
<220> FEATURE:
<221> NAME/KEY: MISC_FEATURE
<222> LOCATION: (53)..(53)
<223> OTHER INFORMATION: Xaa = Lys or Arg
<220> FEATURE:
<221> NAME/KEY: MISC_FEATURE
<222> LOCATION: (54)..(54)
<223> OTHER INFORMATION: Xaa = Lys or Arg
<220> FEATURE:
<221> NAME/KEY: MISC_FEATURE
<222> LOCATION: (55)..(55)
<223> OTHER INFORMATION: Xaa = Glu or Asp
<220> FEATURE:
<221> NAME/KEY: MISC_FEATURE
<222> LOCATION: (55)..(56)
<223> OTHER INFORMATION: Xaa of residue positions 55 and 56 have
      opposite charge of Xaa at positions 59 and 60
<220> FEATURE:
<221> NAME/KEY: MISC_FEATURE
<222> LOCATION: (55)..(60)
<223> OTHER INFORMATION: optionally present
<220> FEATURE:
<221> NAME/KEY: MISC_FEATURE
<222> LOCATION: (56)..(56)
<223> OTHER INFORMATION: Xaa = Glu or Asp
<220> FEATURE:
<221> NAME/KEY: MISC_FEATURE
<222> LOCATION: (59)..(59)
<223> OTHER INFORMATION: Xaa = Lys or Arg
<220> FEATURE:
<221> NAME/KEY: MISC_FEATURE
<222> LOCATION: (60)..(60)
<223> OTHER INFORMATION: Xaa = Lys or Arg

<400> SEQUENCE: 156

Xaa Xaa Ala Ala Xaa Xaa Xaa Xaa Ala Ala Xaa Xaa Xaa Xaa Ala Ala
1               5                   10                  15

Xaa Xaa Xaa Xaa Ala Ala Xaa Xaa Xaa Xaa Ala Ala Xaa Xaa Xaa Xaa
                20                  25                  30

Ala Ala Xaa Xaa Xaa Xaa Ala Ala Xaa Xaa Xaa Xaa Ala Ala Xaa Xaa
            35                  40                  45

Xaa Xaa Ala Ala Xaa Xaa Xaa Xaa Ala Ala Xaa Xaa
    50                  55                  60

<210> SEQ ID NO 157
<211> LENGTH: 55
<212> TYPE: PRT
<213> ORGANISM: artificial sequence
<220> FEATURE:
<223> OTHER INFORMATION: synthetic alpha helix forming sequence
<220> FEATURE:
<221> NAME/KEY: MISC_FEATURE
<222> LOCATION: (1)..(1)
```

-continued

```
<223> OTHER INFORMATION: Xaa = Glu or Asp
<220> FEATURE:
<221> NAME/KEY: MISC_FEATURE
<222> LOCATION: (1)..(1)
<223> OTHER INFORMATION: Xaa of residue position 1 is oppositely
      charged from Xaa of residue position 5.
<220> FEATURE:
<221> NAME/KEY: MISC_FEATURE
<222> LOCATION: (5)..(5)
<223> OTHER INFORMATION: Xaa = Lys or Arg
<220> FEATURE:
<221> NAME/KEY: MISC_FEATURE
<222> LOCATION: (6)..(6)
<223> OTHER INFORMATION: Xaa = Glu or Asp
<220> FEATURE:
<221> NAME/KEY: MISC_FEATURE
<222> LOCATION: (6)..(6)
<223> OTHER INFORMATION: Xaa of residue position 6 is oppositely
      charged from Xaa of residue position 10.
<220> FEATURE:
<221> NAME/KEY: MISC_FEATURE
<222> LOCATION: (10)..(10)
<223> OTHER INFORMATION: Xaa = Lys or Arg
<220> FEATURE:
<221> NAME/KEY: MISC_FEATURE
<222> LOCATION: (11)..(11)
<223> OTHER INFORMATION: Xaa = Glu or Asp
<220> FEATURE:
<221> NAME/KEY: MISC_FEATURE
<222> LOCATION: (11)..(11)
<223> OTHER INFORMATION: Xaa of residue position 11 is oppositely
      charged from Xaa of residue position 15.
<220> FEATURE:
<221> NAME/KEY: MISC_FEATURE
<222> LOCATION: (11)..(15)
<223> OTHER INFORMATION: optionally present
<220> FEATURE:
<221> NAME/KEY: MISC_FEATURE
<222> LOCATION: (15)..(15)
<223> OTHER INFORMATION: Xaa = Lys or Arg
<220> FEATURE:
<221> NAME/KEY: MISC_FEATURE
<222> LOCATION: (16)..(16)
<223> OTHER INFORMATION: Xaa = Glu or Asp
<220> FEATURE:
<221> NAME/KEY: MISC_FEATURE
<222> LOCATION: (16)..(16)
<223> OTHER INFORMATION: Xaa of residue position 16 is oppositely
      charged from Xaa of residue position 20.
<220> FEATURE:
<221> NAME/KEY: MISC_FEATURE
<222> LOCATION: (16)..(20)
<223> OTHER INFORMATION: optionally present
<220> FEATURE:
<221> NAME/KEY: MISC_FEATURE
<222> LOCATION: (20)..(20)
<223> OTHER INFORMATION: Xaa = Lys or Arg
<220> FEATURE:
<221> NAME/KEY: MISC_FEATURE
<222> LOCATION: (21)..(21)
<223> OTHER INFORMATION: Xaa = Glu or Asp
<220> FEATURE:
<221> NAME/KEY: MISC_FEATURE
<222> LOCATION: (21)..(21)
<223> OTHER INFORMATION: Xaa of residue position 21 is oppositely
      charged from Xaa of residue position 25.
<220> FEATURE:
<221> NAME/KEY: MISC_FEATURE
<222> LOCATION: (21)..(25)
<223> OTHER INFORMATION: optionally present
<220> FEATURE:
<221> NAME/KEY: MISC_FEATURE
<222> LOCATION: (25)..(25)
<223> OTHER INFORMATION: Xaa = Lys or Arg
<220> FEATURE:
<221> NAME/KEY: MISC_FEATURE
<222> LOCATION: (26)..(26)
<223> OTHER INFORMATION: Xaa = Glu or Asp
<220> FEATURE:
<221> NAME/KEY: MISC_FEATURE
```

```
<222> LOCATION: (26)..(26)
<223> OTHER INFORMATION: Xaa of residue position 26 is oppositely
      charged from Xaa of residue position 30.
<220> FEATURE:
<221> NAME/KEY: MISC_FEATURE
<222> LOCATION: (26)..(30)
<223> OTHER INFORMATION: optionally present
<220> FEATURE:
<221> NAME/KEY: MISC_FEATURE
<222> LOCATION: (30)..(30)
<223> OTHER INFORMATION: Xaa = Lys or Arg
<220> FEATURE:
<221> NAME/KEY: MISC_FEATURE
<222> LOCATION: (31)..(31)
<223> OTHER INFORMATION: Xaa = Glu or Asp
<220> FEATURE:
<221> NAME/KEY: MISC_FEATURE
<222> LOCATION: (31)..(31)
<223> OTHER INFORMATION: Xaa of residue position 31 is oppositely
      charged from Xaa of residue position 35.
<220> FEATURE:
<221> NAME/KEY: MISC_FEATURE
<222> LOCATION: (31)..(35)
<223> OTHER INFORMATION: optionally present
<220> FEATURE:
<221> NAME/KEY: MISC_FEATURE
<222> LOCATION: (35)..(35)
<223> OTHER INFORMATION: Xaa = Lys or Arg
<220> FEATURE:
<221> NAME/KEY: MISC_FEATURE
<222> LOCATION: (36)..(36)
<223> OTHER INFORMATION: Xaa = Glu or Asp
<220> FEATURE:
<221> NAME/KEY: MISC_FEATURE
<222> LOCATION: (36)..(36)
<223> OTHER INFORMATION: Xaa of residue position 36 is oppositely
      charged from Xaa of residue position 40.
<220> FEATURE:
<221> NAME/KEY: MISC_FEATURE
<222> LOCATION: (36)..(40)
<223> OTHER INFORMATION: optionally present
<220> FEATURE:
<221> NAME/KEY: MISC_FEATURE
<222> LOCATION: (40)..(40)
<223> OTHER INFORMATION: Xaa = Lys or Arg
<220> FEATURE:
<221> NAME/KEY: MISC_FEATURE
<222> LOCATION: (41)..(41)
<223> OTHER INFORMATION: Xaa = Glu or Asp
<220> FEATURE:
<221> NAME/KEY: MISC_FEATURE
<222> LOCATION: (41)..(41)
<223> OTHER INFORMATION: Xaa of residue position 41 is oppositely
      charged from Xaa of residue position 45.
<220> FEATURE:
<221> NAME/KEY: MISC_FEATURE
<222> LOCATION: (41)..(45)
<223> OTHER INFORMATION: optionally present
<220> FEATURE:
<221> NAME/KEY: MISC_FEATURE
<222> LOCATION: (45)..(45)
<223> OTHER INFORMATION: Xaa = Lys or Arg
<220> FEATURE:
<221> NAME/KEY: MISC_FEATURE
<222> LOCATION: (46)..(46)
<223> OTHER INFORMATION: Xaa = Glu or Asp
<220> FEATURE:
<221> NAME/KEY: MISC_FEATURE
<222> LOCATION: (46)..(46)
<223> OTHER INFORMATION: Xaa of residue position 46 is oppositely
      charged from Xaa of residue position 50.
<220> FEATURE:
<221> NAME/KEY: MISC_FEATURE
<222> LOCATION: (46)..(50)
<223> OTHER INFORMATION: optionally present
<220> FEATURE:
<221> NAME/KEY: MISC_FEATURE
<222> LOCATION: (50)..(50)
<223> OTHER INFORMATION: Xaa = Lys or Arg
<220> FEATURE:
```

-continued

```
<221> NAME/KEY: MISC_FEATURE
<222> LOCATION: (51)..(51)
<223> OTHER INFORMATION: Xaa = Glu or Asp
<220> FEATURE:
<221> NAME/KEY: MISC_FEATURE
<222> LOCATION: (51)..(51)
<223> OTHER INFORMATION: Xaa of residue position 51 is oppositely
      charged from Xaa of residue position 55.
<220> FEATURE:
<221> NAME/KEY: MISC_FEATURE
<222> LOCATION: (51)..(55)
<223> OTHER INFORMATION: optionally present
<220> FEATURE:
<221> NAME/KEY: MISC_FEATURE
<222> LOCATION: (55)..(55)
<223> OTHER INFORMATION: Xaa = Lys or Arg

<400> SEQUENCE: 157

Xaa Ala Ala Ala Xaa Xaa Ala Ala Ala Xaa Xaa Ala Ala Ala Xaa Xaa
1               5                   10                  15

Ala Ala Ala Xaa Xaa Ala Ala Xaa Xaa Ala Ala Ala Xaa Xaa Ala
            20                  25                  30

Ala Ala Xaa Xaa Ala Ala Ala Xaa Xaa Ala Ala Ala Xaa Xaa Ala Ala
        35                  40                  45

Ala Xaa Xaa Ala Ala Ala Xaa
    50                  55

<210> SEQ ID NO 158
<211> LENGTH: 77
<212> TYPE: PRT
<213> ORGANISM: artificial sequence
<220> FEATURE:
<223> OTHER INFORMATION: synthetic alpha helix forming sequence
<220> FEATURE:
<221> NAME/KEY: MISC_FEATURE
<222> LOCATION: (1)..(1)
<223> OTHER INFORMATION: Xaa = Glu or Asp
<220> FEATURE:
<221> NAME/KEY: MISC_FEATURE
<222> LOCATION: (1)..(1)
<223> OTHER INFORMATION: Xaa of residue position 1 has opposite charge
      from Xaa at residue position 5
<220> FEATURE:
<221> NAME/KEY: MISC_FEATURE
<222> LOCATION: (5)..(5)
<223> OTHER INFORMATION: Xaa = Lys or Arg
<220> FEATURE:
<221> NAME/KEY: MISC_FEATURE
<222> LOCATION: (6)..(6)
<223> OTHER INFORMATION: Xaa = Leu, Val, Ile, Phe, Trp, Met or Tyr
<220> FEATURE:
<221> NAME/KEY: MISC_FEATURE
<222> LOCATION: (7)..(7)
<223> OTHER INFORMATION: Xaa = Leu, Val, Ile, Phe, Trp, Met or Tyr
<220> FEATURE:
<221> NAME/KEY: MISC_FEATURE
<222> LOCATION: (8)..(8)
<223> OTHER INFORMATION: Xaa = Glu or Asp
<220> FEATURE:
<221> NAME/KEY: MISC_FEATURE
<222> LOCATION: (8)..(8)
<223> OTHER INFORMATION: Xaa of residue position 8 has opposite charge
      from Xaa at residue position 12
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (13)..(13)
<223> OTHER INFORMATION: Xaa = Leu, Val, Ile, Phe, Trp, Met or Tyr
<220> FEATURE:
<221> NAME/KEY: MISC_FEATURE
<222> LOCATION: (14)..(14)
<223> OTHER INFORMATION: Xaa = Leu, Val, Ile, Phe, Trp, Met or Tyr
```

```
<220> FEATURE:
<221> NAME/KEY: MISC_FEATURE
<222> LOCATION: (15)..(15)
<223> OTHER INFORMATION: Xaa = Glu or Asp
<220> FEATURE:
<221> NAME/KEY: MISC_FEATURE
<222> LOCATION: (15)..(15)
<223> OTHER INFORMATION: Xaa of residue position 15 has opposite charge
      from Xaa at residue position 19
<220> FEATURE:
<221> NAME/KEY: MISC_FEATURE
<222> LOCATION: (15)..(21)
<223> OTHER INFORMATION: optionally present
<220> FEATURE:
<221> NAME/KEY: MISC_FEATURE
<222> LOCATION: (19)..(19)
<223> OTHER INFORMATION: Xaa = Lys or Arg
<220> FEATURE:
<221> NAME/KEY: MISC_FEATURE
<222> LOCATION: (20)..(20)
<223> OTHER INFORMATION: Xaa = Leu, Val, Ile, Phe, Trp, Met or Tyr
<220> FEATURE:
<221> NAME/KEY: MISC_FEATURE
<222> LOCATION: (21)..(21)
<223> OTHER INFORMATION: Xaa = Leu, Val, Ile, Phe, Trp, Met or Tyr
<220> FEATURE:
<221> NAME/KEY: MISC_FEATURE
<222> LOCATION: (22)..(22)
<223> OTHER INFORMATION: Xaa = Glu or Asp
<220> FEATURE:
<221> NAME/KEY: MISC_FEATURE
<222> LOCATION: (22)..(22)
<223> OTHER INFORMATION: Xaa of residue position 22 has opposite charge
      from Xaa at residue position 26
<220> FEATURE:
<221> NAME/KEY: MISC_FEATURE
<222> LOCATION: (22)..(28)
<223> OTHER INFORMATION: optionally present
<220> FEATURE:
<221> NAME/KEY: MISC_FEATURE
<222> LOCATION: (26)..(26)
<223> OTHER INFORMATION: Xaa = Lys or Arg
<220> FEATURE:
<221> NAME/KEY: MISC_FEATURE
<222> LOCATION: (27)..(27)
<223> OTHER INFORMATION: Xaa = Leu, Val, Ile, Phe, Trp, Met or Tyr
<220> FEATURE:
<221> NAME/KEY: MISC_FEATURE
<222> LOCATION: (28)..(28)
<223> OTHER INFORMATION: Xaa = Leu, Val, Ile, Phe, Trp, Met or Tyr
<220> FEATURE:
<221> NAME/KEY: MISC_FEATURE
<222> LOCATION: (29)..(29)
<223> OTHER INFORMATION: Xaa = Glu or Asp
<220> FEATURE:
<221> NAME/KEY: MISC_FEATURE
<222> LOCATION: (29)..(29)
<223> OTHER INFORMATION: Xaa of residue position 29 has opposite charge
      from Xaa at residue position 33
<220> FEATURE:
<221> NAME/KEY: MISC_FEATURE
<222> LOCATION: (29)..(35)
<223> OTHER INFORMATION: optionally present
<220> FEATURE:
<221> NAME/KEY: MISC_FEATURE
<222> LOCATION: (33)..(33)
<223> OTHER INFORMATION: Xaa = Lys or Arg
<220> FEATURE:
<221> NAME/KEY: MISC_FEATURE
<222> LOCATION: (34)..(34)
<223> OTHER INFORMATION: Xaa = Leu, Val, Ile, Phe, Trp, Met or Tyr
<220> FEATURE:
<221> NAME/KEY: MISC_FEATURE
<222> LOCATION: (35)..(35)
<223> OTHER INFORMATION: Xaa = Leu, Val, Ile, Phe, Trp, Met or Tyr
<220> FEATURE:
<221> NAME/KEY: MISC_FEATURE
<222> LOCATION: (36)..(36)
<223> OTHER INFORMATION: Xaa = Glu or Asp
<220> FEATURE:
```

-continued

```
<221> NAME/KEY: MISC_FEATURE
<222> LOCATION: (36)..(36)
<223> OTHER INFORMATION: Xaa of residue position 36 has opposite charge
      from Xaa at residue position 40
<220> FEATURE:
<221> NAME/KEY: MISC_FEATURE
<222> LOCATION: (36)..(42)
<223> OTHER INFORMATION: optionally present
<220> FEATURE:
<221> NAME/KEY: MISC_FEATURE
<222> LOCATION: (40)..(40)
<223> OTHER INFORMATION: Xaa = Lys or Arg
<220> FEATURE:
<221> NAME/KEY: MISC_FEATURE
<222> LOCATION: (41)..(41)
<223> OTHER INFORMATION: Xaa = Leu, Val, Ile, Phe, Trp, Met or Tyr
<220> FEATURE:
<221> NAME/KEY: MISC_FEATURE
<222> LOCATION: (42)..(42)
<223> OTHER INFORMATION: Xaa = Leu, Val, Ile, Phe, Trp, Met or Tyr
<220> FEATURE:
<221> NAME/KEY: MISC_FEATURE
<222> LOCATION: (43)..(43)
<223> OTHER INFORMATION: Xaa = Glu or Asp
<220> FEATURE:
<221> NAME/KEY: MISC_FEATURE
<222> LOCATION: (43)..(43)
<223> OTHER INFORMATION: Xaa of residue position 43 has opposite charge
      from Xaa at residue position 47
<220> FEATURE:
<221> NAME/KEY: MISC_FEATURE
<222> LOCATION: (43)..(49)
<223> OTHER INFORMATION: optionally present
<220> FEATURE:
<221> NAME/KEY: MISC_FEATURE
<222> LOCATION: (47)..(47)
<223> OTHER INFORMATION: Xaa = Lys or Arg
<220> FEATURE:
<221> NAME/KEY: MISC_FEATURE
<222> LOCATION: (48)..(48)
<223> OTHER INFORMATION: Xaa = Leu, Val, Ile, Phe, Trp, Met or Tyr
<220> FEATURE:
<221> NAME/KEY: MISC_FEATURE
<222> LOCATION: (49)..(49)
<223> OTHER INFORMATION: Xaa = Leu, Val, Ile, Phe, Trp, Met or Tyr
<220> FEATURE:
<221> NAME/KEY: MISC_FEATURE
<222> LOCATION: (50)..(50)
<223> OTHER INFORMATION: Xaa = Glu or Asp
<220> FEATURE:
<221> NAME/KEY: MISC_FEATURE
<222> LOCATION: (50)..(50)
<223> OTHER INFORMATION: Xaa of residue position 50 has opposite charge
      from Xaa at residue position 54
<220> FEATURE:
<221> NAME/KEY: MISC_FEATURE
<222> LOCATION: (50)..(56)
<223> OTHER INFORMATION: optionally present
<220> FEATURE:
<221> NAME/KEY: MISC_FEATURE
<222> LOCATION: (54)..(54)
<223> OTHER INFORMATION: Xaa = Lys or Arg
<220> FEATURE:
<221> NAME/KEY: MISC_FEATURE
<222> LOCATION: (55)..(55)
<223> OTHER INFORMATION: Xaa = Leu, Val, Ile, Phe, Trp, Met or Tyr
<220> FEATURE:
<221> NAME/KEY: MISC_FEATURE
<222> LOCATION: (56)..(56)
<223> OTHER INFORMATION: Xaa = Leu, Val, Ile, Phe, Trp, Met or Tyr
<220> FEATURE:
<221> NAME/KEY: MISC_FEATURE
<222> LOCATION: (57)..(57)
<223> OTHER INFORMATION: Xaa = Glu or Asp
<220> FEATURE:
<221> NAME/KEY: MISC_FEATURE
<222> LOCATION: (57)..(57)
<223> OTHER INFORMATION: Xaa of residue position 57 has opposite charge
      from Xaa at residue position 61
<220> FEATURE:
```

```
<221> NAME/KEY: MISC_FEATURE
<222> LOCATION: (57)..(63)
<223> OTHER INFORMATION: optionally present
<220> FEATURE:
<221> NAME/KEY: MISC_FEATURE
<222> LOCATION: (61)..(61)
<223> OTHER INFORMATION: Xaa = Lys or Arg
<220> FEATURE:
<221> NAME/KEY: MISC_FEATURE
<222> LOCATION: (62)..(62)
<223> OTHER INFORMATION: Xaa = Leu, Val, Ile, Phe, Trp, Met or Tyr
<220> FEATURE:
<221> NAME/KEY: MISC_FEATURE
<222> LOCATION: (63)..(63)
<223> OTHER INFORMATION: Xaa = Leu, Val, Ile, Phe, Trp, Met or Tyr
<220> FEATURE:
<221> NAME/KEY: MISC_FEATURE
<222> LOCATION: (64)..(64)
<223> OTHER INFORMATION: Xaa = Glu or Asp
<220> FEATURE:
<221> NAME/KEY: MISC_FEATURE
<222> LOCATION: (64)..(64)
<223> OTHER INFORMATION: Xaa of residue position 64 has opposite charge
    from Xaa at residue position 68
<220> FEATURE:
<221> NAME/KEY: MISC_FEATURE
<222> LOCATION: (64)..(70)
<223> OTHER INFORMATION: optionally present
<220> FEATURE:
<221> NAME/KEY: MISC_FEATURE
<222> LOCATION: (68)..(68)
<223> OTHER INFORMATION: Xaa = Lys or Arg
<220> FEATURE:
<221> NAME/KEY: MISC_FEATURE
<222> LOCATION: (69)..(69)
<223> OTHER INFORMATION: Xaa = Leu, Val, Ile, Phe, Trp, Met or Tyr
<220> FEATURE:
<221> NAME/KEY: MISC_FEATURE
<222> LOCATION: (70)..(70)
<223> OTHER INFORMATION: Xaa = Leu, Val, Ile, Phe, Trp, Met or Tyr
<220> FEATURE:
<221> NAME/KEY: MISC_FEATURE
<222> LOCATION: (71)..(71)
<223> OTHER INFORMATION: Xaa = Glu or Asp
<220> FEATURE:
<221> NAME/KEY: MISC_FEATURE
<222> LOCATION: (71)..(71)
<223> OTHER INFORMATION: Xaa of residue position 71 has opposite charge
    from Xaa at residue position 75
<220> FEATURE:
<221> NAME/KEY: MISC_FEATURE
<222> LOCATION: (71)..(77)
<223> OTHER INFORMATION: optionally present
<220> FEATURE:
<221> NAME/KEY: MISC_FEATURE
<222> LOCATION: (75)..(75)
<223> OTHER INFORMATION: Xaa = Lys or Arg
<220> FEATURE:
<221> NAME/KEY: MISC_FEATURE
<222> LOCATION: (76)..(76)
<223> OTHER INFORMATION: Xaa = Leu, Val, Ile, Phe, Trp, Met or Tyr
<220> FEATURE:
<221> NAME/KEY: MISC_FEATURE
<222> LOCATION: (77)..(77)
<223> OTHER INFORMATION: Xaa = Leu, Val, Ile, Phe, Trp, Met or Tyr

<400> SEQUENCE: 158

Xaa Ala Ala Ala Xaa Xaa Xaa Xaa Ala Ala Ala Xaa Xaa Xaa Xaa Ala
1               5                   10                  15

Ala Ala Xaa Xaa Xaa Xaa Ala Ala Ala Xaa Xaa Xaa Xaa Ala Ala Ala
            20                  25                  30

Xaa Xaa Xaa Xaa Ala Ala Ala Xaa Xaa Xaa Xaa Ala Ala Ala Xaa Xaa
        35                  40                  45

Xaa Xaa Ala Ala Ala Xaa Xaa Xaa Xaa Ala Ala Ala Xaa Xaa Xaa Xaa
    50                  55                  60
```

```
Ala Ala Ala Xaa Xaa Xaa Xaa Ala Ala Ala Xaa Xaa Xaa
65                  70                  75

<210> SEQ ID NO 159
<211> LENGTH: 40
<212> TYPE: PRT
<213> ORGANISM: artificial sequence
<220> FEATURE:
<223> OTHER INFORMATION: artificial sequence
<220> FEATURE:
<221> NAME/KEY: MISC_FEATURE
<222> LOCATION: (1)..(1)
<223> OTHER INFORMATION: Xaa = Glu, Asp, Lys or Arg
<220> FEATURE:
<221> NAME/KEY: MISC_FEATURE
<222> LOCATION: (3)..(3)
<223> OTHER INFORMATION: Xaa = Glu, Asp, Lys or Arg
<220> FEATURE:
<221> NAME/KEY: MISC_FEATURE
<222> LOCATION: (5)..(5)
<223> OTHER INFORMATION: Xaa = Glu, Asp, Lys or Arg
<220> FEATURE:
<221> NAME/KEY: MISC_FEATURE
<222> LOCATION: (5)..(6)
<223> OTHER INFORMATION: optionally present
<220> FEATURE:
<221> NAME/KEY: MISC_FEATURE
<222> LOCATION: (7)..(7)
<223> OTHER INFORMATION: Xaa = Glu, Asp, Lys or Arg
<220> FEATURE:
<221> NAME/KEY: MISC_FEATURE
<222> LOCATION: (7)..(8)
<223> OTHER INFORMATION: optionally present
<220> FEATURE:
<221> NAME/KEY: MISC_FEATURE
<222> LOCATION: (9)..(9)
<223> OTHER INFORMATION: Xaa = Glu, Asp, Lys or Arg
<220> FEATURE:
<221> NAME/KEY: MISC_FEATURE
<222> LOCATION: (9)..(10)
<223> OTHER INFORMATION: optionally present
<220> FEATURE:
<221> NAME/KEY: MISC_FEATURE
<222> LOCATION: (11)..(11)
<223> OTHER INFORMATION: Xaa = Glu, Asp, Lys or Arg
<220> FEATURE:
<221> NAME/KEY: MISC_FEATURE
<222> LOCATION: (11)..(12)
<223> OTHER INFORMATION: optionally present
<220> FEATURE:
<221> NAME/KEY: MISC_FEATURE
<222> LOCATION: (13)..(13)
<223> OTHER INFORMATION: Xaa = Glu, Asp, Lys or Arg
<220> FEATURE:
<221> NAME/KEY: MISC_FEATURE
<222> LOCATION: (13)..(14)
<223> OTHER INFORMATION: optionally present
<220> FEATURE:
<221> NAME/KEY: MISC_FEATURE
<222> LOCATION: (15)..(15)
<223> OTHER INFORMATION: Xaa = Glu, Asp, Lys or Arg
<220> FEATURE:
<221> NAME/KEY: MISC_FEATURE
<222> LOCATION: (15)..(16)
<223> OTHER INFORMATION: optionally present
<220> FEATURE:
<221> NAME/KEY: MISC_FEATURE
<222> LOCATION: (17)..(17)
<223> OTHER INFORMATION: Xaa = Glu, Asp, Lys or Arg
<220> FEATURE:
<221> NAME/KEY: MISC_FEATURE
<222> LOCATION: (17)..(18)
<223> OTHER INFORMATION: optionally present
<220> FEATURE:
<221> NAME/KEY: MISC_FEATURE
<222> LOCATION: (19)..(19)
<223> OTHER INFORMATION: Xaa = Glu, Asp, Lys or Arg
<220> FEATURE:
<221> NAME/KEY: MISC_FEATURE
```

-continued

```
<222> LOCATION: (19)..(20)
<223> OTHER INFORMATION: optionally present
<220> FEATURE:
<221> NAME/KEY: MISC_FEATURE
<222> LOCATION: (21)..(21)
<223> OTHER INFORMATION: Xaa = Glu, Asp, Lys or Arg
<220> FEATURE:
<221> NAME/KEY: MISC_FEATURE
<222> LOCATION: (21)..(22)
<223> OTHER INFORMATION: optionally present
<220> FEATURE:
<221> NAME/KEY: MISC_FEATURE
<222> LOCATION: (23)..(23)
<223> OTHER INFORMATION: Xaa = Glu, Asp, Lys or Arg
<220> FEATURE:
<221> NAME/KEY: MISC_FEATURE
<222> LOCATION: (23)..(24)
<223> OTHER INFORMATION: optionally present
<220> FEATURE:
<221> NAME/KEY: MISC_FEATURE
<222> LOCATION: (25)..(25)
<223> OTHER INFORMATION: Xaa = Glu, Asp, Lys or Arg
<220> FEATURE:
<221> NAME/KEY: MISC_FEATURE
<222> LOCATION: (25)..(26)
<223> OTHER INFORMATION: optionally present
<220> FEATURE:
<221> NAME/KEY: MISC_FEATURE
<222> LOCATION: (27)..(27)
<223> OTHER INFORMATION: Xaa = Glu, Asp, Lys or Arg
<220> FEATURE:
<221> NAME/KEY: MISC_FEATURE
<222> LOCATION: (27)..(28)
<223> OTHER INFORMATION: optionally present
<220> FEATURE:
<221> NAME/KEY: MISC_FEATURE
<222> LOCATION: (29)..(29)
<223> OTHER INFORMATION: Xaa = Glu, Asp, Lys or Arg
<220> FEATURE:
<221> NAME/KEY: MISC_FEATURE
<222> LOCATION: (29)..(30)
<223> OTHER INFORMATION: optionally present
<220> FEATURE:
<221> NAME/KEY: MISC_FEATURE
<222> LOCATION: (31)..(31)
<223> OTHER INFORMATION: Xaa = Glu, Asp, Lys or Arg
<220> FEATURE:
<221> NAME/KEY: MISC_FEATURE
<222> LOCATION: (31)..(32)
<223> OTHER INFORMATION: optionally present
<220> FEATURE:
<221> NAME/KEY: MISC_FEATURE
<222> LOCATION: (33)..(33)
<223> OTHER INFORMATION: Xaa = Glu, Asp, Lys or Arg
<220> FEATURE:
<221> NAME/KEY: MISC_FEATURE
<222> LOCATION: (33)..(34)
<223> OTHER INFORMATION: optionally present
<220> FEATURE:
<221> NAME/KEY: MISC_FEATURE
<222> LOCATION: (35)..(35)
<223> OTHER INFORMATION: Xaa = Glu, Asp, Lys or Arg
<220> FEATURE:
<221> NAME/KEY: MISC_FEATURE
<222> LOCATION: (35)..(36)
<223> OTHER INFORMATION: optionally present
<220> FEATURE:
<221> NAME/KEY: MISC_FEATURE
<222> LOCATION: (37)..(37)
<223> OTHER INFORMATION: Xaa = Glu, Asp, Lys or Arg
<220> FEATURE:
<221> NAME/KEY: MISC_FEATURE
<222> LOCATION: (37)..(38)
<223> OTHER INFORMATION: optionally present
<220> FEATURE:
<221> NAME/KEY: MISC_FEATURE
<222> LOCATION: (39)..(39)
<223> OTHER INFORMATION: Xaa = Glu, Asp, Lys or Arg
<220> FEATURE:
<221> NAME/KEY: MISC_FEATURE
```

```
<222> LOCATION: (39)..(40)
<223> OTHER INFORMATION: optionally present

<400> SEQUENCE: 159

Xaa Pro Xaa Pro Xaa Pro Xaa Pro Xaa Pro Xaa Pro Xaa Pro Xaa Pro
1               5                   10                  15

Xaa Pro Xaa Pro Xaa Pro Xaa Pro Xaa Pro Xaa Pro Xaa Pro Xaa Pro
                20                  25                  30

Xaa Pro Xaa Pro Xaa Pro Xaa Pro
        35                  40

<210> SEQ ID NO 160
<211> LENGTH: 40
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa = Glu, Asp, Lys or Arg
<220> FEATURE:
<221> NAME/KEY: MISC_FEATURE
<222> LOCATION: (4)..(4)
<223> OTHER INFORMATION: Xaa = Glu, Asp, Lys or Arg
<220> FEATURE:
<221> NAME/KEY: MISC_FEATURE
<222> LOCATION: (5)..(6)
<223> OTHER INFORMATION: optionally present
<220> FEATURE:
<221> NAME/KEY: MISC_FEATURE
<222> LOCATION: (6)..(6)
<223> OTHER INFORMATION: Xaa = Glu, Asp, Lys or Arg
<220> FEATURE:
<221> NAME/KEY: MISC_FEATURE
<222> LOCATION: (7)..(8)
<223> OTHER INFORMATION: optionally present
<220> FEATURE:
<221> NAME/KEY: MISC_FEATURE
<222> LOCATION: (8)..(8)
<223> OTHER INFORMATION: Xaa = Glu, Asp, Lys or Arg
<220> FEATURE:
<221> NAME/KEY: MISC_FEATURE
<222> LOCATION: (9)..(10)
<223> OTHER INFORMATION: optionally present
<220> FEATURE:
<221> NAME/KEY: MISC_FEATURE
<222> LOCATION: (10)..(10)
<223> OTHER INFORMATION: Xaa = Glu, Asp, Lys or Arg
<220> FEATURE:
<221> NAME/KEY: MISC_FEATURE
<222> LOCATION: (11)..(12)
<223> OTHER INFORMATION: optionally present
<220> FEATURE:
<221> NAME/KEY: MISC_FEATURE
<222> LOCATION: (12)..(12)
<223> OTHER INFORMATION: Xaa = Glu, Asp, Lys or Arg
<220> FEATURE:
<221> NAME/KEY: MISC_FEATURE
<222> LOCATION: (13)..(14)
<223> OTHER INFORMATION: optionally present
<220> FEATURE:
<221> NAME/KEY: MISC_FEATURE
<222> LOCATION: (14)..(14)
<223> OTHER INFORMATION: Xaa = Glu, Asp, Lys or Arg
<220> FEATURE:
<221> NAME/KEY: MISC_FEATURE
<222> LOCATION: (15)..(16)
<223> OTHER INFORMATION: optionally present
<220> FEATURE:
<221> NAME/KEY: MISC_FEATURE
<222> LOCATION: (16)..(16)
<223> OTHER INFORMATION: Xaa = Glu, Asp, Lys or Arg
<220> FEATURE:
<221> NAME/KEY: MISC_FEATURE
<222> LOCATION: (17)..(18)
```

```
<223> OTHER INFORMATION: optionally present
<220> FEATURE:
<221> NAME/KEY: MISC_FEATURE
<222> LOCATION: (18)..(18)
<223> OTHER INFORMATION: Xaa = Glu, Asp, Lys or Arg
<220> FEATURE:
<221> NAME/KEY: MISC_FEATURE
<222> LOCATION: (19)..(20)
<223> OTHER INFORMATION: optionally present
<220> FEATURE:
<221> NAME/KEY: MISC_FEATURE
<222> LOCATION: (20)..(20)
<223> OTHER INFORMATION: Xaa = Glu, Asp, Lys or Arg
<220> FEATURE:
<221> NAME/KEY: MISC_FEATURE
<222> LOCATION: (21)..(22)
<223> OTHER INFORMATION: optionally present
<220> FEATURE:
<221> NAME/KEY: MISC_FEATURE
<222> LOCATION: (22)..(22)
<223> OTHER INFORMATION: Xaa = Glu, Asp, Lys or Arg
<220> FEATURE:
<221> NAME/KEY: MISC_FEATURE
<222> LOCATION: (23)..(24)
<223> OTHER INFORMATION: optionally present
<220> FEATURE:
<221> NAME/KEY: MISC_FEATURE
<222> LOCATION: (24)..(24)
<223> OTHER INFORMATION: Xaa = Glu, Asp, Lys or Arg
<220> FEATURE:
<221> NAME/KEY: MISC_FEATURE
<222> LOCATION: (25)..(26)
<223> OTHER INFORMATION: optionally present
<220> FEATURE:
<221> NAME/KEY: MISC_FEATURE
<222> LOCATION: (26)..(26)
<223> OTHER INFORMATION: Xaa = Glu, Asp, Lys or Arg
<220> FEATURE:
<221> NAME/KEY: MISC_FEATURE
<222> LOCATION: (27)..(28)
<223> OTHER INFORMATION: optionally present
<220> FEATURE:
<221> NAME/KEY: MISC_FEATURE
<222> LOCATION: (28)..(28)
<223> OTHER INFORMATION: Xaa = Glu, Asp, Lys or Arg
<220> FEATURE:
<221> NAME/KEY: MISC_FEATURE
<222> LOCATION: (29)..(30)
<223> OTHER INFORMATION: optionally present
<220> FEATURE:
<221> NAME/KEY: MISC_FEATURE
<222> LOCATION: (30)..(30)
<223> OTHER INFORMATION: Xaa = Glu, Asp, Lys or Arg
<220> FEATURE:
<221> NAME/KEY: MISC_FEATURE
<222> LOCATION: (31)..(32)
<223> OTHER INFORMATION: optionally present
<220> FEATURE:
<221> NAME/KEY: MISC_FEATURE
<222> LOCATION: (32)..(32)
<223> OTHER INFORMATION: Xaa = Glu, Asp, Lys or Arg
<220> FEATURE:
<221> NAME/KEY: MISC_FEATURE
<222> LOCATION: (33)..(34)
<223> OTHER INFORMATION: optionally present
<220> FEATURE:
<221> NAME/KEY: MISC_FEATURE
<222> LOCATION: (34)..(34)
<223> OTHER INFORMATION: Xaa = Glu, Asp, Lys or Arg
<220> FEATURE:
<221> NAME/KEY: MISC_FEATURE
<222> LOCATION: (35)..(36)
<223> OTHER INFORMATION: optionally present
<220> FEATURE:
<221> NAME/KEY: MISC_FEATURE
<222> LOCATION: (36)..(36)
<223> OTHER INFORMATION: Xaa = Glu, Asp, Lys or Arg
<220> FEATURE:
<221> NAME/KEY: MISC_FEATURE
<222> LOCATION: (37)..(38)
```

-continued

```
<223> OTHER INFORMATION: optionally present
<220> FEATURE:
<221> NAME/KEY: MISC_FEATURE
<222> LOCATION: (38)..(38)
<223> OTHER INFORMATION: Xaa = Glu, Asp, Lys or Arg
<220> FEATURE:
<221> NAME/KEY: MISC_FEATURE
<222> LOCATION: (39)..(40)
<223> OTHER INFORMATION: optionally present
<220> FEATURE:
<221> NAME/KEY: MISC_FEATURE
<222> LOCATION: (40)..(40)
<223> OTHER INFORMATION: Xaa = Glu, Asp, Lys or Arg

<400> SEQUENCE: 160

Pro Xaa Pro Xaa Pro Xaa Pro Xaa Pro Xaa Pro Xaa Pro Xaa Pro Xaa
1               5                   10                  15

Pro Xaa Pro Xaa Pro Xaa Pro Xaa Pro Xaa Pro Xaa Pro Xaa Pro Xaa
            20                  25                  30

Pro Xaa Pro Xaa Pro Xaa Pro Xaa
        35                  40

<210> SEQ ID NO 161
<211> LENGTH: 280
<212> TYPE: PRT
<213> ORGANISM: artificial sequence
<220> FEATURE:
<223> OTHER INFORMATION: synthetic construct extended proline dipeptide
      linker
<220> FEATURE:
<221> NAME/KEY: MISC_FEATURE
<222> LOCATION: (1)..(1)
<223> OTHER INFORMATION: Xaa = Glu, Asp, Lys, or Arg
<220> FEATURE:
<221> NAME/KEY: MISC_FEATURE
<222> LOCATION: (3)..(3)
<223> OTHER INFORMATION: Xaa = Glu, Asp, Lys, or Arg
<220> FEATURE:
<221> NAME/KEY: MISC_FEATURE
<222> LOCATION: (5)..(5)
<223> OTHER INFORMATION: Xaa = Glu, Asp, Lys, or Arg
<220> FEATURE:
<221> NAME/KEY: MISC_FEATURE
<222> LOCATION: (7)..(7)
<223> OTHER INFORMATION: Xaa = Glu, Asp, Lys, or Arg
<220> FEATURE:
<221> NAME/KEY: MISC_FEATURE
<222> LOCATION: (9)..(9)
<223> OTHER INFORMATION: Xaa = Glu, Asp, Lys, or Arg
<220> FEATURE:
<221> NAME/KEY: MISC_FEATURE
<222> LOCATION: (11)..(11)
<223> OTHER INFORMATION: Xaa = Glu, Asp, Lys, or Arg
<220> FEATURE:
<221> NAME/KEY: MISC_FEATURE
<222> LOCATION: (15)..(15)
<223> OTHER INFORMATION: Xaa = Glu, Asp, Lys, or Arg
<220> FEATURE:
<221> NAME/KEY: MISC_FEATURE
<222> LOCATION: (15)..(28)
<223> OTHER INFORMATION: optionally present
<220> FEATURE:
<221> NAME/KEY: MISC_FEATURE
<222> LOCATION: (17)..(17)
<223> OTHER INFORMATION: Xaa = Glu, Asp, Lys, or Arg
<220> FEATURE:
<221> NAME/KEY: MISC_FEATURE
<222> LOCATION: (19)..(19)
<223> OTHER INFORMATION: Xaa = Glu, Asp, Lys, or Arg
<220> FEATURE:
<221> NAME/KEY: MISC_FEATURE
<222> LOCATION: (21)..(21)
<223> OTHER INFORMATION: Xaa = Glu, Asp, Lys, or Arg
<220> FEATURE:
<221> NAME/KEY: MISC_FEATURE
<222> LOCATION: (23)..(23)
```

-continued

```
<223> OTHER INFORMATION: Xaa = Glu, Asp, Lys, or Arg
<220> FEATURE:
<221> NAME/KEY: MISC_FEATURE
<222> LOCATION: (25)..(25)
<223> OTHER INFORMATION: Xaa = Glu, Asp, Lys, or Arg
<220> FEATURE:
<221> NAME/KEY: MISC_FEATURE
<222> LOCATION: (29)..(29)
<223> OTHER INFORMATION: Xaa = Glu, Asp, Lys, or Arg
<220> FEATURE:
<221> NAME/KEY: MISC_FEATURE
<222> LOCATION: (29)..(42)
<223> OTHER INFORMATION: optionally present
<220> FEATURE:
<221> NAME/KEY: MISC_FEATURE
<222> LOCATION: (31)..(31)
<223> OTHER INFORMATION: Xaa = Glu, Asp, Lys, or Arg
<220> FEATURE:
<221> NAME/KEY: MISC_FEATURE
<222> LOCATION: (33)..(33)
<223> OTHER INFORMATION: Xaa = Glu, Asp, Lys, or Arg
<220> FEATURE:
<221> NAME/KEY: MISC_FEATURE
<222> LOCATION: (35)..(35)
<223> OTHER INFORMATION: Xaa = Glu, Asp, Lys, or Arg
<220> FEATURE:
<221> NAME/KEY: MISC_FEATURE
<222> LOCATION: (37)..(37)
<223> OTHER INFORMATION: Xaa = Glu, Asp, Lys, or Arg
<220> FEATURE:
<221> NAME/KEY: MISC_FEATURE
<222> LOCATION: (39)..(39)
<223> OTHER INFORMATION: Xaa = Glu, Asp, Lys, or Arg
<220> FEATURE:
<221> NAME/KEY: MISC_FEATURE
<222> LOCATION: (43)..(43)
<223> OTHER INFORMATION: Xaa = Glu, Asp, Lys, or Arg
<220> FEATURE:
<221> NAME/KEY: MISC_FEATURE
<222> LOCATION: (43)..(56)
<223> OTHER INFORMATION: optionally present
<220> FEATURE:
<221> NAME/KEY: MISC_FEATURE
<222> LOCATION: (45)..(45)
<223> OTHER INFORMATION: Xaa = Glu, Asp, Lys, or Arg
<220> FEATURE:
<221> NAME/KEY: MISC_FEATURE
<222> LOCATION: (47)..(47)
<223> OTHER INFORMATION: Xaa = Glu, Asp, Lys, or Arg
<220> FEATURE:
<221> NAME/KEY: MISC_FEATURE
<222> LOCATION: (49)..(49)
<223> OTHER INFORMATION: Xaa = Glu, Asp, Lys, or Arg
<220> FEATURE:
<221> NAME/KEY: MISC_FEATURE
<222> LOCATION: (51)..(51)
<223> OTHER INFORMATION: Xaa = Glu, Asp, Lys, or Arg
<220> FEATURE:
<221> NAME/KEY: MISC_FEATURE
<222> LOCATION: (53)..(53)
<223> OTHER INFORMATION: Xaa = Glu, Asp, Lys, or Arg
<220> FEATURE:
<221> NAME/KEY: MISC_FEATURE
<222> LOCATION: (57)..(57)
<223> OTHER INFORMATION: Xaa = Glu, Asp, Lys, or Arg
<220> FEATURE:
<221> NAME/KEY: MISC_FEATURE
<222> LOCATION: (57)..(70)
<223> OTHER INFORMATION: optionally present
<220> FEATURE:
<221> NAME/KEY: MISC_FEATURE
<222> LOCATION: (59)..(59)
<223> OTHER INFORMATION: Xaa = Glu, Asp, Lys, or Arg
<220> FEATURE:
<221> NAME/KEY: MISC_FEATURE
<222> LOCATION: (61)..(61)
<223> OTHER INFORMATION: Xaa = Glu, Asp, Lys, or Arg
<220> FEATURE:
<221> NAME/KEY: MISC_FEATURE
<222> LOCATION: (63)..(63)
```

-continued

```
<223> OTHER INFORMATION: Xaa = Glu, Asp, Lys, or Arg
<220> FEATURE:
<221> NAME/KEY: MISC_FEATURE
<222> LOCATION: (65)..(65)
<223> OTHER INFORMATION: Xaa = Glu, Asp, Lys, or Arg
<220> FEATURE:
<221> NAME/KEY: MISC_FEATURE
<222> LOCATION: (67)..(67)
<223> OTHER INFORMATION: Xaa = Glu, Asp, Lys, or Arg
<220> FEATURE:
<221> NAME/KEY: MISC_FEATURE
<222> LOCATION: (71)..(71)
<223> OTHER INFORMATION: Xaa = Glu, Asp, Lys, or Arg
<220> FEATURE:
<221> NAME/KEY: MISC_FEATURE
<222> LOCATION: (71)..(84)
<223> OTHER INFORMATION: optionally present
<220> FEATURE:
<221> NAME/KEY: MISC_FEATURE
<222> LOCATION: (73)..(73)
<223> OTHER INFORMATION: Xaa = Glu, Asp, Lys, or Arg
<220> FEATURE:
<221> NAME/KEY: MISC_FEATURE
<222> LOCATION: (75)..(75)
<223> OTHER INFORMATION: Xaa = Glu, Asp, Lys, or Arg
<220> FEATURE:
<221> NAME/KEY: MISC_FEATURE
<222> LOCATION: (77)..(77)
<223> OTHER INFORMATION: Xaa = Glu, Asp, Lys, or Arg
<220> FEATURE:
<221> NAME/KEY: MISC_FEATURE
<222> LOCATION: (79)..(79)
<223> OTHER INFORMATION: Xaa = Glu, Asp, Lys, or Arg
<220> FEATURE:
<221> NAME/KEY: MISC_FEATURE
<222> LOCATION: (81)..(81)
<223> OTHER INFORMATION: Xaa = Glu, Asp, Lys, or Arg
<220> FEATURE:
<221> NAME/KEY: MISC_FEATURE
<222> LOCATION: (85)..(85)
<223> OTHER INFORMATION: Xaa = Glu, Asp, Lys, or Arg
<220> FEATURE:
<221> NAME/KEY: MISC_FEATURE
<222> LOCATION: (85)..(98)
<223> OTHER INFORMATION: optionally present
<220> FEATURE:
<221> NAME/KEY: MISC_FEATURE
<222> LOCATION: (87)..(87)
<223> OTHER INFORMATION: Xaa = Glu, Asp, Lys, or Arg
<220> FEATURE:
<221> NAME/KEY: MISC_FEATURE
<222> LOCATION: (89)..(89)
<223> OTHER INFORMATION: Xaa = Glu, Asp, Lys, or Arg
<220> FEATURE:
<221> NAME/KEY: MISC_FEATURE
<222> LOCATION: (91)..(91)
<223> OTHER INFORMATION: Xaa = Glu, Asp, Lys, or Arg
<220> FEATURE:
<221> NAME/KEY: MISC_FEATURE
<222> LOCATION: (93)..(93)
<223> OTHER INFORMATION: Xaa = Glu, Asp, Lys, or Arg
<220> FEATURE:
<221> NAME/KEY: MISC_FEATURE
<222> LOCATION: (95)..(95)
<223> OTHER INFORMATION: Xaa = Glu, Asp, Lys, or Arg
<220> FEATURE:
<221> NAME/KEY: MISC_FEATURE
<222> LOCATION: (99)..(99)
<223> OTHER INFORMATION: Xaa = Glu, Asp, Lys, or Arg
<220> FEATURE:
<221> NAME/KEY: MISC_FEATURE
<222> LOCATION: (99)..(112)
<223> OTHER INFORMATION: optionally present
<220> FEATURE:
<221> NAME/KEY: MISC_FEATURE
<222> LOCATION: (101)..(101)
<223> OTHER INFORMATION: Xaa = Glu, Asp, Lys, or Arg
<220> FEATURE:
<221> NAME/KEY: MISC_FEATURE
<222> LOCATION: (103)..(103)
```

```
<223> OTHER INFORMATION: Xaa = Glu, Asp, Lys, or Arg
<220> FEATURE:
<221> NAME/KEY: MISC_FEATURE
<222> LOCATION: (105)..(105)
<223> OTHER INFORMATION: Xaa = Glu, Asp, Lys, or Arg
<220> FEATURE:
<221> NAME/KEY: MISC_FEATURE
<222> LOCATION: (107)..(107)
<223> OTHER INFORMATION: Xaa = Glu, Asp, Lys, or Arg
<220> FEATURE:
<221> NAME/KEY: MISC_FEATURE
<222> LOCATION: (109)..(109)
<223> OTHER INFORMATION: Xaa = Glu, Asp, Lys, or Arg
<220> FEATURE:
<221> NAME/KEY: MISC_FEATURE
<222> LOCATION: (113)..(113)
<223> OTHER INFORMATION: Xaa = Glu, Asp, Lys, or Arg
<220> FEATURE:
<221> NAME/KEY: MISC_FEATURE
<222> LOCATION: (113)..(126)
<223> OTHER INFORMATION: optionally present
<220> FEATURE:
<221> NAME/KEY: MISC_FEATURE
<222> LOCATION: (115)..(115)
<223> OTHER INFORMATION: Xaa = Glu, Asp, Lys, or Arg
<220> FEATURE:
<221> NAME/KEY: MISC_FEATURE
<222> LOCATION: (117)..(117)
<223> OTHER INFORMATION: Xaa = Glu, Asp, Lys, or Arg
<220> FEATURE:
<221> NAME/KEY: MISC_FEATURE
<222> LOCATION: (119)..(119)
<223> OTHER INFORMATION: Xaa = Glu, Asp, Lys, or Arg
<220> FEATURE:
<221> NAME/KEY: MISC_FEATURE
<222> LOCATION: (121)..(121)
<223> OTHER INFORMATION: Xaa = Glu, Asp, Lys, or Arg
<220> FEATURE:
<221> NAME/KEY: MISC_FEATURE
<222> LOCATION: (123)..(123)
<223> OTHER INFORMATION: Xaa = Glu, Asp, Lys, or Arg
<220> FEATURE:
<221> NAME/KEY: MISC_FEATURE
<222> LOCATION: (127)..(127)
<223> OTHER INFORMATION: Xaa = Glu, Asp, Lys, or Arg
<220> FEATURE:
<221> NAME/KEY: MISC_FEATURE
<222> LOCATION: (127)..(140)
<223> OTHER INFORMATION: optionally present
<220> FEATURE:
<221> NAME/KEY: MISC_FEATURE
<222> LOCATION: (129)..(129)
<223> OTHER INFORMATION: Xaa = Glu, Asp, Lys, or Arg
<220> FEATURE:
<221> NAME/KEY: MISC_FEATURE
<222> LOCATION: (131)..(131)
<223> OTHER INFORMATION: Xaa = Glu, Asp, Lys, or Arg
<220> FEATURE:
<221> NAME/KEY: MISC_FEATURE
<222> LOCATION: (133)..(133)
<223> OTHER INFORMATION: Xaa = Glu, Asp, Lys, or Arg
<220> FEATURE:
<221> NAME/KEY: MISC_FEATURE
<222> LOCATION: (135)..(135)
<223> OTHER INFORMATION: Xaa = Glu, Asp, Lys, or Arg
<220> FEATURE:
<221> NAME/KEY: MISC_FEATURE
<222> LOCATION: (137)..(137)
<223> OTHER INFORMATION: Xaa = Glu, Asp, Lys, or Arg
<220> FEATURE:
<221> NAME/KEY: MISC_FEATURE
<222> LOCATION: (141)..(141)
<223> OTHER INFORMATION: Xaa = Glu, Asp, Lys, or Arg
<220> FEATURE:
<221> NAME/KEY: MISC_FEATURE
<222> LOCATION: (141)..(154)
<223> OTHER INFORMATION: optionally present
<220> FEATURE:
<221> NAME/KEY: MISC_FEATURE
<222> LOCATION: (143)..(143)
```

-continued

```
<223> OTHER INFORMATION: Xaa = Glu, Asp, Lys, or Arg
<220> FEATURE:
<221> NAME/KEY: MISC_FEATURE
<222> LOCATION: (145)..(145)
<223> OTHER INFORMATION: Xaa = Glu, Asp, Lys, or Arg
<220> FEATURE:
<221> NAME/KEY: MISC_FEATURE
<222> LOCATION: (147)..(147)
<223> OTHER INFORMATION: Xaa = Glu, Asp, Lys, or Arg
<220> FEATURE:
<221> NAME/KEY: MISC_FEATURE
<222> LOCATION: (149)..(149)
<223> OTHER INFORMATION: Xaa = Glu, Asp, Lys, or Arg
<220> FEATURE:
<221> NAME/KEY: MISC_FEATURE
<222> LOCATION: (151)..(151)
<223> OTHER INFORMATION: Xaa = Glu, Asp, Lys, or Arg
<220> FEATURE:
<221> NAME/KEY: MISC_FEATURE
<222> LOCATION: (155)..(155)
<223> OTHER INFORMATION: Xaa = Glu, Asp, Lys, or Arg
<220> FEATURE:
<221> NAME/KEY: MISC_FEATURE
<222> LOCATION: (155)..(168)
<223> OTHER INFORMATION: optionally present
<220> FEATURE:
<221> NAME/KEY: MISC_FEATURE
<222> LOCATION: (157)..(157)
<223> OTHER INFORMATION: Xaa = Glu, Asp, Lys, or Arg
<220> FEATURE:
<221> NAME/KEY: MISC_FEATURE
<222> LOCATION: (159)..(159)
<223> OTHER INFORMATION: Xaa = Glu, Asp, Lys, or Arg
<220> FEATURE:
<221> NAME/KEY: MISC_FEATURE
<222> LOCATION: (161)..(161)
<223> OTHER INFORMATION: Xaa = Glu, Asp, Lys, or Arg
<220> FEATURE:
<221> NAME/KEY: MISC_FEATURE
<222> LOCATION: (163)..(163)
<223> OTHER INFORMATION: Xaa = Glu, Asp, Lys, or Arg
<220> FEATURE:
<221> NAME/KEY: MISC_FEATURE
<222> LOCATION: (165)..(165)
<223> OTHER INFORMATION: Xaa = Glu, Asp, Lys, or Arg
<220> FEATURE:
<221> NAME/KEY: MISC_FEATURE
<222> LOCATION: (169)..(169)
<223> OTHER INFORMATION: Xaa = Glu, Asp, Lys, or Arg
<220> FEATURE:
<221> NAME/KEY: MISC_FEATURE
<222> LOCATION: (169)..(182)
<223> OTHER INFORMATION: optionally present
<220> FEATURE:
<221> NAME/KEY: MISC_FEATURE
<222> LOCATION: (171)..(171)
<223> OTHER INFORMATION: Xaa = Glu, Asp, Lys, or Arg
<220> FEATURE:
<221> NAME/KEY: MISC_FEATURE
<222> LOCATION: (173)..(173)
<223> OTHER INFORMATION: Xaa = Glu, Asp, Lys, or Arg
<220> FEATURE:
<221> NAME/KEY: MISC_FEATURE
<222> LOCATION: (175)..(175)
<223> OTHER INFORMATION: Xaa = Glu, Asp, Lys, or Arg
<220> FEATURE:
<221> NAME/KEY: MISC_FEATURE
<222> LOCATION: (177)..(177)
<223> OTHER INFORMATION: Xaa = Glu, Asp, Lys, or Arg
<220> FEATURE:
<221> NAME/KEY: MISC_FEATURE
<222> LOCATION: (179)..(179)
<223> OTHER INFORMATION: Xaa = Glu, Asp, Lys, or Arg
<220> FEATURE:
<221> NAME/KEY: MISC_FEATURE
<222> LOCATION: (183)..(183)
<223> OTHER INFORMATION: Xaa = Glu, Asp, Lys, or Arg
<220> FEATURE:
<221> NAME/KEY: MISC_FEATURE
<222> LOCATION: (183)..(196)
```

```
<223> OTHER INFORMATION: optionally present
<220> FEATURE:
<221> NAME/KEY: MISC_FEATURE
<222> LOCATION: (185)..(185)
<223> OTHER INFORMATION: Xaa = Glu, Asp, Lys, or Arg
<220> FEATURE:
<221> NAME/KEY: MISC_FEATURE
<222> LOCATION: (187)..(187)
<223> OTHER INFORMATION: Xaa = Glu, Asp, Lys, or Arg
<220> FEATURE:
<221> NAME/KEY: MISC_FEATURE
<222> LOCATION: (189)..(189)
<223> OTHER INFORMATION: Xaa = Glu, Asp, Lys, or Arg
<220> FEATURE:
<221> NAME/KEY: MISC_FEATURE
<222> LOCATION: (191)..(191)
<223> OTHER INFORMATION: Xaa = Glu, Asp, Lys, or Arg
<220> FEATURE:
<221> NAME/KEY: MISC_FEATURE
<222> LOCATION: (193)..(193)
<223> OTHER INFORMATION: Xaa = Glu, Asp, Lys, or Arg
<220> FEATURE:
<221> NAME/KEY: MISC_FEATURE
<222> LOCATION: (197)..(197)
<223> OTHER INFORMATION: Xaa = Glu, Asp, Lys, or Arg
<220> FEATURE:
<221> NAME/KEY: MISC_FEATURE
<222> LOCATION: (197)..(210)
<223> OTHER INFORMATION: optionally present
<220> FEATURE:
<221> NAME/KEY: MISC_FEATURE
<222> LOCATION: (199)..(199)
<223> OTHER INFORMATION: Xaa = Glu, Asp, Lys, or Arg
<220> FEATURE:
<221> NAME/KEY: MISC_FEATURE
<222> LOCATION: (201)..(201)
<223> OTHER INFORMATION: Xaa = Glu, Asp, Lys, or Arg
<220> FEATURE:
<221> NAME/KEY: MISC_FEATURE
<222> LOCATION: (203)..(203)
<223> OTHER INFORMATION: Xaa = Glu, Asp, Lys, or Arg
<220> FEATURE:
<221> NAME/KEY: MISC_FEATURE
<222> LOCATION: (205)..(205)
<223> OTHER INFORMATION: Xaa = Glu, Asp, Lys, or Arg
<220> FEATURE:
<221> NAME/KEY: MISC_FEATURE
<222> LOCATION: (207)..(207)
<223> OTHER INFORMATION: Xaa = Glu, Asp, Lys, or Arg
<220> FEATURE:
<221> NAME/KEY: MISC_FEATURE
<222> LOCATION: (211)..(211)
<223> OTHER INFORMATION: Xaa = Glu, Asp, Lys, or Arg
<220> FEATURE:
<221> NAME/KEY: MISC_FEATURE
<222> LOCATION: (211)..(224)
<223> OTHER INFORMATION: optionally present
<220> FEATURE:
<221> NAME/KEY: MISC_FEATURE
<222> LOCATION: (213)..(213)
<223> OTHER INFORMATION: Xaa = Glu, Asp, Lys, or Arg
<220> FEATURE:
<221> NAME/KEY: MISC_FEATURE
<222> LOCATION: (215)..(215)
<223> OTHER INFORMATION: Xaa = Glu, Asp, Lys, or Arg
<220> FEATURE:
<221> NAME/KEY: MISC_FEATURE
<222> LOCATION: (217)..(217)
<223> OTHER INFORMATION: Xaa = Glu, Asp, Lys, or Arg
<220> FEATURE:
<221> NAME/KEY: MISC_FEATURE
<222> LOCATION: (219)..(219)
<223> OTHER INFORMATION: Xaa = Glu, Asp, Lys, or Arg
<220> FEATURE:
<221> NAME/KEY: MISC_FEATURE
<222> LOCATION: (221)..(221)
<223> OTHER INFORMATION: Xaa = Glu, Asp, Lys, or Arg
<220> FEATURE:
<221> NAME/KEY: MISC_FEATURE
<222> LOCATION: (225)..(225)
```

```
<223> OTHER INFORMATION: Xaa = Glu, Asp, Lys, or Arg
<220> FEATURE:
<221> NAME/KEY: MISC_FEATURE
<222> LOCATION: (225)..(238)
<223> OTHER INFORMATION: optionally present
<220> FEATURE:
<221> NAME/KEY: MISC_FEATURE
<222> LOCATION: (227)..(227)
<223> OTHER INFORMATION: Xaa = Glu, Asp, Lys, or Arg
<220> FEATURE:
<221> NAME/KEY: MISC_FEATURE
<222> LOCATION: (229)..(229)
<223> OTHER INFORMATION: Xaa = Glu, Asp, Lys, or Arg
<220> FEATURE:
<221> NAME/KEY: MISC_FEATURE
<222> LOCATION: (231)..(231)
<223> OTHER INFORMATION: Xaa = Glu, Asp, Lys, or Arg
<220> FEATURE:
<221> NAME/KEY: MISC_FEATURE
<222> LOCATION: (233)..(233)
<223> OTHER INFORMATION: Xaa = Glu, Asp, Lys, or Arg
<220> FEATURE:
<221> NAME/KEY: MISC_FEATURE
<222> LOCATION: (235)..(235)
<223> OTHER INFORMATION: Xaa = Glu, Asp, Lys, or Arg
<220> FEATURE:
<221> NAME/KEY: MISC_FEATURE
<222> LOCATION: (239)..(239)
<223> OTHER INFORMATION: Xaa = Glu, Asp, Lys, or Arg
<220> FEATURE:
<221> NAME/KEY: MISC_FEATURE
<222> LOCATION: (239)..(252)
<223> OTHER INFORMATION: optionally present
<220> FEATURE:
<221> NAME/KEY: MISC_FEATURE
<222> LOCATION: (241)..(241)
<223> OTHER INFORMATION: Xaa = Glu, Asp, Lys, or Arg
<220> FEATURE:
<221> NAME/KEY: MISC_FEATURE
<222> LOCATION: (243)..(243)
<223> OTHER INFORMATION: Xaa = Glu, Asp, Lys, or Arg
<220> FEATURE:
<221> NAME/KEY: MISC_FEATURE
<222> LOCATION: (245)..(245)
<223> OTHER INFORMATION: Xaa = Glu, Asp, Lys, or Arg
<220> FEATURE:
<221> NAME/KEY: MISC_FEATURE
<222> LOCATION: (247)..(247)
<223> OTHER INFORMATION: Xaa = Glu, Asp, Lys, or Arg
<220> FEATURE:
<221> NAME/KEY: MISC_FEATURE
<222> LOCATION: (249)..(249)
<223> OTHER INFORMATION: Xaa = Glu, Asp, Lys, or Arg
<220> FEATURE:
<221> NAME/KEY: MISC_FEATURE
<222> LOCATION: (253)..(253)
<223> OTHER INFORMATION: Xaa = Glu, Asp, Lys, or Arg
<220> FEATURE:
<221> NAME/KEY: MISC_FEATURE
<222> LOCATION: (253)..(266)
<223> OTHER INFORMATION: optionally present
<220> FEATURE:
<221> NAME/KEY: MISC_FEATURE
<222> LOCATION: (255)..(255)
<223> OTHER INFORMATION: Xaa = Glu, Asp, Lys, or Arg
<220> FEATURE:
<221> NAME/KEY: MISC_FEATURE
<222> LOCATION: (257)..(257)
<223> OTHER INFORMATION: Xaa = Glu, Asp, Lys, or Arg
<220> FEATURE:
<221> NAME/KEY: MISC_FEATURE
<222> LOCATION: (259)..(259)
<223> OTHER INFORMATION: Xaa = Glu, Asp, Lys, or Arg
<220> FEATURE:
<221> NAME/KEY: MISC_FEATURE
<222> LOCATION: (261)..(261)
<223> OTHER INFORMATION: Xaa = Glu, Asp, Lys, or Arg
<220> FEATURE:
<221> NAME/KEY: MISC_FEATURE
<222> LOCATION: (263)..(263)
```

```
<223> OTHER INFORMATION: Xaa = Glu, Asp, Lys, or Arg
<220> FEATURE:
<221> NAME/KEY: MISC_FEATURE
<222> LOCATION: (267)..(267)
<223> OTHER INFORMATION: Xaa = Glu, Asp, Lys, or Arg
<220> FEATURE:
<221> NAME/KEY: MISC_FEATURE
<222> LOCATION: (267)..(280)
<223> OTHER INFORMATION: optionally present
<220> FEATURE:
<221> NAME/KEY: MISC_FEATURE
<222> LOCATION: (269)..(269)
<223> OTHER INFORMATION: Xaa = Glu, Asp, Lys, or Arg
<220> FEATURE:
<221> NAME/KEY: MISC_FEATURE
<222> LOCATION: (271)..(271)
<223> OTHER INFORMATION: Xaa = Glu, Asp, Lys, or Arg
<220> FEATURE:
<221> NAME/KEY: MISC_FEATURE
<222> LOCATION: (273)..(273)
<223> OTHER INFORMATION: Xaa = Glu, Asp, Lys, or Arg
<220> FEATURE:
<221> NAME/KEY: MISC_FEATURE
<222> LOCATION: (275)..(275)
<223> OTHER INFORMATION: Xaa = Glu, Asp, Lys, or Arg
<220> FEATURE:
<221> NAME/KEY: MISC_FEATURE
<222> LOCATION: (277)..(277)
<223> OTHER INFORMATION: Xaa = Glu, Asp, Lys, or Arg

<400> SEQUENCE: 161

Xaa Pro Xaa Pro Xaa Pro Xaa Pro Xaa Pro Xaa Pro Gly Gly Xaa Pro
 1               5                  10                  15

Xaa Pro Xaa Pro Xaa Pro Xaa Pro Xaa Pro Gly Gly Xaa Pro Xaa Pro
             20                  25                  30

Xaa Pro Xaa Pro Xaa Pro Xaa Pro Gly Gly Xaa Pro Xaa Pro Xaa Pro
         35                  40                  45

Xaa Pro Xaa Pro Xaa Pro Gly Gly Xaa Pro Xaa Pro Xaa Pro Xaa Pro
     50                  55                  60

Xaa Pro Xaa Pro Gly Gly Xaa Pro Xaa Pro Xaa Pro Xaa Pro Xaa Pro
65                  70                  75                  80

Xaa Pro Gly Gly Xaa Pro Xaa Pro Xaa Pro Xaa Pro Xaa Pro Xaa Pro
             85                  90                  95

Gly Gly Xaa Pro Xaa Pro Xaa Pro Xaa Pro Xaa Pro Xaa Pro Gly Gly
            100                 105                 110

Xaa Pro Xaa Pro Xaa Pro Xaa Pro Xaa Pro Gly Gly Xaa Pro Xaa Pro
            115                 120                 125

Xaa Pro Xaa Pro Xaa Pro Xaa Pro Gly Gly Xaa Pro Xaa Pro Xaa Pro
            130                 135                 140

Xaa Pro Xaa Pro Xaa Pro Gly Gly Xaa Pro Xaa Pro Xaa Pro Xaa Pro
145                 150                 155                 160

Xaa Pro Xaa Pro Gly Gly Xaa Pro Xaa Pro Xaa Pro Xaa Pro Xaa Pro
            165                 170                 175

Xaa Pro Gly Gly Xaa Pro Xaa Pro Xaa Pro Xaa Pro Xaa Pro Xaa Pro
            180                 185                 190

Xaa Pro Gly Gly Xaa Pro Xaa Pro Xaa Pro Xaa Pro Xaa Pro Xaa Pro
            195                 200                 205

Gly Gly Xaa Pro Xaa Pro Xaa Pro Xaa Pro Xaa Pro Xaa Pro Gly Gly
            210                 215                 220

Xaa Pro Xaa Pro Xaa Pro Xaa Pro Xaa Pro Xaa Pro Gly Gly Xaa Pro
225                 230                 235                 240

Xaa Pro Xaa Pro Xaa Pro Xaa Pro Gly Gly Xaa Pro Xaa Pro
            245                 250                 255
```

```
Xaa Pro Xaa Pro Xaa Pro Xaa Pro Gly Gly Xaa Pro Xaa Pro Xaa Pro
            260                 265                 270

Xaa Pro Xaa Pro Xaa Pro Gly Gly
        275                 280

<210> SEQ ID NO 162
<211> LENGTH: 12
<212> TYPE: PRT
<213> ORGANISM: artificial sequence
<220> FEATURE:
<223> OTHER INFORMATION: Synthetic construct

<400> SEQUENCE: 162

Arg Val Pro Asn Lys Thr Val Thr Val Asp Gly Ala
1               5                   10

<210> SEQ ID NO 163
<211> LENGTH: 12
<212> TYPE: PRT
<213> ORGANISM: artificial sequence
<220> FEATURE:
<223> OTHER INFORMATION: Synthetic construct

<400> SEQUENCE: 163

Asp Arg His Lys Ser Lys Tyr Ser Ser Thr Lys Ser
1               5                   10

<210> SEQ ID NO 164
<211> LENGTH: 12
<212> TYPE: PRT
<213> ORGANISM: artificial sequence
<220> FEATURE:
<223> OTHER INFORMATION: Synthetic construct

<400> SEQUENCE: 164

Lys Asn Phe Pro Gln Gln Lys Glu Phe Pro Leu Ser
1               5                   10

<210> SEQ ID NO 165
<211> LENGTH: 12
<212> TYPE: PRT
<213> ORGANISM: artificial sequence
<220> FEATURE:
<223> OTHER INFORMATION: Synthetic construct

<400> SEQUENCE: 165

Gln Arg Asn Ser Pro Pro Ala Met Ser Arg Arg Asp
1               5                   10

<210> SEQ ID NO 166
<211> LENGTH: 12
<212> TYPE: PRT
<213> ORGANISM: artificial sequence
<220> FEATURE:
<223> OTHER INFORMATION: Synthetic construct

<400> SEQUENCE: 166

Thr Arg Lys Pro Asn Met Pro His Gly Gln Tyr Leu
1               5                   10

<210> SEQ ID NO 167
<211> LENGTH: 12
<212> TYPE: PRT
<213> ORGANISM: artificial sequence
<220> FEATURE:
<223> OTHER INFORMATION: Synthetic construct

<400> SEQUENCE: 167
```

Lys Pro Pro His Leu Ala Lys Leu Pro Phe Thr Thr
1               5                   10

<210> SEQ ID NO 168
<211> LENGTH: 12
<212> TYPE: PRT
<213> ORGANISM: artificial sequence
<220> FEATURE:
<223> OTHER INFORMATION: Synthetic construct

<400> SEQUENCE: 168

Asn Lys Arg Pro Pro Thr Ser His Arg Ile His Ala
1               5                   10

<210> SEQ ID NO 169
<211> LENGTH: 12
<212> TYPE: PRT
<213> ORGANISM: artificial sequence
<220> FEATURE:
<223> OTHER INFORMATION: Synthetic construct

<400> SEQUENCE: 169

Asn Leu Pro Arg Tyr Gln Pro Pro Cys Lys Pro Leu
1               5                   10

<210> SEQ ID NO 170
<211> LENGTH: 12
<212> TYPE: PRT
<213> ORGANISM: artificial sequence
<220> FEATURE:
<223> OTHER INFORMATION: Synthetic construct

<400> SEQUENCE: 170

Arg Pro Pro Trp Lys Lys Pro Ile Pro Pro Ser Glu
1               5                   10

<210> SEQ ID NO 171
<211> LENGTH: 12
<212> TYPE: PRT
<213> ORGANISM: artificial sequence
<220> FEATURE:
<223> OTHER INFORMATION: Synthetic construct

<400> SEQUENCE: 171

Arg Gln Arg Pro Lys Asp His Phe Phe Ser Arg Pro
1               5                   10

<210> SEQ ID NO 172
<211> LENGTH: 12
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Thr or Pro

<400> SEQUENCE: 172

Ser Val Pro Asn Lys Xaa Val Thr Val Asp Gly Xaa
1               5                   10

<210> SEQ ID NO 173
<211> LENGTH: 12

```
<212> TYPE: PRT
<213> ORGANISM: artificial sequence
<220> FEATURE:
<223> OTHER INFORMATION: Synthetic construct

<400> SEQUENCE: 173

Thr Thr Lys Trp Arg His Arg Ala Pro Val Ser Pro
1               5                   10

<210> SEQ ID NO 174
<211> LENGTH: 12
<212> TYPE: PRT
<213> ORGANISM: artificial sequence
<220> FEATURE:
<223> OTHER INFORMATION: Synthetic construct

<400> SEQUENCE: 174

Trp Leu Gly Lys Asn Arg Ile Lys Pro Arg Ala Ser
1               5                   10

<210> SEQ ID NO 175
<211> LENGTH: 12
<212> TYPE: PRT
<213> ORGANISM: artificial sequence
<220> FEATURE:
<223> OTHER INFORMATION: Synthetic construct

<400> SEQUENCE: 175

Ser Asn Phe Lys Thr Pro Leu Pro Leu Thr Gln Ser
1               5                   10

<210> SEQ ID NO 176
<211> LENGTH: 12
<212> TYPE: PRT
<213> ORGANISM: artificial sequence
<220> FEATURE:
<223> OTHER INFORMATION: Synthetic construct

<400> SEQUENCE: 176

Ser Val Ser Val Gly Met Lys Pro Ser Pro Arg Pro
1               5                   10

<210> SEQ ID NO 177
<211> LENGTH: 7
<212> TYPE: PRT
<213> ORGANISM: artificial sequence
<220> FEATURE:
<223> OTHER INFORMATION: Synthetic construct

<400> SEQUENCE: 177

Asp Leu His Thr Val Tyr His
1               5

<210> SEQ ID NO 178
<211> LENGTH: 7
<212> TYPE: PRT
<213> ORGANISM: artificial sequence
<220> FEATURE:
<223> OTHER INFORMATION: Synthetic construct

<400> SEQUENCE: 178

His Ile Lys Pro Pro Thr Arg
1               5

<210> SEQ ID NO 179
<211> LENGTH: 7
<212> TYPE: PRT
<213> ORGANISM: artificial sequence
```

```
<220> FEATURE:
<223> OTHER INFORMATION: Synthetic construct

<400> SEQUENCE: 179

His Pro Val Trp Pro Ala Ile
1               5

<210> SEQ ID NO 180
<211> LENGTH: 7
<212> TYPE: PRT
<213> ORGANISM: artificial sequence
<220> FEATURE:
<223> OTHER INFORMATION: Synthetic construct

<400> SEQUENCE: 180

Met Pro Leu Tyr Tyr Leu Gln
1               5

<210> SEQ ID NO 181
<211> LENGTH: 26
<212> TYPE: PRT
<213> ORGANISM: artificial sequence
<220> FEATURE:
<223> OTHER INFORMATION: Synthetic construct

<400> SEQUENCE: 181

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 182
<211> LENGTH: 41
<212> TYPE: PRT
<213> ORGANISM: artificial sequence
<220> FEATURE:
<223> OTHER INFORMATION: Synthetic construct

<400> SEQUENCE: 182

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
            35                  40

<210> SEQ ID NO 183
<211> LENGTH: 7
<212> TYPE: PRT
<213> ORGANISM: artificial sequence
<220> FEATURE:
<223> OTHER INFORMATION: Synthetic construct

<400> SEQUENCE: 183

Lys His Pro Thr Tyr Arg Gln
1               5

<210> SEQ ID NO 184
<211> LENGTH: 7
<212> TYPE: PRT
<213> ORGANISM: artificial sequence
<220> FEATURE:
<223> OTHER INFORMATION: Synthetic construct

<400> SEQUENCE: 184

His Pro Met Ser Ala Pro Arg
```

```
<210> SEQ ID NO 185
<211> LENGTH: 7
<212> TYPE: PRT
<213> ORGANISM: artificial sequence
<220> FEATURE:
<223> OTHER INFORMATION: Synthetic construct

<400> SEQUENCE: 185

Met Pro Lys Tyr Tyr Leu Gln
1               5

<210> SEQ ID NO 186
<211> LENGTH: 7
<212> TYPE: PRT
<213> ORGANISM: artificial sequence
<220> FEATURE:
<223> OTHER INFORMATION: Synthetic construct

<400> SEQUENCE: 186

Met His Ala His Ser Ile Ala
1               5

<210> SEQ ID NO 187
<211> LENGTH: 12
<212> TYPE: PRT
<213> ORGANISM: artificial sequence
<220> FEATURE:
<223> OTHER INFORMATION: Synthetic construct

<400> SEQUENCE: 187

Ala Lys Pro Ile Ser Gln His Leu Gln Arg Gly Ser
1               5                   10

<210> SEQ ID NO 188
<211> LENGTH: 12
<212> TYPE: PRT
<213> ORGANISM: artificial sequence
<220> FEATURE:
<223> OTHER INFORMATION: Synthetic construct

<400> SEQUENCE: 188

Ala Pro Pro Thr Pro Ala Ala Ala Ser Ala Thr Thr
1               5                   10

<210> SEQ ID NO 189
<211> LENGTH: 12
<212> TYPE: PRT
<213> ORGANISM: artificial sequence
<220> FEATURE:
<223> OTHER INFORMATION: Synthetic construct

<400> SEQUENCE: 189

Asp Pro Thr Glu Gly Ala Arg Arg Thr Ile Met Thr
1               5                   10

<210> SEQ ID NO 190
<211> LENGTH: 12
<212> TYPE: PRT
<213> ORGANISM: artificial sequence
<220> FEATURE:
<223> OTHER INFORMATION: Synthetic construct

<400> SEQUENCE: 190

Leu Asp Thr Ser Phe Pro Pro Val Pro Phe His Ala
1               5                   10
```

<210> SEQ ID NO 191
<211> LENGTH: 12
<212> TYPE: PRT
<213> ORGANISM: artificial sequence
<220> FEATURE:
<223> OTHER INFORMATION: Synthetic construct

<400> SEQUENCE: 191

Leu Asp Thr Ser Phe His Gln Val Pro Phe His Gln
1               5                   10

<210> SEQ ID NO 192
<211> LENGTH: 11
<212> TYPE: PRT
<213> ORGANISM: artificial sequence
<220> FEATURE:
<223> OTHER INFORMATION: Synthetic construct

<400> SEQUENCE: 192

Leu Pro Arg Ile Ala Asn Thr Trp Ser Pro Ser
1               5                   10

<210> SEQ ID NO 193
<211> LENGTH: 12
<212> TYPE: PRT
<213> ORGANISM: artificial sequence
<220> FEATURE:
<223> OTHER INFORMATION: Synthetic construct

<400> SEQUENCE: 193

Arg Thr Asn Ala Ala Asp His Pro Ala Ala Val Thr
1               5                   10

<210> SEQ ID NO 194
<211> LENGTH: 12
<212> TYPE: PRT
<213> ORGANISM: artificial sequence
<220> FEATURE:
<223> OTHER INFORMATION: Synthetic construct

<400> SEQUENCE: 194

Ser Leu Asn Trp Val Thr Ile Pro Gly Pro Lys Ile
1               5                   10

<210> SEQ ID NO 195
<211> LENGTH: 12
<212> TYPE: PRT
<213> ORGANISM: artificial sequence
<220> FEATURE:
<223> OTHER INFORMATION: Synthetic construct

<400> SEQUENCE: 195

Thr Asp Met Gln Ala Pro Thr Lys Ser Tyr Ser Asn
1               5                   10

<210> SEQ ID NO 196
<211> LENGTH: 12
<212> TYPE: PRT
<213> ORGANISM: artificial sequence
<220> FEATURE:
<223> OTHER INFORMATION: Synthetic construct

<400> SEQUENCE: 196

Thr Ile Met Thr Lys Ser Pro Ser Leu Ser Cys Gly
1               5                   10

<210> SEQ ID NO 197

<211> LENGTH: 12
<212> TYPE: PRT
<213> ORGANISM: artificial sequence
<220> FEATURE:
<223> OTHER INFORMATION: Synthetic construct

<400> SEQUENCE: 197

Thr Pro Ala Leu Asp Gly Leu Arg Gln Pro Leu Arg
1               5                   10

<210> SEQ ID NO 198
<211> LENGTH: 12
<212> TYPE: PRT
<213> ORGANISM: artificial sequence
<220> FEATURE:
<223> OTHER INFORMATION: Synthetic construct

<400> SEQUENCE: 198

Thr Tyr Pro Ala Ser Arg Leu Pro Leu Leu Ala Pro
1               5                   10

<210> SEQ ID NO 199
<211> LENGTH: 12
<212> TYPE: PRT
<213> ORGANISM: artificial sequence
<220> FEATURE:
<223> OTHER INFORMATION: Synthetic construct

<400> SEQUENCE: 199

Ala Lys Thr His Lys His Pro Ala Pro Ser Tyr Ser
1               5                   10

<210> SEQ ID NO 200
<211> LENGTH: 12
<212> TYPE: PRT
<213> ORGANISM: artificial sequence
<220> FEATURE:
<223> OTHER INFORMATION: Synthetic construct

<400> SEQUENCE: 200

Thr Asp Pro Thr Pro Phe Ser Ile Ser Pro Glu Arg
1               5                   10

<210> SEQ ID NO 201
<211> LENGTH: 12
<212> TYPE: PRT
<213> ORGANISM: artificial sequence
<220> FEATURE:
<223> OTHER INFORMATION: Synthetic construct

<400> SEQUENCE: 201

Ser Gln Asn Trp Gln Asp Ser Thr Ser Tyr Ser Asn
1               5                   10

<210> SEQ ID NO 202
<211> LENGTH: 12
<212> TYPE: PRT
<213> ORGANISM: artificial sequence
<220> FEATURE:
<223> OTHER INFORMATION: Synthetic construct

<400> SEQUENCE: 202

Trp His Asp Lys Pro Gln Asn Ser Ser Lys Ser Thr
1               5                   10

<210> SEQ ID NO 203
<211> LENGTH: 12
<212> TYPE: PRT

<213> ORGANISM: artificial sequence
<220> FEATURE:
<223> OTHER INFORMATION: Synthetic construct

<400> SEQUENCE: 203

Leu Asp Val Glu Ser Tyr Lys Gly Thr Ser Met Pro
1               5                   10

<210> SEQ ID NO 204
<211> LENGTH: 7
<212> TYPE: PRT
<213> ORGANISM: artificial sequence
<220> FEATURE:
<223> OTHER INFORMATION: Synthetic construct

<400> SEQUENCE: 204

Asn Thr Pro Lys Glu Asn Trp
1               5

<210> SEQ ID NO 205
<211> LENGTH: 7
<212> TYPE: PRT
<213> ORGANISM: artificial sequence
<220> FEATURE:
<223> OTHER INFORMATION: Synthetic construct

<400> SEQUENCE: 205

Asn Thr Pro Ala Ser Asn Arg
1               5

<210> SEQ ID NO 206
<211> LENGTH: 7
<212> TYPE: PRT
<213> ORGANISM: artificial sequence
<220> FEATURE:
<223> OTHER INFORMATION: Synthetic construct

<400> SEQUENCE: 206

Pro Arg Gly Met Leu Ser Thr
1               5

<210> SEQ ID NO 207
<211> LENGTH: 7
<212> TYPE: PRT
<213> ORGANISM: artificial sequence
<220> FEATURE:
<223> OTHER INFORMATION: Synthetic construct

<400> SEQUENCE: 207

Pro Pro Thr Tyr Leu Ser Thr
1               5

<210> SEQ ID NO 208
<211> LENGTH: 12
<212> TYPE: PRT
<213> ORGANISM: artificial sequence
<220> FEATURE:
<223> OTHER INFORMATION: Synthetic construct

<400> SEQUENCE: 208

Thr Ile Pro Thr His Arg Gln His Asp Tyr Arg Ser
1               5                   10

<210> SEQ ID NO 209
<211> LENGTH: 7
<212> TYPE: PRT
<213> ORGANISM: artificial sequence
<220> FEATURE:

<223> OTHER INFORMATION: Synthetic construct

<400> SEQUENCE: 209

Thr Pro Pro Thr His Arg Leu
1               5

<210> SEQ ID NO 210
<211> LENGTH: 7
<212> TYPE: PRT
<213> ORGANISM: artificial sequence
<220> FEATURE:
<223> OTHER INFORMATION: Synthetic construct

<400> SEQUENCE: 210

Leu Pro Thr Met Ser Thr Pro
1               5

<210> SEQ ID NO 211
<211> LENGTH: 7
<212> TYPE: PRT
<213> ORGANISM: artificial sequence
<220> FEATURE:
<223> OTHER INFORMATION: Synthetic construct

<400> SEQUENCE: 211

Leu Gly Thr Asn Ser Thr Pro
1               5

<210> SEQ ID NO 212
<211> LENGTH: 12
<212> TYPE: PRT
<213> ORGANISM: artificial sequence
<220> FEATURE:
<223> OTHER INFORMATION: Synthetic construct

<400> SEQUENCE: 212

Thr Pro Leu Thr Gly Ser Thr Asn Leu Leu Ser Ser
1               5                   10

<210> SEQ ID NO 213
<211> LENGTH: 7
<212> TYPE: PRT
<213> ORGANISM: artificial sequence
<220> FEATURE:
<223> OTHER INFORMATION: Synthetic construct

<400> SEQUENCE: 213

Thr Pro Leu Thr Lys Glu Thr
1               5

<210> SEQ ID NO 214
<211> LENGTH: 7
<212> TYPE: PRT
<213> ORGANISM: artificial sequence
<220> FEATURE:
<223> OTHER INFORMATION: Synthetic construct

<400> SEQUENCE: 214

Lys Gln Ser His Asn Pro Pro
1               5

<210> SEQ ID NO 215
<211> LENGTH: 7
<212> TYPE: PRT
<213> ORGANISM: artificial sequence
<220> FEATURE:
<223> OTHER INFORMATION: Synthetic construct

```
<400> SEQUENCE: 215

Gln Gln Ser His Asn Pro Pro
1               5

<210> SEQ ID NO 216
<211> LENGTH: 7
<212> TYPE: PRT
<213> ORGANISM: artificial sequence
<220> FEATURE:
<223> OTHER INFORMATION: Synthetic construct

<400> SEQUENCE: 216

Thr Gln Pro His Asn Pro Pro
1               5

<210> SEQ ID NO 217
<211> LENGTH: 12
<212> TYPE: PRT
<213> ORGANISM: artificial sequence
<220> FEATURE:
<223> OTHER INFORMATION: Synthetic construct

<400> SEQUENCE: 217

Ser Thr Asn Leu Leu Arg Thr Ser Thr Val His Pro
1               5                   10

<210> SEQ ID NO 218
<211> LENGTH: 12
<212> TYPE: PRT
<213> ORGANISM: artificial sequence
<220> FEATURE:
<223> OTHER INFORMATION: Synthetic construct

<400> SEQUENCE: 218

His Thr Gln Pro Ser Tyr Ser Ser Thr Asn Leu Phe
1               5                   10

<210> SEQ ID NO 219
<211> LENGTH: 7
<212> TYPE: PRT
<213> ORGANISM: artificial sequence
<220> FEATURE:
<223> OTHER INFORMATION: Synthetic construct

<400> SEQUENCE: 219

Ser Leu Leu Ser Ser His Ala
1               5

<210> SEQ ID NO 220
<211> LENGTH: 12
<212> TYPE: PRT
<213> ORGANISM: artificial sequence
<220> FEATURE:
<223> OTHER INFORMATION: Synthetic construct

<400> SEQUENCE: 220

Gln Gln Ser Ser Ile Ser Leu Ser Ser His Ala Val
1               5                   10

<210> SEQ ID NO 221
<211> LENGTH: 7
<212> TYPE: PRT
<213> ORGANISM: artificial sequence
<220> FEATURE:
<223> OTHER INFORMATION: Synthetic construct

<400> SEQUENCE: 221
```

Asn Ala Ser Pro Ser Ser Leu
1               5

<210> SEQ ID NO 222
<211> LENGTH: 7
<212> TYPE: PRT
<213> ORGANISM: artificial sequence
<220> FEATURE:
<223> OTHER INFORMATION: Synthetic construct

<400> SEQUENCE: 222

His Ser Pro Ser Ser Leu Arg
1               5

<210> SEQ ID NO 223
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= H, R or N
<220> FEATURE:
<221> NAME/KEY: MISC_FEATURE
<222> LOCATION: (2)..(2)
<223> OTHER INFORMATION: X= His, Arg or Asn

<400> SEQUENCE: 223

Lys Xaa Ser His His Thr His
1               5

<210> SEQ ID NO 224
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X = H, R or N
<220> FEATURE:
<221> NAME/KEY: MISC_FEATURE
<222> LOCATION: (2)..(2)
<223> OTHER INFORMATION: X = His, Arg or Asn

<400> SEQUENCE: 224

Glu Xaa Ser His His Thr His
1               5

<210> SEQ ID NO 225
<211> LENGTH: 12
<212> TYPE: PRT
<213> ORGANISM: artificial sequence
<220> FEATURE:
<223> OTHER INFORMATION: Synthetic construct

<400> SEQUENCE: 225

Ser His His Thr His Tyr Gly Gln Pro Gly Pro Val
1               5                   10

<210> SEQ ID NO 226
<211> LENGTH: 7
<212> TYPE: PRT
<213> ORGANISM: artificial sequence
<220> FEATURE:
<223> OTHER INFORMATION: Synthetic construct

<400> SEQUENCE: 226

Leu Glu Ser Thr Ser Leu Leu
1               5

<210> SEQ ID NO 227
<211> LENGTH: 7
<212> TYPE: PRT
<213> ORGANISM: artificial sequence
<220> FEATURE:
<223> OTHER INFORMATION: Synthetic construct

<400> SEQUENCE: 227

Asp Leu Thr Leu Pro Phe His
1               5

<210> SEQ ID NO 228
<211> LENGTH: 8
<212> TYPE: PRT
<213> ORGANISM: artificial sequence
<220> FEATURE:
<223> OTHER INFORMATION: Synthetic construct

<400> SEQUENCE: 228

Arg Thr Asn Ala Ala Asp His Pro
1               5

<210> SEQ ID NO 229
<211> LENGTH: 12
<212> TYPE: PRT
<213> ORGANISM: artificial sequence
<220> FEATURE:
<223> OTHER INFORMATION: Synthetic construct

<400> SEQUENCE: 229

Ile Pro Trp Trp Asn Ile Arg Ala Pro Leu Asn Ala
1               5                   10

<210> SEQ ID NO 230
<211> LENGTH: 18
<212> TYPE: PRT
<213> ORGANISM: artificial sequence
<220> FEATURE:
<223> OTHER INFORMATION: Synthetic construct

<400> SEQUENCE: 230

Glu Gln Ile Ser Gly Ser Leu Val Ala Ala Pro Trp Glu Gly Glu Gly
1               5                   10                  15

Glu Arg

<210> SEQ ID NO 231
<211> LENGTH: 18
<212> TYPE: PRT
<213> ORGANISM: artificial sequence
<220> FEATURE:
<223> OTHER INFORMATION: Synthetic construct

<400> SEQUENCE: 231

Leu Asp Thr Ser Phe His Gln Val Pro Phe His Gln Lys Arg Lys Arg
1               5                   10                  15

Lys Asp

<210> SEQ ID NO 232
<211> LENGTH: 18
<212> TYPE: PRT
<213> ORGANISM: artificial sequence
<220> FEATURE:
<223> OTHER INFORMATION: Synthetic construct

<400> SEQUENCE: 232

Glu Gln Ile Ser Gly Ser Leu Val Ala Ala Pro Trp Lys Arg Lys Arg
1               5                   10                  15

Lys Asp

<210> SEQ ID NO 233
<211> LENGTH: 18
<212> TYPE: PRT
<213> ORGANISM: artificial sequence
<220> FEATURE:
<223> OTHER INFORMATION: Synthetic construct

<400> SEQUENCE: 233

Thr Pro Pro Glu Leu Leu His Gly Asp Pro Arg Ser Lys Arg Lys Arg
1               5                   10                  15

Lys Asp

<210> SEQ ID NO 234
<211> LENGTH: 13
<212> TYPE: PRT
<213> ORGANISM: artificial sequence
<220> FEATURE:
<223> OTHER INFORMATION: Synthetic construct

<400> SEQUENCE: 234

Asn Thr Ser Gln Leu Ser Thr Glu Gly Glu Gly Glu Asp
1               5                   10

<210> SEQ ID NO 235
<211> LENGTH: 13
<212> TYPE: PRT
<213> ORGANISM: artificial sequence
<220> FEATURE:
<223> OTHER INFORMATION: Synthetic construct

<400> SEQUENCE: 235

Thr Pro Pro Glu Leu Leu His Gly Asp Pro Arg Ser Cys
1               5                   10

<210> SEQ ID NO 236
<211> LENGTH: 15
<212> TYPE: PRT
<213> ORGANISM: artificial sequence
<220> FEATURE:
<223> OTHER INFORMATION: Synthetic construct

<400> SEQUENCE: 236

His Ala His Lys Asn Gln Lys Glu Thr His Gln Arg His Ala Ala
1               5                   10                  15

<210> SEQ ID NO 237
<211> LENGTH: 15
<212> TYPE: PRT
<213> ORGANISM: artificial sequence
<220> FEATURE:
<223> OTHER INFORMATION: Synthetic construct

<400> SEQUENCE: 237

His Glu His Lys Asn Gln Lys Glu Thr His Gln Arg His Ala Ala
1               5                   10                  15

<210> SEQ ID NO 238
<211> LENGTH: 20
<212> TYPE: PRT
<213> ORGANISM: artificial sequence
<220> FEATURE:
<223> OTHER INFORMATION: Synthetic construct

<400> SEQUENCE: 238

His Asn His Met Gln Glu Arg Tyr Thr Glu Pro Gln His Ser Pro Ser
1               5                   10                  15

Val Asn Gly Leu
            20

<210> SEQ ID NO 239
<211> LENGTH: 17
<212> TYPE: PRT
<213> ORGANISM: artificial sequence
<220> FEATURE:
<223> OTHER INFORMATION: Synthetic construct

<400> SEQUENCE: 239

Thr His Ser Thr His Asn His Gly Ser Pro Arg His Thr Asn Ala Asp
1               5                   10                  15

Ala

<210> SEQ ID NO 240
<211> LENGTH: 20
<212> TYPE: PRT
<213> ORGANISM: artificial sequence
<220> FEATURE:
<223> OTHER INFORMATION: Synthetic construct

<400> SEQUENCE: 240

Ala Gln Ser Gln Leu Pro Ala Lys His Ser Gly Leu His Glu Arg Ala
1               5                   10                  15

Pro Gln Arg Tyr
            20

<210> SEQ ID NO 241
<211> LENGTH: 20
<212> TYPE: PRT
<213> ORGANISM: artificial sequence
<220> FEATURE:
<223> OTHER INFORMATION: Synthetic construct

<400> SEQUENCE: 241

Ala Gln Ser Gln Leu Pro Glu Lys His Ser Gly Leu His Glu Arg Ala
1               5                   10                  15

Pro Gln Arg Tyr
            20

<210> SEQ ID NO 242
<211> LENGTH: 12
<212> TYPE: PRT
<213> ORGANISM: artificial sequence
<220> FEATURE:
<223> OTHER INFORMATION: Synthetic construct

<400> SEQUENCE: 242

Arg Leu Leu Arg Leu Leu Arg Leu Leu Arg Leu Leu
1               5                   10

<210> SEQ ID NO 243
<211> LENGTH: 12
<212> TYPE: PRT
<213> ORGANISM: artificial sequence
<220> FEATURE:
<223> OTHER INFORMATION: Synthetic construct

<400> SEQUENCE: 243

```
Thr Pro Pro Glu Leu Leu His Gly Glu Pro Arg Ser
1               5                   10
```

<210> SEQ ID NO 244
<211> LENGTH: 12
<212> TYPE: PRT
<213> ORGANISM: artificial sequence
<220> FEATURE:
<223> OTHER INFORMATION: Synthetic construct

<400> SEQUENCE: 244

```
Thr Pro Pro Glu Leu Leu His Gly Ala Pro Arg Ser
1               5                   10
```

<210> SEQ ID NO 245
<211> LENGTH: 12
<212> TYPE: PRT
<213> ORGANISM: artificial sequence
<220> FEATURE:
<223> OTHER INFORMATION: Synthetic construct

<400> SEQUENCE: 245

```
Glu Gln Ile Ser Gly Ser Leu Val Ala Ala Pro Trp
1               5                   10
```

<210> SEQ ID NO 246
<211> LENGTH: 12
<212> TYPE: PRT
<213> ORGANISM: artificial sequence
<220> FEATURE:
<223> OTHER INFORMATION: Synthetic construct

<400> SEQUENCE: 246

```
Asn Glu Val Pro Ala Arg Asn Ala Pro Trp Leu Val
1               5                   10
```

<210> SEQ ID NO 247
<211> LENGTH: 13
<212> TYPE: PRT
<213> ORGANISM: artificial sequence
<220> FEATURE:
<223> OTHER INFORMATION: Synthetic construct

<400> SEQUENCE: 247

```
Asn Ser Pro Gly Tyr Gln Ala Asp Ser Val Ala Ile Gly
1               5                   10
```

<210> SEQ ID NO 248
<211> LENGTH: 12
<212> TYPE: PRT
<213> ORGANISM: artificial sequence
<220> FEATURE:
<223> OTHER INFORMATION: Synthetic construct

<400> SEQUENCE: 248

```
Ala Lys Pro Ile Ser Gln His Leu Gln Arg Gly Ser
1               5                   10
```

<210> SEQ ID NO 249
<211> LENGTH: 12
<212> TYPE: PRT
<213> ORGANISM: artificial sequence
<220> FEATURE:
<223> OTHER INFORMATION: Synthetic construct

<400> SEQUENCE: 249

```
Leu Asp Thr Ser Phe Pro Pro Val Pro Phe His Ala
```

```
<210> SEQ ID NO 250
<211> LENGTH: 12
<212> TYPE: PRT
<213> ORGANISM: artificial sequence
<220> FEATURE:
<223> OTHER INFORMATION: Synthetic construct

<400> SEQUENCE: 250

Ser Leu Asn Trp Val Thr Ile Pro Gly Pro Lys Ile
1               5                   10

<210> SEQ ID NO 251
<211> LENGTH: 12
<212> TYPE: PRT
<213> ORGANISM: artificial sequence
<220> FEATURE:
<223> OTHER INFORMATION: Synthetic construct

<400> SEQUENCE: 251

Thr Gln Asp Ser Ala Gln Lys Ser Pro Ser Pro Leu
1               5                   10

<210> SEQ ID NO 252
<211> LENGTH: 12
<212> TYPE: PRT
<213> ORGANISM: artificial sequence
<220> FEATURE:
<223> OTHER INFORMATION: Synthetic construct

<400> SEQUENCE: 252

Lys Glu Leu Gln Thr Arg Asn Val Val Gln Arg Glu
1               5                   10

<210> SEQ ID NO 253
<211> LENGTH: 12
<212> TYPE: PRT
<213> ORGANISM: artificial sequence
<220> FEATURE:
<223> OTHER INFORMATION: Synthetic construct

<400> SEQUENCE: 253

Gln Arg Asn Ser Pro Ala Met Ser Arg Arg Asp
1               5                   10

<210> SEQ ID NO 254
<211> LENGTH: 12
<212> TYPE: PRT
<213> ORGANISM: artificial sequence
<220> FEATURE:
<223> OTHER INFORMATION: Synthetic construct

<400> SEQUENCE: 254

Thr Pro Thr Ala Asn Gln Phe Thr Gln Ser Val Pro
1               5                   10

<210> SEQ ID NO 255
<211> LENGTH: 12
<212> TYPE: PRT
<213> ORGANISM: artificial sequence
<220> FEATURE:
<223> OTHER INFORMATION: Synthetic construct

<400> SEQUENCE: 255

Ala Ala Gly Leu Ser Gln Lys His Glu Arg Asn Arg
1               5                   10
```

<210> SEQ ID NO 256
<211> LENGTH: 12
<212> TYPE: PRT
<213> ORGANISM: artificial sequence
<220> FEATURE:
<223> OTHER INFORMATION: Synthetic construct

<400> SEQUENCE: 256

Glu Thr Val His Gln Thr Pro Leu Ser Asp Arg Pro
1               5                   10

<210> SEQ ID NO 257
<211> LENGTH: 12
<212> TYPE: PRT
<213> ORGANISM: artificial sequence
<220> FEATURE:
<223> OTHER INFORMATION: Synthetic construct

<400> SEQUENCE: 257

Lys Asn Phe Pro Gln Gln Lys Glu Phe Pro Leu Ser
1               5                   10

<210> SEQ ID NO 258
<211> LENGTH: 12
<212> TYPE: PRT
<213> ORGANISM: artificial sequence
<220> FEATURE:
<223> OTHER INFORMATION: Synthetic construct

<400> SEQUENCE: 258

Leu Pro Ala Leu His Ile Gln Arg His Pro Arg Met
1               5                   10

<210> SEQ ID NO 259
<211> LENGTH: 12
<212> TYPE: PRT
<213> ORGANISM: artificial sequence
<220> FEATURE:
<223> OTHER INFORMATION: Synthetic construct

<400> SEQUENCE: 259

Gln Pro Ser His Ser Gln Ser His Asn Leu Arg Ser
1               5                   10

<210> SEQ ID NO 260
<211> LENGTH: 12
<212> TYPE: PRT
<213> ORGANISM: artificial sequence
<220> FEATURE:
<223> OTHER INFORMATION: Synthetic construct

<400> SEQUENCE: 260

Arg Gly Ser Gln Lys Ser Lys Pro Pro Arg Pro Pro
1               5                   10

<210> SEQ ID NO 261
<211> LENGTH: 12
<212> TYPE: PRT
<213> ORGANISM: artificial sequence
<220> FEATURE:
<223> OTHER INFORMATION: Synthetic construct

<400> SEQUENCE: 261

Thr His Thr Gln Lys Thr Pro Leu Leu Tyr Tyr His
1               5                   10

<210> SEQ ID NO 262

```
<211> LENGTH: 12
<212> TYPE: PRT
<213> ORGANISM: artificial sequence
<220> FEATURE:
<223> OTHER INFORMATION: Synthetic construct

<400> SEQUENCE: 262

Thr Lys Gly Ser Ser Gln Ala Ile Leu Lys Ser Thr
1               5                   10

<210> SEQ ID NO 263
<211> LENGTH: 7
<212> TYPE: PRT
<213> ORGANISM: artificial sequence
<220> FEATURE:
<223> OTHER INFORMATION: Synthetic construct

<400> SEQUENCE: 263

Thr Ala Ala Thr Thr Ser Pro
1               5

<210> SEQ ID NO 264
<211> LENGTH: 7
<212> TYPE: PRT
<213> ORGANISM: artificial sequence
<220> FEATURE:
<223> OTHER INFORMATION: Synthetic construct

<400> SEQUENCE: 264

Leu Gly Ile Pro Gln Asn Leu
1               5

<210> SEQ ID NO 265
<211> LENGTH: 20
<212> TYPE: PRT
<213> ORGANISM: artificial sequence
<220> FEATURE:
<223> OTHER INFORMATION: Synthetic construct

<400> SEQUENCE: 265

Thr His Ser Thr His Asn His Gly Ser Pro Arg His Thr Asn Ala Asp
1               5                   10                  15

Ala Gly Asn Pro
            20

<210> SEQ ID NO 266
<211> LENGTH: 20
<212> TYPE: PRT
<213> ORGANISM: artificial sequence
<220> FEATURE:
<223> OTHER INFORMATION: Synthetic construct

<400> SEQUENCE: 266

Gln Gln His Lys Val His His Gln Asn Pro Asp Arg Ser Thr Gln Asp
1               5                   10                  15

Ala His His Ser
            20

<210> SEQ ID NO 267
<211> LENGTH: 15
<212> TYPE: PRT
<213> ORGANISM: artificial sequence
<220> FEATURE:
<223> OTHER INFORMATION: Synthetic construct

<400> SEQUENCE: 267

His His Gly Thr His His Asn Ala Thr Lys Gln Lys Asn His Val
```

```
1               5                   10                  15
```

<210> SEQ ID NO 268
<211> LENGTH: 15
<212> TYPE: PRT
<213> ORGANISM: artificial sequence
<220> FEATURE:
<223> OTHER INFORMATION: Synthetic construct

<400> SEQUENCE: 268

```
Ser Thr Leu His Lys Tyr Lys Ser Gln Asp Pro Thr Pro His His
1               5                   10                  15
```

<210> SEQ ID NO 269
<211> LENGTH: 12
<212> TYPE: PRT
<213> ORGANISM: artificial sequence
<220> FEATURE:
<223> OTHER INFORMATION: Synthetic construct

<400> SEQUENCE: 269

```
Ser Val Ser Val Gly Met Lys Pro Ser Pro Arg Pro
1               5                   10
```

<210> SEQ ID NO 270
<211> LENGTH: 12
<212> TYPE: PRT
<213> ORGANISM: artificial sequence
<220> FEATURE:
<223> OTHER INFORMATION: Synthetic construct

<400> SEQUENCE: 270

```
Thr Pro Pro Glu Leu Leu His Gly Asp Pro Arg Ser
1               5                   10
```

<210> SEQ ID NO 271
<211> LENGTH: 15
<212> TYPE: PRT
<213> ORGANISM: artificial sequence
<220> FEATURE:
<223> OTHER INFORMATION: Synthetic construct

<400> SEQUENCE: 271

```
Ser Thr Leu His Lys Tyr Lys Ser Gln Asp Pro Thr Pro His His
1               5                   10                  15
```

<210> SEQ ID NO 272
<211> LENGTH: 20
<212> TYPE: PRT
<213> ORGANISM: artificial sequence
<220> FEATURE:
<223> OTHER INFORMATION: Synthetic construct

<400> SEQUENCE: 272

```
His Asn His Met Gln Glu Arg Tyr Thr Asp Pro Gln His Ser Pro Ser
1               5                   10                  15

Val Asn Gly Leu
            20
```

<210> SEQ ID NO 273
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 273

-continued

Ser Ser Ala Asp Phe Ala Ser Phe Gly Phe Gly Phe Ser Ala Ala
1               5                   10                  15

Ser Ala Asp Ser Arg
            20

<210> SEQ ID NO 274
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 274

Ser Ser Phe Ala Glu Ala Trp Ser Arg Ala Trp Pro Arg Ala Glu Val
1               5                   10                  15

Phe Phe Pro Ser Arg Gly Tyr
            20

<210> SEQ ID NO 275
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 275

Ser Ser Phe Ser Val Asn Glu Pro His Ala Trp Met Ala Pro Leu Ser
1               5                   10                  15

Arg

<210> SEQ ID NO 276
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 276

Ser Ser Phe Ser Trp Val Tyr Gly His Gly Gly Leu Gly Phe Ala Ser
1               5                   10                  15

Arg

<210> SEQ ID NO 277
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 277

Ser Ser Phe Val Ser Trp Ser Pro Tyr Lys Ser Pro Pro Glu Leu Ser
1               5                   10                  15

Arg

<210> SEQ ID NO 278
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 278

Ser Ser Phe Tyr Gly Ser Ser Ala Phe Val Ser Ser Gly Val Ser Val
1               5                   10                  15

```
Ala Tyr Gly Ser Arg
            20

<210> SEQ ID NO 279
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 279

Ser Ser Gly Ser Val Ala Val Ser Ala Glu Ala Ser Trp Phe Ser Gly
1               5                   10                  15

Val Ala Ala Ser Arg
            20

<210> SEQ ID NO 280
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 280

Ser Ser His Asp Glu His Tyr Gln Tyr His Tyr Tyr Ser Ser Arg
1               5                   10                  15

<210> SEQ ID NO 281
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 281

Ser Ser His Tyr Tyr Tyr Asn Asp Tyr Asp His Gln Ser Ser Arg
1               5                   10                  15

<210> SEQ ID NO 282
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 282

Ser Ser Leu Phe Asn Met Tyr Gly His Gln Ser Val Leu Gly Pro Ser
1               5                   10                  15

Arg

<210> SEQ ID NO 283
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 283

Ser Ser Leu Phe Ser Asp Val His Tyr Gly Ser Asn Lys Ala Leu Ser
1               5                   10                  15

Arg

<210> SEQ ID NO 284
<211> LENGTH: 17
<212> TYPE: PRT
<213> ORGANISM: artificial sequence
```

```
<220> FEATURE:
<223> OTHER INFORMATION: Dyed-hair-bindg peptide

<400> SEQUENCE: 284

Ser Ser Leu Leu Ser Asp Phe His Tyr Gly Asp Met Trp Asp Ala Ser
1               5                   10                  15

Arg

<210> SEQ ID NO 285
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 285

Ser Ser Asn Tyr Asn Tyr Asn Tyr Asn Tyr Gln Tyr Ser Ser Arg
1               5                   10                  15

<210> SEQ ID NO 286
<211> LENGTH: 21
<212> TYPE: PRT
<213> ORGANISM: artificial sequence
<220> FEATURE:
<223> OTHER INFORMATION: synethetic construct

<400> SEQUENCE: 286

Ser Ser Asn Tyr Asn Tyr Asn Tyr Asn Tyr Gln Tyr Ser Ser Arg Glu
1               5                   10                  15

Gly Glu Gly Glu Arg
            20

<210> SEQ ID NO 287
<211> LENGTH: 21
<212> TYPE: PRT
<213> ORGANISM: ARTIFICIAL SEQUENCE
<220> FEATURE:
<223> OTHER INFORMATION: Synthetic construct

<400> SEQUENCE: 287

Ser Ser Asn Tyr Asn Tyr Asn Tyr Asn Tyr Gln Tyr Ser Ser Arg Lys
1               5                   10                  15

Arg Lys Arg Lys Asp
            20

<210> SEQ ID NO 288
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 288

Ser Ser Gln Tyr Tyr Gln Asp Tyr Gln Tyr Tyr His Ser Ser Arg
1               5                   10                  15

<210> SEQ ID NO 289
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 289

Ser Ser Ser Cys Met Gly Ser His Asn Pro Arg Met Ser Val Glu Glu
1               5                   10                  15
```

Ser Thr Arg Asn Cys Ser Arg
            20

<210> SEQ ID NO 290
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 290

Ser Ser Ser Cys Asn Asn Asn Trp Phe Tyr Ser Ser Thr Leu Pro Gly
1               5                   10                  15

Gly Asp His Ala Cys Ser Arg
            20

<210> SEQ ID NO 291
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 291

Ser Ser Ser Cys Tyr Asp Val Glu Cys Ser Ser Phe Val Ala Trp Met
1               5                   10                  15

Arg Gly Pro Ser Ser Ser Arg
            20

<210> SEQ ID NO 292
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 292

Ser Ser Ser Phe Ala Ala Ser Ser Ala Phe Ser Phe Leu Val Asp Ala
1               5                   10                  15

Val Ala Trp Ser Arg
            20

<210> SEQ ID NO 293
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 293

Ser Ser Ser Phe Ala Tyr Leu Val Pro Asp Asp Gly Trp Leu Ser Ser
1               5                   10                  15

Arg

<210> SEQ ID NO 294
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 294

Ser Ser Ser Gly Ala Val Phe Ser Ser Gly Gly Ala Asp Ala Gly Trp
1               5                   10                  15

```
Gly Val Trp Ser Arg
            20

<210> SEQ ID NO 295
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 295

Ser Ser Ser Ser Ala Asp Ala Ala Tyr Gly His Cys Cys Gly Ala Gly
1               5                   10                  15

Phe Ser Thr Phe Ser Ser Arg
            20

<210> SEQ ID NO 296
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 296

Ser Ser Ser Ser Asp Val His Asn Ser Ile Ile Gly Trp Asp Phe Tyr
1               5                   10                  15

His Ser Arg Gly Ser Ser Arg
            20

<210> SEQ ID NO 297
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 297

Ser Ser Ser Ser Leu Asp Phe Phe Ser Tyr Ser Ala Phe Ser Gly Gly
1               5                   10                  15

Val Ala Glu Ser Arg
            20

<210> SEQ ID NO 298
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 298

Ser Ser Ser Ser Asn Asp Ser Asn Val Ser Trp Phe His Tyr Tyr Ala
1               5                   10                  15

Ser Gly Leu Thr Ser Ser Arg
            20

<210> SEQ ID NO 299
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 299

Ser Ser Val Asp Tyr Glu Val Pro Leu Ala Val Ala Ala Glu Trp Gly
1               5                   10                  15
```

```
Phe Ser Val Ser Arg
        20

<210> SEQ ID NO 300
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 300

Ser Ser Tyr His Tyr Asp Tyr Asp His Tyr Tyr Glu Ser Ser Arg
1               5                   10                  15

<210> SEQ ID NO 301
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 301

Ser Ser Tyr Tyr Asn Tyr His Tyr Gln Tyr Gln Asp Ser Ser Arg
1               5                   10                  15

<210> SEQ ID NO 302
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 302

Ser Ser Tyr Tyr Tyr Asp Tyr Tyr Gln Gln Asp Tyr Ser Ser Arg
1               5                   10                  15

<210> SEQ ID NO 303
<211> LENGTH: 12
<212> TYPE: PRT
<213> ORGANISM: artificial sequence
<220> FEATURE:
<223> OTHER INFORMATION: Synthetic construct

<400> SEQUENCE: 303

Lys Arg Gly Arg His Lys Arg Pro Lys Arg His Lys
1               5                   10

<210> SEQ ID NO 304
<211> LENGTH: 7
<212> TYPE: PRT
<213> ORGANISM: artificial sequence
<220> FEATURE:
<223> OTHER INFORMATION: Synthetic construct

<400> SEQUENCE: 304

Arg Leu Leu Arg Leu Leu Arg
1               5

<210> SEQ ID NO 305
<211> LENGTH: 12
<212> TYPE: PRT
<213> ORGANISM: artificial sequence
<220> FEATURE:
<223> OTHER INFORMATION: Synthetic construct

<400> SEQUENCE: 305

His Lys Pro Arg Gly Gly Arg Lys Lys Ala Leu His
1               5                   10
```

```
<210> SEQ ID NO 306
<211> LENGTH: 18
<212> TYPE: PRT
<213> ORGANISM: artificial sequence
<220> FEATURE:
<223> OTHER INFORMATION: Synthetic construct

<400> SEQUENCE: 306

Lys Pro Arg Pro Pro His Gly Lys Lys His Arg Pro Lys His Arg Pro
1               5                   10                  15

Lys Lys

<210> SEQ ID NO 307
<211> LENGTH: 18
<212> TYPE: PRT
<213> ORGANISM: artificial sequence
<220> FEATURE:
<223> OTHER INFORMATION: Synthetic construct

<400> SEQUENCE: 307

Arg Gly Arg Pro Lys Lys Gly His Gly Lys Arg Pro Gly His Arg Ala
1               5                   10                  15

Arg Lys

<210> SEQ ID NO 308
<211> LENGTH: 12
<212> TYPE: PRT
<213> ORGANISM: artificial sequence
<220> FEATURE:
<223> OTHER INFORMATION: Synthetic construct

<400> SEQUENCE: 308

Thr Pro Phe His Ser Pro Glu Asn Ala Pro Gly Ser
1               5                   10

<210> SEQ ID NO 309
<211> LENGTH: 13
<212> TYPE: PRT
<213> ORGANISM: artificial sequence
<220> FEATURE:
<223> OTHER INFORMATION: Synthetic construct

<400> SEQUENCE: 309

Thr Pro Phe His Ser Pro Glu Asn Ala Pro Gly Ser Lys
1               5                   10

<210> SEQ ID NO 310
<211> LENGTH: 16
<212> TYPE: PRT
<213> ORGANISM: artificial sequence
<220> FEATURE:
<223> OTHER INFORMATION: Synthetic construct

<400> SEQUENCE: 310

Thr Pro Phe His Ser Pro Glu Asn Ala Pro Gly Ser Gly Gly Gly Ser
1               5                   10                  15

<210> SEQ ID NO 311
<211> LENGTH: 17
<212> TYPE: PRT
<213> ORGANISM: artificial sequence
<220> FEATURE:
<223> OTHER INFORMATION: Synthetic construct

<400> SEQUENCE: 311
```

-continued

Thr Pro Phe His Ser Pro Glu Asn Ala Pro Gly Ser Gly Gly Gly Ser
1               5                   10                  15

Ser

<210> SEQ ID NO 312
<211> LENGTH: 15
<212> TYPE: PRT
<213> ORGANISM: artificial sequence
<220> FEATURE:
<223> OTHER INFORMATION: Synthetic construct

<400> SEQUENCE: 312

Thr Pro Phe His Ser Pro Glu Asn Ala Pro Gly Ser Gly Gly Gly
1               5                   10                  15

<210> SEQ ID NO 313
<211> LENGTH: 7
<212> TYPE: PRT
<213> ORGANISM: artificial sequence
<220> FEATURE:
<223> OTHER INFORMATION: Synthetic construct

<400> SEQUENCE: 313

Phe Thr Gln Ser Leu Pro Arg
1               5

<210> SEQ ID NO 314
<211> LENGTH: 12
<212> TYPE: PRT
<213> ORGANISM: artificial sequence
<220> FEATURE:
<223> OTHER INFORMATION: Synthetic construct

<400> SEQUENCE: 314

Lys Gln Ala Thr Phe Pro Pro Asn Pro Thr Ala Tyr
1               5                   10

<210> SEQ ID NO 315
<211> LENGTH: 12
<212> TYPE: PRT
<213> ORGANISM: artificial sequence
<220> FEATURE:
<223> OTHER INFORMATION: Synthetic construct

<400> SEQUENCE: 315

His Gly His Met Val Ser Thr Ser Gln Leu Ser Ile
1               5                   10

<210> SEQ ID NO 316
<211> LENGTH: 7
<212> TYPE: PRT
<213> ORGANISM: artificial sequence
<220> FEATURE:
<223> OTHER INFORMATION: Synthetic construct

<400> SEQUENCE: 316

Leu Ser Pro Ser Arg Met Lys
1               5

<210> SEQ ID NO 317
<211> LENGTH: 7
<212> TYPE: PRT
<213> ORGANISM: artificial sequence
<220> FEATURE:
<223> OTHER INFORMATION: Synthetic construct

<400> SEQUENCE: 317

```
Leu Pro Ile Pro Arg Met Lys
1               5

<210> SEQ ID NO 318
<211> LENGTH: 7
<212> TYPE: PRT
<213> ORGANISM: artificial sequence
<220> FEATURE:
<223> OTHER INFORMATION: Synthetic construct

<400> SEQUENCE: 318

His Gln Arg Pro Tyr Leu Thr
1               5

<210> SEQ ID NO 319
<211> LENGTH: 7
<212> TYPE: PRT
<213> ORGANISM: artificial sequence
<220> FEATURE:
<223> OTHER INFORMATION: Synthetic construct

<400> SEQUENCE: 319

Phe Pro Pro Leu Leu Arg Leu
1               5

<210> SEQ ID NO 320
<211> LENGTH: 7
<212> TYPE: PRT
<213> ORGANISM: artificial sequence
<220> FEATURE:
<223> OTHER INFORMATION: Synthetic construct

<400> SEQUENCE: 320

Gln Ala Thr Phe Met Tyr Asn
1               5

<210> SEQ ID NO 321
<211> LENGTH: 11
<212> TYPE: PRT
<213> ORGANISM: artificial sequence
<220> FEATURE:
<223> OTHER INFORMATION: Synthetic construct

<400> SEQUENCE: 321

Val Leu Thr Ser Gln Leu Pro Asn His Ser Met
1               5                   10

<210> SEQ ID NO 322
<211> LENGTH: 7
<212> TYPE: PRT
<213> ORGANISM: artificial sequence
<220> FEATURE:
<223> OTHER INFORMATION: Synthetic construct

<400> SEQUENCE: 322

His Ser Thr Ala Tyr Leu Thr
1               5

<210> SEQ ID NO 323
<211> LENGTH: 12
<212> TYPE: PRT
<213> ORGANISM: artificial sequence
<220> FEATURE:
<223> OTHER INFORMATION: Synthetic construct

<400> SEQUENCE: 323

Ala Pro Gln Gln Arg Pro Met Lys Thr Phe Asn Thr
1               5                   10
```

```
<210> SEQ ID NO 324
<211> LENGTH: 12
<212> TYPE: PRT
<213> ORGANISM: artificial sequence
<220> FEATURE:
<223> OTHER INFORMATION: Synthetic construct

<400> SEQUENCE: 324

Ala Pro Gln Gln Arg Pro Met Lys Thr Val Gln Tyr
1               5                   10

<210> SEQ ID NO 325
<211> LENGTH: 7
<212> TYPE: PRT
<213> ORGANISM: artificial sequence
<220> FEATURE:
<223> OTHER INFORMATION: Synthetic construct

<400> SEQUENCE: 325

Pro Pro Trp Leu Asp Leu Leu
1               5

<210> SEQ ID NO 326
<211> LENGTH: 7
<212> TYPE: PRT
<213> ORGANISM: artificial sequence
<220> FEATURE:
<223> OTHER INFORMATION: Synthetic construct

<400> SEQUENCE: 326

Pro Pro Trp Thr Phe Pro Leu
1               5

<210> SEQ ID NO 327
<211> LENGTH: 7
<212> TYPE: PRT
<213> ORGANISM: artificial sequence
<220> FEATURE:
<223> OTHER INFORMATION: Synthetic construct

<400> SEQUENCE: 327

Ser Val Thr His Leu Thr Ser
1               5

<210> SEQ ID NO 328
<211> LENGTH: 7
<212> TYPE: PRT
<213> ORGANISM: artificial sequence
<220> FEATURE:
<223> OTHER INFORMATION: Synthetic construct

<400> SEQUENCE: 328

Val Ile Thr Arg Leu Thr Ser
1               5

<210> SEQ ID NO 329
<211> LENGTH: 12
<212> TYPE: PRT
<213> ORGANISM: artificial sequence
<220> FEATURE:
<223> OTHER INFORMATION: Synthetic construct

<400> SEQUENCE: 329

Asp Leu Lys Pro Pro Leu Leu Ala Leu Ser Lys Val
1               5                   10
```

```
<210> SEQ ID NO 330
<211> LENGTH: 12
<212> TYPE: PRT
<213> ORGANISM: artificial sequence
<220> FEATURE:
<223> OTHER INFORMATION: Synthetic construct

<400> SEQUENCE: 330

Ser His Pro Ser Gly Ala Leu Gln Glu Gly Thr Phe
1               5                   10

<210> SEQ ID NO 331
<211> LENGTH: 12
<212> TYPE: PRT
<213> ORGANISM: artificial sequence
<220> FEATURE:
<223> OTHER INFORMATION: Synthetic construct

<400> SEQUENCE: 331

Phe Pro Leu Thr Ser Lys Pro Ser Gly Ala Cys Thr
1               5                   10

<210> SEQ ID NO 332
<211> LENGTH: 12
<212> TYPE: PRT
<213> ORGANISM: artificial sequence
<220> FEATURE:
<223> OTHER INFORMATION: Synthetic construct

<400> SEQUENCE: 332

Asp Leu Lys Pro Pro Leu Leu Ala Leu Ser Lys Val
1               5                   10

<210> SEQ ID NO 333
<211> LENGTH: 7
<212> TYPE: PRT
<213> ORGANISM: artificial sequence
<220> FEATURE:
<223> OTHER INFORMATION: Synthetic construct

<400> SEQUENCE: 333

Pro Leu Leu Ala Leu His Ser
1               5

<210> SEQ ID NO 334
<211> LENGTH: 7
<212> TYPE: PRT
<213> ORGANISM: artificial sequence
<220> FEATURE:
<223> OTHER INFORMATION: Synthetic construct

<400> SEQUENCE: 334

Val Pro Ile Ser Thr Gln Ile
1               5

<210> SEQ ID NO 335
<211> LENGTH: 12
<212> TYPE: PRT
<213> ORGANISM: artificial sequence
<220> FEATURE:
<223> OTHER INFORMATION: Synthetic construct

<400> SEQUENCE: 335

Tyr Ala Lys Gln His Tyr Pro Ile Ser Thr Phe Lys
1               5                   10

<210> SEQ ID NO 336
<211> LENGTH: 7
```

```
-continued

<212> TYPE: PRT
<213> ORGANISM: artificial sequence
<220> FEATURE:
<223> OTHER INFORMATION: Synthetic construct

<400> SEQUENCE: 336

His Ser Thr Ala Tyr Leu Thr
1               5

<210> SEQ ID NO 337
<211> LENGTH: 12
<212> TYPE: PRT
<213> ORGANISM: artificial sequence
<220> FEATURE:
<223> OTHER INFORMATION: Synthetic construct

<400> SEQUENCE: 337

Ser Thr Ala Tyr Leu Val Ala Met Ser Ala Ala Pro
1               5                   10

<210> SEQ ID NO 338
<211> LENGTH: 12
<212> TYPE: PRT
<213> ORGANISM: artificial sequence
<220> FEATURE:
<223> OTHER INFORMATION: Synthetic construct

<400> SEQUENCE: 338

Ser Val Ser Val Gly Met Lys Pro Ser Pro Arg Pro
1               5                   10

<210> SEQ ID NO 339
<211> LENGTH: 12
<212> TYPE: PRT
<213> ORGANISM: artificial sequence
<220> FEATURE:
<223> OTHER INFORMATION: Synthetic construct

<400> SEQUENCE: 339

Thr Met Gly Phe Thr Ala Pro Arg Phe Pro His Tyr
1               5                   10

<210> SEQ ID NO 340
<211> LENGTH: 12
<212> TYPE: PRT
<213> ORGANISM: artificial sequence
<220> FEATURE:
<223> OTHER INFORMATION: Synthetic construct

<400> SEQUENCE: 340

Asn Leu Gln His Ser Val Gly Thr Ser Pro Val Trp
1               5                   10

<210> SEQ ID NO 341
<211> LENGTH: 15
<212> TYPE: PRT
<213> ORGANISM: artificial sequence
<220> FEATURE:
<223> OTHER INFORMATION: Synthetic construct

<400> SEQUENCE: 341

Gln Leu Ser Tyr His Ala Tyr Pro Gln Ala Asn His His Ala Pro
1               5                   10                  15

<210> SEQ ID NO 342
<211> LENGTH: 12
<212> TYPE: PRT
<213> ORGANISM: artificial sequence
```

```
<220> FEATURE:
<223> OTHER INFORMATION: Synthetic construct

<400> SEQUENCE: 342

Asn Gln Ala Ala Ser Ile Thr Lys Arg Val Pro Tyr
1               5                   10

<210> SEQ ID NO 343
<211> LENGTH: 14
<212> TYPE: PRT
<213> ORGANISM: artificial sequence
<220> FEATURE:
<223> OTHER INFORMATION: Synthetic construct

<400> SEQUENCE: 343

Ser Gly Cys His Leu Val Tyr Asp Asn Gly Phe Cys Asp His
1               5                   10

<210> SEQ ID NO 344
<211> LENGTH: 14
<212> TYPE: PRT
<213> ORGANISM: artificial sequence
<220> FEATURE:
<223> OTHER INFORMATION: Synthetic construct

<400> SEQUENCE: 344

Ala Ser Cys Pro Ser Ala Ser His Ala Asp Pro Cys Ala His
1               5                   10

<210> SEQ ID NO 345
<211> LENGTH: 14
<212> TYPE: PRT
<213> ORGANISM: artificial sequence
<220> FEATURE:
<223> OTHER INFORMATION: Synthetic construct

<400> SEQUENCE: 345

Asn Leu Cys Asp Ser Ala Arg Asp Ser Pro Arg Cys Lys Val
1               5                   10

<210> SEQ ID NO 346
<211> LENGTH: 12
<212> TYPE: PRT
<213> ORGANISM: artificial sequence
<220> FEATURE:
<223> OTHER INFORMATION: Synthetic construct

<400> SEQUENCE: 346

Asn His Ser Asn Trp Lys Thr Ala Ala Asp Phe Leu
1               5                   10

<210> SEQ ID NO 347
<211> LENGTH: 12
<212> TYPE: PRT
<213> ORGANISM: artificial sequence
<220> FEATURE:
<223> OTHER INFORMATION: Synthetic construct

<400> SEQUENCE: 347

Gly Ser Ser Thr Val Gly Arg Pro Leu Ser Tyr Glu
1               5                   10

<210> SEQ ID NO 348
<211> LENGTH: 12
<212> TYPE: PRT
<213> ORGANISM: artificial sequence
<220> FEATURE:
<223> OTHER INFORMATION: Synthetic construct
```

```
<400> SEQUENCE: 348

Ser Asp Thr Ile Ser Arg Leu His Val Ser Met Thr
1               5                   10

<210> SEQ ID NO 349
<211> LENGTH: 12
<212> TYPE: PRT
<213> ORGANISM: artificial sequence
<220> FEATURE:
<223> OTHER INFORMATION: Synthetic construct

<400> SEQUENCE: 349

Ser Pro Leu Thr Val Pro Tyr Glu Arg Lys Leu Leu
1               5                   10

<210> SEQ ID NO 350
<211> LENGTH: 12
<212> TYPE: PRT
<213> ORGANISM: artificial sequence
<220> FEATURE:
<223> OTHER INFORMATION: Synthetic construct

<400> SEQUENCE: 350

Ser Pro Tyr Pro Ser Trp Ser Thr Pro Ala Gly Arg
1               5                   10

<210> SEQ ID NO 351
<211> LENGTH: 12
<212> TYPE: PRT
<213> ORGANISM: artificial sequence
<220> FEATURE:
<223> OTHER INFORMATION: Synthetic construct

<400> SEQUENCE: 351

Val Gln Pro Ile Thr Asn Thr Arg Tyr Glu Gly Gly
1               5                   10

<210> SEQ ID NO 352
<211> LENGTH: 12
<212> TYPE: PRT
<213> ORGANISM: artificial sequence
<220> FEATURE:
<223> OTHER INFORMATION: Synthetic construct

<400> SEQUENCE: 352

Trp Pro Met His Pro Glu Lys Gly Ser Arg Trp Ser
1               5                   10

<210> SEQ ID NO 353
<211> LENGTH: 14
<212> TYPE: PRT
<213> ORGANISM: artificial sequence
<220> FEATURE:
<223> OTHER INFORMATION: Synthetic construct

<400> SEQUENCE: 353

Asp Ala Cys Ser Gly Asn Gly His Pro Asn Asn Cys Asp Arg
1               5                   10

<210> SEQ ID NO 354
<211> LENGTH: 14
<212> TYPE: PRT
<213> ORGANISM: artificial sequence
<220> FEATURE:
<223> OTHER INFORMATION: Synthetic construct

<400> SEQUENCE: 354
```

Asp His Cys Leu Gly Arg Gln Leu Gln Pro Val Cys Tyr Pro
1               5                   10

<210> SEQ ID NO 355
<211> LENGTH: 14
<212> TYPE: PRT
<213> ORGANISM: artificial sequence
<220> FEATURE:
<223> OTHER INFORMATION: Synthetic construct

<400> SEQUENCE: 355

Asp Trp Cys Asp Thr Ile Ile Pro Gly Arg Thr Cys His Gly
1               5                   10

<210> SEQ ID NO 356
<211> LENGTH: 12
<212> TYPE: PRT
<213> ORGANISM: artificial sequence
<220> FEATURE:
<223> OTHER INFORMATION: Synthetic construct

<400> SEQUENCE: 356

Ala Leu Pro Arg Ile Ala Asn Thr Trp Ser Pro Ser
1               5                   10

<210> SEQ ID NO 357
<211> LENGTH: 12
<212> TYPE: PRT
<213> ORGANISM: artificial sequence
<220> FEATURE:
<223> OTHER INFORMATION: Synthetic construct

<400> SEQUENCE: 357

Tyr Pro Ser Phe Ser Pro Thr Tyr Arg Pro Ala Phe
1               5                   10

<210> SEQ ID NO 358
<211> LENGTH: 20
<212> TYPE: PRT
<213> ORGANISM: artificial sequence
<220> FEATURE:
<223> OTHER INFORMATION: Synthetic construct

<400> SEQUENCE: 358

Ala His Pro Glu Ser Leu Gly Ile Lys Tyr Ala Leu Asp Gly Asn Ser
1               5                   10                  15

Asp Pro His Ala
            20

<210> SEQ ID NO 359
<211> LENGTH: 20
<212> TYPE: PRT
<213> ORGANISM: artificial sequence
<220> FEATURE:
<223> OTHER INFORMATION: Synthetic construct

<400> SEQUENCE: 359

Ala Ser Val Ser Asn Tyr Pro Pro Ile His His Leu Ala Thr Ser Asn
1               5                   10                  15

Thr Thr Val Asn
            20

<210> SEQ ID NO 360
<211> LENGTH: 14
<212> TYPE: PRT
<213> ORGANISM: artificial sequence

```
<220> FEATURE:
<223> OTHER INFORMATION: Synthetic construct

<400> SEQUENCE: 360

Asp Glu Cys Met Glu Pro Leu Asn Ala Ala His Cys Trp Arg
1               5                   10

<210> SEQ ID NO 361
<211> LENGTH: 14
<212> TYPE: PRT
<213> ORGANISM: artificial sequence
<220> FEATURE:
<223> OTHER INFORMATION: Synthetic construct

<400> SEQUENCE: 361

Asp Glu Cys Met His Gly Ser Asp Val Glu Phe Cys Thr Ser
1               5                   10

<210> SEQ ID NO 362
<211> LENGTH: 14
<212> TYPE: PRT
<213> ORGANISM: artificial sequence
<220> FEATURE:
<223> OTHER INFORMATION: Synthetic construct

<400> SEQUENCE: 362

Asp Leu Cys Ser Met Gln Met Met Asn Thr Gly Cys His Tyr
1               5                   10

<210> SEQ ID NO 363
<211> LENGTH: 14
<212> TYPE: PRT
<213> ORGANISM: artificial sequence
<220> FEATURE:
<223> OTHER INFORMATION: Synthetic construct

<400> SEQUENCE: 363

Asp Leu Cys Ser Ser Pro Ser Thr Trp Gly Ser Cys Ile Arg
1               5                   10

<210> SEQ ID NO 364
<211> LENGTH: 20
<212> TYPE: PRT
<213> ORGANISM: artificial sequence
<220> FEATURE:
<223> OTHER INFORMATION: Synthetic construct

<400> SEQUENCE: 364

Asp Pro Asn Glu Ser Asn Tyr Glu Asn Ala Thr Thr Val Ser Gln Pro
1               5                   10                  15

Thr Arg His Leu
            20

<210> SEQ ID NO 365
<211> LENGTH: 20
<212> TYPE: PRT
<213> ORGANISM: artificial sequence
<220> FEATURE:
<223> OTHER INFORMATION: Synthetic construct

<400> SEQUENCE: 365

Glu Pro Thr His Pro Thr Met Arg Ala Gln Met His Gln Ser Leu Arg
1               5                   10                  15

Ser Ser Ser Pro
            20
```

```
<210> SEQ ID NO 366
<211> LENGTH: 20
<212> TYPE: PRT
<213> ORGANISM: artificial sequence
<220> FEATURE:
<223> OTHER INFORMATION: Synthetic construct

<400> SEQUENCE: 366

Gly Asn Thr Asp Thr Thr Pro Pro Asn Ala Val Met Glu Pro Thr Val
1               5                   10                  15

Gln His Lys Trp
            20

<210> SEQ ID NO 367
<211> LENGTH: 15
<212> TYPE: PRT
<213> ORGANISM: artificial sequence
<220> FEATURE:
<223> OTHER INFORMATION: Synthetic construct

<400> SEQUENCE: 367

Asn Gly Pro Asp Met Val Gln Ser Val Gly Lys His Lys Asn Ser
1               5                   10                  15

<210> SEQ ID NO 368
<211> LENGTH: 15
<212> TYPE: PRT
<213> ORGANISM: artificial sequence
<220> FEATURE:
<223> OTHER INFORMATION: Synthetic construct

<400> SEQUENCE: 368

Asn Gly Pro Glu Val Arg Gln Ile Pro Ala Asn Phe Glu Lys Leu
1               5                   10                  15

<210> SEQ ID NO 369
<211> LENGTH: 20
<212> TYPE: PRT
<213> ORGANISM: artificial sequence
<220> FEATURE:
<223> OTHER INFORMATION: Synthetic construct

<400> SEQUENCE: 369

Asn Asn Thr Ser Ala Asp Asn Pro Pro Glu Thr Asp Ser Lys His His
1               5                   10                  15

Leu Ser Met Ser
            20

<210> SEQ ID NO 370
<211> LENGTH: 20
<212> TYPE: PRT
<213> ORGANISM: artificial sequence
<220> FEATURE:
<223> OTHER INFORMATION: Synthetic construct

<400> SEQUENCE: 370

Asn Asn Thr Trp Pro Glu Gly Ala Gly His Thr Met Pro Ser Thr Asn
1               5                   10                  15

Ile Arg Gln Ala
            20

<210> SEQ ID NO 371
<211> LENGTH: 20
<212> TYPE: PRT
<213> ORGANISM: artificial sequence
<220> FEATURE:
<223> OTHER INFORMATION: Synthetic construct
```

```
<400> SEQUENCE: 371

Asn Pro Thr Ala Thr Pro His Met Lys Asp Pro Met His Ser Asn Ala
1               5                   10                  15

His Ser Ser Ala
            20

<210> SEQ ID NO 372
<211> LENGTH: 20
<212> TYPE: PRT
<213> ORGANISM: artificial sequence
<220> FEATURE:
<223> OTHER INFORMATION: Synthetic construct

<400> SEQUENCE: 372

Asn Pro Thr Asp His Ile Pro Ala Asn Ser Thr Asn Ser Arg Val Ser
1               5                   10                  15

Lys Gly Asn Thr
            20

<210> SEQ ID NO 373
<211> LENGTH: 15
<212> TYPE: PRT
<213> ORGANISM: artificial sequence
<220> FEATURE:
<223> OTHER INFORMATION: Synthetic construct

<400> SEQUENCE: 373

Asn Pro Thr Asp Ser Thr His Met Met His Ala Arg Asn His Glu
1               5                   10                  15

<210> SEQ ID NO 374
<211> LENGTH: 14
<212> TYPE: PRT
<213> ORGANISM: artificial sequence
<220> FEATURE:
<223> OTHER INFORMATION: Synthetic construct

<400> SEQUENCE: 374

Gln His Cys Ile Thr Glu Arg Leu His Pro Pro Cys Thr Lys
1               5                   10

<210> SEQ ID NO 375
<211> LENGTH: 14
<212> TYPE: PRT
<213> ORGANISM: artificial sequence
<220> FEATURE:
<223> OTHER INFORMATION: Synthetic construct

<400> SEQUENCE: 375

Thr Pro Cys Ala Pro Ala Ser Phe Asn Pro His Cys Ser Arg
1               5                   10

<210> SEQ ID NO 376
<211> LENGTH: 14
<212> TYPE: PRT
<213> ORGANISM: artificial sequence
<220> FEATURE:
<223> OTHER INFORMATION: Synthetic construct

<400> SEQUENCE: 376

Thr Pro Cys Ala Thr Tyr Pro His Phe Ser Gly Cys Arg Ala
1               5                   10

<210> SEQ ID NO 377
<211> LENGTH: 20
```

```
<212> TYPE: PRT
<213> ORGANISM: artificial sequence
<220> FEATURE:
<223> OTHER INFORMATION: Synthetic construct

<400> SEQUENCE: 377

Trp Cys Thr Asp Phe Cys Thr Arg Ser Thr Pro Thr Ser Thr Ser Arg
1               5                   10                  15

Ser Thr Thr Ser
            20

<210> SEQ ID NO 378
<211> LENGTH: 20
<212> TYPE: PRT
<213> ORGANISM: artificial sequence
<220> FEATURE:
<223> OTHER INFORMATION: Synthetic construct

<400> SEQUENCE: 378

Ala Pro Pro Leu Lys Thr Tyr Met Gln Glu Arg Glu Leu Thr Met Ser
1               5                   10                  15

Gln Asn Lys Asp
            20

<210> SEQ ID NO 379
<211> LENGTH: 20
<212> TYPE: PRT
<213> ORGANISM: artificial sequence
<220> FEATURE:
<223> OTHER INFORMATION: Synthetic construct

<400> SEQUENCE: 379

Glu Pro Pro Thr Arg Thr Arg Val Asn Asn His Thr Val Thr Val Gln
1               5                   10                  15

Ala Gln Gln His
            20

<210> SEQ ID NO 380
<211> LENGTH: 14
<212> TYPE: PRT
<213> ORGANISM: artificial sequence
<220> FEATURE:
<223> OTHER INFORMATION: Synthetic construct

<400> SEQUENCE: 380

Gly Tyr Cys Leu Arg Gly Asp Glu Pro Ala Val Cys Ser Gly
1               5                   10

<210> SEQ ID NO 381
<211> LENGTH: 20
<212> TYPE: PRT
<213> ORGANISM: artificial sequence
<220> FEATURE:
<223> OTHER INFORMATION: Synthetic construct

<400> SEQUENCE: 381

Leu Ser Ser Lys Asp Phe Gly Val Thr Asn Thr Asp Gln Arg Thr Tyr
1               5                   10                  15

Asp Tyr Thr Thr
            20

<210> SEQ ID NO 382
<211> LENGTH: 14
<212> TYPE: PRT
<213> ORGANISM: artificial sequence
<220> FEATURE:
```

<223> OTHER INFORMATION: Synthetic construct

<400> SEQUENCE: 382

Asn Phe Cys Glu Thr Gln Leu Asp Leu Ser Val Cys Thr Val
1               5                   10

<210> SEQ ID NO 383
<211> LENGTH: 14
<212> TYPE: PRT
<213> ORGANISM: artificial sequence
<220> FEATURE:
<223> OTHER INFORMATION: Synthetic construct

<400> SEQUENCE: 383

Asn Thr Cys Gln Pro Thr Lys Asn Ala Thr Pro Cys Ser Ala
1               5                   10

<210> SEQ ID NO 384
<211> LENGTH: 20
<212> TYPE: PRT
<213> ORGANISM: artificial sequence
<220> FEATURE:
<223> OTHER INFORMATION: Synthetic construct

<400> SEQUENCE: 384

Pro Ser Glu Pro Glu Arg Arg Asp Arg Asn Ile Ala Ala Asn Ala Gly
1               5                   10                  15

Arg Phe Asn Thr
            20

<210> SEQ ID NO 385
<211> LENGTH: 18
<212> TYPE: PRT
<213> ORGANISM: artificial sequence
<220> FEATURE:
<223> OTHER INFORMATION: Synthetic construct

<400> SEQUENCE: 385

Thr His Asn Met Ser His Phe Pro Pro Ser Gly His Pro Lys Arg Thr
1               5                   10                  15

Ala Thr

<210> SEQ ID NO 386
<211> LENGTH: 14
<212> TYPE: PRT
<213> ORGANISM: artificial sequence
<220> FEATURE:
<223> OTHER INFORMATION: Synthetic construct

<400> SEQUENCE: 386

Thr Thr Cys Pro Thr Met Gly Thr Tyr His Val Cys Trp Leu
1               5                   10

<210> SEQ ID NO 387
<211> LENGTH: 20
<212> TYPE: PRT
<213> ORGANISM: artificial sequence
<220> FEATURE:
<223> OTHER INFORMATION: Synthetic construct

<400> SEQUENCE: 387

Tyr Cys Ala Asp His Thr Pro Asp Pro Ala Asn Pro Asn Lys Ile Cys
1               5                   10                  15

Gly Tyr Ser His
            20

```
<210> SEQ ID NO 388
<211> LENGTH: 20
<212> TYPE: PRT
<213> ORGANISM: artificial sequence
<220> FEATURE:
<223> OTHER INFORMATION: Synthetic construct

<400> SEQUENCE: 388

Ala Ala Asn Pro His Thr Glu Trp Asp Arg Asp Ala Phe Gln Leu Ala
1               5                   10                  15

Met Pro Pro Lys
            20

<210> SEQ ID NO 389
<211> LENGTH: 20
<212> TYPE: PRT
<213> ORGANISM: artificial sequence
<220> FEATURE:
<223> OTHER INFORMATION: Synthetic construct

<400> SEQUENCE: 389

Asp Leu His Pro Met Asp Pro Ser Asn Lys Arg Pro Asp Asn Pro Ser
1               5                   10                  15

Asp Leu His Thr
            20

<210> SEQ ID NO 390
<211> LENGTH: 14
<212> TYPE: PRT
<213> ORGANISM: artificial sequence
<220> FEATURE:
<223> OTHER INFORMATION: Synthetic construct

<400> SEQUENCE: 390

Glu Ser Cys Val Ser Asn Ala Leu Met Asn Gln Cys Ile Tyr
1               5                   10

<210> SEQ ID NO 391
<211> LENGTH: 20
<212> TYPE: PRT
<213> ORGANISM: artificial sequence
<220> FEATURE:
<223> OTHER INFORMATION: Synthetic construct

<400> SEQUENCE: 391

His Asn Lys Ala Asp Ser Trp Asp Pro Asp Leu Pro Pro His Ala Gly
1               5                   10                  15

Met Ser Leu Gly
            20

<210> SEQ ID NO 392
<211> LENGTH: 20
<212> TYPE: PRT
<213> ORGANISM: artificial sequence
<220> FEATURE:
<223> OTHER INFORMATION: Synthetic construct

<400> SEQUENCE: 392

Leu Asn Asp Gln Arg Lys Pro Gly Pro Pro Thr Met Pro Thr His Ser
1               5                   10                  15

Pro Ala Val Gly
            20

<210> SEQ ID NO 393
<211> LENGTH: 14
```

```
<212> TYPE: PRT
<213> ORGANISM: artificial sequence
<220> FEATURE:
<223> OTHER INFORMATION: Synthetic construct

<400> SEQUENCE: 393

Asn Thr Cys Ala Thr Ser Pro Asn Ser Tyr Thr Cys Ser Asn
1               5                   10

<210> SEQ ID NO 394
<211> LENGTH: 14
<212> TYPE: PRT
<213> ORGANISM: artificial sequence
<220> FEATURE:
<223> OTHER INFORMATION: Synthetic construct

<400> SEQUENCE: 394

Ser Asp Cys Thr Ala Gly Leu Val Pro Pro Leu Cys Ala Thr
1               5                   10

<210> SEQ ID NO 395
<211> LENGTH: 20
<212> TYPE: PRT
<213> ORGANISM: artificial sequence
<220> FEATURE:
<223> OTHER INFORMATION: Synthetic construct

<400> SEQUENCE: 395

Thr Ile Glu Ser Ser Gln His Ser Arg Thr His Gln Gln Asn Tyr Gly
1               5                   10                  15

Ser Thr Lys Thr
            20

<210> SEQ ID NO 396
<211> LENGTH: 20
<212> TYPE: PRT
<213> ORGANISM: artificial sequence
<220> FEATURE:
<223> OTHER INFORMATION: Synthetic construct

<400> SEQUENCE: 396

Val Gly Thr Met Lys Gln His Pro Thr Thr Thr Gln Pro Pro Arg Val
1               5                   10                  15

Ser Ala Thr Asn
            20

<210> SEQ ID NO 397
<211> LENGTH: 20
<212> TYPE: PRT
<213> ORGANISM: artificial sequence
<220> FEATURE:
<223> OTHER INFORMATION: Synthetic construct

<400> SEQUENCE: 397

Tyr Ser Glu Thr Pro Asn Asp Gln Lys Pro Asn Pro His Tyr Lys Val
1               5                   10                  15

Ser Gly Thr Lys
            20

<210> SEQ ID NO 398
<211> LENGTH: 12
<212> TYPE: PRT
<213> ORGANISM: Artificial sequence
<220> FEATURE:
<223> OTHER INFORMATION: Polymethylmethacrylate binding peptides

<400> SEQUENCE: 398
```

```
Ile Pro Trp Trp Asn Ile Arg Ala Pro Leu Asn Ala
1               5                   10
```

<210> SEQ ID NO 399
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 399

```
Thr Ala Val Met Asn Val Val Asn Asn Gln Leu Ser
1               5                   10
```

<210> SEQ ID NO 400
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 400

```
Val Pro Trp Trp Ala Pro Ser Lys Leu Ser Met Gln
1               5                   10
```

<210> SEQ ID NO 401
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 401

```
Met Val Met Ala Pro His Thr Pro Arg Ala Arg Ser
1               5                   10
```

<210> SEQ ID NO 402
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 402

```
Thr Tyr Pro Asn Trp Ala His Leu Leu Ser His Tyr
1               5                   10
```

<210> SEQ ID NO 403
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 403

```
Thr Pro Trp Trp Arg Ile Thr
1               5
```

<210> SEQ ID NO 404
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 404

```
Asp Leu Thr Leu Pro Phe His
```

```
1               5
```

<210> SEQ ID NO 405
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 405

```
Gly Thr Ser Ile Pro Ala Met
1               5
```

<210> SEQ ID NO 406
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 406

```
His His Lys His Val Val Ala
1               5
```

<210> SEQ ID NO 407
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 407

```
His His His Lys His Phe Met
1               5
```

<210> SEQ ID NO 408
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 408

```
His His His Arg His Gln Gly
1               5
```

<210> SEQ ID NO 409
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 409

```
His His Trp His Ala Pro Arg
1               5
```

<210> SEQ ID NO 410
<211> LENGTH: 12
<212> TYPE: PRT
<213> ORGANISM: Artificial Sequence
<220> FEATURE:
<223> OTHER INFORMATION: Shampoo-resistant, PMMA-binding peptide

<400> SEQUENCE: 410

```
Ala Pro Trp His Leu Ser Ser Gln Tyr Ser Gly Thr
1               5                   10
```

<210> SEQ ID NO 411
<211> LENGTH: 14
<212> TYPE: PRT
<213> ORGANISM: Artificial Sequence
<220> FEATURE:
<223> OTHER INFORMATION: Shampoo-resistant PMMA-binding peptide

<400> SEQUENCE: 411

Gly Tyr Cys Leu Arg Val Asp Glu Pro Thr Val Cys Ser Gly
1               5                   10

<210> SEQ ID NO 412
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 412

His Ile His Pro Ser Asp Asn Phe Pro His Lys Asn Arg Thr His
1               5                   10                  15

<210> SEQ ID NO 413
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 413

His Thr His His Asp Thr His Lys Pro Trp Pro Thr Asp Asp His Arg
1               5                   10                  15

Asn Ser Ser Val
            20

<210> SEQ ID NO 414
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 414

Pro Glu Asp Arg Pro Ser Arg Thr Asn Ala Leu His His Asn Ala His
1               5                   10                  15

His His Asn Ala
            20

<210> SEQ ID NO 415
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 415

Thr Pro His Asn His Ala Thr Thr Asn His His Ala Gly Lys Lys
1               5                   10                  15

<210> SEQ ID NO 416
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 416

```
Glu Met Val Lys Asp Ser Asn Gln Arg Asn Thr Arg Ile Ser Ser
1               5                   10                  15
```

<210> SEQ ID NO 417
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 417

```
His Tyr Ser Arg Tyr Asn Pro Gly Pro His Pro Leu
1               5                   10
```

<210> SEQ ID NO 418
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 418

```
Ile Asp Thr Phe Tyr Met Ser Thr Met Ser His Ser
1               5                   10
```

<210> SEQ ID NO 419
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 419

```
Pro Met Lys Glu Ala Thr His Pro Val Pro Pro His Lys His Ser Glu
1               5                   10                  15

Thr Pro Thr Ala
            20
```

<210> SEQ ID NO 420
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 420

```
Tyr Gln Thr Ser Ser Pro Ala Lys Gln Ser Val Gly
1               5                   10
```

<210> SEQ ID NO 421
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 421

```
His Leu Pro Ser Tyr Gln Ile Thr Gln Thr His Ala Gln Tyr Arg
1               5                   10                  15
```

<210> SEQ ID NO 422
<211> LENGTH: 20
<212> TYPE: PRT
<213> ORGANISM: Artificial Sequence
<220> FEATURE:
<223> OTHER INFORMATION: Shampoo-resistant PMMA-binding peptide -continued

```
<400> SEQUENCE: 422

Thr Thr Pro Lys Thr Thr Tyr His Gln Ser Arg Ala Pro Val Thr Ala
1               5                   10                  15

Met Ser Glu Val
            20

<210> SEQ ID NO 423
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 423

Asp Arg Ile His His Lys Ser His His Val Thr Thr Asn His Phe
1               5                   10                  15

<210> SEQ ID NO 424
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 424

Trp Ala Pro Glu Lys Asp Tyr Met Gln Leu Met Lys
1               5                   10

<210> SEQ ID NO 425
<211> LENGTH: 12
<212> TYPE: PRT
<213> ORGANISM: Artificial sequence
<220> FEATURE:
<223> OTHER INFORMATION: Polypropylene-binding peptides

<400> SEQUENCE: 425

Thr Ser Asp Ile Lys Ser Arg Ser Pro His His Arg
1               5                   10

<210> SEQ ID NO 426
<211> LENGTH: 12
<212> TYPE: PRT
<213> ORGANISM: Artificial Sequence
<220> FEATURE:
<223> OTHER INFORMATION: Polypropylenebinding peptide

<400> SEQUENCE: 426

His Thr Gln Asn Met Arg Met Tyr Glu Pro Trp Phe
1               5                   10

<210> SEQ ID NO 427
<211> LENGTH: 7
<212> TYPE: PRT
<213> ORGANISM: Artificial Sequence
<220> FEATURE:
<223> OTHER INFORMATION: Polypropylene-binding peptide

<400> SEQUENCE: 427

Leu Pro Pro Gly Ser Leu Ala
1               5

<210> SEQ ID NO 428
<211> LENGTH: 12
<212> TYPE: PRT
<213> ORGANISM: Artificial Sequence
<220> FEATURE:
<223> OTHER INFORMATION: Polypropylene-binding peptide
```

```
<400> SEQUENCE: 428

Met Pro Ala Val Met Ser Ser Ala Gln Val Pro Arg
1               5                   10

<210> SEQ ID NO 429
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 429

Asn Gln Ser Phe Leu Pro Leu Asp Phe Pro Phe Arg
1               5                   10

<210> SEQ ID NO 430
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 430

Ser Ile Leu Ser Thr Met Ser Pro His Gly Ala Thr
1               5                   10

<210> SEQ ID NO 431
<211> LENGTH: 12
<212> TYPE: PRT
<213> ORGANISM: Artificial Sequence
<220> FEATURE:
<223> OTHER INFORMATION: Polypropylenebinding peptide

<400> SEQUENCE: 431

Ser Met Lys Tyr Ser His Ser Thr Ala Pro Ala Leu
1               5                   10

<210> SEQ ID NO 432
<211> LENGTH: 12
<212> TYPE: PRT
<213> ORGANISM: Artificial sequence
<220> FEATURE:
<223> OTHER INFORMATION: Polytetrafluoroethylene-binding peptides

<400> SEQUENCE: 432

Glu Ser Ser Tyr Ser Trp Ser Pro Ala Arg Leu Ser
1               5                   10

<210> SEQ ID NO 433
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 433

Gly Pro Leu Lys Leu Leu His Ala Trp Trp Gln Pro
1               5                   10

<210> SEQ ID NO 434
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 434
```

Asn Ala Leu Thr Arg Pro Val
1               5

<210> SEQ ID NO 435
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 435

Ser Ala Pro Ser Ser Lys Asn
1               5

<210> SEQ ID NO 436
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 436

Ser Val Ser Val Gly Met Lys Pro Ser Pro Arg Pro
1               5                   10

<210> SEQ ID NO 437
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 437

Ser Tyr Tyr Ser Leu Pro Pro Ile Phe His Ile Pro
1               5                   10

<210> SEQ ID NO 438
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 438

Thr Phe Thr Pro Tyr Ser Ile Thr His Ala Leu Leu
1               5                   10

<210> SEQ ID NO 439
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 439

Thr Met Gly Phe Thr Ala Pro Arg Phe Pro His Tyr
1               5                   10

<210> SEQ ID NO 440
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 440

Thr Asn Pro Phe Pro Pro Pro Pro Ser Ser Pro Ala

```
1               5                   10
```

<210> SEQ ID NO 441
<211> LENGTH: 12
<212> TYPE: PRT
<213> ORGANISM: Artificial sequence
<220> FEATURE:
<223> OTHER INFORMATION: Polyethylene-binding peptides

<400> SEQUENCE: 441

```
His Asn Lys Ser Ser Pro Leu Thr Ala Ala Leu Pro
1               5                   10
```

<210> SEQ ID NO 442
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 442

```
Leu Pro Pro Trp Lys His Lys Thr Ser Gly Val Ala
1               5                   10
```

<210> SEQ ID NO 443
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 443

```
Leu Pro Trp Trp Leu Arg Asp Ser Tyr Leu Leu Pro
1               5                   10
```

<210> SEQ ID NO 444
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 444

```
Val Pro Trp Trp Lys His Pro Pro Leu Pro Val Pro
1               5                   10
```

<210> SEQ ID NO 445
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 445

```
His His Lys Gln Trp His Asn His Pro His His Ala
1               5                   10
```

<210> SEQ ID NO 446
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 446

```
His Ile Phe Ser Ser Trp His Gln Met Trp His Arg
1               5                   10
```

<210> SEQ ID NO 447
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 447

Trp Pro Ala Trp Lys Thr His Pro Ile Leu Arg Met
1               5                   10

<210> SEQ ID NO 448
<211> LENGTH: 7
<212> TYPE: PRT
<213> ORGANISM: Artificial sequence
<220> FEATURE:
<223> OTHER INFORMATION: Nylon-binding peptides

<400> SEQUENCE: 448

Lys Thr Pro Pro Thr Arg Pro
1               5

<210> SEQ ID NO 449
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 449

Val Ile Asn Pro Asn Leu Asp
1               5

<210> SEQ ID NO 450
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 450

Lys Val Trp Ile Val Ser Thr
1               5

<210> SEQ ID NO 451
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 451

Ala Glu Pro Val Ala Met Leu
1               5

<210> SEQ ID NO 452
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 452

Ala Glu Leu Val Ala Met Leu
1               5

<210> SEQ ID NO 453

```
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 453

His Ser Leu Arg Leu Asp Trp
1               5

<210> SEQ ID NO 454
<211> LENGTH: 13
<212> TYPE: PRT
<213> ORGANISM: Artificial sequence
<220> FEATURE:
<223> OTHER INFORMATION: Polystyrene-binding peptide

<400> SEQUENCE: 454

Thr Ser Thr Ala Ser Pro Thr Met Gln Ser Lys Ile Arg
1               5                   10

<210> SEQ ID NO 455
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 455

Lys Arg Asn His Trp Gln Arg Met His Leu Ser Ala
1               5                   10

<210> SEQ ID NO 456
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 456

Ser His Ala Thr Pro Pro Gln Gly Leu Gly Pro Gln
1               5                   10

<210> SEQ ID NO 457
<211> LENGTH: 20
<212> TYPE: PRT
<213> ORGANISM: artificial sequence
<220> FEATURE:
<223> OTHER INFORMATION: cellulose acetate-binding peptide

<400> SEQUENCE: 457

Ala Thr Thr Pro Pro Ser Gly Lys Ala Ala His Ser Ala Ala Arg
1               5                   10                  15

Gln Lys Gly Asn
            20

<210> SEQ ID NO 458
<211> LENGTH: 15
<212> TYPE: PRT
<213> ORGANISM: artificial sequence
<220> FEATURE:
<223> OTHER INFORMATION: cellulose acetate-binding peptide

<400> SEQUENCE: 458

Asp Thr Ile His Pro Asn Lys Met Lys Ser Pro Ser Ser Pro Leu
1               5                   10                  15
```

```
<210> SEQ ID NO 459
<211> LENGTH: 20
<212> TYPE: PRT
<213> ORGANISM: artificial sequence
<220> FEATURE:
<223> OTHER INFORMATION: cellulose aceteate-binding peptide

<400> SEQUENCE: 459

Asn Gly Asn Asn His Thr Asp Ile Pro Asn Arg Ser Ser Tyr Thr Gly
1               5                   10                  15

Gly Ser Phe Ala
            20

<210> SEQ ID NO 460
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 460

Met Pro Pro Pro Leu Met Gln
1               5

<210> SEQ ID NO 461
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 461

Phe His Glu Asn Trp Pro Ser
1               5

<210> SEQ ID NO 462
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 462

Arg Thr Ala Pro Thr Thr Pro Leu Leu Leu Ser Leu
1               5                   10

<210> SEQ ID NO 463
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 463

Trp His Leu Ser Trp Ser Pro Val Pro Leu Pro Thr
1               5                   10

<210> SEQ ID NO 464
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 464

Pro His Ala Arg Leu Val Gly
1               5
```

```
<210> SEQ ID NO 465
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 465

Asn Ile Pro Tyr His His Pro
1               5

<210> SEQ ID NO 466
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 466

Thr Thr Met Pro Ala Ile Pro
1               5

<210> SEQ ID NO 467
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 467

His Asn Leu Pro Pro Arg Ser
1               5

<210> SEQ ID NO 468
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 468

Ala His Lys Thr Gln Met Gly Val Arg Gln Pro Ala
1               5                   10

<210> SEQ ID NO 469
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 469

Ala Asp Asn Val Gln Met Gly Val Ser His Thr Pro
1               5                   10

<210> SEQ ID NO 470
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 470

Ala His Asn Ala Gln Met Gly Val Ser His Pro Pro
1               5                   10

<210> SEQ ID NO 471
```

```
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 471

Ala Asp Tyr Val Gly Met Gly Val Ser His Arg Pro
1               5                   10

<210> SEQ ID NO 472
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 472

Ser Val Ser Val Gly Met Lys Pro Ser Pro Arg Pro
1               5                   10

<210> SEQ ID NO 473
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 473

Tyr Pro Asn Thr Ala Leu Val
1               5

<210> SEQ ID NO 474
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 474

Val Ala Thr Arg Ile Val Ser
1               5

<210> SEQ ID NO 475
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 475

His Ser Leu Lys Asn Ser Met Leu Thr Val Met Ala
1               5                   10

<210> SEQ ID NO 476
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 476

Asn Tyr Pro Thr Gln Ala Pro
1               5

<210> SEQ ID NO 477
<211> LENGTH: 7
<212> TYPE: PRT
```

```
<213> ORGANISM: Artificial Sequence
<220> FEATURE:
<223> OTHER INFORMATION: Pigment-binding peptide

<400> SEQUENCE: 477

Lys Cys Cys Tyr Ser Val Gly
1               5

<210> SEQ ID NO 478
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 478

Arg His Asp Leu Asn Thr Trp Leu Pro Pro Val Lys
1               5                   10

<210> SEQ ID NO 479
<211> LENGTH: 12
<212> TYPE: PRT
<213> ORGANISM: artificial sequence
<220> FEATURE:
<223> OTHER INFORMATION: synthetic construct

<400> SEQUENCE: 479

Glu Ile Ser Leu Pro Ala Lys Leu Pro Ser Ala Ser
1               5                   10

<210> SEQ ID NO 480
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 480

Ser Asp Tyr Val Gly Met Arg Pro Ser Pro Arg His
1               5                   10

<210> SEQ ID NO 481
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 481

Ser Asp Tyr Val Gly Met Arg Leu Ser Pro Ser Gln
1               5                   10

<210> SEQ ID NO 482
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 482

Ser Val Ser Val Gly Ile Gln Pro Ser Pro Arg Pro
1               5                   10

<210> SEQ ID NO 483
<211> LENGTH: 12
<212> TYPE: PRT
<213> ORGANISM: Artificial Sequence
<220> FEATURE:
```

<223> OTHER INFORMATION: Pigment-binding peptide

<400> SEQUENCE: 483

Tyr Val Ser Val Gly Ile Lys Pro Ser Pro Arg Pro
1               5                   10

<210> SEQ ID NO 484
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 484

Tyr Val Cys Glu Gly Ile His Pro Cys Pro Arg Pro
1               5                   10

<210> SEQ ID NO 485
<211> LENGTH: 12
<212> TYPE: PRT
<213> ORGANISM: artificial sequence
<220> FEATURE:
<223> OTHER INFORMATION: Iron oxide-binding peptide

<400> SEQUENCE: 485

Trp Ala Pro Glu Lys Asp Tyr Met Gln Leu Met Lys
1               5                   10

<210> SEQ ID NO 486
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 486

Cys Pro Leu Asp Thr Pro Thr His Lys Thr Lys His Glu Tyr Lys Thr
1               5                   10                  15

Arg Cys Arg His
            20

<210> SEQ ID NO 487
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 487

Asp His Asp His Pro Arg Leu His Lys Arg Gln Glu Lys Ser Glu His
1               5                   10                  15

Leu His

<210> SEQ ID NO 488
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 488

Asp Ser His His Asn His Lys Gln Asp Ser Arg Pro Gln His Arg
1               5                   10                  15

Lys Thr Pro Asn
            20

```
<210> SEQ ID NO 489
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 489

Glu Gly Gly Asn Ala Pro His His Lys Pro His His Arg Lys His
1               5                   10                  15

<210> SEQ ID NO 490
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 490

His Asp Ser His Arg Pro Leu Thr Gln His Gly His Arg His Ser His
1               5                   10                  15

Val Pro

<210> SEQ ID NO 491
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 491

His Asp Ser Asn His Cys Ser His Ser Thr Arg Arg Pro Asn Cys Ala
1               5                   10                  15

Arg Thr

<210> SEQ ID NO 492
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 492

Ala Thr Arg Val Asp Asn Thr Pro Ala Ser Asn Pro Pro Ser Leu
1               5                   10                  15

<210> SEQ ID NO 493
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 493

Asp Gly Ile Lys Pro Phe His Leu Met Thr Pro Thr Leu Ala Asn
1               5                   10                  15

<210> SEQ ID NO 494
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 494

Asp Ile Thr Pro Pro Gly Ser Thr His His Arg Lys Pro His Arg His
```

```
1               5                  10                  15
Gln His

<210> SEQ ID NO 495
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 495

Asp Asn Leu Trp Pro Gln Pro Leu Asn Val Glu Asp Asp Arg Tyr
1               5                  10                  15

<210> SEQ ID NO 496
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 496

Glu Asn Glu Lys His Arg His Asn Thr His Glu Ala Leu His Ser His
1               5                  10                  15

Phe Lys

<210> SEQ ID NO 497
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 497

Gly Ala Ile Trp Pro Ala Ser Ser Ala Leu Met Thr Glu His Asn Pro
1               5                  10                  15

Thr Asp Asn His
            20

<210> SEQ ID NO 498
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 498

Gly Asp Thr Asn Gln Asp Thr Val Met Trp Tyr Tyr Thr Val Asn
1               5                  10                  15

<210> SEQ ID NO 499
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 499

His Asn Gly Pro Tyr Gly Met Leu Ser Thr Gly Lys Ile His Phe
1               5                  10                  15

<210> SEQ ID NO 500
<211> LENGTH: 15
<212> TYPE: PRT
<213> ORGANISM: artificial sequence
<220> FEATURE:
```

-continued

<223> OTHER INFORMATION: Iron oxide-binding peptide

<400> SEQUENCE: 500

Leu Asp Gly Gly Tyr Arg Asp Thr Pro Asp Asn Tyr Leu Lys Gly
1               5                   10                  15

<210> SEQ ID NO 501
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 501

Leu His Thr Lys Thr Glu Asn Ser His Thr Asn Met Lys Thr Thr
1               5                   10                  15

<210> SEQ ID NO 502
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 502

Asn Ala Gln Tyr Asp Pro Pro Thr Leu Asn Lys Gly Ala Val Arg Lys
1               5                   10                  15

Ala Ala Ser Thr
            20

<210> SEQ ID NO 503
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 503

Asn Gly Asn Asn His Thr Asp Ile Pro Asn Arg Ser Ser Tyr Thr
1               5                   10                  15

<210> SEQ ID NO 504
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 504

Gln Ser Thr Asn His His His Pro His Ala Lys His Pro Arg Val Asn
1               5                   10                  15

Thr His

<210> SEQ ID NO 505
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 505

Ser Asn Asn Asp Tyr Val Gly Thr Tyr Pro Ala Thr Ala Ile Gln
1               5                   10                  15

<210> SEQ ID NO 506
<211> LENGTH: 15

```
<212> TYPE: PRT
<213> ORGANISM: artificial sequence
<220> FEATURE:
<223> OTHER INFORMATION: Iron oxide-binding peptide

<400> SEQUENCE: 506

Ser Thr Gln His Asn Leu His Asp Arg Asn Ile Tyr Phe Val Ser
1               5                   10                  15

<210> SEQ ID NO 507
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 507

Thr Ala Asn Asn Lys Thr Pro Ala Gly Ala Pro Asn Ala Ala Val Gly
1               5                   10                  15

Leu Ala Gln Arg
            20

<210> SEQ ID NO 508
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 508

Thr Glu Pro Thr Arg Ile Ser Asn Tyr Arg Ser Ile Pro Asn Asp
1               5                   10                  15

<210> SEQ ID NO 509
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 509

Thr His Asn Pro Arg Glu His Ala Arg His His His Asn Glu Tyr
1               5                   10                  15

Lys His

<210> SEQ ID NO 510
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 510

Thr His Pro Pro Cys Trp Tyr Glu Thr Asn Cys Ile Val Gln Glu
1               5                   10                  15

<210> SEQ ID NO 511
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 511

Thr Thr Asn Pro His Lys Pro Ala Ser His His His Asp His Arg Pro
1               5                   10                  15
```

-continued

```
Ala Leu Arg His
        20

<210> SEQ ID NO 512
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 512

Trp Leu Val Ala Asp Asn Ala Thr Asp Gly His Ser His Gln Lys
1               5                   10                  15

<210> SEQ ID NO 513
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 513

Tyr Thr Asp Ser Met Ser Asp Gln Thr Pro Glu Phe Ala Lys Tyr
1               5                   10                  15

<210> SEQ ID NO 514
<211> LENGTH: 7
<212> TYPE: PRT
<213> ORGANISM: Artificial Sequence
<220> FEATURE:
<223> OTHER INFORMATION: Print Media Binding Peptide

<400> SEQUENCE: 514

Ser Ile Leu Pro Tyr Pro Tyr
1               5

<210> SEQ ID NO 515
<211> LENGTH: 7
<212> TYPE: PRT
<213> ORGANISM: Artificial Sequence
<220> FEATURE:
<223> OTHER INFORMATION: Cotton Binding Peptide

<400> SEQUENCE: 515

Ser Thr Ala Ser Tyr Thr Arg
1               5

<210> SEQ ID NO 516
<211> LENGTH: 7
<212> TYPE: PRT
<213> ORGANISM: Artificial Sequence
<220> FEATURE:
<223> OTHER INFORMATION: Polyester/Cotton Binding Peptide

<400> SEQUENCE: 516

Leu Pro Val Arg Pro Trp Thr
1               5

<210> SEQ ID NO 517
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 517

Gly Asn Thr Pro Ser Arg Ala
1               5
```

-continued

<210> SEQ ID NO 518
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 518

His Ala Ile Tyr Pro Arg His
1               5

<210> SEQ ID NO 519
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 519

Tyr Gln Asp Ser Ala Lys Thr
1               5

<210> SEQ ID NO 520
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 520

Val Pro Arg Val Thr Ser Ile
1               5

<210> SEQ ID NO 521
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 521

Met Ala Asn His Asn Leu Ser
1               5

<210> SEQ ID NO 522
<211> LENGTH: 7
<212> TYPE: PRT
<213> ORGANISM: Artificial Sequence
<220> FEATURE:
<223> OTHER INFORMATION: Pigment Binding and Cellulose Binding Peptide

<400> SEQUENCE: 522

Phe His Glu Asn Trp Pro Ser
1               5

<210> SEQ ID NO 523
<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 523

Thr His Lys Thr Ser Thr Gln Arg Leu Leu Ala Ala
1               5                   10

```
<210> SEQ ID NO 524
<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 524

Lys Cys Cys Tyr Val Asn Val Gly Ser Val Phe Ser
1               5                   10

<210> SEQ ID NO 525
<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 525

Ala His Met Gln Phe Arg Thr Ser Leu Thr Pro His
1               5                   10

<210> SEQ ID NO 526
<211> LENGTH: 27
<212> TYPE: PRT
<213> ORGANISM: artificial sequence
<220> FEATURE:
<223> OTHER INFORMATION: Clay-binding peptide

<400> SEQUENCE: 526

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 527
<211> LENGTH: 27
<212> TYPE: PRT
<213> ORGANISM: artificial sequence
<220> FEATURE:
<223> OTHER INFORMATION: Clay-binding peptide

<400> SEQUENCE: 527

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 528
<211> LENGTH: 27
<212> TYPE: PRT
<213> ORGANISM: artificial sequence
<220> FEATURE:
<223> OTHER INFORMATION: Clay-binding peptide

<400> SEQUENCE: 528

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 529
<211> LENGTH: 27
<212> TYPE: PRT
<213> ORGANISM: artificial sequence
<220> FEATURE:
<223> OTHER INFORMATION: Clay-binding peptide
```

-continued

<400> SEQUENCE: 529

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 530
<211> LENGTH: 22
<212> TYPE: PRT
<213> ORGANISM: artificial sequence
<220> FEATURE:
<223> OTHER INFORMATION: Clay-binding peptide

<400> SEQUENCE: 530

Val Gly Arg His His Ser Lys Ala Lys Gln Lys Arg Pro His Gly Gly
1               5                   10                  15

Lys Gly Gln Asn Lys Asn
            20

<210> SEQ ID NO 531
<211> LENGTH: 22
<212> TYPE: PRT
<213> ORGANISM: artificial sequence
<220> FEATURE:
<223> OTHER INFORMATION: Clay-binding peptide

<400> SEQUENCE: 531

Val Gly Arg His His Pro Lys Ala Lys Gln Lys Arg Pro His Gly Gly
1               5                   10                  15

Lys Gly Gln Asn Lys Asn
            20

<210> SEQ ID NO 532
<211> LENGTH: 17
<212> TYPE: PRT
<213> ORGANISM: artificial sequence
<220> FEATURE:
<223> OTHER INFORMATION: Clay-binding peptide

<400> SEQUENCE: 532

Gly Arg Arg Pro Arg Ala Arg Gly Arg Ser Arg Arg Gly Ser Thr Lys
1               5                   10                  15

Thr

<210> SEQ ID NO 533
<211> LENGTH: 19
<212> TYPE: PRT
<213> ORGANISM: artificial sequence
<220> FEATURE:
<223> OTHER INFORMATION: Clay-binding peptide

<400> SEQUENCE: 533

Leu Gly Val Ile Arg Asn His Val Val Arg Gly Arg Arg His His Gln
1               5                   10                  15

His Val Arg

<210> SEQ ID NO 534
<211> LENGTH: 27
<212> TYPE: PRT
<213> ORGANISM: artificial sequence
<220> FEATURE:
<223> OTHER INFORMATION: Clay-binding peptide

<400> SEQUENCE: 534

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 535
<211> LENGTH: 27
<212> TYPE: PRT
<213> ORGANISM: artificial sequence
<220> FEATURE:
<223> OTHER INFORMATION: Clay-binding peptide

<400> SEQUENCE: 535

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 536
<211> LENGTH: 27
<212> TYPE: PRT
<213> ORGANISM: artificial sequence
<220> FEATURE:
<223> OTHER INFORMATION: Clay-binding peptide

<400> SEQUENCE: 536

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 537
<211> LENGTH: 27
<212> TYPE: PRT
<213> ORGANISM: artificial sequence
<220> FEATURE:
<223> OTHER INFORMATION: Clay-binding peptide

<400> SEQUENCE: 537

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25

<210> SEQ ID NO 538
<211> LENGTH: 27
<212> TYPE: PRT
<213> ORGANISM: artificial sequence
<220> FEATURE:
<223> OTHER INFORMATION: Clay-binding peptide

<400> SEQUENCE: 538

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 539
<211> LENGTH: 27
<212> TYPE: PRT
<213> ORGANISM: artificial sequence
<220> FEATURE:
<223> OTHER INFORMATION: Clay-binding peptide

<400> SEQUENCE: 539

```
His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 540
<211> LENGTH: 27
<212> TYPE: PRT
<213> ORGANISM: artificial sequence
<220> FEATURE:
<223> OTHER INFORMATION: Clay-binding peptide

<400> SEQUENCE: 540

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys
            20                  25

<210> SEQ ID NO 541
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 541

Arg Asn Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 542
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 542

Arg Asn Asn Lys Gly Ser Lys Lys Val Asp Asp Lys Arg Arg Lys Thr
1               5                   10                  15

Val His Asn Thr Lys Ser Arg Ala Lys His Ser
            20                  25

<210> SEQ ID NO 543
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 543

Arg Asp Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 544
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 544
```

Arg Asn Asn Lys Gly Ser Lys Val Asp Asp Lys Arg Arg Lys Thr
1               5                   10                  15

Val His Ser Thr Lys Ser Arg Ala Lys Tyr Ser
            20                  25

<210> SEQ ID NO 545
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 545

Arg Asn Asn Lys Gly Ser Arg Lys Val Asp Asp Lys Arg Arg Lys Thr
1               5                   10                  15

Val His Asn Thr Lys Ser Arg Ala Lys Tyr Ser
            20                  25

<210> SEQ ID NO 546
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 546

Arg Asn Asn Lys Gly Ser Lys Lys Ala Asp Asp Lys Arg Arg Lys Thr
1               5                   10                  15

Val His Ser Thr Lys Ser Arg Ala Lys Tyr Ser
            20                  25

<210> SEQ ID NO 547
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 547

Arg Asn Asn Lys Gly Ser Lys Lys Val Asp Lys Arg Arg Lys Ala
1               5                   10                  15

Val His Asn Lys Lys Ser Arg Ala Lys Tyr Ser
            20                  25

<210> SEQ ID NO 548
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 548

Arg Asn Asn Lys Gly Ser Lys Lys Val Asp Asp Lys Arg Arg Lys Thr
1               5                   10                  15

Val His Asn Thr Arg Ser Arg Ala Lys Tyr Ser
            20                  25

<210> SEQ ID NO 549
<211> LENGTH: 27
<212> TYPE: PRT
<213> ORGANISM: artificial sequence
<220> FEATURE:
<223> OTHER INFORMATION: Calcium carbonate binding peptide

```
<400> SEQUENCE: 549

Arg Asn Asn Lys Gly Ser Lys Lys Val Asp Asp Lys Arg Arg Lys Thr
1               5                   10                  15

Val His Asn Thr Lys Ser Arg Ala Lys Phe Ser
            20                  25

<210> SEQ ID NO 550
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 550

Gln Arg Arg Lys Leu Arg His Pro Lys Glu Lys Trp Phe Gly Trp Ser
1               5                   10                  15

Glu Lys Lys Val Ile Lys Lys Trp Ser Arg Lys
            20                  25

<210> SEQ ID NO 551
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (23)..(23)
<223> OTHER INFORMATION: Xaa = any naturally occurring amino acid

<400> SEQUENCE: 551

Gln Arg Arg Lys Phe Arg His Pro Lys Glu Lys Trp Phe Gly Trp Ser
1               5                   10                  15

Glu Lys Lys Val Ile Lys Xaa Asn Gly Arg Pro
            20                  25

<210> SEQ ID NO 552
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 552

His Lys Arg Leu Val Gln Asn Lys Pro His Arg Thr Arg Lys Ile Glu
1               5                   10                  15

Gly Trp Ile Lys His Met Val Lys Arg Gln His
            20                  25

<210> SEQ ID NO 553
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 553

Thr Arg Gly His Ile Met Arg Pro Cys Trp Ile Gly Ala Met Lys Gln
1               5                   10                  15

Gly Val Lys Lys Lys Arg Thr Pro Gly Trp Arg
            20                  25
```

<210> SEQ ID NO 554
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 554

Trp Lys Val Lys Arg Arg Met Val Thr Arg Thr Tyr Glu Phe Met Gly
1               5                   10                  15

Lys Lys Pro Cys Met Met Leu Thr Lys Arg Leu
            20                  25

<210> SEQ ID NO 555
<211> LENGTH: 26
<212> TYPE: PRT
<213> ORGANISM: artificial sequence
<220> FEATURE:
<223> OTHER INFORMATION: Calcium carbonate binding peptide

<400> SEQUENCE: 555

Lys Lys Ser Asn Lys Gly His His Ser Lys Ala Lys Gln Lys Arg Pro
1               5                   10                  15

His Gly Gly Lys Ala Gln Asn Lys Asn Thr
            20                  25

<210> SEQ ID NO 556
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 556

Arg Ala His Lys Glu Arg Phe Val Val Arg Gln Ile Gly Arg Ser Gln
1               5                   10                  15

Gly Tyr Lys Thr Trp Gln Cys Val Arg Val Ala
            20                  25

<210> SEQ ID NO 557
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 557

Ser Gln Lys Pro Lys Gly His Lys Val Lys Val Val Lys Leu Cys
1               5                   10                  15

Lys Arg Pro Tyr Trp Arg Met Leu Asn Thr Ala
            20                  25

<210> SEQ ID NO 558
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (11)..(11)
<223> OTHER INFORMATION: Xaa = any naturally occurring amino acid

```
<400> SEQUENCE: 558

Asn His Gly Cys Pro Val Asn Trp Lys Val Xaa Asn Pro Pro Arg Gly
1               5                   10                  15

Trp Gln Arg Leu Asn His Cys Lys Trp Trp Asn
            20                  25

<210> SEQ ID NO 559
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 559

Arg Asn Ser Arg His Lys Glu Trp Arg Arg Tyr Lys Arg Thr His Val
1               5                   10                  15

His Ser His Glu Phe Tyr His Val Glu Cys Trp
            20                  25

<210> SEQ ID NO 560
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 560

His Arg Ser Glu Lys Pro Lys Asn Val Asn Tyr Lys Arg Gly Tyr Trp
1               5                   10                  15

Glu Arg Gly Asn Gln Lys Lys His Gly Pro Gly
            20                  25

<210> SEQ ID NO 561
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 561

His Glu Arg Thr Arg Arg Gly Lys Pro Asp Arg Gln Lys Thr Thr His
1               5                   10                  15

Glu Lys Arg Arg Gln Gly Leu Trp Ile Phe Met
            20                  25

<210> SEQ ID NO 562
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 562

Pro Trp Gly Thr Asn Lys Arg Gln Lys His Lys Val His Glu Ala Lys
1               5                   10                  15

Ala Leu Lys Lys Ser Leu Trp Tyr Ser Asn Ser
            20                  25

<210> SEQ ID NO 563
<211> LENGTH: 27
<212> TYPE: PRT
<213> ORGANISM: artificial sequence
<220> FEATURE:
<223> OTHER INFORMATION: Calcium carbonate binding peptide
```

-continued

```
<400> SEQUENCE: 563

Arg Arg Gly Val Val Leu Cys His Thr His Arg Asn Lys Arg Ile Arg
1               5                   10                  15

Leu Ala Tyr Ser Val Thr Lys Lys Ala Trp Ala
            20                  25

<210> SEQ ID NO 564
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 564

Glu Arg Ile Arg Trp Arg Arg Leu Ser Ala Glu Ile Arg Ala His Lys
1               5                   10                  15

Trp Ser Val Leu Lys Phe Arg Leu Ser Cys Met
            20                  25

<210> SEQ ID NO 565
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 565

Lys Thr Lys Glu Lys Lys Glu Val Lys Leu His Lys Lys Ser Leu
1               5                   10                  15

Ser Leu Val Leu Leu Ala Asp Leu Trp Arg Leu
            20                  25

<210> SEQ ID NO 566
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 566

Leu Gly Lys Lys His Lys Gln His Ser Lys Val Gly His Gly Lys Leu
1               5                   10                  15

Ser Thr Arg Phe Leu Arg Arg Ser Lys Leu Phe
            20                  25

<210> SEQ ID NO 567
<211> LENGTH: 17
<212> TYPE: PRT
<213> ORGANISM: artificial sequence
<220> FEATURE:
<223> OTHER INFORMATION: Antimicrobial peptide

<400> SEQUENCE: 567

Pro Lys Gly Leu Lys Lys Leu Leu Lys Gly Leu Lys Lys Leu Leu Lys
1               5                   10                  15

Leu

<210> SEQ ID NO 568
<211> LENGTH: 16
<212> TYPE: PRT
<213> ORGANISM: artificial sequence
<220> FEATURE:
<223> OTHER INFORMATION: Antimicrobial peptide
```

```
<400> SEQUENCE: 568

Lys Gly Leu Lys Lys Leu Leu Lys Gly Leu Lys Leu Leu Lys Leu
1               5                   10                  15

<210> SEQ ID NO 569
<211> LENGTH: 16
<212> TYPE: PRT
<213> ORGANISM: artificial sequence
<220> FEATURE:
<223> OTHER INFORMATION: Antimicrobial peptide

<400> SEQUENCE: 569

Lys Gly Leu Lys Lys Leu Leu Lys Leu Leu Lys Leu Leu Lys Leu
1               5                   10                  15

<210> SEQ ID NO 570
<211> LENGTH: 14
<212> TYPE: PRT
<213> ORGANISM: artificial sequence
<220> FEATURE:
<223> OTHER INFORMATION: Antimicrobial peptide

<400> SEQUENCE: 570

Leu Lys Lys Leu Leu Lys Leu Leu Lys Lys Leu Leu Lys Leu
1               5                   10

<210> SEQ ID NO 571
<211> LENGTH: 12
<212> TYPE: PRT
<213> ORGANISM: artificial sequence
<220> FEATURE:
<223> OTHER INFORMATION: Antimicrobial peptide

<400> SEQUENCE: 571

Leu Lys Lys Leu Leu Lys Leu Leu Lys Lys Leu Leu
1               5                   10

<210> SEQ ID NO 572
<211> LENGTH: 17
<212> TYPE: PRT
<213> ORGANISM: artificial sequence
<220> FEATURE:
<223> OTHER INFORMATION: Antimicrobial peptide

<400> SEQUENCE: 572

Val Ala Lys Lys Leu Ala Lys Leu Ala Lys Lys Leu Ala Lys Leu Ala
1               5                   10                  15

Leu

<210> SEQ ID NO 573
<211> LENGTH: 13
<212> TYPE: PRT
<213> ORGANISM: artificial sequence
<220> FEATURE:
<223> OTHER INFORMATION: Antimicrobial peptide

<400> SEQUENCE: 573

Phe Ala Lys Leu Leu Ala Lys Ala Leu Lys Lys Leu Leu
1               5                   10

<210> SEQ ID NO 574
<211> LENGTH: 16
<212> TYPE: PRT
<213> ORGANISM: artificial sequence
<220> FEATURE:
<223> OTHER INFORMATION: Antimicrobial peptide
```

```
<400> SEQUENCE: 574

Lys Gly Leu Lys Gly Leu Lys Leu Leu Lys Leu Leu Lys Leu
1               5                   10                  15

<210> SEQ ID NO 575
<211> LENGTH: 16
<212> TYPE: PRT
<213> ORGANISM: artificial sequence
<220> FEATURE:
<223> OTHER INFORMATION: Antimicrobial peptide

<400> SEQUENCE: 575

Lys Gly Leu Lys Lys Leu Leu Lys Leu Gly Lys Leu Leu Lys Leu
1               5                   10                  15

<210> SEQ ID NO 576
<211> LENGTH: 16
<212> TYPE: PRT
<213> ORGANISM: artificial sequence
<220> FEATURE:
<223> OTHER INFORMATION: Antimicrobial peptide

<400> SEQUENCE: 576

Lys Gly Leu Lys Lys Leu Gly Lys Leu Leu Lys Leu Leu Lys Leu
1               5                   10                  15

<210> SEQ ID NO 577
<211> LENGTH: 16
<212> TYPE: PRT
<213> ORGANISM: artificial sequence
<220> FEATURE:
<223> OTHER INFORMATION: Antimicrobial peptide

<400> SEQUENCE: 577

Lys Gly Leu Lys Lys Leu Leu Lys Leu Leu Lys Lys Gly Leu Lys Leu
1               5                   10                  15

<210> SEQ ID NO 578
<211> LENGTH: 16
<212> TYPE: PRT
<213> ORGANISM: artificial sequence
<220> FEATURE:
<223> OTHER INFORMATION: Antimicrobial peptide

<400> SEQUENCE: 578

Lys Gly Leu Lys Lys Leu Leu Lys Leu Leu Lys Lys Leu Gly Lys Leu
1               5                   10                  15

<210> SEQ ID NO 579
<211> LENGTH: 19
<212> TYPE: PRT
<213> ORGANISM: artificial sequence
<220> FEATURE:
<223> OTHER INFORMATION: Antimicrobial peptide

<400> SEQUENCE: 579

Phe Ala Leu Ala Leu Lys Ala Leu Lys Lys Ala Leu Lys Lys Ala Leu Lys
1               5                   10                  15

Lys Ala Leu

<210> SEQ ID NO 580
<211> LENGTH: 17
<212> TYPE: PRT
<213> ORGANISM: artificial sequence
<220> FEATURE:
<223> OTHER INFORMATION: Antimicrobial peptide
```

```
<400> SEQUENCE: 580

Phe Ala Lys Lys Leu Ala Lys Leu Ala Lys Lys Leu Ala Lys Leu Ala
1               5                   10                  15

Leu

<210> SEQ ID NO 581
<211> LENGTH: 13
<212> TYPE: PRT
<213> ORGANISM: artificial sequence
<220> FEATURE:
<223> OTHER INFORMATION: Antimicrobial peptide

<400> SEQUENCE: 581

Phe Ala Lys Leu Leu Ala Lys Leu Ala Lys Lys Leu Leu
1               5                   10

<210> SEQ ID NO 582
<211> LENGTH: 15
<212> TYPE: PRT
<213> ORGANISM: artificial sequence
<220> FEATURE:
<223> OTHER INFORMATION: Antimicrobial peptide

<400> SEQUENCE: 582

Phe Ala Lys Lys Leu Ala Lys Leu Ala Leu Lys Leu Ala Lys Leu
1               5                   10                  15

<210> SEQ ID NO 583
<211> LENGTH: 10
<212> TYPE: PRT
<213> ORGANISM: artificial sequence
<220> FEATURE:
<223> OTHER INFORMATION: Antimicrobial peptide

<400> SEQUENCE: 583

Phe Ala Lys Lys Leu Ala Lys Lys Leu Leu
1               5                   10

<210> SEQ ID NO 584
<211> LENGTH: 13
<212> TYPE: PRT
<213> ORGANISM: artificial sequence
<220> FEATURE:
<223> OTHER INFORMATION: Antimicrobial peptide

<400> SEQUENCE: 584

Phe Ala Lys Leu Leu Ala Lys Leu Ala Lys Lys Val Leu
1               5                   10

<210> SEQ ID NO 585
<211> LENGTH: 13
<212> TYPE: PRT
<213> ORGANISM: artificial sequence
<220> FEATURE:
<223> OTHER INFORMATION: Antimicrobial peptide

<400> SEQUENCE: 585

Lys Tyr Lys Lys Ala Leu Lys Lys Leu Ala Lys Leu Leu
1               5                   10

<210> SEQ ID NO 586
<211> LENGTH: 12
<212> TYPE: PRT
<213> ORGANISM: artificial sequence
<220> FEATURE:
<223> OTHER INFORMATION: Antimicrobial peptide
```

```
<400> SEQUENCE: 586

Phe Ala Leu Leu Lys Ala Leu Leu Lys Lys Ala Leu
1               5                   10

<210> SEQ ID NO 587
<211> LENGTH: 14
<212> TYPE: PRT
<213> ORGANISM: artificial sequence
<220> FEATURE:
<223> OTHER INFORMATION: Antimicrobial peptide

<400> SEQUENCE: 587

Lys Arg Leu Phe Lys Lys Leu Lys Phe Ser Leu Arg Lys Tyr
1               5                   10

<210> SEQ ID NO 588
<211> LENGTH: 14
<212> TYPE: PRT
<213> ORGANISM: artificial sequence
<220> FEATURE:
<223> OTHER INFORMATION: Antimicrobial peptide

<400> SEQUENCE: 588

Lys Arg Leu Phe Lys Lys Leu Leu Phe Ser Leu Arg Lys Tyr
1               5                   10

<210> SEQ ID NO 589
<211> LENGTH: 14
<212> TYPE: PRT
<213> ORGANISM: artificial sequence
<220> FEATURE:
<223> OTHER INFORMATION: Antimicrobial peptide

<400> SEQUENCE: 589

Leu Leu Leu Phe Leu Leu Lys Lys Arg Lys Lys Arg Lys Tyr
1               5                   10

<210> SEQ ID NO 590
<211> LENGTH: 36
<212> TYPE: PRT
<213> ORGANISM: Hyalophora cecropia

<400> SEQUENCE: 590

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 591
<211> LENGTH: 23
<212> TYPE: PRT
<213> ORGANISM: Xenopus laevis

<400> SEQUENCE: 591

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 592
<211> LENGTH: 22
<212> TYPE: PRT
<213> ORGANISM: Xenopus laevis
```

```
<400> SEQUENCE: 592

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 593
<211> LENGTH: 12
<212> TYPE: PRT
<213> ORGANISM: Bos taurus

<400> SEQUENCE: 593

Arg Leu Cys Arg Ile Val Val Ile Arg Val Cys Arg
1               5                   10

<210> SEQ ID NO 594
<211> LENGTH: 13
<212> TYPE: PRT
<213> ORGANISM: Bos taurus

<400> SEQUENCE: 594

Ile Leu Pro Trp Lys Trp Pro Trp Trp Pro Trp Arg Arg
1               5                   10

<210> SEQ ID NO 595
<211> LENGTH: 24
<212> TYPE: PRT
<213> ORGANISM: Homo sapiens

<400> SEQUENCE: 595

Asp Ser His Ala Lys Arg His His Gly Tyr Lys Arg Lys Phe His Glu
1               5                   10                  15

Lys His His Ser His Arg Gly Tyr
            20
```

PEPTIDE LINKERS FOR EFFECTIVE MULTIVALENT PEPTIDE BINDING

CROSS-REFERENCE TO A RELATED APPLICATION

This application claims the benefit of U.S. Provisional Patent Application No. 61/138,633 filed Dec. 18, 2008, incorporated herein by reference.

FIELD OF THE INVENTION

The invention relates to methods of identifying and using peptide linkers characterized by a high level of rigidity to prepare single chain target surface-binding domains as well as single chain peptide-based reagents. More specifically, target surface-binding domains comprising a plurality of single chain target surface-binding peptides separated by at least one rigid peptide linker exhibit higher affinity for the target surface in comparison to target surface binding domains having flexible peptide linkers. One or more of the target surface binding domains can be incorporated into single chain peptide-based reagents for delivery of a benefit agent to target surface.

BACKGROUND OF THE INVENTION

Proteinaceous materials coupled to one or more cosmetic care benefit agents have been reported in the art. Lang et al. in U.S. Pat. No. 5,192,332 describe temporary coloring compositions that contain an animal or vegetable protein, or hydrolysate thereof, which contain residues of dye molecules (e.g., benefit agents) grafted onto the protein chain. In the Lang et al. compositions, the protein serves as a conditioning agent and does not provided targeted delivery or enhanced durability for coupling the benefit agent to the target surface.

Proteinaceous materials having strong affinity for a body surface have been used for targeted delivery of one or more personal care benefit agents. However, many of the materials used for targeted delivery are comprised or derived from immunoglobulins or immunoglobulin fragments (antibodies, antibody fragments, $F_{ab}$, single-chain variable fragments (scFv), and Camelidae $V_{HH}$) having affinity for the target surface. For example, Horikoshi et al. in JP 08104614 and Igarashi et al. in U.S. Pat. No. 5,597,386 describe hair coloring agents that consist of an anti-keratin antibody covalently attached to a dye or pigment. The antibody binds to the hair, thereby enhancing the binding of the hair coloring agent to the hair. Similarly, Kizawa et al. in JP 09003100 describe an antibody that recognizes the surface layer of hair and its use to treat hair. A hair coloring agent consisting of the anti-hair antibody coupled to colored latex particles is also described. The use of antibodies to enhance the binding of dyes to the hair is effective in increasing the durability of the hair coloring, but the antibodies are difficult and expensive to produce. Terada et al. in JP 2002363026 describe the use of conjugates consisting of single-chain antibodies, preferably anti-keratin, coupled to dyes, ligands, and cosmetic agents for skin and hair care compositions. Although single-chain antibodies may be prepared using genetic engineering techniques, these molecules are expensive to prepare and may not be suitable for use in commercial personal care products due to their conserved structure (i.e., immunoglobulin folds) and large size.

Non-immunoglobulin derived scaffold proteins have also been developed for targeted delivery of benefit agents to a target surface, such as delivery of cosmetic agents to keratin-containing materials (See Binz, H. et al. (2005) *Nature Biotechnology* 23, 1257-1268 for a review of various proteins used in scaffold-assisted binding). Findlay in WO 00/048558 describes the use of calycin-like scaffold proteins, such as β-lactoglobulin, which contain a binding domain for a cosmetic agent and another binding domain that binds to at least a part of the surface of a hair fiber or skin surface, for conditioners, dyes, and perfumes. Houtzager et a. in WO 03/050283 and US 2006/0140889 also describe affinity proteins having a defined core scaffold structure for controlled application of cosmetic substances. As with immunoglobulin-like proteins, these large scaffold proteins are somewhat limited by the requirement to maintain the underlying core structure for effective binding and are expensive to produce.

Short, single chain peptides (i.e., "target surface-binding peptides") having strong affinity for a target surface can be identified and isolated from peptide libraries using any number of biopanning techniques well known to those skilled in the art including, but not limited to bacterial display, yeast display, combinatorial solid phase peptide synthesis, phage display, ribosome display, and mRNA display technology (PROFUSION™, U.S. Pat. No. 6,258,558. Techniques to generate random peptide libraries are described in Dani, M., *J. of Receptor & Signal Transduction Res.*, 21(4):447-468 (2001). Phage display libraries are available commercially from companies such as New England BioLabs (Beverly, Mass.).

The target surface-binding peptides are typically no more than 60 amino acids in length and often have a binding affinity (as measured by an $MB_{50}$ or $K_D$ value) of $10^{-4}$ M or less for the target surface. These short peptides may be used in some applications as an interfacial material to couple one or more benefit agents to the target surface. However, for some commercial applications the individual biopanned peptides (herein referred to as providing a "monovalent" interaction) may not provide the durability necessary to achieve the desired effect. The lack in durability may be especially evident when attempting to couple a particulate benefit agent to the target surface.

Single chain peptide-based reagents lacking a scaffold support or immunoglobulin fold have been developed that can be used to couple benefit agents to a target surface. Examples of target surfaces include, but are not limited to body surfaces such as hair, skin, nail, and teeth (U.S. Pat. Nos. 7,220,405; 7,309,482; and 7,285,264; U.S. Patent Application Publication Nos. 2005-0226839; 2007-0196305; 2006-0199206; 2007-0065387; 2008-0107614; 2007-0110686; and 2006-0073111; and published PCT applications WO2008/054746; WO2004/048399; and WO2008/073368) as well as other surfaces such as pigments and miscellaneous print media (U.S. Patent Application Publication No. 2005-0054752), and various polymers such as polymethylmethacrylate (U.S. Patent Application Publication No. 2007-0265431), polypropylene (U.S. Patent Application Publication No. 2007-0264720), nylon (U.S. Patent Application Publication Nos. 2007-0141629 and 2003-0185870), polytetrafluoroethylene (U.S. patent application Ser. No. 11/607,734), polyethylene (U.S. Patent Application Publication No. 2007-0141628), and polystyrene (U.S. Patent Application Publication No. 2007-0261775). However, some single chain peptide-based reagents may lack the durability required for certain commercial applications, especially when coupling a particulate benefit agent to a body surface in a highly stringent matrix.

Single chain target surface-binding domains (herein referred to as "hands") may be prepared by linking together a plurality of target surface-binding peptides (herein referred to as "fingers"). However, due to the absence of a scaffold or core structure to help control the translational and rotational entropies lost in binding between ligands (e.g., the target surface-binding peptides) and the associated polyvalent receptor (i.e., the target surface, such as a body surface), many single chain target surface-binding domains that are unstructured in solution do not exhibit polyvalent interactions. As such, rationally-designing single chain peptide reagents is often difficult. This is particularly true when attempting to design single chain peptide reagents having affinity for a target surface that is heterogeneous in nature and/or wherein the binding motifs may not be well characterized. As such, rationally-designing target surface binding domains capable of effectively forming (or promoting the formation of) multivalent associations from singe chain target surface-binding peptides remains a problem to be addressed for certain commercial applications. This is especially true for single chain target surface-binding domains lacking a conserved scaffold support, as the entropy associated with the unstructured system may adversely impact the formation of stable multivalent interactions.

Mammen et al., (*Angew. Chem. Int. Ed.* (1998) 37:2754-2794) examines and reviews the theoretical considerations of polyvalent interactions in biological systems and the central role entropy plays in polyvalency. Polyvalent interactions can be collectively much stronger than corresponding monovalent interactions. The increase in affinity observed with multivalent binding vs. monovalent binding is mostly attributed to decreases in the rate of dissociation ($K_{off}$) rather than an increase in the rate of association ($K_{on}$). Mammen et al. provides examples of biological systems involving polyvalent interactions including, but not limited to ligand-receptor interactions between bacterium and host cell matrices, antibody-antigen interactions, virus and host cell receptors, and signal transduction interactions, to name a few.

The entropy of a polyvalent interaction is a combination of the translational and rotational entropies (Mammen et al., *J. Org. Chem.* (1998) 63:3168-3175 and Mammen et al., *J Org. Chem.* (1998) 63:3821-3830). Due to the absence of a scaffold or core structure to help control the translational and rotational entropies present between ligands (e.g., the target surface-binding peptides) and the associated polyvalent receptor (i.e., the target surface, such as a body surface), single chain target surface-binding domains and/or single peptide-based reagents may not exhibit multivalent binding behavior.

One problem to be solved is to provide single chain peptide-based reagents comprising one or more single chain target surface-binding domains exhibiting strong binding affinity for the target surface.

Another problem to be solved is to provide a method of identifying single chain target surface-binding domains having strong affinity for a target surface. Preferably the method provides target surface-binding domains that exhibit multivalent binding characteristics for the target surface.

A method of coupling a benefit agent to a target surface using a single chain peptide-based reagent comprising at least one target surface-binding domain exhibiting strong affinity for the target surface is also needed.

SUMMARY OF THE INVENTION

The stated problems have been solved by discovering that single chain target surface-binding domains comprising a plurality of target surface-binding peptides separated by peptide linkers having limited flexibility (i.e., "rigid peptide linkers") typically provide the highest binding affinity for the respective target surface. Although not bound by theory, it is believed that the use of rigid peptide linkers to separate the various target surface-binding peptides effectively promotes and enhances multivalent binding. Peptide-based reagents comprising one or more of the present target surface-binding domains are also provided.

In one embodiment, a peptide-based reagent is provided comprising at least one target surface-binding domain (TSBD) having the general structure:

i) TSBP1 is a first target surface-binding peptide having affinity for a target surface; wherein the first target-surface-binding peptide ranges in length from about 7 to about 60 amino acids;
ii) TSBP2 is a second target surface-binding peptide having affinity for the target surface; wherein the first target surface-binding peptide and the second target surface-binding peptide are the same or different; wherein the second target-surface-binding peptide ranges in length from about 7 to about 60 amino acids;
iii) $RL_1$ is a first rigid peptide linker; wherein the first rigid peptide linker ranges in length from about 3 to 50 amino acids in length;
iv) $RL_2$ is a second rigid peptide linker; wherein the first rigid peptide linker and the second peptide linker are the same or different; wherein the second rigid linker ranges in length from about 3 to 50 amino acids in length;
v) a=1 to 10; and
vi) b=0 or 1.

The present peptide-based reagents are may be used in personal care applications for delivery of a benefit agent to a body surface.

In another embodiment, a peptide-based reagent is provided comprising at least one body surface-binding domain (B ii) a non-bonded cutoff distance of 14 angstroms with cutoff settings of CTOFNB=12 and CTONNB=10; the SWITCH cutoff method to calculate non-bonded terms;
iii) a Particle Mesh Ewald (PME) summation method to calculate electrostatic interactions; and
iv) a SHAKE algorithm to constrain bonds involving hydrogen atoms; and
v) an integration time step set to 2 femtoseconds;

b. setting an initial peptide configuration for the peptide linker sequence, wherein the initial peptide configuration is selected from the group consisting of an α-helical conformation and a fully extended conformation; wherein the following assumptions are used:
  i) the pH is assumed to be 7; and
  ii) the N-termini and C-termini of the peptide linker are assumed to be charged;

c. conducting an energy minimization on the initial peptide linker configuration comprising the steps of:
  i) performing an initial energy minimization calculation using steepest descent method for 400 steps;
  ii) performing a subsequent energy minimization using a conjugated gradients method for 800 steps or until the gradient of the potential energy converged to 0.1; and
  iii) performing an Adopted Basis Newton-Raphson method for 2000 steps or until the gradient of the potential energy reached 0.1;

d. conducting a peptide solvation simulation comprising the steps of:
  i) placing the peptide linker in the center of a rectangular box of water molecules; wherein the dimension of the rectangular box is determined by adding 16 angstroms to the maximum extent of the peptide linker in each direction;
  ii) adding counter-ions selected from the group consisting of Na+ or Cl− to the system to bring the total charge of the system to zero;
  iii) inputting a set of periodic boundary conditions (PBC) comprising the following settings:
    a) the maximum allowable distance of any group included in an image atom list is set to 14 angstroms; and
    b) the image atom list is updated using the heuristic method;
  iv) performing an energy minimization on the water molecules using the steepest descent method for 50 steps with the peptide linker sequence constrained using a harmonic constraint with a force constant of 25;
  v) removing the harmonic constraint and conducting the energy minimization on the entire system using the steepest descent method for 400 steps or until the total gradient of the potential energy converges to 0.01;

e. conducting a heating simulation run wherein the system is heated from 0 Kelvin to 300 Kelvin with 5 Kelvin increments very 50 steps in 3000 steps;

f. conducting an equilibration simulation run where the system is equilibrated at 300 Kelvin for 5000 steps;

g. conducting a production simulation run in an NVT system at 300 Kelvin for 1,000,000 steps (200 picoseconds) wherein the coordinates of the atoms are saved every 100 steps (0.2 picoseconds) in a trajectory file;

h. calculating room-mean-square (RMS) fluctuations for all phi (φ) and psi (ψ) torsion angles in the peptide using the coordinates of the atoms stored in the trajectory files; and
  i. averaging the phi and psi RMS fluctuations.

In another embodiment, the present peptide-based reagents comprise a binding domain prepared using a rigid peptide linker selected from the group consisting of:

a) a salt bridge stabilized α-helix of the general formula:

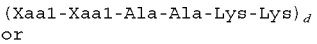
or
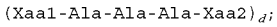
or
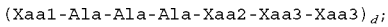

wherein;
Xaa1=Glu or Asp;
Xaa2=Lys or Arg;
Xaa3=Leu, Ile, Val, Phe, Trp, Tyr, and Met; and
d=2 to 10;

b) an extended proline dipeptide of the formula:

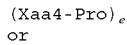
or
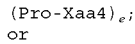
or
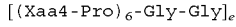

wherein e=2 to 20; and Xaa4 is an acidic or a basic amino acid; and c) a peptide linker having the amino acid sequence SEQ ID NO: 54.

The peptide-based reagent may be coupled directly to a benefit agent, coupled to the benefit agent through a peptide bridge, or may be coupled via a peptide bridge to a benefit agent-binding domain having affinity for the surface on the benefit agent. As such, a peptide-based reagent is also provided comprising the general structure selected from the group consisting of:
  a) $(BSBD)_f$-BA;
  b) $(BSBD)_f$-BR-BA; and
  c) $[(BSBD)_f$-$(BR)_g$-$(BABD)_h]_i$;
wherein
  i) BSBD is a body surface-binding domain comprising at least one rigid peptide linker;
  ii) BA is a benefit agent;
  iii) BR is a peptide bridge ranging from 1 to 60 amino acids in length; and
  iv) BABD is a benefit agent-binding domain; and
wherein
  f=1 to 10;
  g=0 or 1;
  h=1 to 10; and
  i=1 to 10.

In another embodiment, the peptide-based reagent comprises a benefit agent-binding domain having at least one rigid peptide linker, said benefit agent-binding domain have the general struct iii) RL₃ is a third rigid peptide linker; wherein the third rigid peptide linker ranges in length from about 3 to 50 amino acids;

iv) RL₄ is a fourth rigid peptide linker; wherein the third rigid peptide linker and the fourth rigid peptide linker are the same or different; wherein the fourth rigid peptide linker ranges in length from about 3 to 50 amino acids;

v) j=1 to 10; and vi) k=0 or 1.

In another embodiment, personal care compositions comprising the present peptide-based reagents are also provided.

In another embodiment, the target surface-binding peptides (i.e., "fingers") independently have a $K_D$ or $MB_{50}$ value for their respective surface of $10^{-4}$ M or less.

In another embodiment, a method to couple a benefit agent to a body surface is provided comprising:

a) providing a personal care composition comprising:
   i) at least one of the present peptide-based reagents having affinity for a body surface; and
   ii) a benefit agent;
b) contacting the body surface with the personal care composition of (a) whereby the benefit agent is coupled by said at least one peptide-based reagent to the body surface.

In one embodiment, the peptide-based reagent comprises a body surface-binding domain having affinity for hair, said body surface-binding domain comprising an amino acid sequence selected from the group consisting of SEQ ID NOs: 73, 74, 75, 76, 77, 78, 83, 85, 88, 89, 90, 91, 92, 93, 94, 96, 97, 98, 99, 100, 101, and 102.

In another embodiment, the peptide-based reagent comprises a body surface-binding domain having affinity for hair, said body surface binding domain comprises an amino acid sequence provided as SEQ ID NO: 85.

In another embodiment, the peptide-based reagent is peptide HC353 having an amino acid SEQ ID NO: 106.

In another embodiment, a method to couple a pigment to hair is provided comprising:

a) providing a hair care composition comprising:
   i) a peptide-based reagent having an amino acid sequence SEQ ID NO: 106; and
   ii) a pigment comprising iron oxide; and
b) contacting the hair care composition of (a) with hair whereby the pigment is coupled to the hair.

In another embodiment, a method to obtain a target surface-binding domain having affinity for a target surface is provided comprising:

a) providing a monovalent phage display library of combinatorially generated phage peptides; wherein the phage peptides comprise the general structure:

TSBP1-L-TSBP2;

wherein i) TSBP1 is a first target surface-binding peptide having affinity for a target surface;

ii) TSBP2 is a second target surface-binding peptide having affinity for the target surface; wherein the first and second target surface-binding peptides may be the same or different; and iii) L is a rigid peptide linker;

b) contacting the monovalent phage display library of (a) with a target surface sample to form a reaction solution comprising:
   (i) phage-phage peptide-target surface sample complex;
   (ii) unbound target surface sample, and
   (iii) uncomplexed phage-phage peptides;
c) separating phage-phage peptide-target surface sample complex of (b) from the unbound target surface sample and the uncomplexed phage-phage peptides;

d) determining the amino acid sequence of the phage peptide in the phage-phage peptide-target surface sample complex wherein the phage peptide has affinity for the target surface; and e) constructing a target surface-binding domain having the sequence of the phage peptide having affinity for the target surface.

BRIEF DESCRIPTION OF FIGURES AND SEQUENCE DESCRIPTIONS

The various embodiments of the invention can be more fully understood from the following detailed description, figure and the accompanying sequence descriptions, which form a part of this application.

BRIEF DESCRIPTION OF THE BIOLOGICAL SEQUENCES

Figure 1:
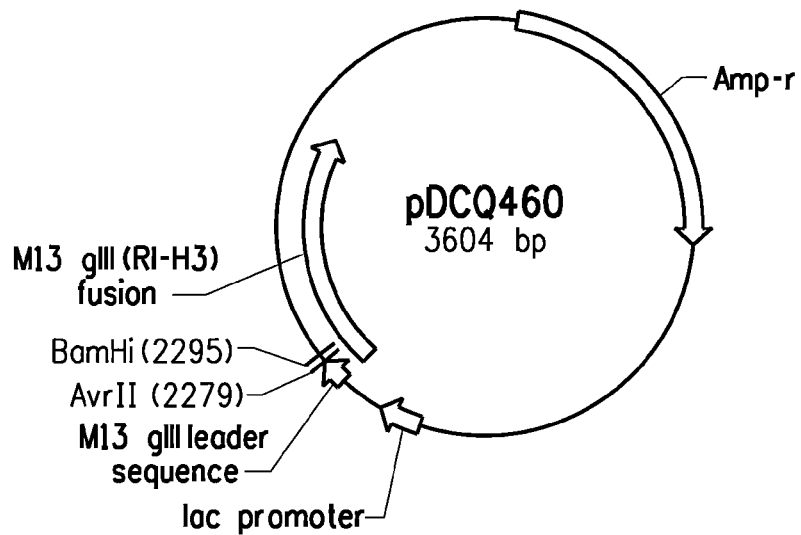
FIG. 1 is a plasmid map of pDCQ460

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822

SEQ ID NO: 1 is the amino acid sequence of peptide linker La3 with N-terminal Gly-Pro and C-terminal Pro-Ala residues.

SEQ ID NO: 2 is the amino acid sequence of peptide linker La3.

SEQ ID NO: 3 is the amino acid sequence of peptide linker La5 with N-terminal Gly-Pro and C-terminal Pro-Ala residues.

SEQ ID NO: 4 is the amino acid sequence of peptide linker La5.

SEQ ID NO: 5 is the amino acid sequence of peptide linker La6 with N-terminal Gly-Pro and C-terminal Pro-Ala residues.

SEQ ID NO: 6 is the amino acid sequence of peptide linker La6.

SEQ ID NO: 7 is the amino acid sequence of peptide linker Lb2 with N-terminal Gly-Pro and C-terminal Pro-Ala residues.

SEQ ID NO: 8 is the amino acid sequence of peptide linker Lb2.

SEQ ID NO: 9 is the amino acid sequence of peptide linker Lb4 with N-terminal Gly-Pro and C-terminal Pro-Ala residues.

SEQ ID NO: 10 is the amino acid sequence of peptide linker Lb4.

SEQ ID NO: 11 is the amino acid sequence of peptide linker Lb5 with N-terminal Gly-Pro and C-terminal Pro-Ala residues.

SEQ ID NO: 12 is the amino acid sequence of peptide linker Lb5.
SEQ ID NO: 13 is the amino acid sequence of peptide linker Lc4 with N-terminal Gly-Pro and C-terminal Pro-Ala residues.
SEQ ID NO: 14 is the amino acid sequence of peptide linker Lc4.
SEQ ID NO: 15 is the amino acid sequence of peptide linker Lc8 with N-terminal Gly-Pro and C-terminal Pro-Ala residues.
SEQ ID NO: 16 is the amino acid sequence of peptide linker Lc8.
SEQ ID NO: 17 is the amino acid sequence of peptide linker Lc12 with N-terminal Gly-Pro and C-terminal Pro-Ala residues.
SEQ ID NO: 18 is the amino acid sequence of peptide linker Lc12.
SEQ ID NO: 19 is the amino acid sequence of peptide linker Lc16 with N-terminal Gly-Pro and C-terminal Pro-Ala residues.
SEQ ID NO: 20 is the amino acid sequence of peptide linker Lc16.
SEQ ID NO: 21 is the amino acid sequence of peptide linker Ld2 with N-terminal Gly-Pro and C-terminal Pro-Ala residues.
SEQ ID NO: 22 is the amino acid sequence of peptide linker Ld2.
SEQ ID NO: 23 is the amino acid sequence of peptide linker Ld4 with N-terminal Gly-Pro and C-terminal Pro-Ala residues.
SEQ ID NO: 24 is the amino acid sequence of peptide linker Ld4.
SEQ ID NO: 25 is the amino acid sequence of peptide linker Ld6 with N-terminal Gly-Pro and C-terminal Pro-Ala residues.
SEQ ID NO: 26 is the amino acid sequence of peptide linker Ld6.
SEQ ID NO: 27 is the amino acid sequence of peptide linker Le2 with N-terminal Gly-Pro and C-terminal Pro-Ala residues.
SEQ ID NO: 28 is the amino acid sequence of peptide linker Le2.
SEQ ID NO: 29 is the amino acid sequence of peptide linker Le4 with N-terminal Gly-Pro and C-terminal Pro-Ala residues.
SEQ ID NO: 30 is the amino acid sequence of peptide linker Le4.
SEQ ID NO: 31 is the amino acid sequence of peptide linker Le6 with N-terminal Gly-Pro and C-terminal Pro-Ala residues.
SEQ ID NO: 32 is the amino acid sequence of peptide linker Le6.
SEQ ID NO: 33 is the amino acid sequence of peptide linker Lf2 with N-terminal Gly-Pro and C-terminal Pro-Ala residues.
SEQ ID NO: 34 is the amino acid sequence of peptide linker Lf2.
SEQ ID NO: 35 is the amino acid sequence of peptide linker Lf4 with N-terminal Gly-Pro and C-terminal Pro-Ala residues.
SEQ ID NO: 36 is the amino acid sequence of peptide linker Lf4.
SEQ ID NO: 37 is the amino acid sequence of peptide linker Lf6 with N-terminal Gly-Pro and C-terminal Pro-Ala residues.
SEQ ID NO: 38 is the amino acid sequence of peptide linker Lf6.
SEQ ID NO: 39 is the amino acid sequence of peptide linker Lg1 with N-terminal Gly-Pro and C-terminal Pro-Ala residues.
SEQ ID NO: 40 is the amino acid sequence of peptide linker Lg1.
SEQ ID NO: 41 is the amino acid sequence of peptide linker Lg2 with N-terminal Gly-Pro and C-terminal Pro-Ala residues.
SEQ ID NO: 42 is the amino acid sequence of peptide linker Lg2.
SEQ ID NO: 43 is the amino acid sequence of peptide linker Lg3 with N-terminal Gly-Pro and C-terminal Pro-Ala residues.
SEQ ID NO: 44 is the amino acid sequence of peptide linker Lg3.
SEQ ID NO: 45 is the amino acid sequence of peptide linker Lh1 with N-terminal Gly-Pro and C-terminal Pro-Ala residues.
SEQ ID NO: 46 is the amino acid sequence of peptide linker Lh1.
SEQ ID NO: 47 is the amino acid sequence of peptide linker Lh2 with N-terminal Gly-Pro and C-terminal Pro-Ala residues.
SEQ ID NO: 48 is the amino acid sequence of peptide linker Lh2.
SEQ ID NO: 49 is the amino acid sequence of peptide linker Lh3 with N-terminal Gly-Pro and C-terminal Pro-Ala residues.
SEQ ID NO: 50 is the amino acid sequence of peptide linker Lh3.
SEQ ID NO: 51 is the amino acid sequence of peptide linker Lj with N-terminal Gly-Pro and C-terminal Pro-Ala residues.
SEQ ID NO: 52 is the amino acid sequence of peptide linker Lj.
SEQ ID NO: 53 is the amino acid sequence of peptide linker Lk with N-terminal Gly-Pro and C-terminal Pro-Ala residues.
SEQ ID NO: 54 is the amino acid sequence of peptide linker Lk.
SEQ ID NO: 55 is the amino acid sequence of peptide linker Lm3 with N-terminal Gly-Pro and C-terminal Pro-Ala residues.
SEQ ID NO: 56 is the amino acid sequence of peptide linker Lm3.
SEQ ID NO: 57 is the amino acid sequence of peptide linker Lm4 with N-terminal Gly-Pro and C-terminal Pro-Ala residues.
SEQ ID NO: 58 is the amino acid sequence of peptide linker Lm4.
SEQ ID NOs: 59-70 are various body surface-binding peptides described in Example 1.
SEQ ID NO: 71 is the nucleic acid sequence of phagemid vector pDCQ460.
SEQ ID NOs: 72-90 are the amino acid sequences of various hair-binding domains identified after $4^{th}$ round of phage biopanning.
SEQ ID NOs: 73-78, 83, 85, 88, and 90-102 are the amino acid sequences of various hair-binding domains identified to bind strongly to hair based on the phage titer and ELISA experiments.
SEQ ID NO: 103 is the amino acid sequence of pigment-binding peptide having affinity for an iron oxide-based pigments.
SEQ ID NO: 104 is the amino sequence of a peptide bridge in peptide reagent HC353.

SEQ ID NO: 105 is the amino acid sequence of a cationic linker used to link together 2 copies of the pigment-binding peptides of SEQ ID NO: 103.

SEQ ID NO: 106 is the amino acid sequence of peptide reagent HC353.

SEQ ID NO: 107 is the nucleic acid sequence encoding peptide reagent HC353.

SEQ ID NO 108 is the nucleic acid sequence of expression vector pLD001.

SEQ ID NO: 109 is the amino acid sequence of inclusion body tag KSI(C4)E.

SEQ ID NO: 110 is the nucleic acid sequence of expression vector pLD1474.

SEQ ID NOs: 111-124 are the amino acid sequences of various modular hair-binding hands comprising a hexahistidine tag.

SEQ ID NOs: 125-145 are PCR primers.

SEQ ID NO: 146 is the amino acid sequence of the hair-binding domain in peptide HC365.

SEQ ID NO: 147 is the amino acid sequence of the hair-binding domain in peptide HC366.

SEQ ID NO: 148 is the amino acid sequence of the hair-binding domain in peptide HC367.

SEQ ID NO: 149 is the amino acid sequence of a cellulose acetate-binding peptide referred to herein as "CA4".

SEQ ID NO: 150-154 are the amino acid sequences of various dimer and trimer constructs comprising multiple copies of cellulose acetate-binding peptide "CA4" covalently linked together using flexible or rigid peptide linkers.

SEQ ID NO: 155 is the amino acid sequence of a Gram negative bacterial cytoplasmic membrane protein "TonB" (GENBANK® Accession No. AAY89716).

SEQ ID NOs: 156-158 are the amino acid sequences of rigid peptide linkers having structures associated with the formation of salt bridge stabilized α-helices.

SEQ ID NOs: 159-161 are the amino acid sequences of rigid peptide linkers comprising extended proline dipeptides.

SEQ ID NOs: 59-70 and 162-307 are the amino acid sequences of hair-binding peptides.

SEQ ID NOs: 303-355 are the amino acid sequences of skin-binding peptides.

SEQ ID NOs: 356-357 are the amino acid sequences of nail-binding peptides.

SEQ ID NOs: 358-397 are the amino acid sequences of tooth-binding peptides.

SEQ ID NOs: 398-424 are the amino acid sequences of polymethylmethacrylate-binding peptides.

SEQ ID NOs: 425-431 are the amino acid sequences of polypropylene-binding peptides.

SEQ ID NOs: 432-440 are the amino acid sequences of polytetrafluoroethylene-binding peptides.

SEQ ID NOs: 441-447 are the amino acid sequences of polyethylene-binding peptides.

SEQ ID NOs: 448-453 are the amino acid sequences of nylon-binding peptides.

SEQ ID NOs: 454-456 are the amino acid sequences of polystyrene-binding peptides.

SEQ ID NOs: 149 and 457-459 are the amino acid sequences of cellulose acetate-binding peptides.

SEQ ID NOs: 460-463 are the amino acid sequences of carbon black-binding peptides.

SEQ ID NOs: 464-472 are the amino acid sequences of CROMOPHTAL® yellow-binding peptides.

SEQ ID NOs: 473-475 are the amino acid sequences of SUNFASV Magenta-binding peptides.

SEQ ID NOs: 476-484 are the amino acid sequences of SUNFAST® Blue-binding peptides.

SEQ ID NOs: 103 and 485-513 are the amino acid sequences of iron oxide-based pigment-binding peptides.

SEQ ID NOs: 514-515 are the amino acid sequences of cotton fabric-binding peptides.

SEQ ID NOs: 514 and 516 are the amino acid sequences of peptides that bind to polyester/cotton blends.

SEQ ID NOs: 514 and 517-519 are the amino acid sequences of peptides that bind to Hammermill paper.

SEQ ID NOs: 520-525 are the amino acid sequences of cellulose-binding peptides.

SEQ ID NOs: 526-540 are the amino acid sequences of clay-binding peptides.

SEQ ID NOs: 541-566 are the amino acid sequences of calcium carbonate-binding peptides.

SEQ ID NOs: 567-595 are the amino acid sequences of antimicrobial peptides.

DETAILED DESCRIPTION OF THE INVENTION

Provided herein are single chain peptide reagents comprising at least one target surface-binding hand formed by covalently linking together two or more target surface-binding peptide fingers using a rigid peptide linker. Target surface-binding domains ("hands") comprising target surface-binding peptides ("fingers") linked together using rigid peptide linkers exhibit stronger affinity for the target surface in comparison to target surface-binding domains having flexible peptide linkers. Although not bound by theory, it is believed that the use of rigid peptide linkers to covalently link together two or more target surface-binding peptides promotes multivalent peptide binding to the target surface.

The single chain peptide-based reagents can be used to couple a benefit agent to a target surface. The target surface may be any surface targeted for the coupling of a benefit agent. Examples of various target surfaces are provided in Table A. In one embodiment, the target surface is a body surface selected from the group consisting of hair, skin, nails, and teeth. The benefit agent may be as cosmetic benefit agent. In another embodiment, the benefit agent may be a particulate benefit agent, such as a pigment (including whitening agents), a polymer coated pigment, a colored microsphere, a particulate conditioning agent, and a sunscreen agent.

The peptide-based reagent may contain one target surface-binding domain having affinity for a target surface and a second domain capable of being coupled to a benefit agent (i.e., a "one-handed" peptide reagent). The peptide reagent may contain a first target surface-binding domain having affinity for a first surface and a second target surface-binding domain having affinity for a second surface wherein the first and second surfaces are different (i.e., a "two-handed" peptide reagent). In a further embodiment, the peptide-based reagent comprises a body surface-binding domain and a benefit agent-binding domain, wherein the body surface-binding domain is linked to the benefit agent-binding domain via an optional peptide bridge; wherein inclusion of a peptide bridge is preferred. In a further embodiment, both the body surface-binding domain and the benefit agent-binding domain comprise at least one rigid peptide linker.

The following definitions are used herein and should be referred to for interpretation of the claims and the specification. Unless otherwise noted, all U.S. Patents and U.S. Patent Applications referenced herein are incorporated by reference in their entirety.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

The term "invention" or "present invention" as used herein is a non-limiting term and is not intended to refer to any single embodiment of the particular invention but encompasses all possible embodiments as described in the specification and the claims.

As used herein, the terms "polypeptide" and "peptide" will be used interchangeably to refer to a polymer of two or more amino acids joined together by a peptide bond. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. In one embodiment, the peptides are comprised of L-amino acids.

As used herein, the term "target surface" refers to a surface of interest. In one embodiment, the target surface is a body surface. In another embodiment, the body surface is the surface of a biological material selected from the group consisting of hair, skin, nail, and teeth.

As used herein, the term "target surface-binding peptide" (TSBP) is a single chain peptide having strong affinity for a target surface. The target surface-binding peptides range from about 7 to about 60 amino acids in length and are typically identified from a random library using biopanning. As described herein, the target surface-binding peptides (as described herein as peptide "fingers") are coupled together via at least one of the present rigid peptide linkers to form at least target surface-binding domain (the "hand"). In one embodiment, the target surface-binding peptide (TSBP) is a body surface-binding peptide.

As used herein, a "body surface-binding peptide" (BSBP) is a single chain peptide having strong affinity for a body surface selected from the group consisting of hair, skin, nails, and teeth.

As used herein, the terms "hand", "target surface hand", and "target surface-binding domain" will refer to a single chain peptide comprising of at least two target surface-binding peptides linked together by at least one rigid peptide linker. In one embodiment, the target surface-binding peptides are biopanned from a random peptide library using a method selected from the group consisting of phage display, bacterial display, yeast display, ribosome display, and mRNA-display. In another embodiment, the target-surface binding hand comprises two target surface-binding peptides linked together by a rigid peptide linker.

As used herein, the term "peptide-based reagent" or "peptide reagent" refers to a single chain peptide comprising at least one target surface-binding domain having strong affinity for a target surface.

As used herein, the term "body surface-binding hand" or "body surface-binding domain" will refer to a single chain peptide comprising two or more body surface-binding peptides (BSBPs) linked together by at least one rigid peptide linker. In one embodiment, the body surface-binding domain comprises two body surface-binding peptides linked together by a rigid peptide linker.

As used herein, the term "benefit agent-binding hand" or "benefit agent-binding domain" will refer to a single chain peptide domain comprising two or more benefit agent-binding peptides (BABPs) coupled together by at least one rigid peptide linker. In one embodiment, the benefit agent-binding domain comprises two benefit agent-binding peptides linked together by a rigid peptide linker.

As used herein, the term "hair" as used herein refers to human hair, eyebrows, and eyelashes.

As used herein, the term "skin" as used herein refers to human skin, or substitutes for human skin, such as pig skin, VITRO-SKIN® and EPIDERM™. Skin, as used herein, will refer to a body surface generally comprising a layer of epithelial cells and may additionally comprise a layer of endothelial cells.

As used herein, the term "nails" as used herein refers to human fingernails and toenails.

As used herein, "HBP" means hair-binding peptide. As used herein, the term "hair-binding peptide" refers to peptide sequences that bind with high affinity to hair. Examples of hair binding peptides have been reported (U.S. patent application Ser. No. 11/074,473 to Huang et al.; WO 0179479; U.S. Patent Application Publication No. 2002/0098524 to Murray et al.; Janssen et al., U.S. Patent Application Publication No. 2003/0152976 to Janssen et al.; WO 2004048399; U.S. application Ser. No. 11/512,910, and U.S. patent application Ser. No. 11/696,380). Examples of hair-binding peptides are provided as SEQ ID NOs: 59-70 and 162-307. The hair-binding peptides may be from about 7 amino acids to about 60 amino acids, more preferably, from about 7 amino acids to about 25 amino acids, most preferably from about 7 to about 20 amino acids in length.

As used herein, "SBP" means skin-binding peptide. As used herein, the term "skin-binding peptide" refers to peptide sequences that bind with high affinity to skin. Examples of skin binding peptides have also been reported (U.S. patent application Ser. No. 11/069,858 to Buseman-Williams; Rothe et. al., WO 2004/000257; and U.S. patent application Ser. No. 11/696,380). Skin as used herein as a body surface will generally comprise a layer of epithelial cells and may additionally comprise a layer of endothelial cells. Examples of skin-binding peptides are provided as SEQ ID NOs: 303-355. The skin-binding peptides may be from about 7 amino acids to about 60 amino acids, more preferably, from about 7 amino acids to about 25 amino acids, most preferably from about 7 to about 20 amino acids in length.

As used herein, "NBP" means nail-binding peptide. As used herein, the term "nail-binding peptide" refers to peptide sequences that bind with high affinity to nail. Examples of nail binding peptides have been reported (U.S. patent application Ser. No. 11/696,380). Examples of nail-binding peptides are provided as SEQ ID NOs: 356-357. The nail-binding peptides may be from about 7 amino acids to about 60 amino acids, more preferably, from about 7 amino acids to about 25 amino acids, most preferably from about 7 to about 20 amino acids in length.

As used herein, "TBP" means tooth-binding peptide. A tooth-binding peptide is a peptide that binds with high affinity to a mammalian or human tooth surface. As used herein, the term "tooth-binding peptide" will refer to a peptide that binds to tooth enamel or tooth pellicle. In one embodiment, the tooth-binding peptides may be from about 7 amino acids to about 60 amino acids in length, more preferably, from about 7 amino acids to about 25 amino acids in length, most preferably from about 7 to about 20 amino acids in length. In a preferred embodiment, the tooth-binding peptides are combinatorially-generated peptides. Examples of tooth-binding peptides having been disclosed in co-pending and co-owned U.S. application Ser. No. 11/877,692. In a preferred embodiment, the tooth-binding peptide is selected from the group consisting of SEQ ID NOs: 358-397.

The term "tooth surface" will refer to a surface comprised of tooth enamel (typically exposed after professional cleaning or polishing) or tooth pellicle (an acquired surface comprising salivary glycoproteins). Hydroxyapatite can be coated with salivary glycoproteins to mimic a natural tooth pellicle surface (tooth enamel is predominantly comprised of hydroxyapatite).

As used herein, the terms "pellicle" and "tooth pellicle" will refer to the thin film (typically ranging from about 1 μm to about 200 μm thick) derived from salivary glycoproteins which forms over the surface of the tooth crown. Daily tooth brushing tends to only remove a portion of the pellicle surface while abrasive tooth cleaning and/or polishing (typically by a dental professional) will exposure more of the tooth enamel surface.

As used herein, the terms "enamel" and "tooth enamel" will refer to the highly mineralized tissue which forms the outer layer of the tooth. The enamel layer is composed primarily of crystalline calcium phosphate (i.e. hydroxyapatite; $Ca_5(PO_4)_3OH$) along with water and some organic material. In one embodiment, the tooth surface is selected from the group consisting of tooth enamel and tooth pellicle.

As used herein, a "polymer" is a natural or synthetic compound of usually high molecular weight consisting of repeated linked units.

As used herein, the term "polymer-binding peptide" refers to peptide sequences that bind with high affinity to a specified polymer (U.S. patent application Ser. No. 11/516,362). Examples include peptides that bind to polyethylene (SEQ ID NOs: 441-447), poly(methyl methacrylate) (SEQ ID NOs: 398-424), nylon (SEQ ID NOs: 448-453), poly(tetrafluoroethylene) (SEQ ID NOs: 432-440), polypropylene (SEQ ID NOs: 425-431, and polystyrene (SEQ ID NOs: 454-456).

As used herein, an "antimicrobial peptide" is a peptide having the ability to kill microbial cell populations (U.S. Pat. No. 7,427,656). Examples of antimicrobial peptides are provided as SEQ ID NOs: 567-595.

As used herein, the term "print medium-binding peptide" will refer to a peptide that binds to a printer medium such as cotton, cellulose, paper, and cotton/polyester blends. Examples of cellulose-binding peptides are provided as SEQ ID NOs: 520-525. Examples of cotton-binding peptides are provided as SEQ ID NOs: 514-516. Examples of Hammermill paper-binding peptides are provided as SEQ ID NOs: 514 and 517-519.

As used herein, "clay-binding peptide" refers to a peptide that binds with strong affinity to clay (U.S. patent application Ser. No. 11/696,380), such as montmorillonite Examples of clay-binding peptides are provided as SEQ ID NOs: 526-540.

As used herein, "calcium carbonate-binding peptide" refers to a peptide that binds with strong affinity of calcium carbonate (U.S. patent application Ser. No. 11/828,539). Examples of calcium carbonate-binding peptides are provided as SEQ ID NOs: 541-566.

As used herein, the term "pigment" means an insoluble colorant. A wide variety of organic and inorganic pigments alone or in combination may be used in the present invention.

As used herein, the terms "iron oxide-based pigment" and "iron oxide pigment" will refer to a pigment particle comprised primarily of an iron oxide. Iron oxide pigments may vary in color (red, yellow, brown, and black tones) due to minor impurities and/or the size of the pigment particle. In one embodiment, the iron oxide pigment is a cosmetically acceptable iron oxide pigment. Cosmetically acceptable iron oxide pigments are commercially available from various companies, such as Sensient Technologies Corp, Milwaukee, Wis. In one embodiment, the iron oxide is selected from the group consisting of ferric oxide ($Fe_2O_3$), ferrous ferric oxide ($Fe_3O_4$), and mixtures of $Fe_2O_3$ and $Fe_3O_4$. In one embodiment, the iron oxide is ferric oxide $Fe_2O_3$. In another embodiment, the iron oxide-based pigment is at least partially coated with silica.

As used herein, the term "pigment-binding peptide" refers to a peptide that binds with high affinity to a pigment particle. Examples of pigment-binding peptides are provided in Table A as SEQ ID NO: 149 and 460-513. SEQ ID NOs: 460-463 bind to carbon black, SEQ ID NOs: 464-472 bind to CROMOPHTAL® yellow, SEQ ID NOs: 473-475 bind to SUNFAST® magenta, SEQ ID NOs: 472 and 476-484 bind to SUNFAST® blue, and SEQ ID NO: 103 and 485-513 bind to iron oxide-based pigments.

As used herein, the term "pigment lake" or "lake" refers to a pigment manufactured by precipitating a dye with an inert binder, usually a metallic salt.

As used herein, the term "operably-linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). In a further embodiment, the definition of "operably linked" may also be extended to describe the products of chimeric genes. As such, "operably-linked" may also refer to the linking of two or more target surface-binding peptides by at least one rigid peptide linker.

As used herein, the "benefit agent" refers to a molecule that imparts a desired functionality or benefit when applied or coupled to a target surface. The present peptide reagents may be used to couple a benefit agent to a target surface, such as a body surface. In one embodiment, the peptide reagent is used to couple a benefit agent to a body surface by forming a complex between the peptide reagent, the benefit agent, and the body surface. In one embodiment, the peptide reagent is applied to the body surface prior to the application of the benefit agent (i.e., a sequential application). The benefit agent may be a peptide or the peptide reagent (e.g., condition peptides or antimicrobial peptides) or may be one or more molecules bound to (covalently or non-covalently), or associated with, a peptide reagent having affinity for a target surface. The benefit agent may be a particulate benefit agent. In one embodiment, the term "particulate benefit agent' is a general term relating to a particulate substance, which when applied to a body surface provides a cosmetic or prophylactic effect. Particulate benefit agents typically include pigments, particulate conditioners, inorganic sunscreens and the like along with other particulate substances commonly used in the personal care industry.

As used herein, the term "effective amount" is that amount of a specified material or combination of materials (e.g., a least one peptide-based reagent and the amount of at least one benefit agent) incorporated into a composition to achieve the desired effect.

The particulate benefit agent may comprise an applied coating, such as a polymeric coating. Examples of benefits agents may include, but are not limited to conditioners for personal care products, pigments, dyes, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few. In a preferred aspect, the benefit agent is cosmetically acceptable pigment or coated pigment.

As used herein, the term "$MB_{50}$" refers to the concentration of the binding peptide that gives a signal that is 50% of the maximum signal obtained in an ELISA-based binding assay (see Example 9 of U.S. Published Patent Application No. 2005-0226839; hereby incorporated by reference). The $MB_{50}$ provides an indication of the strength of the binding interaction or affinity of the components of the complex. The lower the value of $MB_{50}$, the stronger the interaction of the peptide with its corresponding substrate.

As used herein, the terms "binding affinity" or "affinity" refers to the strength of the interaction of a binding peptide (e.g. target surface-binding peptides, target surface-binding domains, and peptide reagents) with its respective substrate. The binding affinity may be reported in terms of the $MB_{50}$ value as determined in an ELISA-based binding assay or as a $K_D$ (equilibrium dissociation constant) value, which may be deduced using surface plasmon resonance (SPR). The lower the value of $MB_{50}$ or $K_D$, the stronger affinity of the peptide interacting with its corresponding substrate.

As used herein, the term "strong affinity" refers to a binding affinity, as measured as an $MB_{50}$ or $K_D$ value, of $10^{-4}$ M or less, preferably $10^{-6}$ M or less, preferably less than $10^{-6}$ M, more preferably less than $10^{-7}$ M, more preferably less than $10^{-8}$ M, even more preferably less than $10^{-9}$ M, and most preferably less than $10^{-10}$ M.

As used herein, the term "avidity" means the combined strength of multiple bond interactions ("multivalent associations").

As used herein, the terms "root-mean-square (RMS) fluctuation" ($RMS^{fluct}$) of a torsion angle is the standard deviation of the torsion angle value about the time-averaged value in a CHARMm molecular dynamics simulation, wherein the torsion angle is calculated was follows:

$$RMS^{fluct} = \sqrt{\frac{1}{N_f}\sum_f (\theta^f - \theta^{ave})^2}$$

where f refers to the frame number, N is the total number of frames in the trajectory file, and $\theta^f$ and $\theta^{ave}$ are the current value and the average value for the torsion angle, respectively.

As used herein, "CHARMm" (Chemistry at HARvard Macromolecular Mechanics) refers to a computer simulation engine (see Brooks B R et al. (1983) *J Comp Chem* 4: 187-217; MacKerell, A. D. et al. (1998) *J. Phys. Chem. B* 102(18): 3586-3616; and "CHARMM: The Energy Function and Its Parameterization with an Overview of the Program", by A. D. MacKerell, Jr., B. Brooks, C. L. Brooks, III, L. Nilsson, B. Roux, Y. Won, and M. Karplus in *The Encyclopedia of Computational Chemistry*, Volume 1, 271-277, by Paul von Raque Schleyer et al., editors (John Wiley & Sons: Chichester, United Kingdom (1998)); and Brooks, B. R., et al., (2009) *J. Comp. Chem.*, 30:1545-1615 (2009).

As used herein, "peptide rigidity" will refer to degree of flexibility of the peptide backbone over the entire length of a short, single chain peptide as measured by the average RMS fluctuation ($RMS^{fluct}$) of all internal torsion angles ($\phi, \psi$) over the length of a given single chain peptide linker. More specifically, the average $RMS^{fluct}$ can be calculated using the formula: (average $RMS^{fluct}$ phi ($\phi$)+average $RMS^{fluct}$ psi ($\psi$)/2. The average RMS fluctuation of all internal backbone torsion angles over the length of the peptide can be used to quantify the rigidity of the peptide linker. The more rigid the peptide is the smaller the average RMS fluctuation should be due to a more limited conformational space accessible to the peptide.

As used herein, the terms "peptide linker", "linker" and "peptide spacer" will refer to a peptide used to link together two or more target surface-binding peptides.

As used herein, "rigid peptide linker", "semi-rigid linker", "rigid linker", and "peptide having limited flexibility" will refer to a short single chain peptide linkers having an average $RMS^{fluct}$ of 25 or less when measured using the present CHARMm modeling over a production run of 200 ps.

As used herein, the term "α-helix" is a right-handed coiled conformation in which every backbone N—H group donates a hydrogen bond to the backbone C=O group of the amino acid four residues earlier (i+4→i hydrogen bonding). Amino acids that have a propensity for forming α-helical structure are typically methionine, alanine, leucine, glutamate, histidine, valine, tryptophan, glutamine, and lysine. In a preferred embodiment, the amino acids having a propensity for forming an α-helical structure are selected from the group consisting of alanine, glutamate (glutamic acid), and leucine.

As used herein, the term "$3_{10}$ helix" is a right-handed coiled conformation in which backbone N—H group donates a hydrogen bond to the backbone C=O group of the amino acid three residues toward the N-terminus (i+3→i hydrogen bonding).

As used herein, the term "salt bridge-stabilized α-helix" refers to a peptide that has the propensity to form an α-helix wherein the peptide comprises oppositely charged residues every 1 o 4 residue apart (i+4) or 3 or 2 residues apart (i+3) (Marqusee, S. and Baldwin, R., *Proc. Natl. Acad. Sci. USA* (1987) 84:8898-8902).

As used herein, the term "bridge", "peptide bridge", and "bridging element" will refer to a linear peptide used to couple a target-surface binding domain ("target surface-binding hand") to a peptide domain coupled to the surface of particulate benefit agent (i.e., covalent or non-covalent coupling). The peptide bridge may range in size from 1 to 60 amino acids in length, preferably 6 to 40 amino acids in length. In one embodiment, the peptide bridge is not rigid and has an average $RMS^{fluct}$ greater than 25, preferably greater than 30.

The terms "coupling" and "coupled" as used herein refer to any chemical association and include both covalent and non-covalent interactions. In one embodiment, the term coupling means a covalent interaction. In another embodiment, the term coupling means a non-covalent interaction.

The term "peptide-based conjugate" refers to a composition formed by coupling a peptide reagent with a particulate benefit agent.

The term "stringency" as it is applied to the selection of the binding peptides, refers to the concentration of the eluting agent used to elute binding peptides from the target surface. Higher concentrations of the eluting agent provide more stringent conditions.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Miscellaneous (or as defined herein) | Xaa | X |

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

The term "monovalent phage display" refers to phage display in which at most a single copy of a functional foreign peptide or small protein is displayed on the surface of each phage particle.

As used herein, the term "peptide-based" refers to an interfacial material comprised of a compound pertaining to or having the nature or the composition of the peptide class. Interfacial refers to the quality of the peptide-based material described herein as connecting one material to another.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5th Ed. Current Protocols and John Wiley and Sons, Inc., N.Y., 2002.

Target Surface-Binding Peptides

The present peptide-based reagent are comprised of at least one target surface-binding domain comprising two or more target surface-binding peptides linked together by at least one rigid peptide linker.

As described herein, target surface-binding peptides are single chain peptides having strong affinity for a target surface. The target surface-binding peptide are from about 7 amino acids to about 60 amino acids in length, more preferably, from about 7 amino acids to about 25 amino acids in length, most preferably from about 7 to about 20 amino acids in length. In one embodiment, the target surface-binding peptide is selected from a peptide library based on affinity for the target surface (i.e., a biopanned peptide). In another embodiment, the target surface-binding peptide may be identified using phage display. In another embodiment, the target surface-binding peptide may be empirically generated (Rothe et al., supra).

The target surface-binding peptide may have strong affinity for a particulate benefit agent surface (such as pigment(s), sunscreen agent(s), and whitening agent(s)), a polymeric coating applied to a particulate benefit agent (i.e., a coated pigment), a clay, calcium carbonate, silica, a metal oxide (such as iron oxide) or a body surface. Examples of various target surface-binding peptides can be found in U.S. Pat. Nos. 7,220,405; 7,285,264; and 7,585,495; U.S. Patent Application Publication Nos. US 2005/0226839; US 2005/0249682; US 2005/0054752; US 2006/0199206; US 2006/0073111; US 2007/0065387; US 2007/0067924; US 2007/0110686; US 2007/0141628; US 2007/0141629; US 2007-0053857; US 2007/0196305; US 2007/0249805; US 2007/0261775; US 2007/0265431; US 2007/0264720; US 2008-0207872; US 2008-0280810; US 2008-0175798; US 2009-0074694; US 2002-0098524; US 2003-0185870; and US 2009-0029902; PCT Publication No. WO2004/048399; and U.S. Provisional Patent Application No. 61/138,623; U.S. 61/138,631; and U.S. 61/016,708.

In one embodiment, the target surface-binding peptide is a body surface-binding peptide selected from the group consisting of a hair-binding peptide, a skin-binding peptide, a nail-binding peptide, and a tooth-binding peptide. Tooth-binding peptides as defined herein as peptides that bind with high affinity to mammalian teeth, preferably human teeth. The tooth surface may be tooth enamel or tooth pellicle (the acquired glycoprotein coating on teeth).

Rigid Peptide Linkers

Individual target surface-binding peptides may lack the binding affinity to durably couple a benefit agent to a target surface for some cosmetic applications (referred to herein as a "monovalent" interaction based one the use of a single target surface-binding peptide). Linking together a plurality of single chain target surface-binding peptides via peptide linkers is one approach to produce single chain peptides having improved affinity for the target surface. The formation of target surface-binding domains (also referred to herein as binding "hands") promote multivalent interactions between the single chain peptide and the target surface.

It has been discovered that rigid peptide linkers can be used to promote multivalent binding when linking together single chain target surface-binding peptides lacking a defined tertiary structure or protein scaffold. Single chain target surface-binding domains prepared using rigid peptide linkers exhibit superior binding affinity when compared to substantially flexible peptide linkers.

Initial experiments using monovalent phage display identified a family of linkers associated with the target surface binding domain having stronger affinity for a target surface. Target surface binding domains exhibiting a higher affinity for the target surface were typically comprised of peptide linkers having limited flexibility. As such, the use of rigid peptide linkers to couple together target surface-binding peptides appears to promote and/or enhance multivalent associations between the single chain target surface-binding domain and the target surface. Molecular dynamics modeling was then used to establish a parameter associated with limited linker flexibility. It was determined that average value of the root-mean-square fluctuations ($RMS^{fluct}$) of all internal torsion angles ($\phi$, $\psi$) of the peptide can be used to characterize and identify rigid peptide linkers.

Suitable rigid peptide linkers have an average $RMS^{fluct}$ of 25 or less over a production run of 200 ps using the present CHARMm model. In one embodiment, the average $RMS^{fluct}$ value is less than 25, more preferably no more than 20, and most preferably no more than 15 when measured over a production run of 200 picoseconds (ps). The present rigid linkers may range from 3 amino acid to 50 amino acids in length, preferably 3 amino acids to 40 amino acids in length, and most preferably 3 amino acids to 30 amino acids in length. In one embodiment, the rigid peptide linker has an average $RMS^{fluct}$ of 25 or less over a production run of 200 ps using the CHARMm model and ranges in length from 3 to 30 amino acids.

The rigid peptide linkers identified from the monovalent phage display experiments generally fell into 3 categories: (1) sequences designed to form a salt bridge-stabilized α-helix confirmation (i+4→i hydrogen bonding) in solution, (2) those having an extended confirmation of repeated proline dipeptide motif, and (3) a rigid linker comprising a peptide sequence herein referred to as the "Lk" linker or "Ton B" linker (SEQ ID NO: 54). The "TonB" linker is derived from the intermediate domain of the Gram-negative bacterial cytoplasmic membrane protein TonB (*Escherichia coli*; GENBANK® Accession No. AAY89716; SEQ ID NO: 155).

In one embodiment, the salt bridge-stabilized linker comprises a repeating motif having oppositely charged residues. In one embodiment, a salt bridge-stabilized α-helix is provided having the general formula:

```
(Xaa1-Xaa1-Ala-Ala-Xaa2-Xaa2)_d      (SEQ ID NO: 156)
or (Xaa1-Ala-Ala-Ala-Xaa2)_d;           (SEQ ID NO: 157)
or (Xaa1-Ala-Ala-Ala-Xaa2-Xaa3-         (SEQ ID NO: 158)
Xaa3)_d;
``` wherein;
  Xaa1 is independently Glu or Asp;
  Xaa2 is independently Lys or Arg; and
  Xaa3 is independently Ala, Leu, Val, Ile, Phe, Trp, Met or Tyr; and
  wherein d=2 to 10.

Xaa1 and Xaa2 are oppositely charged amino acid residues spaced 3 or 4 residues apart. In another embodiment, Xaa1 is glutamine and Xaa2 is lysine. In another embodiment, d=2 to 6.

The salt bridge-stabilized α-helix forming sequence may include hydrophobic amino acid residues at Xaa3. In one embodiment, Xaa3 is independently selected from the group Ala, Leu, Val, Ile, Phe, Trp, Met or Tyr. In a preferred embodiment, Xaa3 is selected from the group consisting of Leu, Val, and Ile, wherein Leu is preferred.

In a preferred embodiment, the salt bridge-stabilized sequence is selected from the group consisting of SEQ ID NOs: 2, 4, 6, 8, 10, 12, 56, 58, 156, 157, and 158. In a further preferred embodiment, the salt bridge stabilized α-helix sequence comprises at least one proline residue flanking the N- and/or C-terminus (a proline "cap") of the salt bridge stabilized α-helix sequence.

In one embodiment, the rigid peptide linker may comprise a repeated proline dipeptide motif having the formula:

```
(Xaa4-Pro)_e           (SEQ ID NO: 159)
or (Pro-Xaa4)_e;          (SEQ ID NO: 160)
or ((Xaa-Pro)_6GG]_e      (SEQ ID NO: 161)
``` wherein Xaa is an acidic or basic amino acid and wherein r is 2 to 20, preferably 2 to 16, more preferably 4 to 16. In another embodiment, e=2 for SEQ ID NO: 161.

In another embodiment, Xaa4 is selected from the group consisting of lysine, arginine, glutamic acid, and combinations thereof. In a further embodiment, Xaa is selected from the group consisting of glutamic acid, lysine, and combinations thereof. In another embodiment, the proline dipeptide comprises a peptide selected from the group consisting of SEQ ID NOs: 14, 16, 18, 20, 52, 159, 160, and 161. The extended proline dipeptide linker may comprise one or more flexible hinge regions as long as the average $RMS^{fluct}$ value is no more than 25, preferable less than 20. In one embodiment, the extended proline dipeptide comprises the amino acid sequence of SEQ ID NO: 52 or SEQ ID NO: 161.

One rigid peptide linker that was also identified from monovalent phage display experiments was the linker "Lk" or "TonB" linker. This linker appears to be particularly suitable for linking together target surface-binding peptides, including both body surface-binding domains and non-biological surfaces, such as cellulose acetate as shown in Example 8. In one embodiment, the rigid peptide linker is the TonB linker. In further embodiment, the TonB linker comprises SEQ ID NO: 54.

A hair-binding domain has been identified comprising the formula HP2-TonB-Gray3 that exhibits strong affinity for hair. In one embodiment, a hair-binding domain is provided as SEQ ID NO: 85. The HP2-TonB-Gray3 hair-binding domain has been linked, via a peptide bridge, to a pigment-binding domain comprising 2 iron oxide-binding peptides (2 copies of iron oxide-binding peptide "Rfe1"; SEQ ID NO: 103) identified by phage display.

Target Surface-Binding Domains Comprising Rigid Peptide Linkers

Target surface-binding domains prepared using rigid peptide linkers typically have stronger affinity for the target surface when compared to target surface-binding domains prepared with flexible peptide linkers. Monovalent phage display was used to isolate hair-binding domain having stronger affinity for the hair based on ELISA experiments. The majority of the hair-binding domains having stronger affinity for the surface of hair were comprised of rigid peptide linkers. Although not bound by theory, it is believed that the stronger affinity attributed to the hair-binding domains having rigid peptide linkers correlates with enhanced multivalent peptide binding by decreasing the translational and rotational entropies of the single chain peptides for the target surface.

The target-surface binding domains may be prepared from target surface-binding peptides identified and isolated from a combinatorially generated peptide library. The peptide linkers that promote the formation of target surface-binding domains with high affinity for the target surface can be identified using the monovalent phage display process described herein.

The monovalent phage display process described herein was used to identify linker rigidity as important factor in creating effective target surface-binding domains. The present monovalent phage display process may also be used to identify rigid peptide linkers having optimal length and composition by creating target surface-binding domain libraries incorporating rigid peptide linkers of varying length and amino acid content. In one embodiment, the rigid peptide linkers are selected from the group consisting of SEQ ID NOs: 2, 4, 6, 8, 10, 12, 14, 16, 18, 20, 52, 54, 56, 58, 156, 157, 158, 159, 160, and 161. In another embodiment, the rigid peptide linker are selected from the group consisting of 2, 4, 6, 8, 10, 12, 14, 16, 18, 20, 52, 54, 56, and 58.

Rigid peptide linkers may be used to prepare single chain binding domains (binding "hands") for any number of target surfaces including, but not limited to body surfaces such hair, skin, nails, and teeth as well as surfaces of pigments, polymers, sunscreen agents, clay, calcium carbonate, print media, and other target surfaces suitable for biopanning. The present examples illustrate the ability to use rigid linker to prepare body surface-binding domains, such as hair-binding domains, as well as a cellulose acetate-binding domain. Regardless of the target surface-binding domain, the incorporation of rigid peptide linkers in the target surface-binding domain typically enhances affinity and promotes multivalent peptide binding.

In one embodiment, a target surface-binding domain (TSBD) is provided comprising the general structure:

[(TSBP1)-RL$_1$-(TSBP2)-(RL$_2$)$_b$]$_a$ wherein i) TSBP1 is a first target surface-binding peptide having affinity for a target surface; wherein the first target-surface-binding peptide ranges in length from about 7 to about 60 amino acids;
ii) TSBP2 is a second target surface-binding peptide having affinity for the target surface; wherein the first target surface-binding peptide and the second target surface-binding peptide are the same or different; wherein the second target-surface-binding peptide ranges in length from about 7 to about 60 amino acids;
iii) RL$_1$ is a first rigid peptide linker; wherein the first rigid peptide linker ranges in length from about 3 to 50 amino acids in length;
iv) RL$_2$ is a second rigid peptide linker; wherein the first rigid peptide linker and the second peptide linker is the same or different; wherein the second rigid linker ranges in length from about 3 to 50 amino acids in length;
v) a=1 to 10; and
vi) b=0 or 1.

In another embodiment, at least one body surface-binding domain (BSBD) is provided having the general structure:

[(BSBP1)-RL$_1$-(BSBP2)-(RL$_2$)$_y$]$_x$ wherein i) BPBP1 is a first body surface-binding peptide having affinity for a body surface; wherein the first body-surface-binding peptide ranges in length from about 7 to about 60 amino acids;
ii) BSBP2 is a second body surface-binding peptide having affinity for the body surface; wherein the first body surface-binding peptide and the second body surface-binding peptide are the same or different; wherein the second body-surface-binding peptide ranges in length from about 7 to about 60 amino acids;
iii) RL$_1$ is a first rigid peptide linker; wherein the first rigid peptide linker ranges in length from about 3 to 50 amino acids in length;
iv) RL$_2$ is a second rigid peptide linker; wherein the first rigid peptide linker and the second peptide linker is the same or different; wherein the second rigid linker ranges in length from about 3 to 50 amino acids in length;
v) x=1 to 10; and
vi) y=0 or 1.

In another embodiment, the present peptide-based reagents comprise a binding domain prepared using a rigid peptide linker selected from the group consisting of:
a) a salt bridge-stabilized α-helix of the general formula:

(Xaa1-Xaa1-Ala-Ala-Xaa2-Xaa2)$_d$    (SEQ ID NO: 156)
or
(Xaa1-Ala-Ala-Ala-Xaa2)$_d$;    (SEQ ID NO: 157)
or
(Xaa1-Ala-Ala-Ala-Xaa2-Xaa3-Xaa3)$_d$;    (SEQ ID NO: 158)

wherein;
   Xaa1=Glu or Asp;
   Xaa2=Lys or Arg; and
   Xaa3=Leu, Val, Ile, Phe, Trp, Met or Tyr;
   wherein d=2 to 10;
b) an extended proline dipeptide of the formula:

(Xaa4-Pro)$_e$    (SEQ ID NO: 159)
or
(Pro-Xaa4)$_e$    (SEQ ID NO: 160)
or
[(Xaa4-Pro)$_6$-Gly-Gly]$_e$    (SEQ ID NO: 161)

wherein e=2 to 20; and Xaa4 is an acidic or basic amino acid; and
c) a peptide linker having the amino acid sequence of SEQ ID NO: 54.

In another embodiment, the peptide-based reagent comprises a benefit agent-binding domain having at least one rigid peptide linker, said benefit agent-binding domain have the general structure:

[(BABP1)-RL$_3$-(BABP2)-(RL$_4$)$_k$]$_j$;

wherein;
i) BABP1 is a first benefit agent-binding peptide having affinity for a particulate benefit agent surface; wherein the first benefit agent-binding peptide ranges in length from about 7 to about 60 amino acids;
ii) BABP2 is a second benefit agent-binding peptide having affinity for the particulate benefit agent surface; wherein the first benefit agent-binding peptide and the second benefit agent-binding peptide are the same or different; wherein the second benefit agent-binding peptide ranges in length from about 7 to about 60 amino acids;
iii) RL$_3$ is a third rigid peptide linker; wherein the third rigid peptide linker ranges in length from about 3 to 50 amino acids in length;
iv) RL$_4$ is a fourth rigid peptide linker; wherein the third rigid peptide linker and the fourth rigid peptide linker are the same or different; wherein the fourth rigid peptide linker ranges in length from about 3 to 50 amino acids in length;
v) j=1 to 10; and
vi) k=0 or 1.

In one embodiment, the peptide-based reagent comprises a body surface-binding domain having affinity for hair, said body surface binding domain comprises an amino acid sequence selected from the group consisting of SEQ ID NOs: 73, 74, 75, 76, 77, 78, 83, 85, 88, 90, 91, 92, 93, 94, 95, 96, 97, 98, 99, 100, 101, and 102.

In another embodiment, the peptide-based reagent comprises a body surface-binding domain having affinity for hair, said body surface binding domain comprises an amino acid sequence provided as SEQ ID NO: 85.

In another embodiment, a peptide-based reagent is provided having an amino acid provided as SEQ ID NO: 106.

Peptide-Based Reagents

Peptide-based reagents are also provided comprising at least one target surface-binding domain prepared by linking together two or more target surface-binding peptides using a rigid peptide linker.

One-Handed Peptide-Based Reagents

As used herein, the term one-handed peptide based reagent refers to a peptide reagent comprising a single target surface-binding domain prepared by linking together (using at least one of the present rigid peptide linkers) two or more target surface-binding peptides having strong affinity for the target surface. The peptide-based reagent may be comprised of a single target surface-binding domain coupled to a benefit agent, a single target surface-binding domain coupled through a peptide bridge to a benefit agent, or a single target surface-binding domain coupled (through an optional peptide bridge) to a peptide domain capable of binding to the benefit agent.

In one embodiment, a peptide-based reagent is provided comprising the general structure selected from the group consisting of:

a) $(BSBD)_f$-BA;
b) $(BSBD)_f$-BR-BA; and
c) $[(BSBD)_f$-$(BR)_g$-$(BABD)_h]_i$;

wherein
i) BSBD is a body surface-binding domain comprising at least one rigid peptide linker;
ii) BA is a benefit agent;
iii) BR is a peptide bridge; and
iv) BABD is a benefit agent-binding domain; and
wherein
$f=1$ to 10;
$g=0$ or 1;
$h=1$ to 10; and
$i=1$ to 10.

In one embodiment, the target surface-binding domain is a body surface-binding domain. In another embodiment, the body surface-binding domain has strong affinity for a body surface selected from the group consisting of hair, skin, nails, and teeth. In a further embodiment, the body surface-binding domain is used to couple a benefit agent to a body surface. In further embodiment, the benefit agent is selected from the group consisting of pigments, dyes, lakes, conditioning agents, antimicrobial agents (including antimicrobial peptides), and the like. In one embodiment, the antimicrobial peptide is selected from the group consisting of SEQ ID NOs: 567-595.

Two-Handed Peptide-Based Reagents

The present peptide-based reagents may comprise two different target surface-binding domains (i.e., the first and the second target surface-binding domains have affinity for different target surfaces) formed by linking together target surface-binding peptides so long as at least one of the two target surface-binding domains comprises at least one rigid peptide linkers. In another embodiment, both the first and the second target-surface binding domains are prepared by linking together their respective target surface-binding peptides using one or more rigid peptide linkers. The first and the second target surface-binding domains may be linked together using an optional peptide bridge, wherein the inclusion of a peptide bridge is preferred.

In one embodiment, the first target surface-binding domain is a body surface-binding domain and the second target surface-binding domain is a benefit agent-binding domain. In another embodiment, the body surface-binding domain has strong affinity for a body surface selected from the group consisting of hair, skin, nails, and teeth. In a further embodiment, the body surface-binding domain is used to couple a benefit agent to a body surface.

In another embodiment, a peptide based reagent is provided comprising a benefit agent binding domain having the general structure the general structure:

$[(BABP1)\text{-}RL_3\text{-}(BABP2)]\text{-}(RL_4)_k]_j$ wherein i) BABP1 is a first benefit agent-binding peptide having affinity for a particulate benefit agent surface; wherein the first benefit agent-binding peptide ranges in length from about 7 to about 60 amino acids;
ii) BABP2 is a second benefit agent-binding peptide having affinity for the particulate benefit agent surface; wherein the first benefit agent-binding peptide and the second benefit agent-binding peptide are the same or different; wherein the second benefit agent-binding peptide ranges in length from about 7 to about 60 amino acids;
iii) $RL_3$ is a third rigid peptide linker; wherein the third rigid peptide linker ranges in length from about 3 to 50 amino acids in length;
iv) $RL_4$ is a fourth rigid peptide linker; wherein the third rigid peptide linker and the fourth rigid peptide linker are the same or different; wherein the fourth rigid peptide linker ranges in length from about 3 to 50 amino acids in length;
v) $j=1$ to 10; and
vi) $k=0$ or 1.

Measurement of Rigidity of Short Peptides Using Molecular Dynamics

A rigid peptide linker can be designed by incorporating conformational constraints.

For example:
(1) an stable α-helical conformation as residues in regular helices have confined backbone torsion angles, the rigidity (stability) of the helices can be further enhanced by the formation of salt-bridges;
(2) an extended conformation with restricted backbone torsion angles, such as peptides consisting of alternating Xaa4-Pro or Pro-Xaa4 dipeptide units, which will adopt relatively stiff elongated conformation; or
(3) a conformationally-constrained peptide linker such as SEQ ID NO: 54.

Reports show that simple physical models can reproduce the structural biases of certain peptide fragments. Molecular dynamics (MD) simulations have been used to study the conformation or folding of small peptides. As described below, a MD simulation was used to quantify the rigidity of peptides.

The rigidity of a peptide can be related to its conformational fluctuations during the MD simulation. Specifically, the averaged value of root-mean-square (RMS) fluctuations of the peptide backbone torsion angles can be used to quantify the rigidity of the peptide.

Torsion Angles

The backbone of a (poly)peptide chain consists of a repeated sequence of three atoms of each residue in the chain—the amide N, the $C^α$, and the carbonyl C.

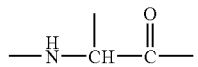

These atoms are generally represented as $N_i$, $C^α$, and $C_i'$, respectively, where i is the residue number, starting from the amino end of the chain. The peptide bond is usually planar because of its partial double bond, and the group of atoms usually acts as a rigid unit. This group is designated a peptide unit. Thus the polypeptide chain can be divided into peptide units that go from one $C^\alpha$ atom to the next $C^\alpha$.

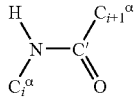

The only degrees of freedom the peptide units have are rotations around the bonds linking consecutive units. Rotations about bonds are described as torsion or dihedral angles, which are usually taken to lie in the range −180° to 180°. Each peptide unit can rotate around two such bonds: the $C^\alpha$—C' and the N—$C^\alpha$ bonds. Rotation about the N—$C^\alpha$ bond is denoted by torsion angle phi (φ), and rotation about the $C^\alpha$—C' bond by psi (ψ). The maximum value of 180° (which is the same as −180° is given to each of the torsion angles in the maximally extended chain, when the N, $C^\alpha$, and C' atoms are all trans to each other. When these atoms are all cis to each other, the torsion angles have the value of zero.

In this way, each amino acid is associated with only two conformational angles φ and ψ, thus the backbone conformation of the polypeptide is completely determined when the φ and ψ angles are defined. In other words, a peptide backbone structure can be represented as a sequence of torsion angle values.

Molecular Dynamics Simulation

The method of molecular dynamics (MD) simulation is one of the principal tools in the theoretical study of biological molecules. This computational method calculates the time dependent behavior of a molecular system. MD simulations have provided detailed information on the fluctuations and conformational changes of proteins and nucleic acids. These methods are now routinely used to investigate the structure, dynamics and thermodynamics of biological molecules and their complexes.

The MD simulation method is based on Newton's second law or the equation of motion. Once the force on each atom is known, it is possible to determine the acceleration of each atom in the system. MD simulations generate successive configurations of the system by integrating the equation of motion. The result is a trajectory that specifies how the positions and velocities of the atoms in the system vary with time. The trajectory is obtained by solving the following equation:

$$F_i = m_i a_i$$

where $F_i$ is the force exerted on atom i, $m_i$ is the mass of atom i and $a_i$ is the acceleration of atom i. The force can also be expressed as the gradient of the potential energy:

$$F_i = -\Delta_i V$$

where V is the potential energy of the system.

Combining the two equations yields:

$$\frac{d^2 V}{dr_i} = m_i \frac{d^2 r_i}{dt^2}$$

where $r_i$ is the position of atom i.

Thus, the derivative of the potential energy can be related to the changes in position as a function of time.

Verlet Integration Method

Numerous numerical algorithms have been developed for integrating the equations of motion. All the integration algorithms assume the positions, velocities and accelerations can be approximated by a Taylor series expansion:

$$r(t+\delta t) = r(t) + \delta t v(t) + \frac{1}{2}\delta t^2 a(t) + \frac{1}{6}\delta t^3 b(t) + \frac{1}{24}\delta t^4 c(t) + \ldots$$

$$v(t+\delta t) = v(t) + \delta t a(t) + \frac{1}{2}\delta t^2 b(t) + \frac{1}{6}\delta t^3 c(t) + \ldots$$

$$a(t+\delta t) = a(t) + \delta t b(t) + \frac{1}{2}\delta t^2 c(t) + \ldots$$

$$b(t+\delta t) = b(t) + \delta t c(t) + \ldots$$

Where r is the position, v is the velocity (the first derivative with respect to time), a is the acceleration (the second derivative with respect to time), etc. The Verlet algorithm is the most widely used method for integrating the equations of motions in a MD simulation (Verlet, L. (1967) *Physical Review* 159 (1): 98-103). The Verlet algorithm calculates the new positions at t+δt, r(t+δt) using the positions and accelerations at time t, and the positions from the previous time step, r(t−δt).

$$r(t+\delta t) = r(t) + \delta t v(t) + \frac{1}{2}\delta t^2 a(t) + \ldots$$

$$r(t-\delta t) = r(t) - \delta t v(t) + \frac{1}{2}\delta t^2 a(t) - \ldots$$

Adding the two equations gives:

$$r(t+\delta t) = 2r(t) - r(t-\delta t) + \delta t^2 a(t)$$

The velocities can be then calculated by dividing the difference in positions at times t+δt and t−δt by 2δt:

$$v(t) = |r(t+\delta t) - r(t-\delta t)|/2\delta t$$

Force Field

Most of the MD simulation methods are force field methods (also known as statistical mechanics). The force field methods ignore the motion of the electrons and calculate the energy of a system as a function of the nuclear positions only.

A force field consists of the functional form and parameter sets used to describe the potential energy of a system of atoms. The basic functional form of a force field includes both bonded terms relating to atoms that are linked by covalent bonds, and non-bonded terms describing the long-range electrostatic and van der Waals forces. The specific decomposition of the terms depends on the force field, but generally the total energy in an additive force field can be written as $$E_{total} = E_{bonded} + E_{nonbonded}$$

$$E_{bonded} = E_{bond} + E_{angle} + E_{dihedral}$$

$$E_{nonbonded} = E_{electrostatic} + E_{vanderWaals}$$

The bond and angle terms are usually modeled as harmonic oscillators in force fields. The functional form for the rest of the bonded terms is highly variable in different force fields.

Non-Bonded Interactions

The non-bonded terms in a force field are generally considered in two groups, one comprising electrostatic interactions, and the other van der Waals interactions. The non-bonded terms are most computationally intensive because they include many more interactions per atom. Typically interactions are limited to pairwise energies. The van der Waals term is usually computed with a Lennard-Jones potential and the electrostatic term with Coulomb's law.

The Lennard-Jones 12-6 function is the best known potential function for van der Waals interactions. It takes the following form:

$$v(r) = 4\varepsilon\left[\left(\frac{\sigma}{r}\right)^{12} - \left(\frac{\sigma}{r}\right)^6\right]$$

Where $\sigma$ is the collision diameter (the separation for which the energy is zero) and $\in$ is the well depth.

The electrostatic interaction between two molecules or between different parts of the same molecule is calculated as a sum of interactions between pairs of point charges using Coulomb's law:

$$F = \sum_{i=1}^{N_A}\sum_{j=1}^{N_B} \frac{q_i q_j}{4\pi\varepsilon_{eff} r_{ij}}$$

$N_A$ and $N_B$ are the numbers of point charges in the two molecules, $q_i$, and $q_j$ are the partial atomic charges, $\in_{eff}$ is the effective dielectric constant, $r_{ij}$ is the relative distance between the two point charges.

Cutoff Method

In principle, the non-bonded terms between every pair of atoms should be evaluated. To speed up the computation, the interactions between two atoms separated by a distance greater than a pre-defined distance, the cutoff distance (CUTNB), are ignored. There are different methods to terminate the interactions between two atoms. In the truncation method, the interactions are simply set to zero for inter-atomic distances greater than the cutoff distance. In the SHIFT cutoff method, the entire potential energy surface is modified such that the interaction potential is zero at the cutoff distance. In the SWITCH method, the interaction potential tapers off over a pre-defined range of distance. The potential takes its usual value up to the first cutoff (CTONNB), and is then switched to zero between the first the last cutoff (CTOFNB). In one embodiment, CTONNB is 10 and the CTOFNB is 12.

Treatment of Solvent

Solvent, usually water, has a fundamental effect on the structure and dynamics of biological molecules. One of the most important effects of the solvent is the screening of electrostatic interactions. Thus it is important to include solvent effects in a MD simulation. In the implicit treatment of the solvent, water molecules are not included in the simulation but an effective dielectric constant is used in the calculation of electrostatic interactions. The effective dielectric constant can be modeled to be distance dependent, $\in_{eff} = r_{ij}\in$.

In the explicit solvent model, water molecules are explicitly included in the simulation ($\in_{eff}$ is 1 in the electrostatic term). In this case, the solvent boundary conditions must be imposed. The purpose is to prevent the water molecules from diffusing away from the protein during the simulation, and to allow simulation using a limited number of solvent molecules.

Boundary Conditions

Periodic boundary conditions (PBC) are a set of boundary conditions that enables a simulation to be performed using a relatively small number of atoms in such a way that the atoms experience forces as though they were in a bulk solution. The center cell, or the primary cell, is replicated in all directions to give a periodic array. If a particle leaves the primary cell during the simulation, then it is replaced by an image particle that enters from the opposite side. Thus the number of particles within the primary cell remains constant.

The cube cell is the simplest periodic system to program. Other cell shapes can be used as well, for example, the hexagonal prism, the truncated octahedron, and the rhombic dodecahedron. It is often recommended to choose a periodic cell that reflects the underlying geometry of the system.

The size of the unit cell must be chosen such that an atom in the primary box does not see its images in the surrounding boxes. Usually this is achieved by specifying the shortest side of the box greater than twice of the non-bonded cutoff distance.

Long-Range Electrostatic Interactions

A major approximation made in the conventional MD simulations is the neglect of long-range electrostatic force. However, the long range electrostatic interactions play important roles in biological molecules. Increasing the cutoff distance to include the longer range electrostatic interactions in a MD simulation can dramatically raise the computational cost.

One solution is to calculate the full electrostatic energy of the unit cell in a macroscopic lattice of repeating images using the Ewald summation convention (Ewald, P. P. (1921) *Annalen der Physik* 369(3): 253-287). The Ewald summation is the method of choice to compute electrostatic interactions in system with PBC. It avoids all problems associated with the use of a cutoff distance. The Particle Mesh Ewald (PME) method is an approximate method to computer Ewald sums and has been shown as an efficient algorithm (Darden, T., D. and York, et al. (1993) *J. Chem. Phys.* 98(12): 10089-10092).

Constraint Dynamics

The conformational behavior of a molecule is a superposition of different motions. The high frequency motions (e.g. bond vibrations) are usually of less interest than the low frequency motions, which often correspond to major conformational changes. The timestep of a MD simulation is dictated by the highest frequency motion present in the system. The timestep can be increased if one can remove the high frequency vibrations without sacrificing accuracy.

SHAKE algorithm (Ryckaert, J.- P. and G. Ciccotti, et al. (1977) *J. Comp. Phys.* 23(3): 327-341) is the most commonly used method for applying constraints. SHAKE can be applied to just the bonds involving hydrogen atoms which have much higher vibrational frequencies. This can enable the time step in a MD simulation to be increased, for example, from typical 1 fs (femtosecond) to 2 fs.

Energy Minimization

When the starting configuration is very far from the equilibrium, large forces can cause the simulation to crash or distort the system, thus, it is often necessary to run energy minimization of the system before starting the MD simulation. Energy minimization methods are used to identify configurations of the system that corresponds to minimum points in the energy surface. Minimum energy arrangements of the atoms correspond to stable states of the system.

Energy minimization algorithms generally start from an arbitrary state of molecules. These methods work by gradually changing the coordinates of the atoms as they move the system closer and closer to the minimum point. The updated coordinates are then used to evaluate the potential energy again.

Two first-order minimization algorithms that are frequently used in molecular modeling are the steepest descents and the conjugate gradient method. In the steepest descents method, each atom is moved a short distance in the direction of decreasing energy (Payne, M. C. and J. D. Joannopoulos, et al. (1986) *Phys. Rev. Lett.* 56(24): 2656). The direction of the gradient is determined by the largest inter-atomic forces, so steepest descent is a good method for relieving the highest-energy features in an initial configuration. The disadvantage of the steepest descents method is that it does not converge well. The conjugate gradient method produces a set of mutually conjugate directions so that each successive step continually refines the direction toward the minimum without oscillations (Stich, I., and R. Car, et al. (1989) *Phys. Rev. B* 39(8): 4997-5004). The conjugate gradient method has the advantage of more efficient convergence to minimum.

Adopted Basis Newton-Raphson (ABNR) method calculates the $2^{nd}$ derivative matrix and then uses steepest descents to find new direction for next iteration (Chu, J.-W., and B. L. Trout, et al. (2003) *J. Chem Phys* 119(24): 12708-12717.).

Constant Temperature Dynamics

It is usually desirable to perform a simulation at a specified temperature. Simulations at constant temperature (NVT) are useful to study the system behaviors at different temperatures. As the temperature of a system is related to the average kinetic energy of the particles, the temperature can be controlled by scaling the velocities.

A dynamics run typically consists of four parts: initialization, heating, equilibration, and the simulation itself (or production). Initialization means establishing an initial configuration and velocity for all the atoms. Heating is the process of increasing the kinetic energy of the system up to the temperature at which the simulation will be conducted. Equilibration is the process where the system evenly distributes its kinetic and the potential energy throughout the system. The production phase can begin when the average temperature of the system stabilizes and this is when one can collect the trajectory information for analysis.

The initial configuration can be obtained from experimental data, from a theoretical model, or from a combination of the two. The initial velocities are usually assigned by randomly selecting from a Maxwell-Boltzmann distribution at the temperature of interest.

$$p(v_{ix}) = \left(\frac{m_i}{2\pi k_B T}\right)^{1/2} \exp\left[-\frac{1}{2}\frac{m_i v_{ix}^2}{k_B T}\right]$$

The Maxwell-Boltzmann equation provides the probability that at atom i of mass $m_i$ has a velocity $v_{ix}$ in the x direction at a temperature T.

Heating the system is performed gradually by increasing the kinetic energy by a small amount periodically. During the heating phase, initial velocities are assigned at a low temperature. Periodically new velocities are assigned at a slightly higher temperature and the simulation is allowed to continue. This process is repeated until the desired temperature is reached.

Once the desired temperature is reached, the simulation of the system continues and several properties are being monitored: the structure, pressure, temperature, and energy. The goal of the equilibration phase is to run the simulation until these properties become stable with respect to time. One typically specifies a temperature window around the final temperature where velocity adjustment will be made. If the temperature increases or decreases significantly, the velocities are scaled such that the temperature returns to near its desired value.

The final step of a MD simulation is to run the simulation in production phase (production "run") for the time length desired. The temperature window can be set larger, so that if there are gross conformational changes which result in large changes in the potential energy, the temperature can be maintained.

A production phase of 200 ps was used in the present models. The average RMS fluctuation is calculated from the trajectory file from the production run.

Particulate Benefit Agents

The method of the invention may be used in conjunction with a wide variety of particulate benefit agents. In one embodiment, the particulate benefit agents are those known in the art of personal care. Examples of particulate benefit agents may include, but are not limited to, pigments, particulate conditioning agents, and inorganic sunscreens.

As used herein, the term "pigment" means an insoluble colorant. A wide variety of organic and inorganic pigments alone or in combination may be used in the present invention. Pigments for coloring hair and skin are well known in the art (see for example Green et al. (WO 0107009), incorporated herein by reference, *CFTA International Color Handbook*, $2^{nd}$ ed., Micelle Press, England (1992) and *Cosmetic Handbook*, US Food and Drug Administration, FDA/IAS Booklet (1992)), and are available commercially from various sources (for example Bayer, Pittsburgh, Pa.; Ciba-Geigy, Tarrytown, N.Y.; ICI, Bridgewater, N.J.; Sandoz, Vienna, Austria; BASF, Mount Olive, N.J.; and Hoechst, Frankfurt, Germany).

Metallic and semiconductor nanoparticles may also be used as hair coloring agents due to their strong emission of light (Vic et al., U.S. Patent Application Publication No. 2004/0010864). The metallic nanoparticles include, but are not limited to, particles of gold, silver, platinum, palladium, iridium, rhodium, osmium, iron, copper, cobalt, and alloys composed of these metals. An "alloy" is herein defined as a homogeneous mixture of two or more metals. The "semiconductor nanoparticles" include, but are not limited to, particles of cadmium selenide, cadmium sulfide, silver sulfide, cadmium sulfide, zinc oxide, zinc sulfide, zinc selenide, lead sulfide, gallium arsenide, silicon, tin oxide, iron oxide, and indium phosphide. The nanoparticles are stabilized and made water-soluble by the use of a suitable organic coating or monolayer. As used herein, monolayer-protected nanoparticles are one type of stabilized nanoparticle. Methods for the preparation of stabilized, water-soluble metal and semiconductor nanoparticles are known in the art, and suitable examples are described by Huang et al. in U.S. Patent Application Publication No. 2004/0115345, which is incorporated herein by reference. The color of the nanoparticles depends on the size of the particles. Therefore, by controlling the size of the nanoparticles, different colors may be obtained.

The particulate benefit agent may also be nanoparticles, such as organic nanoparticles; inorganic nanoparticles, such as silica nanoparticles; polymer nanoparticles; and metallic and semiconductor nanoparticles, which serve as hair conditioning agents, specifically, hair straightening aids, hair strengthening aids, and hair volumizing agents.

The particulate benefit agent may also be an inorganic UV sunscreen, which absorbs, reflects, or scatters ultraviolet light at wavelengths from 290 to 400 nanometers. Inorganic UV sunscreen materials are typically inorganic pigments and metal oxides including, but not limited to, titanium dioxide (such as SunSmart available from Cognis Co.), zinc oxide, and iron oxide. A preferred sunscreen is titanium dioxide nanoparticles. Suitable titanium dioxide nanoparticles are described in U.S. Pat. Nos. 5,451,390; 5,672,330; and 5,762,914. Titanium dioxide P25 is an example of a suitable commercial product available from Degussa (Parsippany, N.J.). Other commercial suppliers of titanium dioxide nanoparticles include Kemira (Helsinki, Finland), Sachtleben (Duisburg, Germany) and Tayca (Osaka, Japan).

The titanium dioxide nanoparticles typically have an average particle size diameter of less than 100 nanometers (nm) as determined by dynamic light scattering which measures the particle size distribution of particles in liquid suspension. The particles are typically agglomerates which may range from about 3 nm to about 6000 nm. Any process known in the art can be used to prepare such particles. The process may involve vapor phase oxidation of titanium halides or solution precipitation from soluble titanium complexes, provided that titanium dioxide nanoparticles are produced.

A preferred process to prepare titanium dioxide nanoparticles is by injecting oxygen and titanium halide, preferably titanium tetrachloride, into a high-temperature reaction zone, typically ranging from 400 to 2000° C. Under the high temperature conditions present in the reaction zone, nanoparticles of titanium dioxide are formed having high surface area and a narrow size distribution. The energy source in the reactor may be any heating source such as a plasma torch.

Polymer-Coated Particulate Benefit Agents

The particulate benefit agent may be coated with a polymer coating such that peptides having an affinity for the polymer will bind to the polymer coating. The polymer coating may be formed from many different organic and biological polymers including, but not limited to cellulose acetate, polyacrylates, polymethacrylates, polymethylmethacrylates, polycarbonates, polystyrene, polypropylene, polyethylene terephthalate, polyurethanes, polypeptides, lignin, polysaccharides, polyamides, polyimides, polyaramides, and copolymers, (e.g., block and graft copolymers) comprising at least one monomer from methacylates, acrylates or styrene.

If a pigment dispersed with a polymer dispersant is used as the particulate benefit agent, the polymer dispersant, may serve as the polymer coating. Any of the polymer dispersants described above may be used. For example, pigments dispersed with a polyacrylate-containing dispersant may be used in conjunction with a polyacrylate-binding peptide. Alternatively, the dispersed pigment may be coated with another polymer as described below.

For pigments and self-dispersing pigments and other particulate benefit agents that are not typically used with a polymer dispersant, the particles may be coated with the polymer using particle coating methods known in the art. Typically, methods used for coating particles are solution-based methods that rely on the application of a polymer coating solution onto the particle surface, followed by the removal of the solvent. For example, the particulate benefit agent may be coated with a polymer by simply mixing the particles with a solution containing the polymer for a time sufficient to coat the particles and then removing the solvent.

Identification of Peptide Linkers Characterized by the Ability to Enhance Binding Affinity by Monovalent Phage Display Target surfaces, such as various body surfaces, may have a heterogeneous surface. As such, many different surface-binding epitopes (the surface features where target surface-binding peptides non-covalently associate) may be present on the target surface. The number and the relative distance between the various binding epitopes may not be known. As such, the optimal length and/or selection of the optimal rigid peptide linker may vary depending upon the surface characteristics of the target surface and the target surface-binding peptides used to prepare the target surface-binding domain.

As illustrated herein, the use of rigid peptide linkers generally enhances the multivalent characteristics of a target surface-binding domain. Molecular Dynamics (MD) modeling can be used to identify peptides having limited flexibility. However, the selection of the rigid linker that provides the strongest affinity may require additional screening.

As illustrated in the present examples, monovalent phage display can be used to identify peptide linkers that provide exhibited stronger affinity for the target surface.

Production of Peptides

Peptides may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the peptides may be prepared using recombinant DNA and molecular cloning techniques. Genes encoding the peptides may be produced in heterologous host cells, particularly in the cells of microbial hosts, as described by Huang et al. (U.S. Patent Application Publication No. 2005/0050656) and O'Brien et al., supra. The peptides may further comprise a proline (P) residue at the N-terminus and optionally an aspartic acid (D) residue at the C-terminus to enable acid cleavage of the peptide when produced as a fusion peptide. These additional residues result from the use of acid labile DP cleavage sites to separate the desired peptide sequence from peptide tags, used to promote inclusion body formation, and between tandem repeats of the peptide sequences.

Personal Care Compositions Comprising a Peptide-Based Reagent and a Benefit Agent The peptide-based reagent may be applied to a body surface from various compositions, such as an aqueous solution or a personal care composition. It is understood that when referring to personal care compositions comprising a peptide-based reagent, the personal care compositions will comprise at least one benefit agent capable of being coupled via the peptide-based reagent to the target body surface.

For example, a peptide-based reagent may be applied to the hair from an aqueous solution comprising the peptide-based reagent. Alternatively, the peptide-based reagent may be applied to the hair from a hair care composition (described below). In either case, the peptide-based reagent is used in the composition at a concentration of about 0.01% to about 10%, preferably about 0.01% to about 5% by weight relative to the total weight of the composition. Suitable peptide-based reagents are described above. Additionally, a mixture of different peptide-based reagents may be used in the composition. The peptide-based reagents in the mixture need to be chosen so that there is no interaction between the reagents that mitigates the beneficial effect. Suitable mixtures of peptide-based reagents may be determined by one skilled in the art using routine experimentation. If a mixture of peptide-based reagents is used in the composition, the total concentration of the peptide-based reagent is about 0.01% to about 10% by weight relative to the total weight of the composition.

Hair care compositions are herein defined as compositions for the treatment of hair including, but not limited to, shampoos, conditioners, rinses, lotions, aerosols, gels, mousses, and hair dyes. The hair care composition may comprise a cosmetically acceptable medium for hair care compositions, examples of which are described for example by Philippe et al. in U.S. Pat. No. 6,280,747, and by Omura et al. in U.S. Pat. No. 6,139,851 and Cannell et al. in U.S. Pat. No. 6,013,250, all of which are incorporated herein by reference. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions may contain one or more conventional cosmetic or dermatological additives or adjuvants including, but not limited to, antioxidants, preserving agents, fillers, surfactants, UVA and/or UVB sunscreens, fragrances, thickeners, wetting agents and anionic, nonionic or amphoteric polymers, and dyes or pigments.

Similarly, the peptide-based reagent may be applied to the skin from an aqueous solution comprising the peptide-based reagent. Alternatively, the peptide-based reagent may be applied to the skin from a skin care composition. In either case, the peptide-based reagent is used in the composition at a concentration of about 0.01% to about 10%, preferably about 0.01% to about 5% by weight relative to the total weight of the composition. Suitable peptide-based reagent are described above. Additionally, a mixture of peptide-based reagent may be used in the composition. The peptide-based reagents in the mixture need to be chosen so that there is no interaction between the peptides that would mitigate the beneficial effect. Suitable mixtures of peptide-based reagents may be determined by one skilled in the art using routine experimentation. If a mixture of peptide-based reagents is used in the composition, the total concentration of the peptide-based reagent is about 0.01% to about 10% by weight relative to the total weight of the composition.

Skin care compositions are herein defined as compositions for the treatment of skin including, but not limited to, skin care, skin cleansing, make-up, sunscreens, skin lightening, and anti-wrinkle products. The skin care composition may be in the form of conventional skin-care products such as a cream, gel or lotion, capsules or the like. The composition can also be in the form of a so-called "wash-off" product e.g. a bath or shower gel, possibly containing a delivery system for the actives to promote adherence to the skin during rinsing. Most preferably the product is a "leave-on" product, i.e. a product to be applied to the skin without a deliberate rinsing step soon after its application to the skin.

The skin care composition may comprise a cosmetically acceptable medium for skin care compositions, examples of which are described for example by Philippe et al. supra. For example, the cosmetically acceptable medium may be an anhydrous composition containing a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants including, but not limited to, antioxidants, preserving agents, fillers, surfactants, UVA and/or UVB sunscreens, fragrances, thickeners, wetting agents and anionic, nonionic or amphoteric polymers, and dyes or pigments.

The present invention includes oral care compositions comprising an effective amount of one or more of the present peptide-based reagents and an effective amount of at least one orally-acceptable benefit agent. In one embodiment, the orally-acceptable benefit agent is a whitening agent.

In another embodiment, the peptide-based reagent is used to detect the presence of a particular surface on teeth (e.g., a diagnostic application). For example, the peptide-based reagent may be used to detect the presence of a pellicle coating on teeth immediately after an abrasive cleaning/polishing procedure (e.g. a dental office cleaning/polishing procedure).

The oral care compositions of the invention may be in the form of powder, paste, gel, liquid, ointment, or tablet. Exemplary oral care compositions include, but are not limited to toothpaste, dental cream, gel or tooth powder, mouth wash, breath freshener, and dental floss. The oral care compositions comprise an effective amount of the peptide-based reagent of the invention in an orally acceptable carrier medium. An effective amount of a peptide-based reagent for use in an oral care composition may vary depending on the type of product. Typically, the effective amount of the peptide-based reagent is a proportion from about 0.01% to about 90% by weight relative to the total weight of the composition. Additionally, a mixture of different peptide-based reagents having affinity for different benefit agents (e.g. tooth whitening colorants) may be used in the composition. The peptide-based reagents in the mixture need to be chosen so that there is no interaction between the peptides that mitigates the whitening effect. Suitable mixtures of peptide-based reagents may be determined by one skilled in the art using routine experimentation. If a mixture of peptide-based reagents is used in the composition, the total concentration of the peptide-based reagents and the benefit agent(s) is about 0.001% to about 90% by weight relative to the total weight of the composition.

Components of an orally-acceptable carrier medium are described by White et al. in U.S. Pat. No. 6,740,311; Lawler et al. in U.S. Pat. No. 6,706,256; Fuglsang et al. in U.S. Pat. No. 6,264,925; and Ibrahim et al., U.S. Patent Application Publication No. 2005/0069501, each of which is incorporated herein by reference. For example, the oral care composition may comprise one or more of the following: abrasives, surfactants, antioxidants, chelating agents, fluoride sources, thickening agents, buffering agents, solvents, humectants, carriers, bulking agents, and oral benefit agents, such as enzymes, anti-plaque agents, anti-staining agents, anti-microbial agents, anti-caries agents, anti-inflammatory agents, desensitizing agents, sweetening agents, flavoring agents, breath-freshening agents, coolants, nutrients, and salivating agents.

Nail care compositions are also provided. The nail care compositions may be in the form of a nail polish or a nail protectant. In on embodiment, the nail care composition is a nail polish comprising at least one coloring agent (i.e. "a peptide-based nail colorant"). The peptide-based reagent may be used to increase the durability of a coloring agent for the a nail surface.

In the peptide-based nail colorants, any of the coloring agents described above may be used. The preferred coloring agents for use in the peptide-based nail colorants include D&C Red Nos. 8, 10, 30 and 36, the barium lakes of D&C Red Nos. 6, 9 and 12, the calcium lakes of D&C Red Nos. 7, 11, 31 and 34, the strontium lake of D&C Red No. 30 and D&C Orange No. 17 and D&C Blue No. 6.

The peptide-based nail colorants may be used in nail polish compositions for coloring fingernails and toenails. Nail polish compositions are herein defined as compositions for the treatment and coloring of nails, comprising an effective amount of a peptide-based nail colorant or a mixture of different peptide-based nail colorants in a cosmetically acceptable medium. An effective amount of a peptide-based nail colorant for use in a nail polish composition is herein defined as a proportion of from about 0.001% to about 20% by weight relative to the total weight of the composition. Components of a cosmetically acceptable medium for nail polishes are described by Philippe et al. supra. The nail polish composition typically contains a solvent and a film forming substance, such as cellulose derivatives, polyvinyl derivatives, acrylic polymers or copolymers, vinyl copolymers and polyester polymers. Additionally, the nail polish may contain a plasticizer, such as tricresyl phosphate, benzyl benzoate, tributyl phosphate, butyl acetyl ricinoleate, triethyl citrate, tributyl acetyl citrate, dibutyl phthalate or camphor.

Methods for Applying a Particulate Benefit Agent to a Body Surface

Peptide-based reagents may be used to enhance the durability of common particulate benefit agents, for example, pigments, whitening agents, particulate conditioners, and inorganic sunscreens, and the like, on one or more body surfaces according to the method of the invention. The particulate benefit agent may be coated with a polymer or other suitable coating.

In one embodiment, the particulate benefit agent is applied to the body surface prior to the application of the peptide-based reagent. In another embodiment, the peptide-based reagent is applied prior to the application of the particulate benefit agent. In yet a further embodiment, the particulate benefit agent and the peptide-based reagent are applied concomitantly to a body surface as described in U.S. Patent Application Publication NOs. 2007/0067924 and 2007/0065387; U.S. Pat. No. 7,285,264; and International Patent Application Publication NO. WO2008/054746. The particulate benefit agent may be applied to the body surface from any suitable solution, such as an aqueous solution or a conventional personal care composition, for example a coloring composition. These personal care compositions are well known in the art. The particulate benefit agent is left on the body surface for a time sufficient for the particulate benefit agent to bind to the body surface, typically between about 5 seconds to about 60 minutes.

In any of the methods described above, the composition comprising the peptide-based reagent having affinity for the particulate benefit agent may optionally be reapplied to the body surface.

Additionally, in any of the methods described above, a composition comprising a polymeric sealant may optionally be applied to the body surface after the application of the composition comprising a particulate benefit agent and the peptide-based reagent to further enhance the durability of the benefit agent. The composition comprising the polymeric sealant may be an aqueous solution or a hair, skin or oral care or skin care composition comprising the polymeric sealant. Typically, the polymeric sealant is present in the composition at a concentration of about 0.25% to about 10% by weight based on the total weight of the composition. Polymeric sealants are well know in the art of personal care products and include, but are not limited to, poly(allylamine), acrylates, acrylate copolymers, methacrylates, methacrylate copolymers, polyurethanes, carbomers, methicones, amodimethicones, polypeptides, polyethylenene glycol, beeswax, siloxanes, and the like. The choice of polymeric sealant depends on the specific particulate benefit agent and the peptide-based reagent used. The optimum polymeric sealant may be readily determined by one skilled in the art using routine experimentation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "M" means molar, "mmol" means millimole(s), "µmole" means micromole(s), "g" means gram(s), "µg" means microgram(s), "mg" means milligram(s), "g" means the gravitation constant, "rpm" means revolution(s) per minute, "pfu" means plaque forming unit(s), "BSA" means bovine serum albumin, "ELISA" means enzyme linked immunosorbent assay, "IPTG" means isopropyl δ-D-thiogalactopyranoside, "A" means absorbance, "$A_{450}$" means the absorbance measured at a wavelength of 450 nm, "TBS" means Tris-buffered saline, "TBST" means Tris-buffered saline containing TWEEN® 20, "TMB" means 3,3',5,5'-tetramethylbenzidine, "HRP" means horse radish peroxidase.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, $5^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.), Sigma-Aldrich Chemical Company (St. Louis, Mo.) or Pierce Chemical Co. (A division of Thermo Fisher Scientific Inc., Rockford, Ill.) unless otherwise specified. unless otherwise specified.

Example 1

Construction of a Combinatorial Modular Peptide Library

Peptide sequences with binding affinity for hair were discovered by phage display as described in U.S. Patent Application Publication NOs. 2007/0067924, 2008/0175798, 2007/0196305, 2006/0073111, 2007/0065387, and U.S. Pat. No. 7,285,264). The binding affinities that characterize those sequences, as determined by half-saturation levels of biotinylated peptide binding to hair, are in the range between approximately 0.1 and 1 micromolar.

One strategy for improving those binding affinities makes use of avidity effects of multiple catenated binding sequences. For the maximal avidity effect, two binding sequences must be joined by a linker that is of an appropriate length to span the separation of the target binding epitopes on the surface of hair. Since no information is available regarding the spacing of epitopes or its regularity, flexibility in the linker is desirable. However, as argued by Mammen et al. (supra) entropic effects of fixing a flexible linker can easily negate the free energy of a second binding sequence. Therefore a balance must be struck between linker length and linker stiffness.

The structure of a prototypical single chain binding peptide "hand" or "domain" is composed of two single chain binding "fingers" (the target surface-binding peptides; TSBPs) joined by a single chain peptide linker. As described in the present example, the target surface-biding peptides are body surface-binding peptides (BSBPs; such as hair-binding peptides). As such, the prototypical binding body surface-binding domain has the general structure:

BSBP1-Linker-BSBP2

This catenated peptide structure is designed to facilitate production of the entire "hand" or "binding domain" linked to additional functional sequences as a single gene product encoded by a single, contiguous DNA sequence.

A library was designed in which the body surface-binding peptides were selected from a list of 12 hair-binding peptides ("fingers") and the linker was selected from a list of 29 linkers (SEQ ID NOs: 1-58; Table 1). The linker list was composed of 12 different sequence motifs of varying hypothetical stiffness, with several different lengths of individual motifs. The lists of body surface-binding peptides (e.g. hair-binding peptides) and Linkers are shown in Tables 1 and 2.

TABLE 1

Peptide Linkers Tested

| Linker names | Linker Formula | SEQ ID NOs (bold)[2] |
|---|---|---|
| La3, La5, La6 | GP[EAAAK]$_n$PA (n = 3, 5, 6) | 1, 2, 3, 4, 5, 6 |
| Lb2, Lb4, Lb5 | GP[EEAAKK]$_n$PA (n = 2, 4, 5) | 7, 8, 9, 10, 11, 12 |
| Lc4, Lc8, Lc12, Lc16 | GP(KP)$_n$GPA (n = 4, 8, 12, 16) | 13, 14, 15, 16, 17, 18, 19, 20 |
| Ld2, Ld4, Ld6 | GP[GGGS]$_n$PA (n = 2, 4, 6) | 21, 22, 23, 24, 25, 26 |
| Le2, Le4, Le6 | GP[EGGGS]$_n$PA (n = 2, 4, 6) | 27, 28, 29, 30, 31, 32 |
| Lf2, Lf4, Lf6 | GP[KGGGS]$_n$PA (n = 2, 4, 6) | 33, 34, 35, 36, 37, 38 |
| Lg1, Lg2, Lg3 | GP[GAGGAGGSGGS]$_n$PA (n = 1, 2, 3) | 39, 40, 41, 42, 43, 44 |
| Lh1, Lh2, Lh3 | GP[AGPAPGSPGSP]$_n$PA (n = 1, 2, 3) | 45, 46, 47, 48, 49, 50 |
| Lj | GP[(KP)$_6$GG]$_2$PA | 51, 52 |
| Lk (TonB)[1] | GP(EP)$_4$IPEPPKEAPVVIE(KP)$_6$PA | 53, 54 |
| Lm3, Lm4 | GP(EAAAKLL)$_n$PA (n = 3, 4) | 55, 56, 57, 58 |

[1]= Linker "Lk" also referred to herein as the "TonB" linker.
[2]= Linker sequences without flanking N-terminus GP or C-terminus PA residues are bolded.

TABLE 2

Body Surface-binding Peptides (hair-binding peptides): 12 options for each position

| Peptide (SEQ ID NO.)* | N-terminus* | C-terminus* |
|---|---|---|
| IB5A (SEQ ID NO: 59) | PSTPPELLHGAPRSGP | PATPPELLHGAPRSGS |
| HB1 (SEQ ID NO: 60) | PSTPPTNVLMLATKGP | PATPPTNVLMLATKGS |
| KF11 (SEQ ID NO: 61) | PSNTSQLSTGP | PANTSQLSTGS |

TABLE 2-continued

Body Surface-binding Peptides (hair-binding peptides):
12 options for each position

| Peptide (SEQ ID NO.)* | N-terminus* | C-terminus* |
|---|---|---|
| Gray1 (SEQ ID NO: 62) | PSGMPAMHWIHPFAGP | PAGMPAMHWIHPFAGS |
| Gray3 (SEQ ID NO: 63) | PSHDHKNQKETHQRHAAGP | PAHDHKNQKETHQRHAAGS |
| Gray4A (SEQ ID NO: 64) | PSHNHMQERYTAPQHSPSVNGLGP | PAHNHMQERYTAPQHSPSVNGLGS |
| Gray5 (SEQ ID NO: 65) | PSTAEIQSSKNPNPHPQRSWTNGP | PATAEIQSSKNPNPHPQRSWTNGS |
| HP1 (SEQ ID NO: 66) | PSGSCVDTHKADSCVANNGPATGP | PAGSCVDTHKADSCVANNGPATGS |
| HP2 (SEQ ID NO: 67) | PSAQSQLPDKHSGLHERAPQRYGP | PAAQSQLPDKHSGLHERAPQRYGS |
| HP3 (SEQ ID NO: 68) | PSTDMMHNHSDNSPPHRRSPRNGP | PATDMMHNHSDNSPPHRRSPRNGS |
| HP4 (SEQ ID NO: 69) | PSTPPELAHTPHHLAQTRLTDRGP | PATPPELAHTPHHLAQTRLTDRGS |
| MEA4 (SEQ ID NO: 70) | PSHINKTNPHQGNHHSEKTQRQGP | PAHINKTNPHQGNHHSEKTQRQGS |

*= sequences of hair-binding peptides identified by phage display are underlined.
The dipeptides flanking the hair-binding sequences are provided to illustrate the design strategy.

The genetic constructs were designed to include unique restriction sequences flanking the construct or 6-base overhangs with no restriction sites.
The general structure used for all genetic modules:

```
AvrII(X) - PeptN - Linker - PeptC - BamHI
CCTAGC                               GGATCC
Pro-Ser                              Gly-Ser Pro-Ser = (C)CTAGCNNN
               NNN Gly-Ser = NNNG
          NNNCCTAG(G)
```

6-base overhangs, no restriction sites:

```
Gly-Pro(N-term) = GGTCCANNN
                         NNN

Gly-Pro(C-term) = NNN
                  NNNTGGACC

Pro-Ala(N-term) = CCGGCANNN
                         NNN

Pro-Ala(C-term) = NNN
                  NNNTGCCGG
```

The library was constructed by DNA2.0, Inc (Menlo Park, Calif.) by ligating synthetic oligonucleotides using standard methods. First 29 separate sub-libraries of 144 members each were constructed by random combination of any of the 12 N- and C-terminal Binding Sequences (Table 2) with a single linker (Table 1). Those libraries were checked and verified for quality by DNA sequencing random members. Each sub-library was cloned separately into the phagemid vector pDCQ460 (SEQ ID NO: 71) between AvrII and BamHI sites. The structure of pDCQ460 is illustrated in FIG. 1.

Ligated DNA was inserted into electrocompetent *E. coli* 10GF' (Lucigen Corp., Middleton, Wis.) by electroporation. A small aliquot from the transformed *E. coli* was plated out to assess the colony yield from each sub-library, also 3 random clones picked for DNA sequencing to assess the complexity of each sub-library.

The 29 sub-libraries were combined in approximately equal cell titers, and a phage library was obtained by super-infecting the entire library of phagemid clones with helper bacteriophage VCSM13 (Stratagene, La Jolla, Calif.), isolating phage particles, and re-infecting *E. coli* 10GF' cells. A small aliquot from the re-infected *E. coli* was plated out to assess the phagemid titer. A second complexity test of the phage library was performed by sequencing plasmid DNA isolated from randomly picked individual clones. This library was used for phage display panning against human hair.

Example 2

Phage Display Biopanning

The hair surface was prepared by bundling 50 strands of Caucasian 50% gray hair (International Hair Importers and Products, Bellerose, N.Y.; pre-cleaned with Neutrogena Clean Replenishing® Moisturizing shampoo Neutrogena Corp., Los Angeles, Calif.) with 3M (3M Corp., St. Paul, Minn.) surgical tape on one end. The bundled hairs were 1.5 cm in length and were either pre-blocked with 1% bovine serum albumin (BSA) at room temperature (~21° C.) for 30 minutes or were not pre-blocked.

Round 1

The hair bundles were contacted with 1-mL of binding solution ($1 \times 10^8$ pfu library) for 1 hour at room temperatures (~21° C.) with gentle mixing followed by a 1 hour contact at 42° C. without mixing.

The hair bundles were then washed twice with 1 mL of TBST buffer (0.5% TWEEN®-20) with gentle shaking at room temperature for 2 min each. The hair was then cut off and the 3M surgical tape was removed. Phage particles were eluted by either (1) adding 1 mL elution buffer (0.2M Glycine-HCl, pH 2.2, 1% BSA) for 10 min at room temp (~21° C.), then neutralized with 160 μL 1 M Tris-Cl, pH 9.1 followed by infection of *E. coli* cells and amplification or (2) directly infect *E. coli* cells with the neutralized loose hair after acid elution step The *E. coli* cells from both elution methods were collected. The phage library was amplified with helper phage VCSM13 and titered.

Round 2

A hair bundle (pre-block with 1% BSA) was contacted with 1 mL of binding solution comprising $1\times10^8$ pfu from the $1^{st}$ round phage. The contacting conditions included (1) 1 hour at room temperature with gentle mixing followed by (2) 1 hour at 42° C. without mixing. The hair was then rinsed 3 times with 1 mL of TBST buffer (0.5% TWEEN®-20) with gentle shaking at room temperature for 2 min each.

The hair ends were cut off as described above. Phage particles were eluted by either (1) adding 1 mL elution buffer (0.2M Glycine-HCl, pH 2.2, 1% BSA) for 10 min at room temp (~21° C.), then neutralized with 160 μL 1 M Tris-Cl, pH 9.1 followed by infection of *E. coli* cells and amplification or (2) directly infect *E. coli* cells with the neutralized loose hair after acid elution step. The *E. coli* cells from both elution methods were collected. The phage library was amplified with helper phage VCSM13 and then titered.

Round 3

A hair bundle (pre-block with 1% BSA) was contacted with 1 mL of binding solution comprising $1\times10^8$ pfu from the 2nd round phage. The contacting conditions included (1) 1 hour at room temperature with gentle mixing followed by (2) 1 hour at 42° C. without mixing. The hair was then rinsed 5 times with 1 mL of TBST buffer (0.5% TWEEN®-20) with gentle shaking at room temperature for 2 min each.

A duplicate set of hair bundles were then washed with 1 mL of 25% Neutrogena Clean Replenishing® Moisturizing shampoo at room temp for 5 min with shaking, followed by 5× buffer rinses and 3× $H_2O$ rinses.

The hair ends were cut off as described above. Phage particles were eluted by either (1) adding 1 mL elution buffer (0.2M Glycine-HCl, pH 2.2, 1% BSA) for 10 min at room temp (~21° C.), then neutralized with 160 μL 1 M Tris-Cl, pH 9.1 followed by infection of *E. coli* cells and amplification or (2) directly infect *E. coli* cells with the neutralized loose hair after acid elution step. The *E. coli* cells from both elution methods were collected. The phage library was amplified with helper phage VCSM13 and then titered.

Round 4

A hair bundle (pre-block with 1% BSA) was contacted with 1 mL of binding solution comprising $1\times10^8$ pfu from the $3^{rd}$ round phage. The contacting conditions included (1) 1 hour at room temperature with gentle mixing followed by (2) 1 hour at 42° C. without mixing. The hair was then rinsed 5 times with 1 mL of TBST buffer (0.5% TWEEN®-20) with gentle shaking at room temperature for 2 min each.

A duplicate set of hair bundles were then washed with 1 mL of 25% Neutrogena Clean Replenishing® Moisturizing shampoo at room temp for 5 min with shaking, followed by 5× buffer rinses and 3× $H_2O$ rinses.

The hair ends were cut off as described above. Phage particles were eluted by either (1) adding 1 mL elution buffer (0.2M Glycine-HCl, pH 2.2, 1% BSA) for 10 min at room temp (~21° C.), then neutralized with 160 μL 1 M Tris-Cl, pH 9.1 followed by infection of *E. coli* cells and amplification or (2) directly infect *E. coli* cells with the neutralized loose hair after acid elution step. The *E. coli* cells from both elution methods were collected. The phage library was amplified with helper phage VCSM13 and then titered.

Sequence Analysis

Ninety-five (95) random colonies were picked for DNA sequencing. The sequence analysis results from the $4^{th}$ round of panning are provide in Table 3

TABLE 3

Sequence analysis of phage from $4^{th}$ round panning.

| Peptide ID (SEQ NO.) | N-terminal Binding Peptide | Linker Sequence | C-terminal Binding Peptide | Linker Type |
|---|---|---|---|---|
| F1 (SEQ ID NO: 72) | HP2 | (GAGGAGGSGGS)$_2$ | Gray3 | Flexible |
| R1 (SEQ ID NO: 73) | HP2 | (EEAAKK)$_4$ | Gray1 | Rigid |
| R2 (SEQ ID NO: 74) | HP2 | (EEAAKK)$_5$ | Gray4A | Rigid |
| R3 (SEQ ID NO: 75) | HP2 | (EEAAKK)$_4$ | MEA4 | Rigid |
| R4 (SEQ ID NO: 76) | HP2 | (EEAAKK)$_2$ | MEA4 | Rigid |
| SR1 (SEQ ID NO: 77) | Gray1 | (KP)$_8$ | Gray1 | Semi-rigid |
| HSR1 (SEQ ID NO: 78) | Gray5 | (KPKPKPKPKPGG)$_2$ | Gray4A | Hinged Semi-rigid |
| HSR2 (SEQ ID NO: 79) | KF11 | (KPKPKPKPKPGG)$_2$ | Gray4A | Hinged Semi-Rigid |
| HSR3 (SEQ ID NO: 80) | KF11 | (KPKPKPKPKPGG)$_2$ | Gray5 | Hinged Semi-Rigid |

TABLE 3-continued

Sequence analysis of phage from 4th round panning.

| Peptide ID (SEQ NO.) | N-terminal Binding Peptide | Linker Sequence | C-terminal Binding Peptide | Linker Type |
|---|---|---|---|---|
| HSR4 (SEQ ID NO: 81) | KF11 | (KPKPKPKPKPKPGG)$_2$ | Gray5 (Q-->R mutation) | Hinged Semi-Rigid |
| HSR5 (SEQ ID NO: 82) | KF11 | (KPKPKPKPKPKPGG)$_2$ | HB1 | Hinged Semi-Rigid |
| HSR6 (SEQ ID NO: 83) | Gray3 | (KPKPKPKPKPKPGG)$_2$ | KF11 | Hinged Semi-Rigid |
| HSR7 (SEQ ID NO: 84) | HP3 | (KPKPKPKPKPKPGG)$_2$ | KF11 | Hinged Semi-Rigid |
| HSR8 (SEQ ID NO: 85) | HP2 | (EP)$_4$IPEP-PKEAPVVIE-(KP)$_6$ | Gray3 | Hinged Semi-Rigid |
| HSR9 (SEQ ID NO: 86) | Gray3 | (EP)$_4$IPEP-PKEAPVVIE-(KP)$_6$ | HP1 | Hinged Semi-Rigid |
| HSR10 (SEQ ID NO: 87) | HP2 | (EP)$_4$IPEP-PKEAPVVIE-(KP)$_6$ | HB1 | Hinged Semi-Rigid |
| HSR11 (SEQ ID NO: 88) | HP2 | (EP)$_4$IPEP-PKEAPVVIE-(KP)$_6$ | IB5A | Hinged Semi-Rigid |
| HSR12 (SEQ ID NO: 89) | HP2 | (EP)$_4$IPEP-PKEAPVVIE-(KP)$_6$ | MEA4 | Hinged Semi-Rigid |
| FR1 (SEQ ID NO: 90) | Gray5 | (EAAAKLL)$_3$ | MEA4 | Semi-rigid |

Example 3

Assay of Phage Binding to Hair

Phage particles recovered from panning (Example 2) were used to infect *E. coli* 10GF' and transformants were purified by colony isolation. Purified phagemid clones were infected with helper phage VCSM13 and phage particles were isolated. Those purified phage clones were assayed for binding to hair by two methods.

a. Phage Titer

Six gray hair strands (1.5 cm long) were blocked with BSA (1 mg/mL) at room temperature (~21° C.) for 30 min in 1.5 mL microfuge tubes, then washed twice with tris buffered saline (TBS). Phage particles were added in TBS plus 0.1% TWEEN®-20 and incubated at room temperature for 1 hour with gentle shaking. The hair was then washed 3 times with TBS plus 0.5% TWEEN®-20, and centrifuged briefly to remove excess liquid. *E. coli* 10GF' (1 mL; $OD_{600nm}$=0.5) was added for 15 min. Aliquots were plated on selective plates and phagemid-containing colonies were counted (Table 4)

b. Phage ELISA

Gray hair (200 strands, 1.5 cm long per bundle were blocked with BSA (1 mg/mL) at room temperature (~21° C.) for 30 min in 1.5 mL microfuge tubes, then washed 3 times with TBS. Phage particles (1×10$^{11}$ pfu) were added in TBS plus 0.1% TWEEN®-20 and incubated at room temperature for 1 hr with gentle shaking. The hair was then washed 5 times with TBS plus 0.5% TWEEN®-20. Hair with bound phage was incubated with HRP/Anti-M13 monoclonal conjugate (GE Healthcare Bio-Science Corp, Piscataway, N.J.) at room temperature (~21° C.) for 1 hr with gentle shaking, then washed 6 times with TBS plus 0.5% TWEEN®-20. IMMU-NOPURE® TMB substrate kit (High sensitivity, Pierce, Rockford, Ill.; a division of Thermo Scientific) was used for colorimetric assay. After 15~20 min development with gentle shaking, the reaction was stopped, and absorbance was determined at 450 nm. The Phage titer and ELISA data were reported relative to the activity observed for the hair-binding domain HP2-TonB-Gray3. (Table 4).

TABLE 4

Phage Titer and ELISA of Phage Binding to Hair Relative to the Activity of HP2-TonB-Gray3.

| Peptide Formula | SEQ ID NO: | Phage Titer (%)[1] | ELISA (%)[1] | Linker Type |
|---|---|---|---|---|
| HP2-(EEAAKK)$_2$-MEA4 | 76 | 330 | 130 | Rigid |
| HP2-(EEAAKK)$_4$-MEA4 | 75 | 80 | 170 | Rigid |
| HP2-TonB-Gray3[1] | 85 | 100 | 100 | Semi-rigid |
| HP2-TonB-IB5A | 88 | 50 | 100 | Semi-rigid |

TABLE 4-continued

Phage Titer and ELISA of Phage Binding to Hair Relative to the Activity of HP2-TonB-Gray3.

| Peptide Formula | SEQ ID NO: | Phage Titer (%)[1] | ELISA (%)[1] | Linker Type |
|---|---|---|---|---|
| Gray5-(EAAAKLL)$_3$-MEA4 | 90 | 25 | 115 | Semi-rigid |
| HP2-(EEAAKK)$_5$-Gray4A | 74 | 50 | 80 | Rigid |
| HP2-TonB-HP2 | 91 | 55 | 55 | Semi-rigid |
| Gray5-(EAAAKLL)$_3$-Gray3 | 92 | 10 | 60 | Semi-rigid |
| HP2-(EEAAKK)$_4$-Gray1 | 73 | 40 | 8 | Rigid |
| HP2-TonB-HB1 | 93 | 30 | 1 | Semi-rigid |
| MEA4-(EAAAKLL)$_3$-IB5A | 94 | 10 | 20 | Semi-rigid |
| HB1-(KGGGS)$_4$-HP2 | 95 | 10 | 1 | Flexible |
| HB1-(KP)$_{12}$-IB5A | 96 | 5 | 1 | Rigid |
| Gray1-(KP)8-Gray1 | 77 | 1 | 1 | Rigid |
| Gray5-[(KP)$_6$GG]$_2$-Gray4A | 78 | 1 | 1 | Semi-rigid |
| KF11-[(KP)$_6$GG]$_2$-Gray4A | 97 | 1 | 1 | Semi-rigid |
| Gray3-TonB-HP1 | 98 | 1 | 1 | Semi-rigid |
| Gray5-[(KP)$_6$GG]$_2$-HP2 | 99 | 1 | 1 | Semi-rigid |
| Gray3-(EAAAKLL)$_4$-HB1 | 100 | 1 | 1 | Semi-rigid |
| Gray3-[(KP)$_6$GG]$_2$-KF11 | 83 | 1 | 1 | Semi-rigid |
| KF11-[(KP)$_6$GG]$_2$-KF11 | 101 | 1 | 1 | Semi-rigid |
| HP2-TonB-MEA4 | 89 | 1 | 1 | Semi-rigid |
| MEA4-[(KP)$_6$GG]$_2$-MEA4 | 102 | 1 | 1 | Semi-rigid |

[1] = Activity relative to HP2-TonB (linker "Lk")-Gray3, the hair-binding domain also found in peptide HC353.

Example 4

Construction of Peptide HC353

The sequences designated HP2 (SEQ ID NO: 67) and Gray3 (SEQ ID NO: 63) were selected from random peptide libraries displayed fused to the pill protein of bacteriophage M13 for their ability to bind to human hair, using conventional phage display technology (Tim Clackson and Henry B. Lowman, Eds., *Phage Display: A Practical Approach*, Oxford University Press, New York, N.Y. (2004)). The sequence designated "Rfe1" (SEQ ID NO: 103) was identified using phage display for its ability to bind to red iron oxide-based pigment particles (SENSIENT® Unipure Red LC381EM, red iron oxide, Sensient Technologies, Milwaukee, Wis.).

The combination of hair-binding peptides HP2 and Gray3 and the linker joining them were selected from a combinatorial library consisting of module combinations of the type [binding sequence-linker-binding sequence], using conventional "monovalent" phage display technology (Clackson and Lowman, supra).

The HP2-TonB-Gray3 (SEQ ID NO: 85) hair-binding hand was coupled via a peptide bridge (GSGGGGSP; SEQ ID NO: 104) to an iron oxide-based pigment binding hand comprising two iron oxide-based pigment-binding peptides (Rfe1) linked together by a cationic linker (GKGKGKGKGKGKGKGKGKGKG; SEQ ID NO: 105), to form peptide HC353. The target surface-binding peptides are in bold. The rigid linker is italicized.

Formula for HC353

```
PS-HP2-GP-TonB-PA-Gray3-GSGGGGSP-Rfe1-
GKGKGKGKGKGKGKGKGKGKG-Rfe1-GK
```

Corresponding Peptide Sequence for HC353

(SEQ ID NO: 106)
PSAQSQLPDKHSGLHERAPQRYGPEPEPEPEPIPEPPKEAPVVIEKPKP

KPKPKPKPPAHDHKNQKETHQRHAAGSGGGGSPWAPEKDHMQLMKG

KGKGKGKGKGKGKGKGKGKGWAPEKDHMQLMKGK

Construction of the DNA Coding Sequence

The DNA sequence (SEQ ID NO: 107) encoding the HC353 peptide sequence was assembled by DNA2.0 Inc. (Menlo Park, Calif.) using conventional chemical synthesis of DNA and assembly from oligonucleotides by annealing and ligation. Candidate sequences were cloned into a vector and verified by DNA sequencing by DNA2.0.

Recloning into Expression Vector pLD001

Figure 2:
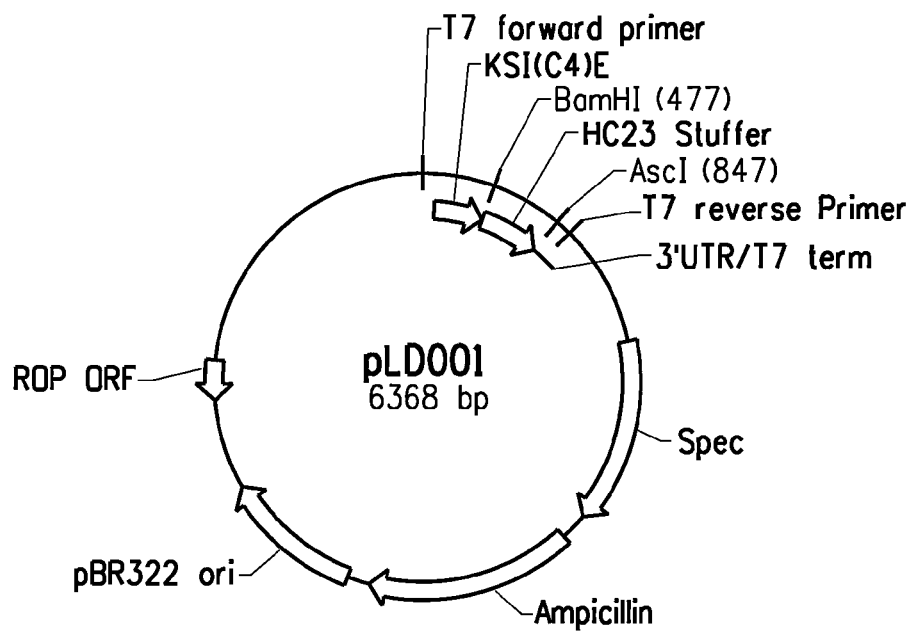
FIG. 2 is a plasmid map of pLD001

The cloned peptide-coding DNA sequence was recloned into the expression vector pLD001 (FIG. 2; SEQ ID NO: 108)

for expression in *E. coli*. For that purpose, the coding sequence on a restriction endonuclease fragment bounded by BamHI and AscI sites was ligated between BamHI and AscI sites in pLD001 using standard recombinant DNA methods. The resulting gene fusion resulted in a gene product in which the HC353 coding sequence was fused downstream from a modified fragment of ketosteroid isomerase [(KSI(C4)E); SEQ ID NO 109] that served to drive the peptide into insoluble inclusion bodies in *E. coli* (See U.S. patent application Ser. Nos. 12/172,385 and 12/172,395; each herein incorporated by reference)

The vector pLD001 was derived from the commercially available vector pDEST17 (Invitrogen, Carlsbad, Calif.). It includes sequences derived from the commercially available vector pET31 b (Novagen, Madison, Wis.) that encode a fragment of the enzyme ketosteroid isomerase (KSI). The KSI fragment was included as a fusion partner to promote partition of the peptides into insoluble inclusion bodies in *E. coli*. The KSI-encoding sequence from pET31 b was modified using standard mutagenesis procedures (QuickChange II, Stratagene, La Jolla, Calif.) to include three additional Cys codons, in addition to the one Cys codon found in the wild type KSI sequence. In addition, all Asp codons in the coding sequence were replaced by Glu codons. The plasmid pLD001, given by SEQ ID NO: 108 was constructed using standard recombinant DNA methods, which are well known to those skilled in the art.

Figure 3:
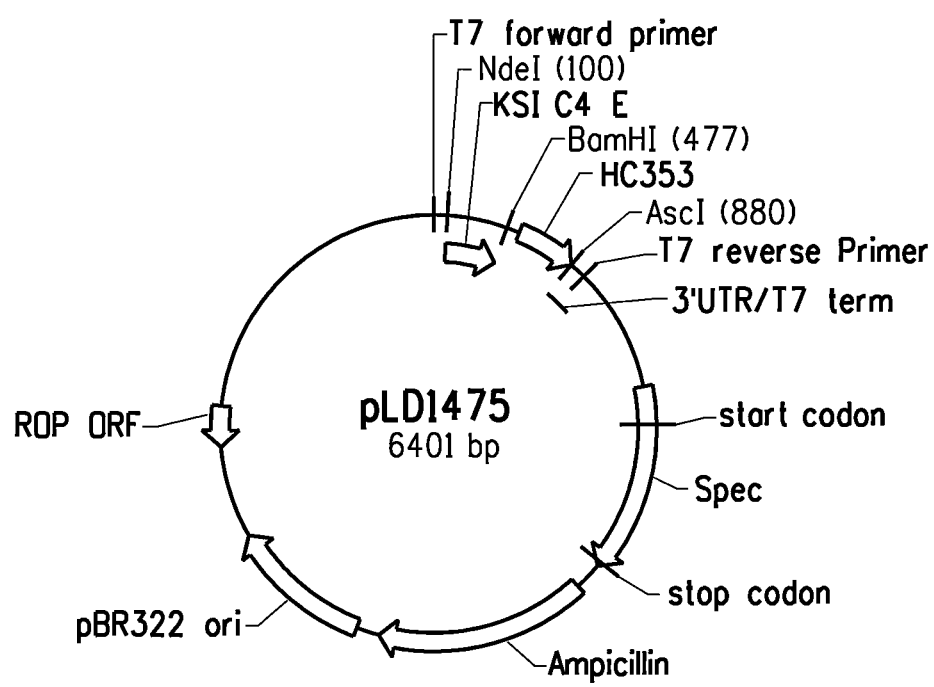
FIG. 3 is a plasmid map of pLD1475

The DNA sequence (SEQ ID NO: 107) encoding peptide HC353 was inserted into pLD001 by substituting for sequences in the vector between the BamHI and AscI sites. Plasmid DNA containing the peptide encoding sequences and vector DNA were digested with endonuclease restriction enzymes BamHI and AscI, then the peptide-encoding sequences and vector DNA were mixed and ligated by phage T4 DNA ligase using standard DNA cloning procedures, which are well known to those skilled in the art. Correct constructs, in which the sequences encoding the peptide HC353 were inserted into pLD001, were identified by restriction analysis and verified by DNA sequencing, using standard methods. The DNA sequence of the expression plasmid pLD1474 encoding the KSI(C4)E-HC353 peptide fusion is provided as SEQ ID NO: 110 (FIG. 3).

Example 5

Production of Peptides Corresponding to Phage Hits

The modular peptide-coding sequences (Tables 1, 2, and 3) were transferred from phagemids isolated from cells infected as described above (Example 3) into a plasmid vector derived from pLD001 as described in Example 4. The vector fused the modular peptide sequences downstream from sequences encoding a protein tag to render them insoluble (an inclusion body tag) and upstream from a six-histidine tag. For that purpose, the coding sequence on a restriction endonuclease fragment bounded by BamHI and AscI sites was ligated between BamHI and AscI sites in pLD001 using standard recombinant DNA methods. The resulting gene fusion resulted in a gene product in which the coding sequence was fused downstream of KSI(C4)E, a solubility tag that served to drive the peptide into insoluble inclusion bodies in *E. coli* (see U.S. patent application Ser. No. 12/172,385; incorporated herein by reference). Modular peptides comprising various hair-binding constructs linked to a hexahistidine tag are provided in Table 5.

TABLE 5

Modular peptides coupled to hexahistidine tag.

| Peptide ID | Peptide Formula[1] | Amino Acid Sequence (SEQ ID NO.) |
|---|---|---|
| HC205 | PG-IB5A-GGGGSGGGGSG-HHHHHH | PGTPPELLHGAPRSGGGGSGGGGS GHHHHHH (SEQ ID NO: 111) |
| HC206 | PG-IB5A-GGG-IB5A-GGGGSGGGGSG-HHHHHH | PGTPPELLHGAPRSGGGTPPELLHG APRSGGGGSGGGGSGHHHHHH (SEQ ID NO: 112) |
| HC208 | PG-GRAY3A-GGGGSGGGGSG-HHHHHH | PGHAHKNQKETHQRHAAGGGGSG GGGSGHHHHHH (SEQ ID NO: 113) |
| HC209 | PG-GRAY3A-GGG-GRAY3A-GGGGSGGGGSG-HHHHHH | PGHAHKNQKETHQRHAAGGGHAH KNQKETHQRHAAGGGGSGGGGSG HHHHHH (SEQ ID NO: 114) |
| HC214 | PG-Gray3-GGG-Gray3-GGGGSGGGGSG-HHHHHH | PGHDHKNQKETHQRHAAGGGHDH KNQKETHQRHAAGGGGSGGGGSG HHHHHH (SEQ ID NO: 115) |
| HC257 | PS-HP2-GP-*Lg2*-PA-Gray3-GSGGGGSP-HHHHHH | PSAQSQLPDKHSGLHERAPQRYGP GAGGAGGSGGSGAGGAGGSGGSP AHDHKNQKETHQRHAAGSGGGGS PHHHHHH (SEQ ID NO: 116) |
| HC263 | PS-HP2-GP-*TonB*-PA-Gray3-GSGGGGSP-HHHHHH | PSAQSQLPDKHSGLHERAPQRYGP EPEPEPEPIPEPPKEAPVVIEKPKPK PKPKPKPPAHDHKNQKETHQRHAA GSGGGGSPHHHHHH (SEQ ID NO: 117) |

TABLE 5-continued

Modular peptides coupled to hexahistidine tag.

| Peptide ID | Peptide Formula[1] | Amino Acid Sequence (SEQ ID NO.) |
|---|---|---|
| HC281 | PS-HP4-GP-*Le4*-PA-KF11-GSGGGGSP-HHHHHH | PSTPPELAHTPHHLAQTRLTDRGPE GGGSEGGGSEGGGSEGGGSPANT SQLSTGSGGGGSPHHHHHH (SEQ ID NO: 118) |
| HC362 | PR-HP2-GP-*TonB*-PA-IB5A-GSGGGGSP-HHHHHH | PRAQSQLPDKHSGLHERAPQRYGP EPEPEPEPIPEPPKEAPVVIEKPKPK PKPKPKPPATPPELLHGAPRSGSGG GGSPHHHHHH (SEQ ID NO: 119) |
| HC364 | PR-HP2-GP-*TonB*-PA-HP2-GSGGGGSP-HHHHHH | PRAQSQLPDKHSGLHERAPQRYGP EPEPEPEPIPEPPKEAPVVIEKPKPK PKPKPKPPAAQSQLPDKHSGLHER APQRYGSGGGGSPHHHHHH (SEQ ID NO: 120) |
| HC365 | PR-HP2-GP-*Lb4*-PA-MEA4-GSGGGGSP-HHHHHH | PRAQSQLPDKHSGLHERAPQRYGP EEAAKKEEAAKKEEAAKKEEAAKKP AHINKTNPHQGNHHSEKTQRQGSG GGGSPHHHHHH (SEQ ID NO: 121) |
| HC375 | PR-HP2-GP-*TonB*-PA-HB1-GSGGGGSP-HHHHHH | PRAQSQLPDKHSGLHERAPQRYGP EPEPEPEPIPEPPKEAPVVIKKPKPK PKPKPKPPATPPTNVLMLATKGSGG GGSPHHHHHH (SEQ ID NO: 122) |
| HC376 | PR-HP2-GP-*Lb5*-PA-Gray4A-GSGGGGSP-HHHHHH | PRAQSQLPDKHSGLHERAPQRYGP EEAAKKEEAAKKEEAAKKEEAAKKE EAAKKPAHNHMQERYTAPQHSPSV NGLGSGGGGSPHHHHHH (SEQ ID NO: 123) |
| HC380 | PR-HP2-GP-*Lb2*-PA-MEA4-GSGGGGSP-HHHHHH | PRAQSQLPDKHSGLHERAPQRYGP EEAAKKEEAAKKPAHINKTNPHQGN HHSEKTQRQGSGGGGSPHHHHHH (SEQ ID NO: 124) |

[1] = Hair-binding peptide units are in bold and the peptide linkers are italicized.

The modular peptide-coding sequences were transferred from phagemids isolated from cells infected as described above into a modified expression plasmid, pKK263. pKK263 was derived from pLD263, which fused the modular peptide sequences (HP2-TonB-Gray3; SEQ ID NO: 83) downstream from sequences encoding a protein tag KSI(C4)E to render them insoluble and upstream from a six-histidine tag. A 980 bp HindIII fragment conferring spectinomycin resistance was removed from pLD263, resulting in pKK263.

Oligonucleotide PCR primers incorporating AvrII (CCTAGG) or BamHI (GGATCC) sites were designed to amplify specifically the 24 selected new modular peptide-coding sequences from the phagemids, and pKK263 plasmid except without the hair binding domain (HP2-TonB-Gray3) (Tables 6 and 7). AccuPrime Pfx Supermix (Invitrogen, Carlsbad, Calif.) was used for all PCR reactions. DNA Clean & Concentrator-25 kit (Zymo Research, Orange, Calif.) was used for all DNA and fragment purifications. Both the amplified vector and 24 PCR fragments representing the modular peptide-coding sequences were first digested with AvrII, then BamHI restriction enzyme. Peptide-encoding sequences and vector DNA were mixed and ligated by phage T4 DNA ligase at room temperature (~21° C.) for 30 min, then transformed using standard DNA techniques. All correct constructs were identified by restriction analysis and verified by DNA sequencing, using standard methods.

TABLE 6

PCR Primers Used to Confirm Vector Backbone Sequence[1,2]

| Primer Name | Sequence | SEQ ID NO: |
|---|---|---|
| KK233 | CGCG*CCTAGG*ATCGGAACCCTGACAAGCATGGA TGTTC | 125 |
| KK236 | AATGGATCCGGTGGCGGCGGTAGCCC | 126 |

[1] = Vector backbone (template = pKK263) was amplified by PCR using primer pair KK233 + KK236.
[2] = AvrII sequence in italics, BamHI is in bold type.

TABLE 7

PCR Primers Used to Confirm Insert Sequences[3]

| Primer Name | Sequence | SEQ ID NO. |
|---|---|---|
| NG1 | CGGCC*TAGG*GGTATGCCTGCTATGCATTGG | 127 |
| NG3 | CGGCC*TAGG*CATGATCATAAAAACCAAAAG | 128 |
| NG5 | CGGCC*TAGG*ACTGCAGAAATCCAATCTAG | 129 |

TABLE 7-continued

PCR Primers Used to Confirm Insert Sequences[3]

| Primer Name | Sequence | SEQ ID NO. |
|---|---|---|
| NH2 | CGGCCTAGGGCACAATCTCAACTGCCTGA | 130 |
| NH3 | CGGCCTAGGACTGATATGATGCACAACC | 131 |
| NHB1 | CGGCCTAGGACTCCACCAACTAATGTTCTG | 132 |
| NKF11 | CGGCCTAGGAATACCTCCCAGCTGTCCAC | 133 |
| NM4 | CGGCCTAGGCATATCAATAAAACTAATCC | 134 |
| CG1 | AATGGATCCTGCGAACGGATGAATC | 135 |
| CG3 | AATGGATCCCGCAGCGTGACGCTGG | 136 |
| CG4A | AATGGATCCCAGACCGTTCACAG | 137 |
| CG5 | AATGGATCCGTTAGTCCAGGAGC | 138 |
| CH1 | AATGGATCCCGTCGCTGGACCG | 139 |
| CH2 | AATGGATCCGTAGCGTTGCGGTG | 140 |
| CH4 | AATGGATCCACGGTCAGTCAGAC | 141 |
| CHB1 | AATGGATCCTTTGGTTGCCAGC | 142 |
| CIB5A | AATGGATCCGGAGCGTGGAGCAC | 143 |
| CKF11 | AATGGATCCGGTGGACAGCTGGC | 144 |
| CM4 | AATGGATCCCTGACGCTGAGTTTTCTCG | 145 |

[3] = AvrII sequence in italics, BamHI is in bold type.

Peptide coding sequences from phagemids were PCR-amplified using respective primer pairs, depending on where the binding domain was in either N or C terminal end (Table 7). Examples of constructs and prior pairs is provided in Table 8. The expression plasmid DNA was inserted into the expression host *E. coli* BL21-AI (Invitrogen Corp, Carlsbad, Calif.) by transformation.

TABLE 8

Examples of Primer Pairs Used to Amplify Peptide Coding Sequences

| Construct Name | Formula of Binding Domain (SEQ ID NO.) | Primer 1 | Primer 2 |
|---|---|---|---|
| HC365 | HP2-GP(EEAAKK)$_4$PA-MEA4 (SEQ ID NO: 146) | NH2 | CM4 |
| HC366 | KF11-GP[(KP)$_6$GG]$_2$PA-Gray4a (SEQ ID NO: 147) | NKF11 | GC4A |
| HC367 | Gray5-GP[(KP)$_6$GG]$_2$PA-Gray4a (SEQ ID NO: 148) | NG5 | CG4A |

Example 6

Preparation, Isolation and Processing of Fusion Protein

Growth Conditions

The BL21-AI *E. coli* cells containing expression plasmids were grown for 20 hours at 37° C. with agitation (200 rpm) in 2.8-L Fernbach flasks containing 1-L of modified ZYP-5052 auto-induction media (Studier, F. William, *Protein Expression and Purification* (2005) 41:207-234). The media composition per liter was as follows: 10 g/L Tryptone, 5 g/L Yeast Extract, 5 g/L NaCl, 50 mM $Na_2HPO_4$, 50 mM $KH_2PO_4$, 25 mM $(NH4)_2SO_4$, 3 mM $MgSO_4$, 0.75% glycerol, 0.075% glucose and 0.05% Arabinose (inducer for BL21 AI T7 system). Under these conditions about 20 g/L wet weight of cells are obtained per liter.

Inclusion Body Isolation

The entire process was performed in one 500-mL bottle. Cells were separated from the growth media by centrifugation and washed with 200-mL (10 g cell paste/100-mL buffer) 20 mM Tris buffer and 10 mM EDTA at pH 8.0. The cell paste was resuspended in 200 mL of 20 mM Tris buffer and 10 mM EDTA at pH 8.0 with added lysozyme (5 mg/200-mL) and taken through at lease one freeze-thaw cycles to facilitate lysis. Lysis is completed by sonication and the inclusion body paste is recovered by centrifugation (9000 RCF 20 minutes 4° C.). Each additional wash step includes resuspension of the inclusion body paste, followed by sonication and centrifugation (9000 RCF 20 minutes 4° C.). Wash steps include a high pH wash (50 mM Tris HCL pH 9.0) followed by additional washes with 20 mM Tris-HCl pH 8.0. Typically 5 g/L inclusion body paste was recovered.

Acid Cleavage

The recovered inclusion body paste was resuspended in 100-mL of pure water and the pH of the mixture adjusted to 2.2 using HCl. The acidified suspension was heated to 70° C. for 14 hours with agitation to complete cleavage of the DP site separating the fusion peptide from the product peptide.

Oxidative Cross-Linking to Separate the IBT from the Peptide of Interest

The product was cooled ~5° C. then the pH neutralized to 5.3 using NaOH and cooled for an additional 1 hour at ~5° C. to facilitate precipitation of cysteine cross-linked KSI (C4)E tag (see U.S. patent application Ser. No. 12/172,395; herein incorporated by reference). The mixture was then centrifuged at 10000 RCF for 30 minutes 4° C. The pellet contains the inclusion body fusion partner KSI (C4)E. The supernatant containing the peptide of interest was then lyophilized.

Example 7

Peptide ELISA

Figure 4:
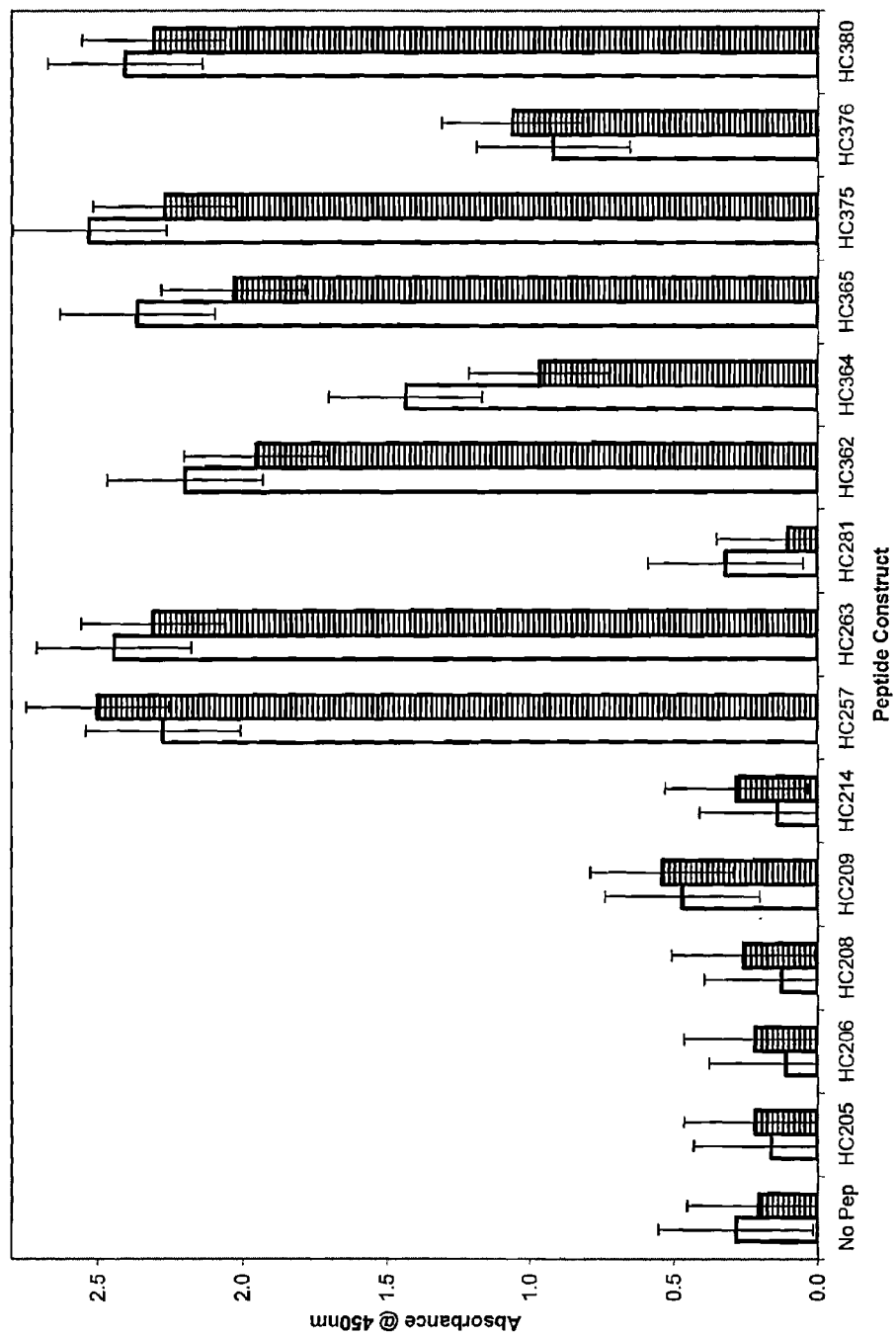
FIG. 4 is a bar graph of the hair-binding ELISA results.

Gray hair bundles 1 cm long, 150 strands per bundle, were blocked with BSA (1 mg/mL in TBS) at room temperature (~21° C.) for 30 min, then washed once with TBS. Peptide (2-20 µM in TBST plus 0.1% TWEEN®-20) was added and incubated at room temp for 1 hr, then washed 5 times with TBS plus 0.5% TWEEN®-20. HISPROBE™ HRP conjugate (Pierce, Rockford, Ill.) (1:4000 dilution in TBS plus 0.1% TWEEN®-20) was added and incubated at room temperature (~21° C.) for 1 hr, then washed 6 times with TBS plus 0.5% TWEEN®-20. Hair bundles were blotted between paper towels and transferred to a fresh microtiter plate. Freshly prepared IMMUNOPURE® TMB (3,3',5,5'-tetramethylbenzidine) substrate (High Sensitivity, Pierce) (150 µL) was added and incubated at room temperature (~21° C.) for 15-20 min. Hair bundles were removed and discarded, and 150 µL stop solution (2M $H_2SO_4$) was added to the microtiter wells. Absorbance was read at 450 nm immediately. Results are shown in FIG. 4.

Example 8

Engineered Peptides for Cellulose Acetate Binding

Cellulous Acetate (referred as "CA" hereafter)-binding peptides were identified by using phage display against particles coated with cellulose acetate (U.S. Provisional Patent Application No. 61/038,272). Several CA-binding peptides were identified. One particular CA-binding peptide ("CA4"; SEQ ID NO: 149) was selected for preparation of a cellulose acetate-binding "domain", also referred to herein as a "binding hand".

Multimers (dimers and trimers) comprising CA4 were prepared by linking together 2 or 3 copies of the CA4 peptide together using peptide linkers of different length and flexibility (Table 9)

wash. Surface regeneration and stabilization procedure was performed after each peptide solution injection as such: 90 seconds of 1% SLES (sodium laureth sulfate) solution injection and 90 seconds of 2 M NaCl solution injection at flow rate of 10 μL/minute, and 25 minutes stabilization in TBS. For the samples of each peptide at different concentrations, a new sensor chip flow cell was used.

Because a monolithic CA surface made from spin-coating on the whole sensor chip was used as ligand for peptides, no ligand-free reference cell was possible to have in these tests in order to take bulk response out as in conventional SPR protein

TABLE 9

Cellulose Acetate-binding Domains

| Peptide name | Description | Sequence |
|---|---|---|
| CA4 | CA binding peptide identified from phage display | SDETGPQIPHRRPTW (SEQ ID NO: 149) |
| CA4 dimer 1 | CA4-GGG-CA4 (flexible linker) | SDETGPQIPHRRPTWGGGSDETGPQIPHRRPTW (SEQ ID NO: 150) |
| CA4 dimer 2 | CA4-GSPGGG-CA4 (flexible linker) | SDETGPQIPHRRPTWGSPGGGSDETGPQIPHRRPTW (SEQ ID NO: 151) |
| CA4 dimer 3 | CA4-GSPGGGTGG-CA4 (flexible linker) | SDETGPQIPHRRPTWGSPGGGTGGSDETGPQIPHRRPTW (SEQ ID NO: 152) |
| CA4 dimer 4 | CA4-TonB-CA4 (rigid linker) | SDETGPQIPHRRPTWGPEPEPEPEPIPEPPKEAPVVIEKPKPKPKPKPPASDETGPQIPHRRPTW (SEQ ID NO: 153) |
| CA4 trimer | CA4-GGG-CA4-GGG-CA4 (flexible linker) | SDETGPQIPHRRPTWGGGSDETGPQIPHRRPTWGGGSDETGPQIPHRRPTW (SEQ ID NO: 154) |
| TonB linker | Linker peptide with flanking N-terminal GP and C-terminal PA residues | GPEPEPEPEPIPEPPKEAPVVIEKPKPKPKPKPKPA (SEQ ID NO: 53) |

The TonB linker peptide in "CA4 dimer 4" was the only rigid linker peptide, which consisted of alternating Pro-Glu and Pro-Lys repeats and derived from the intermediate domain of the Gram-negative bacterial cytoplasmic membrane protein TonB (SEQ ID NO: 155).

Binding affinity of CA4 peptide and CA4 multimers were assessed by Surface Plasmon Resonance (SPR). The CA surface was prepared by spin-coating 0.75% CA solution in mixed cyclohexanone/methyl ethyl ketone (1/9 weight ratio) solvent at 2000 rpm for 1 minute twice on the Biacore bare gold sensor chip (Biacore Inc., Catalogue number BR-1004-05; General Electric Corp., Fairfield, Conn.), followed by 80° C. annealing for 15 minutes. The CA resin used was CA-398-10 from Eastman Chemical Company (Kingsport, Tenn.), and the solution prepared was filtered with 0.2 μm PTFE membrane before use. The thickness of the spin-coated CA thin film was measured by Atomic Force Microscope (AFM) to be 26-30 nm.

Figure 5:
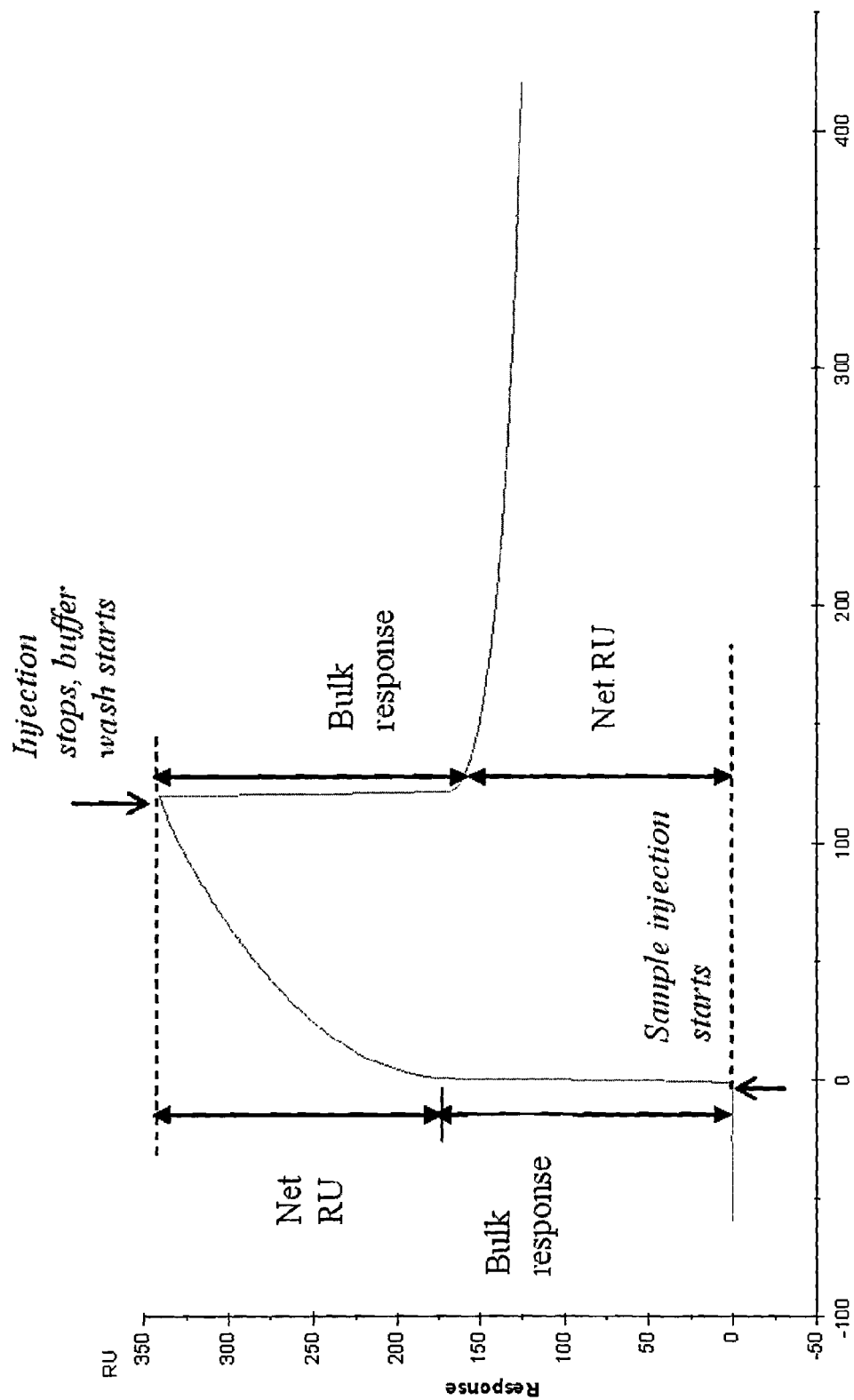
FIG. 5 is a typical binding kinetics curve for injection and buffer wash phases in Surface Plasmon Resonance sensorgram.

Binding of each peptide to the CA surface was tested at various concentration ranges in Tris Buffered Saline (TBS, 25 mM Tris, 150 mM NaCl, pH 7.5), using Biacore X100 system. Each peptide solution sample was injected for 2 minutes at flow rate of 30 μL/minute followed by 10 minutes buffer assay using Biacore instruments. Bulk response refers to the SPR response to the refractive index difference between the sample solution and the running buffer, but not caused by sample binding to the surface. Bulk response completely disappears once sample injection is finished and buffer wash starts. So the response units (RU) remained right after injection was caused by binding and proportional to the mass of peptide bound to the surface, and was named as "net RU" in binding data. FIG. 5 shows a typical binding kinetics curve for injection and buffer wash phases in SPR sensorgram, with indication of bilk response and net RU. Typically, association and dissociation rate constant (ka and kd) can be obtained from binding kinetics curve fitting, and dissociation constant ($K_D$). can be determined from the ratio of dissociation rate constant to association rate constant. The $K_D$ values derived from the binding kinetics curves for all peptides under study are listed in Table 10. The use of short linkers (3-6 amino acid residues) in CA4 dimer 1, CA4 dimer 2 and CA4 trimer gave 5 fold improvement on binding affinity compared to CA4 monomer. The use of long rigid linker (TonB linker) in CA4 dimer 4 gave 50 fold improvement on binding affinity compared to CA4 monomer. By contrast, the use of flexible linker in CA4 dimer 3 had detrimental effect on its binding affinity to CA surface. As control, the TonB linker peptide was tested in the same way. It showed no binding affinity to the CA surface.

TABLE 10

Dissociation constant ($K_D$) derived from kinetic curve.

| Peptide name | Description | ka (1/mS) | kd (1/S) | KD(M) from kinetics |
|---|---|---|---|---|
| CA4 | CA binding peptide identified from phage display (SEQ ID NO: 149) | 11.9 | 1.2E-03 | 1.0E-04 |
| CA4 dimer 1 | CA4-GGG-CA4 (flexible linker) (SEQ ID NO: 150) | 44.2 | 9.5E-04 | 2.1E-05 |
| CA4 dimer 2 | CA4-GSPGGG-CA4 (flexible linker) (SEQ ID NO: 151) | 26.49 | 7.1E-04 | 2.7E-05 |
| CA4 dimer 3* | CA4-GSPGGGTGG-CA4 (flexible linker) (SEQ ID NO: 152) | | | undetectable |
| CA4 dimer 4 | CA4-TonB-CA4 (rigid linker) (SEQ ID NO: 153) | 441.5 | 8.9E-04 | 2.0E-06 |
| CA4 trimer | CA4-GGG-CA4-GGG-CA4 (flexible linker) (SEQ ID NO: 154) | 23.46 | 7.9E-04 | 3.4E-05 |
| TonB linker* | Linker peptide (SEQ ID NO: 53) | | | undetectable |

Figure 6:
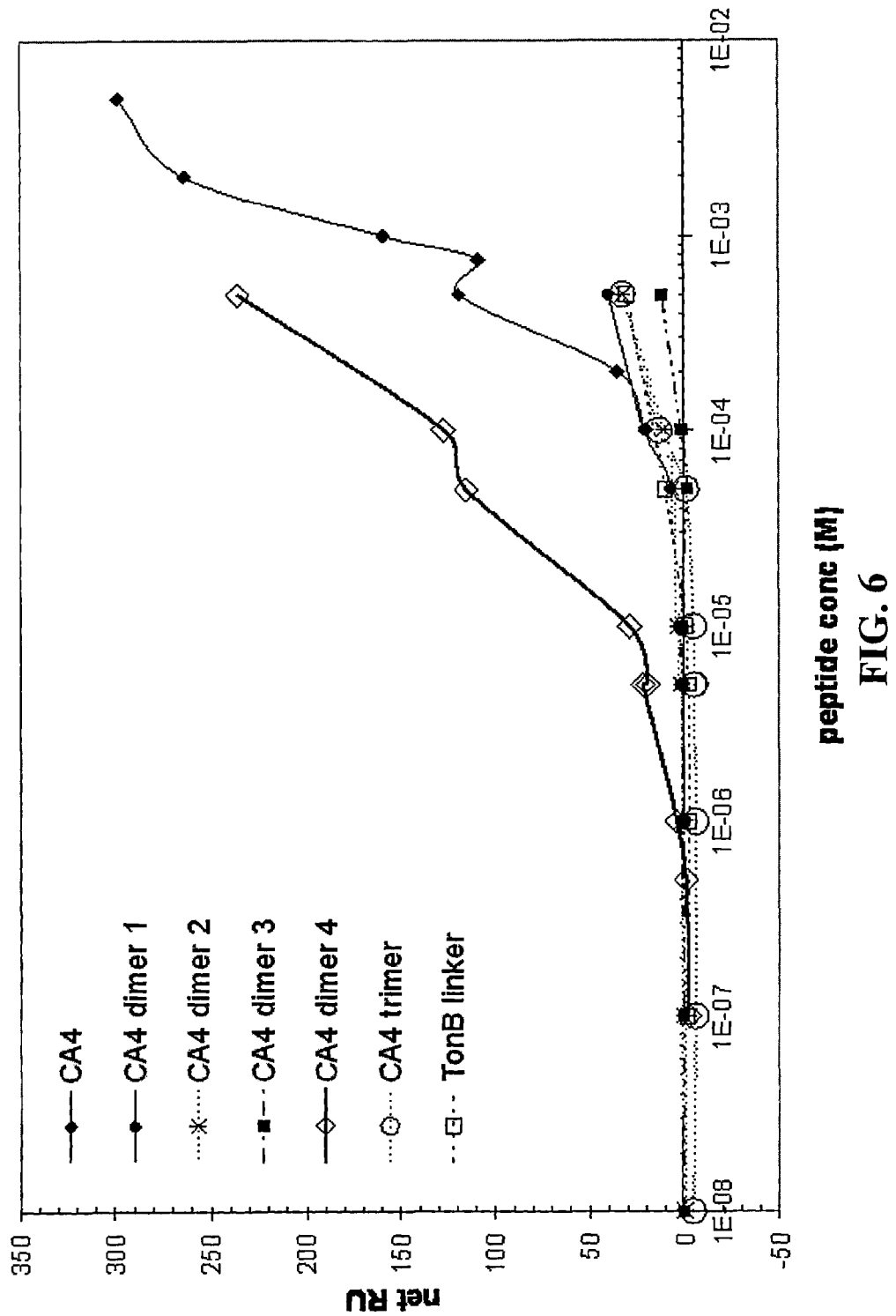
FIG. 6 is shows the net response units (RU) for various peptide concentration plots for all tested cellulose acetate-binding peptides described in Example 8.

Net RU versus peptide concentration plots also reflect peptide-binding affinity to the surface. FIG. 6 shows the net RU-peptide concentration plots for all tested CA binding peptides. Only CA4 dimer 4 which had a rigid peptide linker TonB between two CA4 domains showed significant binding affinity improvement: binding response started rising at 5 µM for CA4 dimer 4, while binding response for rest of CA4, CA4 dimer and CA4 trimer peptides started rising at about 100-500 µM range. As control, the TonB linker peptide showed no binding to the CA surface up to 50 µM. The comparison of CA4 multimers linked by flexible and rigid linker shown in FIG. 6 and Table 10 clearly indicated that peptide-surface binding affinity was improved by using rigid linker to connect individual binding domains, while the insertion of flexible linkers was detrimental to the binding affinity as illustrated by CA4 dimer 3.

Example 9

Simulation Protocol to Determine Linker Rigidity

The purpose of this experiment was to show that a computer simulation can be used to calculate and quantify the rigidity of various single chain peptide linkers.

All the energy calculations and simulations were done using CHARMm (Accelrys, CHARMm31b1) with the CHARMM27 force field. CHARMm is a simulation engine (Brooks B R et al. (1983) *J Comp Chem* 4: 187-217). CHARMM22 (released in 1991) and CHARMM27 (released in 1999) are the most recent versions of the force field. For purely protein systems, the two are equivalent (MacKerell, A. D. et al. (1998) *J. Phys. Chem. B* 102(18): 3586-3616).

For the cutoff model for non-bonded interactions, a non-bonded cutoff distance of 14 Å was used with CTOFNB=12 and CTONNB=10. The SWITCH cutoff method is used for the calculations of both the van der Waals and electrostatic interactions. The non-bonded lists are updated using the heuristic method. Particle Mesh Ewald summation is used to calculate the electrostatics interactions. Bonds involving hydrogen atoms are constrained using SHAKE.

All the simulations were done in explicit solvent with PBC.

Initialization of Peptides

All peptides were constructed using the Biopolymer module in InsightII (Accelrys). For those that have been designed to form one of the two stable conformations (alpha-helical or extended conformation), the peptides were constructed with the designed conformation as the initial conformation. For those peptides presumed to be flexible, two initial configurations were constructed for each peptide, one in the α-helical conformation, and the other in the extended conformation.

The ionization states of the titratable amino acids of the peptides were specified as follows:

Glu is assumed unprotonated (negatively charged); Lys assumed protonated (positively charged). The pH was set to 7, with both N- and C-termini set as charged.

Initial Energy Minimization

Energy minimization was performed on the initial structure. The initial phase of the minimization employs the steepest descent method for 400 steps to effectively quench the system towards the nearest local minimum. Further minimization was done using the conjugate gradients method for 800 steps or until the average gradient of the potential energy was below 0.1, followed by the Adopted Basis Newton-Raphson (ABNR) method for 2000 steps or until the average energy gradient was below 0.1.

Solvation of the Peptide

All the MD simulations were performed in explicit water using the periodic boundary conditions. The unit cell was a rectangular box, and its dimension was determined by adding 16 Å to the maximum extent of the peptide in each direction. The entire box of water molecules was overlaid onto the protein and water molecules that overlap with the protein were removed. The images were built using the Crystal facility in CHARMm. The frequency of updating the image atom list during the dynamics was done using the heuristic method. The maximum allowable distance of any group to be included in the image atom list was set to 14A.

If the total charge of the system was not zero, counter-ions ($Na^+$ or $Cl^-$) were added to bring the total charge of the system to zero. The counter-ions were randomly placed in the solvent box without overlapping with the peptide.

First, the energy minimization was done on water molecules only using the steepest descent method for 50 steps with the peptide fixed (constrained by a harmonic constraint with a force constant of 25). This helped to remove the bad contacts among water molecules. The constraint on the peptide was then removed and a minimization on the entire system was done using the steepest descent method for 400 steps or until the total gradient of the potential energy reached below 0.01.

Molecular Dynamics Simulation

The integration of the Newtonian equations of motion was performed with the Verlet algorithm and a step size of 2 fs (femtoseconds). A total of 216 ps (picoseconds) molecular dynamics simulation was performed, with the last 200 ps as the production run.

Heating

Next, the system was heated up from 0 Kelvin to 300 Kelvin using 5 Kelvin increments every 50 steps. The global rotation-translation was stopped every 200 steps. The entire heating process was run for 3000 steps (6 picoseconds (ps)).
Equilibration
After heating the system to 300K, equilibration was done to ensure that the system was stable. The system was equilibrated at 300K. The temperature was checked every 100 steps to see if it moved out of the desired window of +/−10K. If so, the velocities were scaled to bring the temperature back within the range of the target temperate (300 Kelvin+/−10 Kelvin). The equilibration process was run for 5000 steps (10 ps).
Production
The production phase was run in an NVT system (constant temperature) for 1,000,000 steps (200 ps) at 300 Kelvin. The coordinates were saved every 100 steps (0.2 ps) into the trajectory file.
Method of Analysis
Molecular Dynamics simulations provided detailed information about the pathways between different molecular conformations. The results of MD simulations were saved in a trajectory file, which contains coordinate sets (or "frames") of the peptide structure saved at regular intervals during the simulation.

The root-mean-square (RMS) fluctuation of a torsion angle is the standard deviation of the torsion angle value about its time-averaged value. The RMS fluctuation was calculated for all the torsion angles in the peptide and these values were averaged for torsion angle φ, ψ, or both φ and ψ combined.

The average value of the RMS fluctuations of the backbone torsion angles was then used to quantify the rigidity of the peptide. The more rigid the peptide is the smaller the average value of the RMS fluctuations is expected to be, due to a more limited conformational space accessible to the peptide.

RMS fluctuation ($RMS^{fluct}$) of the torsion angle was calculated as follows:

$$RMS^{fluct} = \sqrt{\frac{1}{N_f} \sum_f (\theta^f - \theta^{ave})^2}$$

where f refers to the frame number, N is the total number of frames in the trajectory file, and $\theta^f$ and $\theta^{ave}$ are the current value and the average value for the torsion angle, respectively.

Because the torsion angles have a periodicity of 2π (360°, the average value for the torsion angle cannot be calculated directly. Instead, the average value for the torsion angle was calculated after adjusting the observed values such that all the observed values take on the same sign as the majority do in the trajectory. This was done by adding or subtracting 360° from the original value if its sign is the opposite of that of the majority values (if the original value was greater than zero, then 360° was subtracted from it; otherwise, 360° was added). The average value was then the averaged value of the adjusted values of the torsion angle over time. The results of the modeling of various peptide linkers are provided in Table 11.

The results from the phage display selection results in Example 2 (Table 3) and Example 3 (Table 4) show that the majority of the selected peptide binding domains were comprised of rigid peptide linkers belonging to the Lb-series, Lc-series, Lj, Lk ("TonB"), and Lm-series of peptide linkers. In comparison to the 200 ps run in Table 10, each of these rigid peptide linker had an average RMS fluctuation over the length of the linker of less than 25 (usually less than 20) whether or not the initial conformation was α-helical conformation or an extended conformation. Generally absent from the phage display selection results were binding domains comprising flexible linkers (see linker series Ld, Le, Lf, Lg, and Lh). Except for the Lh1, all of the flexible linkers had 200 ps run average RMS fluctuations over 25; see Table 11).

TABLE 11

RMS fluctuations for various peptide linkers over a 200 ps run using different initial conformations.

| | | | 200 ps Run | | |
|---|---|---|---|---|---|
| Identifier | Peptide (SEQ ID NO) | Initial Conformation | Average RMS Fluctuation (Phi) | Average RMS Fluctuation (Psi) | Average RMS Fluctuation |
| La3 | (EAAAK)$_3$ (SEQ ID NO: 2) | α-helix | 10.66 | 16.11 | 13.38 |
| La5 | (EAAAK)$_5$ (SEQ ID NO: 4) | α-helix | 11.29 | 23.73 | 17.51 |
| La6 | (EAAAK)$_6$ (SEQ ID NO: 6) | α-helix | 10.66 | 14.94 | 12.8 |
| Lb2 | (EEAAKK)$_2$ (SEQ ID NO: 8) | α-helix | 11.06 | 14.84 | 12.95 |
| Lb4 | (EEAAKK)$_4$ (SEQ ID NO: 10) | α-helix | 9.75 | 12.85 | 11.3 |
| Lb5 | (EEAAKK)$_5$ (SEQ ID NO: 12) | α-helix | 10.2 | 13.03 | 11.61 |
| Lc4 | (KP)$_4$ (SEQ ID NO: 14) | extended | 14.55 | 16.29 | 15.42 |
| Lc8 | (KP)$_8$ (SEQ ID NO: 16) | extended | 13.63 | 15.57 | 14.8 |

TABLE 11-continued

RMS fluctuations for various peptide linkers over a 200 ps run using different initial conformations.

| Identifier | Peptide (SEQ ID NO) | Initial Conformation | 200 ps Run Average RMS Fluctuation (Phi) | Average RMS Fluctuation (Psi) | Average RMS Fluctuation |
|---|---|---|---|---|---|
| Lc12 | (KP)₁₂ (SEQ ID NO: 18) | extended | 13.0 | 14.18 | 13.59 |
| Lc16 | (KP)₁₆ (SEQ ID NO: 20) | extended | 12.96 | 12.92 | 12.94 |
| Ld2 | (GGGS)₂ (SEQ ID NO: 22) | α-helix | 43.63 | 68.28 | 55.95 |
| Ld2 | (GGGS)₂ (SEQ ID NO: 22) | extended | 39.45 | 53.29 | 46.37 |
| Ld4 | (GGGS)₄ (SEQ ID NO: 24) | α-helix | 46.64 | 86.17 | 66.41 |
| Ld4 | (GGGS)₄ (SEQ ID NO: 24) | extended | 39.61 | 51.01 | 45.31 |
| Ld6 | (GGGS)₆ (SEQ ID NO: 26) | α-helix | 39.69 | 67.77 | 53.73 |
| Ld6 | (GGGS)₆ (SEQ ID NO: 26) | extended | 36.49 | 53.89 | 45.19 |
| Le2 | (EGGGS)₂ (SEQ ID NO: 28) | α-helix | 47.98 | 70.46 | 59.22 |
| Le2 | (EGGGS)₂ (SEQ ID NO: 28) | extended | 40.95 | 58.45 | 49.7 |
| Le4 | (EGGGS)₄ (SEQ ID NO: 30) | α-helix | 36.26 | 74.95 | 55.6 |
| Le4 | (EGGGS)₄ (SEQ ID NO: 30) | extended | 36.25 | 47.95 | 42.1 |
| Le6 | (EGGGS)₆ (SEQ ID NO: 32) | α-helix | 27.94 | 67.18 | 47.56 |
| Le6 | (EGGGS)₆ (SEQ ID NO: 32) | extended | 34.4 | 39.68 | 35.73 |
| Lf2 | (KGGGS)₂ (SEQ ID NO: 34) | α-helix | 38.31 | 61.35 | 49.83 |
| Lf2 | (KGGGS)₂ (SEQ ID NO: 34) | extended | 34.79 | 66.62 | 50.7 |
| Lf4 | (KGGGS)₄ (SEQ ID NO: 36) | α-helix | 25.64 | 54.63 | 40.13 |
| Lf4 | (KGGGS)₄ (SEQ ID NO: 36) | extended | 34.74 | 44.04 | 39.39 |
| Lf6 | (KGGGS)₆ (SEQ ID NO: 38) | α-helix | 26.16 | 60.12 | 43.14 |
| Lf6 | (KGGGS)₆ (SEQ ID NO: 38) | extended | 36.34 | 48.85 | 42.59 |
| Lg1 | (GAGGAGGSGGS)₁ (SEQ ID NO: 40) | α-helix | NA | NA | NA |
| Lg1 | (GAGGAGGSGGS)₁ (SEQ ID NO: 40) | extended | NA | NA | NA |
| Lg2 | (GAGGAGGSGGS)₂ (SEQ ID NO: 42) | α-helix | 29.33 | 50.67 | 40.0 |

TABLE 11-continued

RMS fluctuations for various peptide linkers over a 200 ps run using different initial conformations.

| Identifier | Peptide (SEQ ID NO) | Initial Conformation | 200 ps Run Average RMS Fluctuation (Phi) | Average RMS Fluctuation (Psi) | Average RMS Fluctuation |
|---|---|---|---|---|---|
| Lg2 | (GAGGAGGSGGS)$_2$ (SEQ ID NO: 42) | extended | 37.1 | 53.6 | 45.35 |
| Lg3 | (GAGGAGGSGGS)$_3$ (SEQ ID NO: 44) | α-helix | 21.18 | 52.93 | 37.06 |
| Lg3 | (GAGGAGGSGGS)$_3$ (SEQ ID NO: 44) | extended | 36.12 | 46.76 | 41.44 |
| Lh1 | (AGPAPGSPGSP)$_1$ (SEQ ID NO: 46) | α-helix | 24.81 | 60.23 | 42.52 |
| Lh1 | (AGPAPGSPGSP)$_1$ (SEQ ID NO: 46) | extended | 22.21 | 23.58 | 22.9 |
| Lh2 | (AGPAPGSPGSP)$_2$ (SEQ ID NO: 48) | α-helix | 14.59 | 68.54 | 41.57 |
| Lh2 | (AGPAPGSPGSP)$_2$ (SEQ ID NO: 48) | extended | 22.41 | 30.15 | 26.28 |
| Lh3 | (AGPAPGSPGSP)$_3$ (SEQ ID NO: 50) | α-helix | 15.73 | 74.89 | 45.31 |
| Lh3 | (AGPAPGSPGSP)$_3$ (SEQ ID NO: 50) | extended | 21.66 | 28.45 | 25.05 |
| Lj | (KP)$_6$GG(KP)$_6$GG (SEQ ID NO: 52) | extended | 16.6 | 17.57 | 17.09 |
| Lk "(TonB)" | (EP)$_4$IPEPPKEAPVVIE(KP)$_6$ (SEQ ID NO: 54 | extended | 14.18 | 16.72 | 15.45 |
| Lm3 | (EAAAKLL)$_3$ (SEQ ID NO: 56 | α-helix | 10.78 | 15.93 | 13.35 |
| Lm4 | (EAAAKLL)$_4$ (SEQ ID NO: 58 | α-helix | 10.11 | 12.85 | 11.48 |

NA = not available

What is claimed is:

1. A peptide-based reagent comprising at least one body surface-binding domain (BSBD) consisting essentially of the general structure:

[(BSBP1)-RL$_1$-(BSBP2)-(RL$_2$)$_y$]$_x$ wherein,
- i) BSBP1 is a first body surface-binding peptide having affinity for a body surface;
- ii) BSBP2 is a second body surface-binding peptide having affinity for the body surface; wherein the BSBP1 and the BSBP2 are the same or different and each ranges in length from about 7 to about 60 amino acids;

wherein the BSBP1 and the BSBP2 are selected from the group consisting of: hair-binding peptides, skin-binding peptides, nail-binding peptides, and tooth-binding peptides provided that both the first body surface-binding peptide and the second body surface-binding peptide have high affinity for the same body surface;
- iii) RL$_1$ is a first rigid peptide linker;
- iv) RL$_2$ is a second rigid peptide linker; wherein the RL1 and the RL2 is the same or different and each ranges in length from about 3 to 50 amino acids in length;

wherein, the RL$_1$ and the RL$_2$ are selected from the group consisting of:
- a) an extended proline dipeptide of the formula:

(Xaa4-Pro)$_e$
or
(Pro-Xaa4)$_e$
or
[(Xaa4-Pro)$_6$-Gly-Gly]$_e$ wherein e=2 to 20; and Xaa4 is an acidic or basic amino acid; and
- b) a peptide linker having the amino acid sequence of SEQ ID NO: 54;
- v) x=1 to 10; and
- vi) y=0 or 1.

2. The peptide-based reagent of claim 1 wherein the first body surface-binding peptide and the second body-surface binding peptide individually have an MB$_{50}$ value for the body surface of no more than $10^{-4}$ M.

3. The peptide-based reagent of claim 1 wherein said peptide-based reagent comprises a general structure (BSBD)$_f$-BR-BA;

wherein
- i) BSBD is the body surface-binding domain of claim 1;
- ii) BR is a peptide bridge ranging from 1 to 60 amino acids in length;

iii) BA is a benefit agent coupled to the peptide-based reagent; and iv) f=1 to 10.

4. The peptide-based reagent of claim 3 wherein the benefit agent is covalently or non-covalently coupled to the peptide-based reagent.

5. The peptide-based reagent of claim 4 wherein the benefit agent is selected from the group consisting of conditioning agents, colorants, and antimicrobial agents.

6. The peptide-based reagent of claim 5 wherein the colorants are selected from the group consisting of dyes, pigments, and lakes.

7. The peptide-based reagent of claim 6 wherein the colorant is a pigment.

8. A personal care composition comprising;

a) at least one peptide-based reagent of claim 1; and b) a benefit agent.

9. The personal care composition of claim 8 wherein the personal care composition is selected from the group consisting of hair care compositions, skin care compositions, nail care compositions, and oral care compositions.

10. The personal care composition of claim 8 wherein the benefit agent is a particulate benefit agent.

11. The personal care composition of claim 10 wherein the particulate benefit agent is coated with at least one polymer.

12. The personal care composition of claim 8 wherein the benefit agent is covalently or non-covalently coupled to the peptide-based reagent.

13. The personal care composition of claim 12 wherein the benefit agent is selected from the group consisting of conditioning agents, colorants, and antimicrobial agents.

14. The personal care composition of claim 13 wherein the colorants are selected from the group consisting of dyes, pigments, and lakes.

15. The personal care composition of claim 14 wherein the colorant is a pigment.

16. The personal care composition of claim 15 wherein the pigment is a white pigment.

17. The personal care composition of claim 9 wherein the hair care composition is in the form of a shampoo, a conditioner, a rinse, a lotion, an aerosol, a gel, a mousse or a hair dye.

18. The personal care composition of claim 9 wherein the skin care composition is in the form of a cream, a gel, a lotion, a capsule or a rinse.

19. The personal care composition of claim 9 wherein the oral cue composition is in the form of a toothpaste, a dental cream, a gel or tooth powder, a mouth wash, a breath freshener or a dental floss.

20. The personal care composition of claim 9 wherein the nail care composition is in the form of a nail polish or a nail protectant.

21. The peptide-based reagent comprising a body surface-binding domain according claim 1, having affinity for hair, wherein said body surface-binding domain comprises an amino acid sequence provided as SEQ ID NO: 85.

* * * * *